(12) United States Patent
Wu et al.

(10) Patent No.: US 11,389,543 B2
(45) Date of Patent: Jul. 19, 2022

(54) PROCESS FOR THE PREPARATION OF TUBULYSINS AND INTERMEDIATES THEREOF

(71) Applicant: SEAGEN INC., Bothell, WA (US)

(72) Inventors: Kun-Liang Wu, Bothell, WA (US); Qingwu Jin, Bothell, WA (US); Wendel Doubleday, Snohomish, WA (US)

(73) Assignee: Seagen Inc., Bothell, WA (US)

( * ) Notice: Subject to any disclaimer, the term of this patent is extended or adjusted under 35 U.S.C. 154(b) by 179 days.

(21) Appl. No.: 16/645,369

(22) PCT Filed: Sep. 7, 2018

(86) PCT No.: PCT/US2018/050095
§ 371 (c)(1),
(2) Date: Mar. 6, 2020

(87) PCT Pub. No.: WO2019/051322
PCT Pub. Date: Mar. 14, 2019

(65) Prior Publication Data
US 2020/0297864 A1    Sep. 24, 2020

Related U.S. Application Data

(60) Provisional application No. 62/556,234, filed on Sep. 8, 2017.

(51) Int. Cl.
| *C07D 277/56* | (2006.01) |
| *A61K 38/00* | (2006.01) |
| *A61K 47/68* | (2017.01) |
| *C07K 5/02* | (2006.01) |

(52) U.S. Cl.
CPC ...... *A61K 47/6851* (2017.08); *A61K 47/6811* (2017.08); *A61K 47/6889* (2017.08); *C07D 277/56* (2013.01); *C07K 5/021* (2013.01); *A61K 38/00* (2013.01)

(58) Field of Classification Search
CPC ............ A61K 47/6851; A61K 47/6889; A61K 47/6811; A61K 38/00; C07D 277/56; C07K 5/021
See application file for complete search history.

(56) References Cited

U.S. PATENT DOCUMENTS

| 8,343,928 B2 | 1/2013 | Doronina |
| 2014/0127197 A1 | 5/2014 | Ebens |

FOREIGN PATENT DOCUMENTS

| CN | 101663044 A | 3/2010 |
| CN | 104379602 A | 2/2015 |
| CN | 104822656 A | 8/2015 |
| CN | 105358573 A | 2/2016 |
| CN | 105358574 A | 2/2016 |
| EP | 2708243 A1 | 3/2014 |
| WO | 2004005269 A1 | 1/2004 |
| WO | 2008106080 A2 | 9/2008 |
| WO | 2008106080 A3 | 12/2008 |
| WO | 2013134743 A1 | 9/2013 |
| WO | 2013173337 A2 | 11/2013 |
| WO | 2013173392 A1 | 11/2013 |
| WO | 2014193722 A1 | 12/2014 |
| WO | 2014194247 A1 | 12/2014 |
| WO | 2013173337 A3 | 6/2015 |
| WO | 2016040684 A1 | 3/2016 |
| WO | 2016090050 A1 | 6/2016 |
| WO | 2016138288 A1 | 9/2016 |

OTHER PUBLICATIONS

Behrens, C.R. et al. (2014, e-pub. Sep. 27, 2013). "Methods For Site-Specific Drug Conjugation To Antibodies," mAB 6(1):46-53.
Columbo, R. et al. (Nov. 2016, e-pub. Aug. 5, 2016). "Total Synthesis and Biological Evaluation of Tubulysin Analogues," J. Org. Chem. 81(21):10302-10320.
Corey, E.J. et al. (1987). "Highly Enantioselective Borane Reduction Of Ketones Catalyzed By Chiral Oxazaborolidines. Mechanism And Synthetic Implications," J. Amer. Chem. Soc. 109(18):5551-5553.
Corey, E.J. et al. (Aug. 17, 1998). "Reduction of Carbonyl Compounds with Chiral Oxazaborolidine Catalysts: A New Paradigm for Enantioselective Catalysis and a Powerful New Synthetic Method," Angew. Chem, Int'l. Ed. 37 (15):1986-2012.
Doronina, S.O. et al. (Jul. 2003). "Development of Potent Monoclonal Antibody Auristatin Conjugates for Cancer Therapy," Nat. Biotechnol. 21(7)778-784.
Han, S.-Y. et al. (2004). "Recent Development Of Peptide Coupling Agents In Organic Synthesis," Tet. 60:2447-2476.
Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMI) for Use With ADEPT and GDEPT," Bioorganic & Medicinal Chemistry Letters 9(15):2237-2242.
Inami, K. et al. (1985). "Total Synthesis Of Antibiotic Althiomycin," Chem. Soc. (Jpn) 58(1):352-360.
International Preliminary Report on Patentability, dated Mar. 10, 2020, for PCT Application No. PCT/US2018/050095, filed Sep. 7, 2018, 10 pages.
International Search Report and Written Opinion, dated Jan. 16, 2019, for PCT Application No. PCT/US2018/050095, filed Sep. 7, 2018, 18 pages.
International Union of Pure and Applied Chemistry (Nov. 5, 1960). "Definitive Rules for Nomenclature of Organic Chemistry," J. Am. Chem. Soc. 82:5545-5473, 30 pages.
Jeffrey, S.C. et al. (May-Jun. 2006, e-pub. May 3, 2006). "Development and Properties of Beta-Glucuronide Linkers for Monoclonal Antibody-Drug Conjugates," American Chemical Society 17(3):A-J.

(Continued)

*Primary Examiner* — Timothy R Rozof
(74) *Attorney, Agent, or Firm* — Morrison & Foerster LLP

(57) ABSTRACT

Improved processes for the preparation of tubulysin compounds, tubulysin drug linker compounds, and their intermediates are disclosed.

22 Claims, No Drawings

(56) References Cited

OTHER PUBLICATIONS

Korenaga, T. et al. (Dec. 7, 2010, e-pub. Oct. 12, 2010). "Rational Electronic Tuning Of CBS Catalyst For Highly Enantioselective Borane Reduction Of Trifluoroacetophenone," Chem. Comm. 46(45):8624-8626.

Lee, W. et al. (Jun. 6, 2008, e-pub. Apr. 24, 2008). "Synthesis and Characterization Of Polyaromatic Compounds Using tri(naphthyl)indium," J. Org. Client. 73(11):4326-4396.

Parker, J.S. (Aug. 1, 2017). "The Development and Scale-Up of an Antibody Drug Conjugate Tubulysin Payload," Organic Process Research And Development 21 (10):1602-1609.

Parker, J.S. et al. (Aug. 1, 2017). "Supporting Information—The Development and Scale-Up of an Antibody Drug Conjugate Tubulysin Payload," Organic Process Research & Development, 21(10):1602-1609.

Patterson et al. (Jun. 20, 2008, e-pub. May 15, 2008). "Expedient Synthesis of N-Methyl Tubulysin Analogues with High Cytotoxicity," J. Org. Chem., 73(12):4362-4369.

Peltier, H.M. et al. (Dec. 20, 2006). "The Total Synthesis Of Tubulysin D," J. Amer. Chem. Soc. 128 (50):16018-16019.

PUBCHEM: (Mar. 21, 2013). "2- [(1S,3R)-1-acetyloxy-4-methyl-3- [methyl- [(2-methylpropan-2-yl )oxycarbonyl] amino]pentyl]-1,3-thiazole-4-carboxylic acid," Pubchem Retrieved from the Internet: URL:https://pubchem.ncbi.nlm.nih.gov/compo und/70952754#secti on=Top, last visited Oct. 2, 2020, 9 pages.

Sani, M et al. (2007). "Total Synthesis of Tubulysins U and V," Angew. Chem. Int. Ed. 46(19):3526-3529.

Sasse, F. et al. (Sep. 2000). "Tubulysins, New Cytostatic Peptides from Myxobacteria Acting on Microtubuli: Production, Isolation, Physico-Chemical and Biological Properties," J. of Antibiotics 53(9):879-885.

Shankar, S.P. et al. (2013). "Synthesis And Structure-Activity Relationship Studies Of Novel Tubulysin U Analogs—Effect On Cytotoxicity Of Structural Variations In The Tubuvaline Fragment," Org. Biomol. Chem. 11:2273-2287.

Shankar, S.P. et al. (Nov. 6, 2013, e-pub. Sep. 11, 2013). "Synthesis and Cytotoxicity Evaluation of Diastereoisomers and N-Terminal Analogues of Tubulysin-U," Tetrahedron Letters 54(45):6137-6141.

Turk, V. et al. (2012, e-pub. Oct. 12, 2011). "Cysteine Cathepsins: From Structure, Function, and Regulations to New Frontiers," Biochimica et Biophysica Acta 1824:68-88.

PROCESS FOR THE PREPARATION OF TUBULYSINS AND INTERMEDIATES THEREOF

CROSS REFERENCE TO RELATED APPLICATIONS

This patent application is a U.S. national stage filing under 35 USC § 371 of International Application No. PCT/US2018/050095, filed Sep. 7, 2018, which claims the benefit of priority to U.S. Provisional Application No. 62/556,234, filed Sep. 8, 2017 each of which are incorporated by reference in their entireties for all purposes.

BACKGROUND OF THE INVENTION

The invention relates to synthetic methods for producing tubulysin compounds having substitution of the amide nitrogen atom of the tubuvaline component, and intermediates thereof.

Tubulysins are a class of powerful cytostatic agents that exhibit their activity through inhibition of tubulin polymerization. Naturally-occurring tubulysins are linear tetrapeptides consisting of N-methyl D-pipecolic acid (Mep), isoleucine (Ile), tubuvaline (Tuv), an unnatural amino acid, and either tubutyrosine (Tut, an analog of tyrosine) or tubuphenylalanine (Tup, an analog of phenylalanine), both of which are unnatural amino acids, as shown in Formula T:

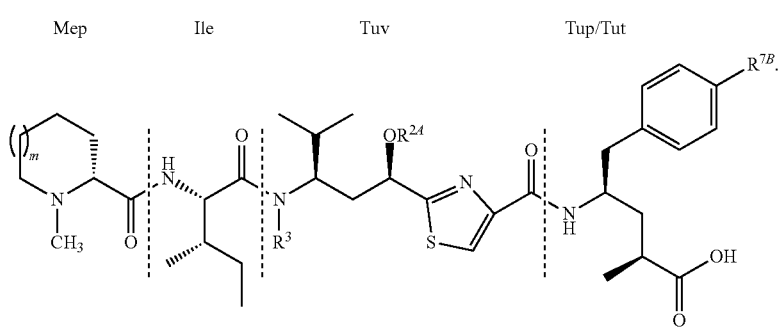

(T)

Tubulysins have been explored as potential cancer chemotherapeutics and as payloads on ligand-drug conjugates (LDCs). Tubulysins comprising an N-substituted tubuvaline are of particular interest because of their potency (Sasse, F. et al. *J. Antibiot. (Tokyo)* (2000) 53(9): 879-885. The development of N-substituted tubulysin analogs and methods of more efficient preparations is of clinical importance.

Generally, N-substituted tubulysins are assembled via peptide synthesis starting from N-substituted tubuvaline derivatives. An exemplary method of preparing such tubuvaline intermediates and the corresponding tubulysin compounds is provided by Patterson et al. "Expedient Synthesis of N-Methyl Tubulysin Analogues with High Cytotoxicity" *J. Org. Chem.* (2008) 73(12): 4362-4369.

The methods of synthesis of tubulysin compounds having substitution of the amide nitrogen atom of the tubuvaline component reported in the literature to date involve multiple steps that are not easily scalable. Therefore, a need exists in the art for improved processes in producing N-substituted tubuvaline for the preparation of the tubulysin compounds. The methods described herein address that unmet need.

SUMMARY OF THE INVENTION

A principal embodiment of the invention provides for a method for preparing a tubuvaline compound of Formula 2:

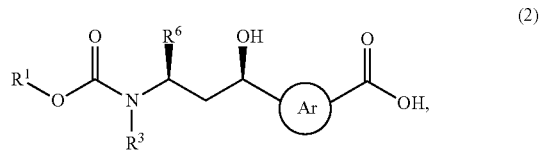

(2)

or a composition comprised or consisting essentially of that compound, optionally in salt form, wherein: the circled Ar is a 1,3-phenylene or a nitrogen-containing 5- or 6-membered 1,3-heteroarylene, optionally substituted at the remaining positions; $R^1$ is t-butyl, 9-fluorenyl, allyl, optionally substituted phenyl or other moiety so that $R^1$—OC(=O)— is a suitable nitrogen protecting group; $R^3$ is optionally substituted saturated $C_1$-$C_8$ alkyl, optionally substituted unsaturated $C_3$-$C_8$, or optionally substituted $C_3$-$C_8$ heteroalkyl; and $R^6$ is optionally substituted $C_1$-$C_8$ alkyl, the method comprising the steps of: (a) contacting a tubuvaline intermediate of Formula A:

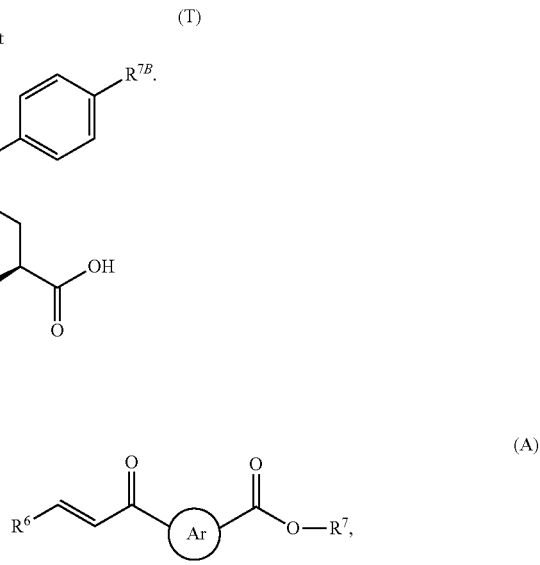

(A)

optionally in salt for, wherein $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moiety so that $R^7$—O— provides a suitable carboxylic acid protecting group, with a compound of Formula B:

$R^3NHC(O)OR^1$  (B), in a suitable polar, aprotic solvent in the presence of a suitable transition metal (II) or transition metal (III) catalyst, in particular, one comprising a transition metal selected from the group consisting of Cu(II), Zn(II) and Yb(III), so as to form a mixture of two enantiomeric tubuvaline intermediates represented by Formula AB:

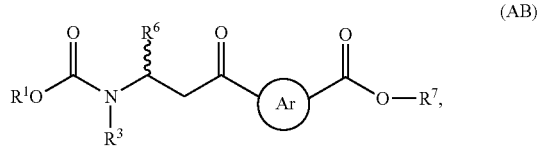
(AB)

or a composition comprised or consisting essentially of these enantiomeric intermediates, each optionally in salt form; and (b) contacting the enantiomeric Formula AB tubuvaline intermediates, or composition comprised or consisting essentially of these intermediates, each optionally in salt form, with a suitable reducing agent, in particular, a chiral reducing agent, so as to form a mixture of two diastereomeric tubuvaline compounds, each optionally in salt form, represented by the structure of Formula R-1a:

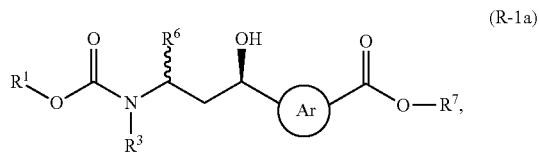
(R-1a)

or a composition comprised or consisting essentially of these diastereomers or salts thereof; and (c) contacting the diastereomeric mixture of Formula R-1a, or the composition comprising or consisting essentially of that mixture with a suitable hydrolysis agent so as to form a mixture of two tubuvaline diastereomeric compounds, each optionally in salt form, represented by Formula R-2 having the structure of:

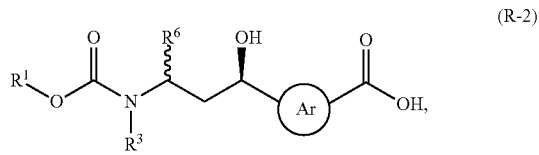
(R-2)

or composition comprised or consisting essentially of these diastereomers or salts thereof, wherein the variable groups of Formulae A, B and AB are as defined for Formula 2.

Other principle embodiments provide methods for preparing a tubuvaline composition comprised or consisting essentially of a diastereomer indicated as Formula R-1a or Formula R-2, either optionally in salt form, as the predominate optical isomer in which $R^6$ is in the R-configuration, which are described herein by (R,R)-Formula 1a or (R,R)-Formula 2, respectively, wherein the composition contains a diastereomeric impurity or salt thereof of no more than about 10% w/w, preferably no more than about 5% w/w, more preferably no more than about 1% w/w or about 0.5% w/w, relative to the total amount of the Formula 1a or Formula 2 optical isomers present in the composition, which is attributable to these diastereomers and their respective enantiomers, or is essentially free of that diastereomer in which $R^6$ of Formula R-1a or Formula R-2 is in the S-configuration, which is described herein as (R,S)-Formula 1a or (R,S)-Formula 2, respectively, and is essentially or substantially free of the corresponding enantiomer, which is indicated as (S,R)-Formula 1a or (S,R)-Formula 2, each optionally in salt form, and optionally containing as the major optical impurity the enantiomer or salt thereof of the predominate optical isomer, which is described as (S,S)-Formula 1a or (S,S)-Formula 2, respectively. In related embodiments provided are those Formula 1a and Formula 2 optical isomers each in purified form useful as analytical standards in the development of other methods for stereoselective preparation of tubuvaline compounds of (R,R)-Formula 1a or (R,R)-Formula 2 tubuvaline compounds obtained therefrom by hydrolysis.

Other principle embodiments provides for methods of preparing from tubuvaline compounds of Formula R-1a or Formula R-2 tubuvaline compounds of related structure in which another O-linked substituent replaces the hydroxyl group. Those embodiments include replacement of the hydroxyl group in Formula R-1a by an ether group of formula —$OR^2$, wherein $R^2$ is optionally substituted saturated $C_1$-$C_8$ alkyl, optionally substituted unsaturated $C_3$-$C_8$ alkyl, optionally substituted $C_2$-$C_8$ alkenyl or optionally substituted $C_2$-$C_8$ alkynyl, or wherein $R^2$ is $R^{2A}$, wherein $R^{2A}$ is —$CH_2R^{2C}$, wherein $R^{2C}$ is optionally substituted saturated $C_1$-$C_8$ ether, optionally substituted unsaturated $C_3$-$C_8$ ether, optionally substituted $C_2$-$C_8$ alkenyl or optionally substituted $C_2$-$C_8$ alkynyl, followed by hydrolysis of the carboxylic acid protecting group, which is provided by —$OR^1$, and further include embodiments in which the hydroxyl group in Formula 2 is replaced by an ester substituent of formula —$OR^{2A}$ wherein $R^{2A}$ is $R^{2B}C(=O)$—, wherein $R^{2B}$ is optionally substituted saturated $C_1$-$C_8$ alkyl, optionally substituted unsaturated $C_3$-$C_8$ alkyl, optionally substituted $C_2$-$C_8$ alkenyl or optionally substituted $C_2$-$C_8$ alkynyl.

Still other principle embodiments provide for Drug Linker compositions, wherein the compounds of the composition have a quaternized tubulysin Drug Unit, that are prepared from the tubuvaline compositions and further provide for Ligand Drug Conjugate compositions derived therefrom.

Those and other embodiments of the invention are described in more detail in the following "Detailed Description of the Invention" and "Claims".

DETAILED DESCRIPTION OF THE INVENTION

General

The present invention is based, in part, on the discovery that tubuvaline analogs can be prepared using a significantly simplified sequence of synthetic steps from commercially available starting materials that significantly shortens the route. Specifically, the present invention provides tubuvaline derivatives that are readily generated using a transition metal (II)-catalyzed Michael addition that introduces a suitably protected secondary amine into a tubuvaline precursor without the need for an inert atmosphere and difficult to control reaction conditions, thus increasing yields and shortening overall reaction times. Thus, the present invention further provides improved processes for preparing certain tubulysin compounds and related Drug Linker compounds and Ligand Drug Conjugates.

1. Definitions

Unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means and/or where permitted by context. Thus, as presented in the specification and the appended claims, the singular forms "a," "an," and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Invention embodiments also specifically include those compounds, compositions, compositions or methods that are, or that consist of, or that consist essentially of those specified components, elements or steps. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. The term "comprised of" is used interchangeably with the term "comprising" and are stated as equivalent terms. Similarly, disclosed compositions, devices, articles of manufacture or methods that "consist of" a component or step are closed and they would not include or read on those compositions or methods having appreciable amounts of an additional component(s) or an additional step(s). Furthermore, the term "consisting essentially of" admits for the inclusion of unrecited elements or steps that have no material effect on the functionality of the disclosed compositions, devices, articles of manufacture or methods for its intended purpose as further defined herein. The section headings used herein are for organizational purposes only and are not to be construed as limiting the subject matter described. Unless otherwise indicated, conventional methods of mass spectroscopy, NMR, HPLC, protein chemistry, biochemistry, recombinant DNA techniques, and pharmacology are employed.

"About", as used herein in connection with a numeric value or range of values o describe a particular property of a compound or composition, indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicate that the numeric value or range of values can vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, or 0.01% of the recited value or range of values, typically by 10% to 0.5%, more typically by 5% to 1%, while still describing the particular property.

With respect to subscript p, which denotes the average number of drug linker moieties in a Ligand Drug Conjugate composition as further defined herein, the term "about" reflects the accepted uncertainty in the art for determining that value from a distribution of Ligand Drug Conjugate compounds within that composition as determined by standard methods of size exclusion or HIC chromatography or HPLC-MS.

"Essentially retains", "essentially retaining" and like terms, as used herein, refers to a property, characteristic, function or activity of a compound or composition or moiety thereof that has not detectably changed or is within experimental error of determination of that same activity, characteristic or property of a compound or composition or moiety of related structure.

"Substantially retains", "substantially retaining" and like terms, as used herein, refers to a measured value of a physical property or characteristic of a compound or composition or moiety thereof that may be statistically different from the determination of that same physical property of another compound or composition or moiety of related structure, but which such difference does not translate to a statistically significant or meaningful difference in biological activity or pharmacological property in a suitable biological test system for evaluating that activity or property (i.e., biological activity or property is essentially retained). Thus the phrase "substantially retains" is made in reference to the effect that a physical property or characteristic of a compound or composition has on a physiochemical or pharmacological property or biological activity that is explicitly associated with that physical property or characteristic.

"Negligibly" or "negligible", as used herein, is an amount of an impurity below the level of quantification by HPLC analysis and if optical impurities are present represents from about 0.5% to about 0.1 w/w % of the composition that it contaminates. Depending on context, those terms may alternatively mean that no statistically significant difference is observed between measured values or outcomes or are within experimental error of the instrumentation used to obtain those values. Negligible differences in values of a parameter determined experimentally do not imply that an impurity characterized by that parameter is present in negligible amount.

"Predominately containing", "predominately having" and like terms, as used herein, refers to the major component of a mixture. When the mixture is of two components, then the major component represents more than 50% by weight of the mixture. With a mixture of three or more components the predominant component is the one present in greatest amount in the mixture and may or may not represent a majority of the mass of the mixture.

"Electron-withdrawing group", as the term is used herein, refers to a functional group or electronegative atom that draws electron density away from an atom to which it is bonded either inductively and/or through resonance, whichever is more dominant (i.e. a functional group or atom may be electron-donating through resonance but may overall be electron withdrawing inductively), and tends to stabilize anions or electron-rich moieties. The electron-withdrawing effect is typically transmitted inductively, albeit in attenuated form, to other atoms attached to the bonded atom that has been made electron-deficient by the electron-withdrawing group (EWG), thus reducing the electron density of a more remote reactive center.

An electron-withdrawing group (EWG) is typically selected from the group consisting of —C(=O), —CN, —NO$_2$, —CX$_3$, —X, —C(=O)OR', —C(=O)NH$_2$, —C(=O)N(R')R$^{op}$, —C(=O)R', —C(=O)X, —S(=O)$_2$R$^{op}$, —S(=O)$_2$OR', —SO$_3$H$_2$, —S(=O)$_2$NH$_2$, —S(=O)$_2$N(R')R$^{op}$, —PO$_3$H$_2$, —P(=O)(OR')(OR$^{op}$)$_2$, —NO, —NH$_{3+}$, —N(R')(R$^{op}$), —N(R$^{op}$)$_3$+, and salts thereof as appropriate, wherein X is —F, —Br, —Cl, or —I, and R$^{op}$ is, at each occurrence, independently selected from a grouping previously described for optional substituents and in some aspects is independently selected from the group consisting of C$_1$-C$_6$ alkyl and phenyl, and wherein R' is hydrogen and R$^{op}$ is selected from a grouping as described elsewhere for optional substituents and in some aspects is a $C_1$-$C_{12}$ alkyl, $C_1$-$C_8$ alkyl, $C_1$-$C_6$ alkyl or $C_1$-$C_4$ alkyl. An EWG can also be an aryl (e.g., phenyl) or heteroaryl depending on its substitution and certain electron deficient heteroaryl groups (e.g., pyridine). Thus, in some aspects, an "electron-withdrawing group" further encompasses electron-deficient $C_5$-$C_{24}$ heteroaryls and $C_6$-$C_{24}$ aryls that electron-deficient due to substituted with electron-withdrawing substituents. More typically, an electron-withdrawing group is independently selected from the group consisting of —C(=O), —CN, —NO$_2$, —CX$_3$, and —X, wherein X is halogen, typically selected from the group consisting of —F and —Cl. Depending on its substituents, an optionally substituted alkyl moiety may also be an electron withdrawing group and thus in such cases would be encompassed by the term for an electron-withdrawing group.

"Electron-donating group", as the term is used herein, refers to a functional group or electropositive atom that increases electron density of an atom to which it is bonded either inductively and/or through resonance, whichever is more dominant (i.e., a functional group or atom may be electron-withdrawing inductively but may overall be electron-donating through resonance), and tends to stabilize cations or electron poor systems. The electron-donating effect is typically transmitted through resonance to other atoms attached to the bonded atom that has been made electron rich by the electron-donating group (EDG) thus increasing the electron density of a more remote reactive center. Typically, an electron donating group is selected from the group consisting of —OH, —OR' and —NH$_2$, —NHR', and N(R')$_2$, provided that the nitrogen atom is not protonated, wherein each R' is an independently selected from $C_1$-$C_{12}$ alkyl, typically $C_1$-$C_6$ alkyl. Depending on its substituents, a $C_6$-$C_{24}$ aryl, $C_5$-$C_{24}$ heteroaryl, or unsaturated $C_1$-$C_{12}$ alkyl moiety may also be an electron-donating group and in some aspects such moieties are encompassed by the term for an electron-donating group. In certain aspects, an electron donating group is a substituent of PAB or PAB-type self-immolative Spacer Unit that accelerates its fragmentation on activation, which is believed to occur through stabilization of the quinone methide byproduct.

"Compound" as the term is used herein, refers to and encompasses the chemical compound itself, either named or represented by structure, and salt form(s) thereof, whether explicitly stated or not, unless context makes clear that such salt forms are to be excluded. Compound salts include zwitterionic salt forms and acid addition and base addition salt forms having organic counterions or inorganic counterions and salt forms involving two or more counterions, which may be the same or different. In some aspects, the salt form is a pharmaceutically acceptable salt form of the compound. The term "compound" further encompasses solvate forms of the compound, in which solvent is noncovalently associated with the compound or is reversibly associated covalently with the compound, as when a carbonyl group of the compound is hydrated to form a gem-diol or an imine bond of the compound is hydrated to form a carbinolamine. Solvate forms include those of the compound itself and its salt form(s) and are inclusive of hemisolvates, monosolvates, disolvates, including hemihydrates, hydrates and dihydrates; and when a compound can be associated with two or more solvent molecules, the two or more solvent molecules may be the same or different. In some instances, a compound of the invention will include an explicit reference to one or more of the above forms, e.g., salts and/or solvates, which typically does not imply solid state forms of the compound; however, this reference is for emphasis only, and is not to be construed as excluding any other of the forms as identified above. Furthermore, when explicit reference to a salt and/or solvate form of a compound or a Ligand Drug Conjugate composition or compound thereof is not made, that omission is not to be construed as excluding the salt and/or solvate form(s) of the compound or Conjugate unless context make clear that such salt and/or solvate forms are to be excluded.

"Optical isomer", as the term is used herein, refers to a related compound in comparison to a reference compound both having identical atom connectivities but differing structurally by one or more chiral centers in opposite stereochemical configuration(s). For example, a reference compound having two chiral centers in the R,R-configuration, will be related to its optical isomers in which those centers are in the R,S-, S,S- and S,R-configurations. Optical isomer having the R,R- and R,S-configurations are related as diastereomers as are optical isomers having the S,S- and S,R-configurations. If no other chiral centers are present then the R,R- and R,S-diastereomers are related as enantiomers to the S,S- and S,R-diastereomers, respectively. In those instances in which a reference compound has only two chiral centers in the R,R-configuration, related compounds with the R,S and S,R-configuration are diastereomeric to that reference compound whereas the related compound with the S,S-configuration will be its enantiomer.

"Moiety", as used herein, means a specified segment, fragment, or functional group of a molecule or compound. Chemical moieties are sometimes indicated as chemical entities that are embedded in or appended to (i.e., a substituent or variable group) a molecule, compound or chemical formula.

Unless indicated otherwise or implied by context, for any substituent group or moiety described herein by a given range of carbon atoms, the designated range means that any individual number of carbon atoms is described. Thus, reference to, e.g., "optionally substituted $C_1$-$C_4$ alkyl" or "optionally substituted $C_2$-$C_6$ alkenyl" specifically means that a 1, 2, 3, or 4 carbon alkyl moiety, optionally substituted, as defined herein, is present, or a 2, 3, 4, 5, or 6 carbon alkenyl moiety, optionally substituted, as defined herein, is present, respectively. All such numerical designations are expressly intended to disclose all of the individual carbon atom groups; and thus "optionally substituted $C_1$-$C_4$ alkyl" includes, methyl, ethyl, 3-carbon alkyls, and 4-carbon alkyls, including all of their positional isomers, whether substituted or unsubstituted. Thus, when an alkyl moiety is substituted, the numerical designations refer to an unsubstituted base moiety and are not intended to include carbon atoms not directly attached to the base moeity that may be present in the substituents of that base moiety. For esters, carbonates, carbamates, and ureas as defined herein that are identified by a given range of carbon atoms, the designated range includes the carbonyl carbon of the respective functional group. Thus, a $C_1$ ester refers to a formate ester and a $C_2$ ester refers to an acetate ester.

The organic substituents, moieties, and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as used herein, by itself or as part of another term, unless otherwise stated or implied by context, refers to methyl or a collection of contiguous carbon atoms, one of which is monovalent, wherein one or more of the carbon atoms are saturated (i.e., is comprised of one or more $sp^3$ carbons) and are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are, in some aspects, referred to as carbocyclyls as further defined herein.

When referring to an alkyl moiety or group as an alkyl substituent, that alkyl substituent to a Markush structure or another organic moiety with which it is associated is methyl or a chain of contiguous carbon atoms unless otherwise indicated or implied by context is non-cyclic, that is covalently attached to the structure or moiety through a $sp^3$ monovalent carbon of the alkyl substituent. An alkyl substituent, as used herein, therefore contains at least one saturated moiety and may also be optionally substituted with cycloalkyl or aromatic or heteroaromatic moieties or groups or by an alkenyl or alkynyl moiety resulting in an unsaturated alkyl. Thus, an optionally substituted alkyl substituent may additionally contain one, two, three or more independently selected double bonds and/or triple bonds or may be substituted by alkenyl or alkynyl moieties or some combination thereof to define an unsaturated alkyl substituent and may be substituted by other moieties that include appropriate optional substituents as described herein. The number of carbon atoms in a saturated alkyl can vary and typically is 1-50, 1-30 or 1-20, and more typically is 1-8 or 1-6, and in an unsaturated alkyl moiety or group typically varies between 3-50, 3-30 or 3-20, and more typically varies between 3-8 or 3-6.

A saturated alkyl moiety contains saturated, acyclic carbon atoms (i.e., acyclic $sp^3$ carbons) and no $sp^2$ or sp carbon atoms, but may be substituted with an optional substituent as described herein, provided that such substitution unless specifically recited is not through an $sp^3$, $sp^2$ or sp carbon atom of the optional substituent as that would affect the identity of the base alkyl moiety so substituted. Unless otherwise indicated or implied by context, the term "alkyl" will indicate a saturated, non-cyclic hydrocarbon radical, wherein the hydrocarbon radical has the indicated number of covalently linked saturated carbon atoms so that terms such as "$C_1$-$C_6$ alkyl" or "$C_1$-$C_6$ alkyl" means an alkyl moiety or group containing 1 saturated carbon atom (i.e., is methyl) or 2, 3, 4, 5 or 6 contiguous, non-cyclic saturated carbon atoms and "$C_1$-$C_8$ alkyl" refers to an alkyl moiety or group having 1 saturated carbon atom or 2, 3, 4, 5, 6, 7 or 8 contiguous saturated, non-cyclic carbon atoms. Typically a saturated alkyl is a $C_1$-$C_6$ or $C_1$-$C_4$ alkyl moiety containing no $sp^2$ or sp carbon atoms in its contiguous carbon chain, with the latter sometimes referred to as lower alkyl and in some aspects when the number of carbon atoms is not indicated will refer to a saturated $C_1$-$C_8$ alkyl moiety having from 1 to 8 contiguous acyclic $sp^3$ carbon atoms containing no $sp^2$ or sp carbon atoms in its contiguous carbon chain. In other aspects, when a range of contiguous carbon atoms defines the term "alkyl" but without specifying it as saturated or unsaturated, then that term encompasses saturated alkyl with the specified range and unsaturated alkyl in which the lower limit of the range is increased by two carbon atoms. For example, the term "$C_1$-$C_8$ alkyl, without further limitation refers, to a saturated $C_1$-$C_8$ alkyl and $C_3$-$C_8$ unsaturated alkyl.

When a saturated alkyl substituent, moiety or group is specified, species include those derived from removing a hydrogen atom from a parent alkane (i.e., an alkyl moiety is monovalent) and may include methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, sec-amyl and other linear and branch chain alkyl moieties.

"Alkylene," as used herein, by itself of as part of another term, unless otherwise stated or implied by context, refers to a saturated, branched or straight chain hydrocarbon diradical, substituted or unsubstituted, wherein one or more of the carbon atoms is saturated (i.e., is comprised of one or more $sp^3$ carbons), of the stated number of carbon atoms ranging from 1 to 50 or 1 to 30, typically 1 to 20 or 1 to 12 carbon atoms, more typically 1 to 8, 1 or 6, or 1 to 4 carbon atoms and having two radical centers (i.e., is divalent) derived by the removal of two hydrogen atoms from the same or two different saturated (i.e., $sp^3$) carbon atoms of a parent alkane. An alkylene moiety in some aspects is an alkyl radical as described herein in which a hydrogen atom has been removed from another of its saturated carbons or from the radical carbon atom of an alkyl radical to form a diradical. In other aspects, an alkylene moiety is or is further encompassed by a divalent moiety derived from removing a hydrogen atom from a saturated carbon atom of a parent alkyl moiety and are exemplified without limitation by methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and like diradicals. Typically, an alkylene is a branched or straight chain hydrocarbon containing only $sp^3$ carbons (i.e., is fully saturated notwithstanding the radical carbon atoms) and in some aspects is unsubstituted. In other aspects, an alkylene contains an internal site of unsaturation(s) in the form of one or more double and/or triple bond functional groups, typically 1 or 2, more typically 1, such functional groups so that the terminal carbons of the unsaturated alkylene moiety are monovalent $sp^3$ carbon atoms. In still other aspects, the alkylene is substituted with 1 to 4, typically 1 to 3, or 1 or 2 substituents, as defined herein for optional substituents, excluding, unless specifically reciting otherwise, alkyl, arylalkyl, alkenyl, alkynyl and any other moiety at saturated carbon atom(s) of a saturated alkylene moiety or saturated and/or unsaturated carbon atom(s) of an unsaturated alkylene moiety, so that the number of contiguous non-aromatic carbon atom of the substituted alkylene does not differ relative to the unsubstituted alkylene, "Carbocyclyl" as used herein, by itself of as part of another term, unless otherwise stated or implied by context, refers to a radical of a monocyclic, bicyclic, tricyclic or polycyclic ring system, wherein each of the atoms forming the ring system (i.e., skeletal atoms) is a carbon atom and wherein one or more of these carbon atoms in each ring of the cyclic ring system is saturated (i.e., is comprised of one or more $sp^3$ carbons). Thus, a carbocyclyl is a cyclic arrangement of saturated carbons but may also contain unsaturated carbon atom(s) and therefore its carbocyclic ring may be saturated or partially unsaturated or may be fused with an aromatic moiety, wherein the points of fusion to the cycloalkyl and aromatic rings are to adjacent unsaturated carbons of the carbocyclyl moiety and adjacent aromatic carbons of the aromatic moiety.

Unless otherwise specified, a carbocyclyl can be substituted (i.e., optionally substituted) with moieties described for alkyl, alkenyl, alkynyl, aryl, arylalkyl, alkylaryl and the like or can be substituted with another cycloalkyl moiety. Cycloalkyl moieties, groups or substituents include cyclopropyl, cyclopentyl, cyclohexyl, adamantly or other cyclic moieties that have only carbon atoms in their cyclic ring systems.

When carbocyclyl is used as a Markush group (i.e., a substituent) the carbocyclyl is attached to a Markush formula or another organic moiety with which it is associated through a carbon that is involved in the carbocyclic ring system of the carbocyclyl moiety provided that carbon is not an aromatic carbon. When an unsaturated carbon of an alkene moiety comprising the carbocyclyl substituent is attached to a Markush formula with which it is associated that carbocyclyl is sometimes referred to as a cycloalkenyl substituent. The number of carbon atoms in a carbocyclyl substituent is defined by the total number of skeletal atoms of its carbocyclic ring system. That number can vary and typically ranges from 3 to 50, 1-30 or 1-20, and more typically 3-8 or 3-6 unless otherwise specified, e.g., $C_3$-$C_8$ carbocyclyl means an carbocyclyl substituent, moiety or group containing 3, 4, 5, 6, 7 or 8 carbocyclic carbon atoms and $C_3$-$C_6$ carbocyclyl means an carbocyclyl substituent, moiety or group containing 3, 4, 5 or 6 carbocyclic carbon atoms. A carbocyclyl may be derived by the removal of one hydrogen atom from a ring atom of a parent cycloalkane or cycloalkene. Representative $C_3$-$C_8$ carbocyclyls include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Therefore, carbocyclyl substituents, moieties or groups typically have 3, 4, 5, 6, 7, 8 carbon atoms in its carbocyclic ring system and may contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share two carbon atoms and a tricyclic ring system may share a total of 3 or 4 carbon atoms. In some aspects, a carbocyclyl is a $C_3$-$C_8$ or $C_3$-$C_6$ carbocyclyl that may be substituted (i.e. optionally substituted) with one or more, 1 to 4, typically 1 to 3, or 1 or 2 moieties described herein for alkyl, alkenyl, alkynyl, aryl, arylalkyl, and alkylaryl and/or with other moieties as including substituent(s) as defined herein for optional substituents, and in some aspects is unsubstituted. In other aspects, a cycloalkyl moiety, group or substituent is a $C_3$-$C_6$ cycloalkyl selected from the group consisting of cyclopropyl, cyclopentyl and cyclohexyl, or is a $C_3$-$C_8$ cycloalkyl that encompasses that group and is further encompasses other cyclic moieties that have no more than 8 carbon atoms in their cyclic ring systems. When the number of carbon atoms is not indicated, a carbocyclyl moiety, group or substituent has from 3 to 8 carbon atoms in its carboxcylic ring system.

"Carbocyclo," by itself or as part of another term, unless otherwise stated or implied by context, refers to an optionally substituted carbocyclyl as defined above wherein another hydrogen atom of its cycloalkyl ring system has been removed (i.e., it is divalent) and is a $C_3$-$C_{50}$ or $C_3$-$C_{30}$ carbocyclo, typically a $C_3$-$C_{20}$ or $C_3$-$C_{12}$ carbocyclo, more typically a $C_3$-$C_8$ or $C_3$-$C_6$ carbocyclo and in some aspects is unsubstituted or an optionally substituted $C_3$, $C_5$ or $C_6$ carbocyclo. When the number of carbon atoms is not indicated, a carbocyclo moiety, group or substituent has from 3 to 8 carbon atoms in its carboxcylic ring system.

In some aspects removal of that other hydrogen atom is from the monovalent carbon atom of the cycloalkyl to provide a divalent carbon atom, which in some instances is a spiro carbon atom that interrupts an alkyl moeity with that carbocyclic carbon atom. In such instances, the spiro carbon atom is attributed to the carbon atom count of the interrupted alkyl moeity and the carbocyclo ring system with the carbocyclo indicated as being incorporated into the alkyl moeity. In those aspects, a carbocyclo moiety, group or substituent is a $C_3$-$C_6$ carbocyclo in the form of a spiro ring system and is selected from the group consisting of cycloprop-1,1-diyl, cyclobutyl-1,1-diyl, cyclopent-1,1-diyl and cyclohex-1,1-diyl, or is a $C_3$-$C_8$ carbocyclo or other divalent cyclic moiety that has no more than 8 carbon atoms in its cyclic ring systems. A carbocyclo may be a saturated or an unsaturated carbocyclo, and/or may be substituted or unsubstituted in the same manner as described for a carbocyclyl moeity. If unsaturated, one or both monovalent carbon atoms of the carbocyclo moiety may be $sp^2$ carbon atoms from the same or a different double bond functional group or both monovalent carbon atoms may be adjacent or non-adjacent $sp^3$ carbon atoms.

"Alkenyl" as the terms are used herein, by itself or as part of another term, unless otherwise stated or implied by context, refers to an organic moiety, substituent or group that comprises one or more double bond functional groups (e.g., a —CH═CH— moiety) or 1, 2, 3, 4, 5 or 6 or more, typically 1, 2 or 3 of such functional groups, more typically one such functional group, and in some aspects may be substituted (i.e., is optionally substituted) with an aryl moiety or group such as phenyl, or may contain non-aromatic linked normal, secondary, tertiary or cyclic carbon atoms, i.e., linear, branched, cyclic or any combination thereof, as part of the base moeity unless the alkenyl substituent, moiety or group is a vinyl moiety (e.g., a —CH═$CH_2$ moiety). An alkenyl moiety, group or substituent having multiple double bonds may have the double bonds arranged contiguously (i.e., a 1,3-butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

An alkenyl moiety, group or substituent contains at least one $sp^2$ carbon atom in which that carbon atom is divalent and is doubly bonded to another organic moeity or Markush structure to which it is associated, or contains at least two $sp^2$ carbon atoms in conjugation to each other in which one of the $sp^2$ carbon atoms is monovalent and is singly bonded to another organic moiety or Markush structure to which it is associated. Typically, when alkenyl is used as a Markush group (i.e., is a substituent) the alkenyl is singly bonded to a Markush formula or another organic moiety with which it is associated through a $sp^2$ carbon of an alkene functional group of the alkenyl moiety. In some aspects, when an alkenyl moiety is specified, species encompasses those corresponding to any of the optionally substituted alkyl or carbocyclyl, groups moieties or substituents described herein that has one or more endo double bonds in which a $sp^2$ carbon atom thereof is monovalent, and monovalent moieties derived from removal of a hydrogen atom from a $sp^2$ carbon of a parent alkene compound. Such monovalent moieties are exemplified without limitation by vinyl (—CH═$CH_2$), allyl, 1-methylvinyl, butenyl, iso-butenyl, 3-methyl-2-butenyl, 1-pentenyl, cyclopentenyl, 1-methylcyclopentenyl, 1-hexenyl, 3-hexenyl, and cyclohexenyl. In some aspects, the term alkenyl encompasses those and/or other linear, cyclic and branched chained, all carbon-containing moieties containing at least one double bond functional group in which one of the $sp^2$ carbon atoms is monovalent.

The number of carbon atoms in an alkenyl moiety is defined by the number of $sp^2$ carbon atoms of the alkene functional group(s) that defines it as an alkenyl substituent and the total number of contiguous non-aromatic carbon atoms appended to each of these $sp^2$ carbons not including any carbon atom of the other moiety or Markush structure for which the alkenyl moiety is a variable group and from any optional substituent to the alkenyl moiety. That number ranges from 1 to 50 or 1 to 30, typically 1 to 20 or 1 to 12, more typically, 1 to 8, 1 to 6 or 1 to 4 carbon atoms when a double bond functional group of the alkenyl moiety is doubly bonded to a Markush structure (e.g. =CH$_2$), or ranges from 2 to 50, typically 2 to 30, 2 to 20 or 2 to 12, more typically 2 to 8, 2 to 6 or 2 to 4 carbon atoms, when a double bond functional group of the alkenyl moiety is singly bonded to the Markush structure (e.g., —CH=CH$_2$). For example, $C_2$-$C_8$ alkenyl or $C_2$-$C_8$ alkenyl means an alkenyl moiety containing 2, 3, 4, 5, 6, 7 or 8 carbon atoms in which at least two are $sp^2$ carbon atoms in conjugation with each other with one of these carbon atoms being monovalent, and $C_2$-$C_6$ alkenyl or $C_2$-$C_6$ alkenyl means an alkenyl moiety containing 2, 3, 4, 5 or 6 carbon atoms in which at least two are $sp^2$ carbons that are in conjugation with each other with one of these carbon atoms being monovalent. In some aspects, an alkenyl substituent or group is a $C_2$-$C_6$ or $C_2$-$C_4$ alkenyl moiety having only two $sp^2$ carbons that are in conjugation with each other with one of these carbon atoms being monovalent, and in other aspects that alkenyl moiety is unsubstituted or is substituted with 1 to 4 or more, typically 1 to 3, more typically 1 or 2, independently selected moieties as disclosed herein, including substituents as defined herein for optional substituents, excluding, unless specifically recited otherwise, alkyl, arylalkyl, heteroarylalkyl, alkenyl, alkynyl and any other moiety so that the substituted alkenyl differs only by the number of contiguous non-aromatic carbon atoms relative to the unsubstituted alkenyl, wherein the substitution(s) may be at any of the alkenyl moiety's contiguous $sp^2$ carbon and $sp^3$ carbon atoms, if any. Typically, an alkenyl substituent is a $C_2$-$C_6$ or $C_2$-$C_4$ alkenyl moiety having only two $sp^2$ carbons that are in conjugation with each other. When the number of carbon atoms is not indicated, an alkenyl moiety has from 2 to 8 carbon atoms.

"Alkenylene" as used herein, by itself of as part of another term, unless otherwise stated or implied by context, refers to an organic moiety, substituent or group that comprises one or more double bond moieties, as previously described for alkenyl, of the stated number of carbon atoms and has two radical centers derived by the removal of two hydrogen atoms from the same or two different $sp^2$ carbon atoms of an alkene functional group in a parent alkene. In some aspects, an alkenylene moiety is that of an alkenyl radical as described herein in which a hydrogen atom has been removed from the same or different $sp^2$ carbon atom of a double bond functional group of the alkenyl radical, or from a $sp^2$ carbon from a different double bonded moiety to provide a diradical. Typically, alkenylene moieties encompass diradicals containing the structure of —C=C— or —C=C—X$^1$—C=C— wherein X$^1$ is absent or is an optionally substituted saturated alkylene as defined herein, which is typically a $C_1$-$C_6$ alkylene, which is more typically unsubstituted. The number of carbon atoms in an alkenylene moiety is defined by the number of $sp^2$ carbon atoms of its alkene functional group(s) that defines it as an alkenylene moiety and the total number of contiguous non-aromatic carbon atoms appended to each of its $sp^2$ carbons not including any carbon atoms of the other moiety or Markush structure in which the alkenyl moiety is a present as a variable group. That number, unless otherwise specified, ranges from 2 to 50 or 2 to 30, typically from 2 to 20 or 2 to 12, more typically from 2 to 8, 2 to 6 or 2 to 4 carbon atoms. For example, $C_2$-$C_8$ alkenylene or $C_2$-$C_8$ alkenylene means an alkenylene moiety containing 2, 3, 4, 5, 6, 7 or 8 carbon atoms, in which at least two are $sp^2$ carbons, in which one is divalent or both are monovalent, that are in conjugation with each other and $C_2$-$C_6$ alkenylene or $C_2$-$C_6$ alkenylene means an alkenyl moiety containing 2, 3, 4, 5 or 6 carbon atoms in which at least two are $sp^2$ carbons, in which at least two are $sp^2$ carbons in which one is divalent or both are monovalent, that are in conjugation with each other. In some aspects, an alkenylene moiety is a $C_2$-$C_6$ or $C_2$-$C_4$ alkenylene having two $sp^2$ carbons that are in conjugation with each other in which both $sp^2$ carbon atoms are monovalent, and in some aspects is unsubstituted. When the number of carbon atoms is not indicated, an alkenylene moiety has from 2 to 8 carbon atoms and is unsubstituted or substituted in the same manner described for an alkenyl moiety.

"Alkynyl" as the terms are used herein, by itself or as part of another term, unless otherwise stated or implied by context, refers to an organic moiety, substituent or group that comprises one or more triple bond functional groups (e.g., a —C≡C— moiety) or 1, 2, 3, 4, 5, or 6 or more, typically 1, 2, or 3 of such functional groups, more typically one such functional group, and in some aspects may be substituted (i.e., is optionally substituted) with an aryl moiety such as phenyl, or by an alkenyl moiety or linked normal, secondary, tertiary or cyclic carbon atoms, i.e., linear, branched, cyclic or any combination thereof unless the alkynyl substituent, moiety or group is —C≡CH). An alkynyl moiety, group or substituent having multiple triple bonds may have the triple bonds arranged contiguously or non-contiguously with one or more intervening saturated or unsaturated carbon atoms or a combination thereof, provided that a cyclic, contiguous arrangement of triple bonds do not form a cyclic conjugated system of 4n+2 electrons (i.e., is not aromatic).

An alkynyl moiety, group or substituent contains at least two sp carbon atom in which the carbon atoms are conjugation to each other and in which one of the sp carbon atoms is singly bonded, to another organic moeity or Markush structure to which it is associated. When alkynyl is used as a Markush group (i.e., is a substituent) the alkynyl is singly bonded to a Markush formula or another organic moiety with which it is associated through a triple-bonded carbon (i.e., a sp carbon) of a terminal alkyne functional group. In some aspects when an alkynyl moiety, group or substituent is specified, species encompasses are any of the optionally substituted alkyl or carbocyclyl, groups moieties or substituents described herein that has one or more endo triple bonds and monovalent moieties derived from removal of a hydrogen atom from a sp carbon of a parent alkyne compound. Such monovalent moieties are exemplified without limitation by —C≡CH, and —C≡C—CH$_3$, —C≡C—Cl, and —C≡C-Ph.

The number of carbon atoms in an alkynyl substituent is defined by the number of sp carbon atoms of the alkene functional group that defines it as an alkynyl substituent and the total number of contiguous non-aromatic carbon atoms appended to each of these sp carbons not including any carbon atom of the other moiety or Markush structure for which the alkenyl moiety is a variable group. That number can vary ranging from 2 to 50, typically 2 to 30, 2 to 20, or 2 to 12, more typically 2 to 8, 2 to 6, or 2 to 4 carbon atoms, wherein the triple bond functional group is singly bonded to the Markush structure (e.g., —CH≡CH). For example, $C_2$-$C_8$ alkynyl or $C_2$-$C_8$ alkynyl means an alkynyl moiety containing 2, 3, 4, 5, 6, 7, or 8 carbon atoms in which at least two are sp carbon atoms in conjugation with each other with one of these carbon atoms being monovalent, and $C_2$-$C_6$ alkynyl or $C_2$-$C_6$ alkynyl means an alkynyl moiety containing 2, 3, 4, 5, or 6 carbon atoms in which at least two are sp carbons that are in conjugation with each other with one of these carbon atoms being monovalent. In some aspects, an alkynyl substituent or group is a $C_2$-$C_6$ or $C_2$-$C_4$ alkynyl moiety having two sp carbons that are in conjugation with each other with one of these carbon atoms being monovalent, and in other aspects that alkynyl moeity is unsubstituted. When the number of carbon atoms is not indicated, an alkynyl moiety, group or substituent has from 2 to 8 carbon atoms. An alkynyl moiety may be substituted or unsubstituted in the same manner as described for an alkenyl moiety, except that substitution at the monovalent sp carbon is not permitted.

"Aryl" as the terms are used herein, by itself or as part of another term, unless otherwise stated or implied by context, refers to an organic moiety, substituent or group having an aromatic or fused aromatic ring system with no ring heteroatoms comprising or consisting of 1, 2, 3 or 4 to 6 aromatic rings each of which are independently optionally substituted, typically consisting of 1 to 3 aromatic rings, more typically 1 or 2 aromatic rings each of which are independently optionally substituted, wherein the rings are composed of only carbon atoms that participate in a cyclically conjugated system of 4n+2 electrons (Hickel rule), typically 6, 10 or 14 electrons, some of which may additionally participate in exocyclic conjugation with a heteroatom (cross-conjugated, e.g., quinone). Aryl substituents, moieties or groups are typically formed by six, eight, ten or more contiguous aromatic carbon atoms up to 24 to include $C_6$-$C_{24}$ aryl and in some aspects is a $C_6$-$C_{20}$ or $C_6$-$C_{12}$ aryl. Aryl substituents, moieties or groups are optionally substituted and in some aspects are unsubstituted or substituted with 1, 2, 3 or more, typically 1 or 2, independently selected substituents as defined herein for alkyl, alkenyl, alkynyl or other moiety described herein including another aryl or a hetereoaryl to form a biaryl or heterobiaryl and other optional substituents as defined herein. In other aspects, aryls are $C_6$-$C_{10}$ aryls such as phenyl and naphthalenyl and phenanthryl. As aromaticity in a neutral aryl moiety requires an even number or electrons, it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group.

"Heterocyclyl" as the terms is used herein, by itself or as part of another term, unless otherwise stated or implied by context, refers to a carbocyclyl in which one or more, but not all of the skeletal carbon atoms with their attached hydrogen atoms within the carbocyclic ring system are replaced by independently selected heteroatoms or heteroatom moieties, optionally substituted where permitted, including without limitation N/NH, O, S, Se, B, Si and P, wherein two or more heteroatoms or heteroatom moieties, typically 2, may be adjacent to each other or separated by one or more carbon atoms within the same ring system, typically by 1 to 3 carbon atoms. Those heteroatoms or heteroatom moieties typically are N/NH, O and S. A heterocyclyl typically contains a monovalent skeletal carbon atom or a monovalent heteroatom or heteroatom moeity and has a total of one to ten heteroatoms and/or heteroatom moieties, typically a total of 1 to 5, or more typically a total of 1 to 3, or 1 or 2, provided that not all of the skeletal atoms in any one of the heterocyclic ring(s) in the heterocyclyl are heteroatoms and/or heteroatom moieties (i.e. at least one carbon atom is not replaced in each ring with at least one having been replaced in one of the rings), wherein each heteroatom or heteroatom moeity in the ring(s), optionally substituted where permitted, is independently selected from the group consisting of N/NH, O and S, with the proviso that any one ring does not contain two adjacent O or S atoms. Exemplary heterocyclyls and heteroaryls, which are collectively referred to as heterocycles, are provided by Paquette, Leo A.; "*Principles of Modern Heterocyclic Chemistry*" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5545-5473 particularly 5566-5573).

When heterocyclyl is used as a Markush group (i.e., a substituent) a saturated or partially unsaturated heterocyclic ring of the heterocyclyl is attached to a Markush structure or other moiety with which it is associated through a carbon atom or a heteroatom of that heterocyclic ring, wherein such attachment does not result in an unstable or disallowed formal oxidation state of that carbon or heteroatom. A heterocyclyl in that context is a monovalent moiety in which a heterocyclic ring of the heterocyclic ring system defining it as a heterocyclyl is non-aromatic, but may be fused with a carbocyclic, aryl or heteroaryl ring and includes phenyl- (i.e., benzo) fused heterocyclic moieties.

A heterocyclyl is a $C_3$-$C_{50}$ or $C_3$-$C_{30}$ carbocyclyl, typically a $C_3$-$C_{20}$ or $C_3$-$C_{12}$ carbocyclyl, more typically a $C_3$-$C_8$ or $C_3$-$C_6$ carbocyclyl wherein 1, 2 or 3 or more, but not all of its carbons of its cycloalkyl ring system are replaced along with its attached hydrogens, typically 1, 2, 3 or 4, more typically 1 or 2, are replaced with a heteroatom or heteroatom moiety independently selected from the group consisting of N/NH, O and S, optionally substituted where permitted, and thus is a $C_3$-$C_{50}$ or $C_3$-$C_{30}$ heterocyclyl, typically a $C_3$-$C_{20}$ or $C_3$-$C_{12}$ heterocyclyl, more typically a $C_3$-$C_6$, or $C_5$-$C_6$ heterocyclyl, in which the subscript indicates the total number of skeletal atoms (inclusive of its carbon atoms and heteroatoms) of the heterocyclic ring system(s) of the heterocyclyl. In some aspects, a heterocyclyl contains 0 to 2 N, 0 to 2 O or 0 to 1 S skeletal heteroatoms, optionally substituted or some combination thereof provided at least one of said heteroatoms is present in a heterocyclic ring system of the heterocyclyl. A heterocyclyl may be saturated or partially unsaturated and/or unsubstituted or substituted at a skeletal carbon atom with an oxo (=O) moiety, as in pyrrolidin-2-one, and/or at a skeletal heteroatom with one or two oxo moieties, which are exemplary heteroatom optional substituents that are present, so as to contain an oxidized heteroatom as exemplified, but not limited to, —N(=O), —S(=O)— or —S(=O)$_2$—. A fully saturated or partially unsaturated heterocyclyl may be substituted or further substituted with an alkyl, (hetero)aryl, (hetero)arylalkyl, alkenyl, alkynyl or other moiety as described herein, including optional substituents as defined herein or a combination of 2, 3 or more, typically 1 or 2, such substituents. In certain aspects, heterocyclyl is selected from the group consisting of pyrrolidinyl, piperidinyl, morpholinyl and piperazinyl.

"Heterocyclo", as the term is used herein, by itself or as part of another term, unless otherwise stated or implied by context, refers to a heterocyclyl moiety, group or substituent as defined above, wherein a hydrogen atom from its monovalent carbon atom, a hydrogen atom from a different skeletal atom (carbon or nitrogen atom if the latter is present), or an electron from a skeletal nitrogen atom, where permitted is removed or an electron from a nitrogen ring atom that is not already monovalent is removed and is replaced with a bond (i.e., it is divalent). In some aspects, the replaced second hydrogen is that of the monovalent carbon atom of the parent heterocyclyl thus forming a spiro carbon atom, which in some instances may interrupt an alkyl moeity with that carbocyclic carbon atom. In such instances, the spiro carbon atom is attributed to the carbon atom count of the interrupted alkyl moiety and the skeletal atom count of the heterocyclic ring system with the heterocyclo indicated as being incorporated into the alkyl moeity.

"Heteroaryl" as the term is used herein, by itself or as part of another term, unless otherwise stated or implied by context, refers to an aryl moiety, group or substituent as defined herein in which one or more but not all of the aromatic carbons of an aromatic ring system of an aryl is replaced by a heteroatom. A heteroaryl typically contains a total one to four skeletal heteroatoms in the ring(s) of the heteroaryl ring system, provided that not all of the skeletal atoms of any one ring system in the heteroaryl are heteroatoms, which are optionally substituted where permitted, and have 0 to 3 N, 1 to 3 N or 0 to 3 N skeletal heteroatoms, typically 0 to 1 O and/or 0 to 1 S skeletal heteroatoms, provided that at least one skeletal heteroatom is present. A heteroaryl may be monocyclic, bicyclic or polycyclic. A polycyclic heteroaryl is typically a $C_5$-$C_{50}$ or $C_5$-$C_{30}$ heteroaryl, more typically a $C_5$-$C_{20}$ or $C_5$-$C_{12}$ heteroaryl, a bicyclic heteroaryl is typically a $C_5$-$C_{10}$ heteroaryl, and a monocyclic heteroaryl is a typically is $C_5$-$C_6$ heteroaryl, in which the subscript indicates the total number of skeletal atoms (inclusive of its carbon atoms and heteroatoms) of the aromatic ring system(s) of the heteroaryl. In some aspects, a heteroaryl is a bicyclic aryl moiety wherein one 1, 2, 3, 4 or more, typically 1, 2 or 3, of the carbon atoms of the aromatic ring(s) and their attached hydrogen atoms of a parent bicyclic aryl moiety are replaced by independently selected heteroatom(s) or heteroatom moiety(ies), or is a monocyclic aryl moiety wherein one 1, 2, 3 or more, typically 1 or 2, of the carbon atoms of the aromatic ring(s) and their attached hydrogen atoms of a parent monocyclic aryl moiety are replaced by an independently selected heteroatom and/or heteroatom moeity, wherein the heteroatom or heteroatom moiety is optionally substituted where permitted, including N/NH, O and S, provided that not all of the skeletal atoms of any one aromatic ring system in the parent aryl moiety are replaced by heteroatoms and more typically are replaced by oxygen (—O—), sulfur (—S—) nitrogen (=N—) or —NR—, which is a heteroatom moiety, so that the nitrogen heteroatom is optionally substituted, wherein R is —H, a nitrogen protecting group or optionally substituted $C_1$-$C_{20}$ alkyl or is an optionally substituted $C_6$-$C_{24}$ aryl or $C_5$-$C_{24}$ heteroaryl to form a heterobiaryl. In other aspects, 1, 2 or 3 of the carbon atoms of the aromatic ring(s) and their attached hydrogen atoms of a parent aryl moiety are replaced by nitrogen substituted with another organic moiety in a manner which retains the cyclic conjugated system. In still other aspects, the aromatic carbon radical of a parent aryl moiety is replaced with an aromatic nitrogen radical. In either of those aspects, the nitrogen, sulfur or oxygen heteroatom participates in the conjugated system either through pi-bonding with an adjacent atom in the ring system or through a lone pair of electrons on the heteroatom. In still other aspects, a heteroaryl has the structure of a heterocyclyl as defined herein in which its ring system has been aromatized.

Typically, a heteroaryl is monocyclic, which in some aspects has a 5-membered or 6-membered heteroaromatic ring system. A 5-membered heteroaryl is a monocyclic $C_5$-heteroaryl containing 1 to 4 aromatic carbon atoms and the requisite number of aromatic heteroatoms within its heteroaromatic ring system. A 6-membered heteroaryl is a monocyclic $C_6$ heteroaryl containing 1 to 5 aromatic carbon atoms and the requisite number of aromatic heteroatoms within its heteroaromatic ring system. Heteroaryls that are 5-membered have four, three, two or one aromatic heteroatom(s), and heteroaryls that are 6-membered include heteroaryls having five, four, three, two or one aromatic heteroatom(s).

$C_5$-heteroaryls, also referred to as 5-membered heteroaryl, are monovalent moieties derived from removing a hydrogen atom from a skeletal aromatic carbon or an electron from a skeletal aromatic heteroatom, where permitted, from a parent aromatic heterocycle compound, which is some aspects is selected from the group consisting of pyrrole, furan, thiophene, oxazole, isoxazole, thiazole, isothiazole, imidazole, pyrazole, triazole and tetrazole. In other aspects, the parent heterocycle is selected from the group consisting of thiazole, imidazole, oxazole, and triazole and is typically thiazole or oxazole, more typically thiazole.

$C_6$ heteroaryls, which are 6-membered, are monovalent moieties derived from removing a hydrogen atom from an aromatic carbon or an electron from an aromatic heteroatom, where permitted, from a parent aromatic heterocycle compound, which is certain aspects is selected from the group consisting of pyridine, pyridazine, pyrimidine, and triazine. A heteroaryl may be substituted or further substituted with an alkyl, (hetero)arylalkyl, alkenyl or alkynyl, or with an aryl or another heteroaryl to form a heterobiaryl, or with other moieties as described herein, including optional substituents as defined herein, or a combination of 2, 3 or more, typically 1 or 2, such substituents.

A "5-membered nitrogen heteroaryl" as the terms are used herein, by itself or as part of another term, unless otherwise stated or implied by context, refers to a monovalent 5-membered heteroaromatic moiety containing at least one nitrogen atom in its aromatic ring system and is typically a monocyclic heteroaryl or is fused to an aryl or another heteroaryl ring system, wherein the 5-membered heteroaromatic moiety contains one or more other independently selected heteroatoms and/or heteroatom moieties such as N/NH, O or S, optionally substituted where permitted. Exemplary 5-membered heteroarylenes include those in which the parent heterocycle is thiazole, imidazole, oxazole, and triazole and is typically thiazole or oxazole, more typically thiazole.

"Arylalkyl" or "heteroarylalkyl" as the terms are used herein, by itself or as part of another term, refers to an aryl or heteroaryl moiety bonded to an alkyl moiety, i.e., (aryl)-alkyl-, where alkyl and aryl groups are as described above. Typically, an arylalkyl is a ($C_6$-$C_{24}$ aryl)-$C_1$-$C_{12}$ alkyl-moeity, group or substituent, and heteroarylalkyl is a ($C_5$-$C_{24}$ heteroaryl)-$C_1$-$C_{12}$ alkyl-moeity, group or substituent. When (hetero)arylalkyl is used as a Markush group (i.e., a substituent) the alkyl moiety of the (hetero)arylalkyl is attached to a Markush formula with which it is associated through a sp³ carbon of its alkyl moiety. In some aspects, an arylalkyl is a ($C_6$-$C_{24}$ aryl)-$C_1$-$C_{12}$ alkyl- or a ($C_6$-$C_{20}$ aryl)-$C_1$-$C_{20}$ alkyl-, typically a ($C_6$-$C_{12}$ aryl)-$C_1$-$C_{12}$ alkyl- or ($C_6$-$C_{10}$ aryl)-$C_1$-$C_{12}$ alkyl-, more typically a ($C_6$-$C_{10}$ aryl)-$C_1$-$C_6$ alkyl-exemplified without limitation, by $C_6H_5$—$CH_2$—, $C_6H_5$—$CH(CH_3)CH_2$— and $C_6H_5$—$CH_2$—$CH(CH_2CH_2CH_3)$—. An (hetero)arylalkyl- may be unsubstituted or substituted in the same manner as described for (hetero)aryl and/or alkyl moieties. An optionally substituted alkyl moiety as defined herein that is substituted by an optionally substituted aryl is is also an optionally substituted arylalkyl, and therefore falls within the definition of an optionally substituted alkyl unless otherwise stated or implied by context.

"Arylene," or "heteroarylene" as used herein, by itself or as part of another term, unless otherwise stated or implied by context, is an aromatic or heteroaromatic diradical moiety that forms two covalent bonds (i.e., it is divalent) within another organic moiety, the bonds of which are in the ortho, meta, or para configuration. Arylene and some heteroarylenes include divalent species by removal of a hydrogen atom from a parent aryl or heteroaryl moiety, group or substituent as defined herein. Other heteroarylenes are divalent species in which hydrogen atoms have been removed from two different aromatic carbon atoms of a parent aromatic heterocycle to form a diradical species, or from removal of a hydrogen atom from an aromatic carbon atom or heteroatom and of another hydrogen atom or electron from a different aromatic heteroatom from a parent aromatic heterocycle to form a diradical species in which one aromatic carbon atom and one aromatic heteroatom is monovalent or two different aromatic heteroatoms are each monovalent. Heteroarylene further include those in which heteroatom(s) and/or heteroatom moiety(ies) replace one or more but not all of the aromatic carbon atoms of a parent arylene.

Non-limiting exemplary arylenes, which are optionally substituted at the remaining positions, are phenyl-1,2-ene, phenyl-1,3-ene, and phenyl-1,4-ene, as shown in the following structures:

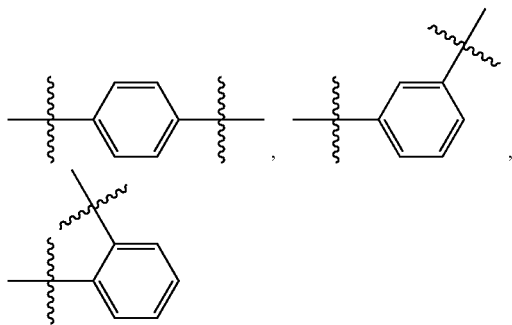

A "5-membered nitrogen heteroarylene" as the terms are used herein, by itself or as part of another term, unless otherwise stated or implied by context, refers to a divalent 5-membered heteroaromatic moiety containing at least one nitrogen atom in its aromatic ring system and is typically a monocyclic heteroarylene or is fused to an aryl or another heteroaryl ring system, wherein the 5-membered heteroaromatic moiety may additionally contains one or more other independently selected heteroatoms and/or heteroatom moieties such as N/NH, O or S, optionally substituted where permitted. Exemplary 5-membered heteroarylenes include those in which the parent heterocycle is thiazole, imidazole, oxazole, and triazole and is typically thiazole or oxazole, more typically thiazole.

"Heteroalkyl," as used herein by itself or in combination with another term, unless otherwise stated or implied by context, refers to an optionally substituted straight or branched chain hydrocarbon, fully saturated or containing from 1 to 3 degrees of unsaturation and having 1 to 12 carbon atom and 1 to 6 heteroatoms, typically 1 to 5 heteroatoms, more typically one or two heteroatoms or heteroatom moieties, selected from the group consisting of O, N/NH, Si and S, optionally substituted where permitted, and includes each nitrogen and sulfur atom independently optionally oxidized to an N-oxide, a sulfoxide or sulfone, or wherein one or more of the nitrogen atoms is optionally substituted or quaternized. The heteroatom(s) or heteroatom moeity(ies) O, N/NH, S, and/or Si may be placed at any interior position of the heteroalkyl group or at a terminal position of the optionally substituted alkyl group of the heteroalkyl. In some aspects, the heteroalkyl is fully saturated or contains 1 degree of unsaturation and contain 1 to 6 carbon atoms and 1 to 2 heteroatoms, and in other aspects that heteroalkyl is unsubstituted. Non-limiting examples are —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, as exemplified by —$CH_2$—NH—$OCH_3$ and —$CH_2$—O—Si($CH_3$)$_3$.

A heteroalkyl is typically denoted by the number of its contiguous heteroatom(s) and non-aromatic carbon atoms, which includes those contiguous carbon atom(s) attached to the heteroatom(s), unless indicated otherwise or by context. Thus, —$CH_2$—$CH_2$—O—$CH_3$ and —$CH_2$—$CH_2$—S(O)—$CH_3$ are both $C_4$-heteroalkyls and —$CH_2$—CH=N—O—$CH_3$, and —CH=CH—N($CH_3$)$_2$ are both $C_5$ heteroalkyls. A heteroalkyl may be unsubstituted or substituted (i.e., optionally substituted) at its heteroatom or heteroatom component with any one of the moieties described herein, including an optional substituent as defined herein, and/or at its alkyl component with 1 to 4 or more, typically 1 to 3 or 1 or 2 independently selected moieties as described herein, including optional substituent(s) as defined herein, excluding alkyl, (hetero)arylalkyl, alkenyl, alkynyl and another heteroalkyl unless specifically recited otherwise.

An aminoalkyl as defined herein is an exemplary heteroalkyl in which a carbon atom the alkyl moeity of the aminoalkyl is monovalent for attachment to another organic moiety with which it is to be associated, but differs by denotation in numbering by only indicating the number of contiguous carbon atoms of its alkyl moiety.

"Heteroalkylene" as used herein by itself or in combination with another term, unless otherwise stated or implied by context, means a divalent group derived from a heteroalkyl (as discussed above), by removal of a hydrogen atom or a heteroatom electron form a parent heteroalkyl to provide a divalent moeity exemplified by, but not limited to, —$CH_2$—$CH_2$—S—$CH_2$—$CH_2$— and —$CH_2$—S—$CH_2$—$CH_2$—NH—$CH_2$—. For a heteroalkylene, heteroatom(s) thereof may be interior to or may occupy either or both termini of its optionally substituted alkylene chain so that one or both of these heteroatoms are monovalent. When a heteroalkylene is a component of a Linker Unit both orientations of that component within the Linker Unit is permitted unless indicated or implied by context.

"Aminoalkyl" as used herein by itself or in combination with another term, unless otherwise stated or implied by context, refers to a moiety, group or substituent having a basic nitrogen bonded to one radical terminus of an alkylene moiety as defined above to provide a primary amine in which the basic nitrogen is not further substituted, or to provide a secondary or tertiary amine in which the basic amine is further substituted by one or two independent selected optional substituted $C_1$-$C_{12}$ alkyl moieties, respectively, as described above. In some aspects, each optionally substituted alkyl moiety is independently a $C_1$-$C_8$ alkyl or $C_1$-$C_6$ alkyl and in other aspects one or both alkyl moieties are unsubstituted. In still other aspects, the basic nitrogen of the aminoalkyl together with those nitrogen substituents defines an optionally substituted $C_3$-$C_8$ heterocyclyl containing the basic nitrogen as a skeletal atom, typically in the form of a nitrogen-containing $C_3$-$C_6$ or $C_5$-$C_6$ heterocyclyl, optionally substituted. When aminoalkyl is used as a variable group to a Markush structure, the alkylene moiety of the aminoalkyl is attached to a Markush formula with which it is associated through a $sp^3$ carbon of that moiety, which in some aspects is a different radical terminus of the aforementioned alkylene. An aminoalkyl is typically denoted by the number of contiguous carbon atoms of its alkylene moiety. Thus, a $C_1$ aminoalkyl is exemplified without limitation by —$CH_2NH_2$, —$CH_2NHCH_3$ and —$CH_2N(CH_3)_2$ and a $C_2$ amino alkyl is exemplified without limitation by —$CH_2CH_2NH_2$, —$CH_2CH_2NHCH_3$ and —$CH_2CH_2N(CH_3)_2$.

"Optionally substituted alkyl", "optionally substituted alkenyl", "optionally substituted alkynyl", "optionally substituted arylalkyl", "optionally substituted heterocycle", "optionally substituted aryl", "optionally substituted heteroaryl", "optionally substituted heteroarylalkyl" and like terms refer to an alkyl, alkenyl, alkynyl, arylalkyl, heterocycle, aryl, heteroaryl, heteroarylalkyl, or other substituent, moiety or group as defined or disclosed herein wherein hydrogen atom(s) of that substituent, moiety or group has been optionally replaced with different moiety(ies) or group(s), or wherein an alicyclic carbon chain that comprise one of those substituents, moiety or group is interrupted by replacing carbon atom(s) of that chain with different moiety(ies) or group(s). In some aspects, an alkene functional group replaces two contiguous $sp^3$ carbon atoms of an alkyl substituent, provided that the radical carbon of the alkyl moiety is not replaced, so that the optionally substituted alkyl becomes an unsaturated alkyl substituent.

Optional substituents replacing hydrogen(s) in any one of the foregoing substituents, moieties, or groups is independently selected from the group consisting of $C_6$-$C_{24}$ aryl, $C_5$-$C_{24}$ heteroaryl, hydroxyl, $C_1$-$C_{20}$ alkoxy, $C_6$-$C_{24}$ aryloxy, cyano, halogen, nitro, $C_1$-$C_{20}$ fluoroalkoxy, and amino, which encompasses —$NH_2$ and mono-, di-, and tri-substituted amino groups, and the protected derivatives thereof, or is selected from the group consisting of —X, —OR', —SR', —$NH_2$, —N(R')($R^{op}$), —N($R^{op}$)$_3$, =NR', —$CX_3$, —CN, —$NO_2$, —NR'C(=O)H, —NR'C(=O)$R^{op}$, —NR'C(=O)$R^{op}$, —C(=O)R', —C(=O)$NH_2$, —C(=O)N(R')$R^{op}$, —S(=O)$_2$R', —S(=O)$_2$$NH_2$, —S(=O)$_2$N(R')$R^{op}$, —S(=O)$_2$$NH_2$, —S(=O)$_2$N(R')RP, —S(=O)$_2$OR', —S(=O)$R^{op}$, —OP(=O)(OR')(O$R^{op}$), —OP(OH)$_3$, —P(=O)(OR')(O$R^{op}$), —$PO_3H_2$, —C(=O)R', —C(=S)$R^{op}$, —$CO_2$R', —C(=S)O$R^{op}$, —C(=O)SR', —C(=S)SR', —C(=S)$NH_2$, —C(=S)N(R')($R^{op}$)$_2$, —C(=NR')$NH_2$, —C(=NR')N(R')$R^{op}$, and salts thereof, wherein each X is independently selected from the group consisting of halogens: —F, —Cl, —Br, and —I; and wherein each $R^{op}$ is independently selected from the group consisting of $C_1$-$C_{20}$ alkyl, $C_2$-$C_{20}$ alkenyl, $C_2$-$C_{20}$ alkynyl, $C_6$-$C_{24}$ aryl, $C_3$-$C_{24}$ heterocyclyl, $C_5$-$C_{24}$ heteroaryl, a protecting group, and a prodrug moiety or two of $R^{op}$ together with the heteroatom to which both are attached define a $C_3$-$C_{24}$ heterocyclyl; and R' is hydrogen or $R^{op}$, wherein $R^{op}$ is selected from the group consisting of $C_1$-$C_{20}$ alkyl, $C_6$-$C_{24}$ aryl, $C_3$-$C_{24}$ heterocyclyl, $C_5$-$C_{24}$ heteroaryl, and a protecting group.

Typically, optional substituents that are present are selected from the group consisting of —X, —OH, —O$R^{op}$, —SH, —S$R^{op}$, —$NH_2$, —NH($R^{op}$), —NR'($R^{op}$)$_2$, —N($R^{op}$)$_3$, =NH, =N$R^{op}$, —$CX_3$, —CN, —$NO_2$, —NR'C(=O)H, NR'C(=O)$R^{op}$, —$CO_2H$, —C(=O)H, —C(=O)$R^{op}$, —C(=O)$NH_2$, —C(=O)NR'$R^{op}$, —S(=O)$_2$$R^{op}$, —S(=O)$_2$$NH_2$, —S(=O)$_2$N(R')$R^{op}$, —S(=O)$_2$$NH_2$, —S(=O)$_2$N(R')($R^{op}$), —S(=O)$_2$OR', —S(=O)$R^{op}$, —C(=S)$R^{op}$, —C(=S)$NH_2$, —C(=S)N(R')RP, —C(=NR')N($R^{op}$)$_2$, and salts thereof, wherein each X is independently selected from the group consisting of —F and —Cl, wherein $R^{op}$ is typically selected from the group consisting of $C_1$-$C_6$ alkyl, $C_6$-$C_{10}$ aryl, $C_3$-$C_{10}$ heterocyclyl, $C_5$-$C_{10}$ heteroaryl, and a protecting group; and R' is independently selected from the group typically consisting of hydrogen, $C_1$-$C_6$ alkyl, $C_6$-$C_{10}$ aryl, $C_3$-$C_{10}$ heterocyclyl, $C_5$-$C_{10}$ heteroaryl, and a protecting group, independently selected from $R^{op}$.

More typically, optional substituents that are present are selected from the group consisting of —X, —$R^{op}$, —OH, —O$R^{op}$, —$NH_2$, —NH($R^{op}$), —N($R^{op}$)$_2$, —N($R^{op}$)$_3$, —$CX_3$, —$NO_2$, —NHC(=O)H, —NHC(=O)$R^{op}$, —C(=O)$NH_2$, —C(=O)NH$R^{op}$, —C(=O)N($R^{op}$)$_2$, —$CO_2H$, —$CO_2$$R^{op}$, —C(=O)H, —C(=O)$R^{op}$, —C(=O)$NH_2$, —C(=O)NH($R^{op}$), —C(=O)N($R^{op}$)$_2$, —C(=NR')$NH_2$, —C(=NR')NH($R^{op}$), —C(=NR')N($R^{op}$)$_2$, a protecting group and salts thereof, wherein each X is —F, wherein $R^{op}$ is independently selected from the group consisting of $C_1$-$C_6$ alkyl, $C_6$-$C_{10}$ aryl, $C_5$-$C_{10}$ heteroaryl and a protecting group; and R' is selected from the group consisting of hydrogen, $C_1$-$C_6$ alkyl and a protecting group, independently selected from $R^{op}$.

In some aspects, an optional alkyl substituent that is present is selected from the group consisting —$NH_2$, —NH($R^{op}$), —N($R^{op}$)$_2$, —N($R^{op}$)$_3$, —C(=NR')$NH_2$, —C(=NR')NH(RP), and —C(=NR')N($R^{op}$)$_2$, wherein R' and $R^{op}$ is as defined for any one of the R' or $R^{op}$ groups above. In some of those aspects, the R' and/or $R^{op}$ substituents together with the nitrogen atom to which they are attached provide for the basic functional group of a Basic Unit (BU), as when $R^{op}$ is independently selected from the group consisting of hydrogen and $C_1$-$C_6$ alkyl. Alkylene, carbocyclyl, carbocyclo, aryl, arylene, heteroalkyl, heteroalkylene, heterocyclyl, heterocyclo, heteroaryl, and heteroarylene groups as described above are similarly substituted or are unsubstituted, with exceptions, if any, as described in the definitions of these moieties.

In other aspects an optional alkyl substituent that is present is an optionally substituted $C_6$-$C_{10}$ aryl or $C_5$-$C_{10}$ heteroaryl to define an optionally substituted (hetero)arylalkyl-, as further defined herein, wherein the alkyl component is a saturated $C_1$-$C_8$ alkyl or an unsaturated $C_3$-$C_8$ alkyl.

"Optionally substituted heteroatom", as used herein, unless otherwise stated or implied by context, refers to a heteroatom or heteroatom moeity within a functional group or other organic moiety in which the heteroatom or heteroatom moeity is not further substituted or is substituted by any one of the aforementioned moieties having a monovalent carbon atom including, but not limited to alkyl, cycloalkyl, alkenyl, aryl, heterocyclyl, heteroaryl, heteroalkyl and (hetero)arylalkyl- or is oxidized by substitution with one or two =O substituents. In some aspects, "optionally substituted heteroatom" refers an aromatic or non-aromatic —NH— moeity that is unsubstituted or in which the hydrogen atom is replaced by any one of the aforementioned substituents. In other aspects, "optionally substituted heteroatom" refers to an aromatic skeletal nitrogen atom of a heteroaryl in which an electron of that heteroatom is replaced by any one of the aforementioned substituents. For encompassing both of those aspects, the nitrogen heteroatom or heteroatom moiety is sometime referred to as optionally substituted N/NH.

Therefore, in some aspects, an optional substituent of a nitrogen atom that is present is selected from the group consisting of $C_1$-$C_{20}$ alkyl, $C_2$-$C_{20}$ alkenyl, $C_2$-$C_{20}$ alkynyl, $C_6$-$C_{24}$ aryl, $C_5$-$C_{24}$ heteroaryl, ($C_6$-$C_{24}$ aryl)-$C_1$-$C_{20}$ alkyl-, and ($C_5$-$C_{24}$ heteroaryl)-$C_1$-$C_{20}$ alkyl-, optionally substituted, as those terms are defined herein. In other aspects, optional substituents of a nitrogen atom that are present are independently selected from the group consisting of $C_1$-$C_{12}$ alkyl, $C_2$-$C_{12}$ alkenyl, $C_2$-$C_{12}$ alkynyl, $C_6$-$C_{24}$ aryl, $C_5$-$C_{24}$ heteroaryl, ($C_6$-$C_{24}$ aryl)-$C_1$-$C_{12}$ alkyl-, and ($C_5$-$C_{24}$ heteroaryl)-$C_1$-$C_{12}$ alkyl-, optionally substituted, from the group consisting of $C_1$-$C_8$ alkyl, $C_2$-$C_8$ alkenyl, $C_2$-$C_8$ alkynyl, $C_6$-$C_{10}$ aryl, $C_5$-$C_{10}$ heteroaryl, ($C_6$-$C_{10}$ aryl)-$C_1$-$C_8$ alkyl-, and ($C_5$-$C_{10}$ heteroaryl)-$C_1$-$C_8$ alkyl, or from the group consisting of $C_1$-$C_6$ alkyl, $C_2$-$C_6$ alkenyl, $C_2$-$C_6$ alkynyl, $C_6$-$C_{10}$ aryl, $C_5$-$C_{10}$ heteroaryl, ($C_6$-$C_{10}$ aryl)-$C_1$-$C_6$ alkyl-, and ($C_5$-$C_{10}$ heteroaryl)-$C_1$-$C_6$ alkyl-.

In some aspects, an optional substituent that is present replaces a carbon atom in the acyclic carbon chain of an alkyl or alkylene moiety, group or substituent to provide for a $C_3$-$C_{12}$ heteroalkyl or $C_3$-$C_{12}$ heteroalkylene and for that purpose is typically selected from the group consisting of —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$—, —OC(=O)NH—, and —NHC(=O)O, optionally substituted in which —NH— is an optionally substituted heteroatom moiety wherein substitution is by replacement of its hydrogen atom by an independently selected substituent from a group previously described for heteroatom moieties.

In other aspects, when variable group J/J' of a PAB or PAB-type self-immolative Spacer Unit within a self-immolative Spacer Unit, as described by the embodiments of the invention, is optionally substituted —NH—, the nitrogen atom is so substituted by replacement of its hydrogen atom with a substituent that suitably retains the localization of its nitrogen lone pair electrons so that on cleavage of the W-J bond in a Linker Unit in which W is a Peptide Cleavable Unit allows for self-immolation of the PAB or PAB-type moiety of the self-immolative Spacer Unit comprised of that optionally substituted nitrogen atom. In other aspects, when variable group E' of a glycosidic bond between W' and Y of a Glucuronide Unit, as described by the embodiments of the invention, is an optionally substituted —NH— moiety, the nitrogen atom when substituted has its attached hydrogen atom replaced by a substituent that suitably retains the localization of its nitrogen lone pair electrons in its participation in the glycosidic bond so as to allow for self-immolation of the PAB or PAB-type moiety of the self-immolative Spacer Unit of that Glucuronide Unit upon cleavage of the glycosidic bond and provides for a recognition site for glycosidase cleavage so that cleavage effectively competes with spontaneous hydrolysis of that bond. In a Glucuronide Unit, J', which is the attachment site to the remainder of the Linker Unit (LU), is —O—, —S— or optionally substituted NH, wherein the bond from J' to the remainder of LU is not subject to enzymatic or non-enzymatic cleavage under normal physiological conditions or within the vicinity of targeted abnormal cells.

"O-linked moiety", as used herein, unless otherwise stated or implied by context, refers to a moiety, group or substituent that is attached to a Markush structure or another organic moiety with which it is associated directly through an oxygen atom of the O-linked moiety. A monovalent O-linked moiety has that attachment through a monovalent oxygen atom and is typically —OH, —OC(=O)$R^b$ (acyloxy), wherein $R^b$ is —H, optionally substituted saturated $C_1$-$C_{20}$ alkyl, optionally substituted unsaturated $C_1$-$C_{20}$ alkyl, optionally substituted $C_3$-$C_{20}$ cycloalkyl, wherein the cycloalkyl moiety is saturated or partially unsaturated, optionally substituted $C_3$-$C_{20}$ alkenyl, optionally substituted $C_2$-$C_{20}$ alkynyl, optionally substituted $C_6$-$C_{24}$ aryl, optionally substituted $C_5$-$C_{24}$ heteroaryl or optionally substituted $C_3$-$C_{24}$ heterocyclyl, or $R^b$ is optionally substituted $C_1$-$C_{12}$ alkyl, optionally substituted $C_3$-$C_{12}$ cycloalkyl, optionally substituted $C_3$-$C_{12}$ alkenyl or optionally substituted $C_2$-$C_{12}$ alkynyl, and wherein an monovalent O-linked moiety further encompasses ether groups which are $C_1$-$C_{12}$ alkyloxy (i.e., $C_1$-$C_{12}$ aliphatic ether) moieties, optionally substituted, wherein the alkyl moiety is saturated or unsaturated.

In other aspects, a monovalent O-linked moiety is a monovalent moiety selected from the group consisting of optionally substituted phenoxy, optionally substituted $C_1$-$C_8$ alkyloxy (i.e., $C_1$-$C_8$ aliphatic ether) and —OC(=O)$R^b$, wherein $R^b$ is optionally substituted $C_1$-$C_8$ alkyl, which is typically saturated or is an unsaturated $C_3$-$C_8$ alkyl, optionally substituted.

In still other aspects, an O-linked moiety is a monovalent moiety selected from the group consisting of —OH, and saturated $C_1$-$C_6$ alkyl ether, unsaturated $C_3$-$C_6$ alkyl ether, optionally substituted, and —OC(=O)$R^b$, wherein $R^b$ is typically $C_1$-$C_6$ saturated alkyl, $C_3$-$C_6$ unsaturated alkyl, $C_3$-$C_6$ cycloalkyl, $C_2$-$C_6$ alkenyl, or phenyl, optionally substituted, or is selected from that group excluding —OH and/or —OC(=O)$R^b$ in which $R^b$ is phenyl, or $R^b$ is a monovalent moiety selected from the group consisting of $C_1$-$C_6$ saturated alkyl, $C_3$-$C_6$ unsaturated alkyl and $C_2$-$C_6$ alkenyl, optionally substituted, or an monovalent O-linked moiety is an unsubstituted O-linked substituent selected from the group consisting of saturated $C_1$-$C_6$ alkyl ether, unsaturated $C_3$-$C_6$ alkyl ether, and —OC(=O)$R^b$, wherein $R^b$ is an unsubstituted, saturated $C_1$-$C_6$ alkyl or unsubstituted, unsaturated $C_3$-$C_6$ alkyl.

Other exemplary O-linked substituents are provided by definitions for carbamate, ether and carbonate as disclosed herein in which the monovalent oxygen atom of the carbamate, ether and carbonate functional group is bonded to the Markush structure or other organic moiety with which it is associated.

In other aspects, an O-linked moiety to carbon is divalent and encompasses =O and —X—(CH$_2$)$_n$—Y—, wherein X and Y independently are S and O and subscript n is 2 or 3, to form a spiro ring system with the carbon to which X and Y are both attached.

"Halogen" as used herein, unless otherwise stated or implied by context, refers to fluorine, chlorine, bromine or iodine and is typically —F or —Cl.

"Protecting group" as used herein, unless otherwise stated or implied by context, refers to a moiety that prevents or substantially reduces the ability of the atom or functional group to which it is linked from participating in unwanted reactions. Typical protecting groups for atoms or functional groups are given in Greene (1999), "Protective groups in organic synthesis, $3^{rd}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is typically protected as an ester (e.g., acetate, propionate or benzoate). Other protecting groups for hydroxyl avoid its interference with the nucleophilicity of organometallic reagents or other highly basic reagents, for which purpose hydroxyl is typically protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$, wherein at least one of R$^{PR}$ is a nitrogen atom protecting group or both R$^{PR}$ together define a nitrogen atom protecting group.

A protecting group is a suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. In some aspects, suitable protecting groups are those previously described for protecting functional groups. In other aspects, a suitable protecting group is a protecting group used in peptide coupling reactions. For example, a suitable protecting group for the basic nitrogen atom of a tubuvaline compound's acyclic or cyclic Basic Unit is an acid-labile carbamate protecting group such as t-butyloxycarbonyl (BOC).

"Ester" as used herein, unless otherwise stated or implied by context, refers to a substituent, moiety or group having the structure of —C(=O)—O— to define an ester functional group in which the carbonyl carbon atom of that structure is not directly connected to another heteroatom but is directly connected to hydrogen or another carbon atom of an organic moiety with which it is associated, and wherein the monovalent oxygen atom is either attached to the same organic moiety at a different carbon atom to provide a lactone or to a Markush structure or to some other organic moiety. Typically, esters in addition to the ester functional group comprise or consist of an organic moiety containing 1 to 50 carbon atoms, typically 1 to 20 carbon atoms or more typically 1 to 8, 1 to 6 or 1 to 4 carbon atoms and 0 to 10 independently selected heteroatoms (e.g., O, S, N, P, Si, but usually O, S and N), typically 0 to 2 heteroatoms, wherein the organic moiety is bonded to the —C(=O)—O— structure (i.e., through the ester functional group) so as to provide structure having the formula of organic moiety-C(=O)—O— or —C(=O)—O— organic moiety.

When an ester is a substituent or variable group of a Markush structure or other organic moeity with which it is associated, that substituent is bonded to the structure or other organic moiety through the monovalent oxygen atom of the ester functional group so that it is an monovalent O-linked substituent, which sometimes referred to as an acyloxy. In such instances, the organic moiety attached to the carbonyl carbon of the ester functional group typically is a C$_1$-C$_{20}$ alkyl, C$_2$-C$_{20}$ alkenyl, C$_2$-C$_{20}$ alkynyl, C$_6$-C$_{24}$ aryl, C$_5$-C$_{24}$ heteroaryl, C$_3$-C$_{24}$ heterocyclyl or is a substituted derivative of any one of these, e.g., having 1, 2, 3 or 4 substituents, more typically is C$_1$-C$_{12}$ alkyl, C$_2$-C$_{12}$ alkenyl, C$_2$-C$_{12}$ alkynyl, C$_6$-C$_{10}$ aryl, C$_5$-C$_{10}$ heteroaryl, C$_3$-C$_{10}$ heterocyclyl or a substituted derivative of one any of these, e.g., having 1, 2, or 3 substituents or is C$_1$-C$_8$ alkyl, C$_2$-C$_8$ alkenyl, C$_2$-C$_8$ alkynyl, or phenyl or a substituted derivative of any one of these, e.g., having 1 or 2 substituents, wherein each independently selected substituent is as defined herein for optional alkyl substituents, or is unsubstituted C$_1$-C$_6$ alkyl or unsubstituted C$_2$-C$_6$ alkenyl.

Exemplary esters by way of example and not limitation, are acetate, propionate, isopropionate, isobutyrate, butyrate, valerate, isovalerate, caproate, isocaproate, hexanoate, heptanoate, octanoate, phenylacetate esters and benzoate esters or have the structure of —OC(=O)R$^b$ in which R$^b$ is as defined for acyloxy O-linked substituents and is typically selected from the group consisting of methyl, ethyl, propyl, iso-propyl, 2-methyl-prop-1-yl, 2,2-dimethyl-prop-1-yl, prop-2-ene-1-yl, and vinyl.

"Ether" as used herein, unless otherwise stated or implied by context, refers to an organic moiety, group or substituent that comprises 1, 2, 3, 4 or more —O— (i.e., oxy) moieties that are not bonded to carbonyl moiety(ies), typically 1 or 2, wherein no two —O-moieties are immediately adjacent (i.e., directly attached) to each other. Typically, an ether contains the formula of —O-organic moiety wherein organic moiety is as described for an organic moiety bonded to an ester functional group, e.g., organic moiety-O—C(=O)—O—, or is as described herein for an optionally substituted alkyl group. When ether is recited as a substituent or variable group of a Markush structure or other organic moeity with which it is associated, the oxygen of the ether functional group is attached to a Markush formula with which it is associated and is sometimes designated as an "alkoxy" group, which is an exemplary O-linked substituent. In some aspects, an ether O-linked substituent is a C$_1$-C$_{20}$ alkoxy or a C$_1$-C$_{12}$ alkoxy, optionally substituted with 1, 2, 3 or 4 substituents, typically 1, 2 or 3, and in other aspects is a C$_1$-C$_8$ alkoxy or C$_1$-C$_6$ alkoxy, optionally substituted with 1 or 2 substituents, wherein each independently selected substituent is as defined herein for optional alkyl substituents, and in still other aspects an ether O-linked substituent is an unsubstituted, saturated or unsaturated C$_1$-C$_4$ alkoxy such as, by way of example and not limitation, methoxy, ethoxy, propoxy, iso-propoxy, butoxy and allyloxy (i.e., —OCH$_2$CH=CH$_2$).

"Amide" as used herein, unless otherwise stated or implied by context, refers to a moiety having an optionally substituted functional group having the structure of R—C(=O)N(R$^c$)— or —C(=O)N(R$^c$)$_2$ to which no other heteroatom is directly attached to the carbonyl carbon and wherein each R$^c$ is independently hydrogen, a protecting group or an independently selected organic moiety, and R is hydrogen or an organic moiety, wherein organic moiety, independently selected from R$^c$, is as described herein for an organic moiety bonded to an ester functional group (e.g., R—C(=O)N(R$^c$)-organic moiety or organic moiety-C(=O)N(R$^c$)$_2$) or is as described herein for an optionally substituted alkyl group. When an amide is recited as a substituent or variable group of a Markush structure or other organic moeity with which it is associated, the amide nitrogen atom or carbonyl carbon atom of the amide functional group is bonded to that structure or other organic moiety. Amides are typically prepared by condensing an acid halide, such an acid chloride, with a molecule containing a primary or secondary amine. Alternatively, amide coupling reactions well-known in the art of peptide synthesis, which in some aspects proceeds through an activated ester of a carboxylic acid-containing molecule, are used. Exemplary preparations of amide bonds through peptide coupling methods are provided in Benoiton (2006) "Chemistry of peptide synthesis", CRC Press; Bodansky (1988) "Peptide synthesis: A practical textbook" Springer-Verlag; Frinkin, M. et al. "Peptide Synthesis" *Ann. Rev. Biochem.* (1974) 43: 419-443.

Reagents used in the preparation of activated carboxylic acids is provided in Han, et al. "Recent development of peptide coupling agents in organic synthesis" *Tet.* (2004) 60: 2447-2476.

Thus, in some aspects, amides are be prepared by reacting a carboxylic acid with an amine in the presence of a coupling agent. As used herein, "in the presence of a coupling agent" includes contacting the carboxylic acid with the coupling agent thereby converting the acid to its activated derivative, such as an activated ester or a mixed anhydride, with or without isolation of the resulting activated derivative of the acid, followed by or simultaneously contacting the resulting activated derivative with the amine. In some instances, the activated derivative is prepared in situ. In other instances, the activated derivative may be isolated to remove any undesired impurities.

"Carbonate" as used here means a substituent, moiety or group that contains a functional group having the structure —O—C(=O)—O—. Typically, carbonate groups as used herein are comprised of an organic moiety bonded to the —O—C(=O)—O— structure, wherein the organic moiety is as described herein for an organic moiety bonded to an ester functional group (e.g., organic moiety-O—C(=O)—O—). When carbonate is recited as a substituent or variable group of a Markush structure or other organic moeity with which it is associated, one of the monovalent oxygen atoms of the carbonate functional group is attached to that structure or organic moeity and the other is bonded to a carbon atom of another organic moiety as previously described for an organic moiety bonded to an ester functional group or is as described herein for an optionally substituted alkyl group. In such instances, carbonate is an exemplary O-linked substituent.

"Carbamate" as used here means a substituent, moiety or group that contains a optionally substituted carbamate functional group structure represented by —O—C(=O)N(R$^c$)— or —O—C(=O)N(R$^c$)$_2$, or —O—C(=O)NH (optionally substituted alkyl)- or —O—C(=O)N (optionally substituted alkyl)$_2$ in which the independently selected optionally substituted alkyl(s) are exemplary carbamate functional group substituents, and typically are C$_1$-C$_{12}$ alkyl or C$_1$-C$_8$ alkyl, optionally substituted, more typically C$_1$-C$_6$ alkyl or C$_1$-C$_4$ alkyl, optionally substituted, wherein each R$^c$ is independently selected, wherein independently selected R$^c$ is hydrogen, a protecting group or an organic moiety, wherein the organic moiety is as described herein for an organic moiety bonded to an ester functional group (e.g., by —O—C(=O)N(R$^c$)-organic moiety or organic moiety-O—C(=O) N(R$^c$)$_2$, or is as described herein for an optionally substituted alkyl group. Typically, carbamate groups are additionally comprised of an organic moiety, independently selected from R$^c$, wherein the organic moiety is as described herein for an organic moiety bonded to an ester functional group, e.g., organic moiety-O—C(=O)—O—, bonded through the —O—C(=O)—N(R$^c$)— structure, wherein the resulting structure has the formula of organic moiety-O—C(=O)—N(R$^c$)— or —O—C(=O)—N(R$^c$)-organic moiety. When carbamate is recited as a substituent or variable group of a Markush structure or other organic moeity with which it is associated, the monovalent oxygen (O-linked) or nitrogen (N-linked) of the carbamate functional group is attached to that Markush formula or other organic moiety. The linkage of the carbamate substituent is either explicitly stated (N- or O-linked) or implicit in the context to which this substituent is referred. O-linked carbamates described herein are exemplary monovalent O-linked substituents.

"Tubulysin drug" or "tubulysin compound" as used herein is a peptide-based tubulin-disrupting agent having cytotoxic, cytostatic, or anti-inflammatory activity and is comprised of one natural or un-natural amino acid component and three other un-natural amino acid components wherein one of those un-natural components is characterized by a central 5-membered or 6-membered heteroarylene moiety and another un-natural component provides for a tertiary amine, which can be used for linking to a targeting agent to form a Ligand Drug Conjugate (LDC) in the form of a quaternized amine so that the tubulysin drug becomes a quaternized Drug Unit.

Tubulysin compounds generally have the structure of D$_G$ or D$_H$:

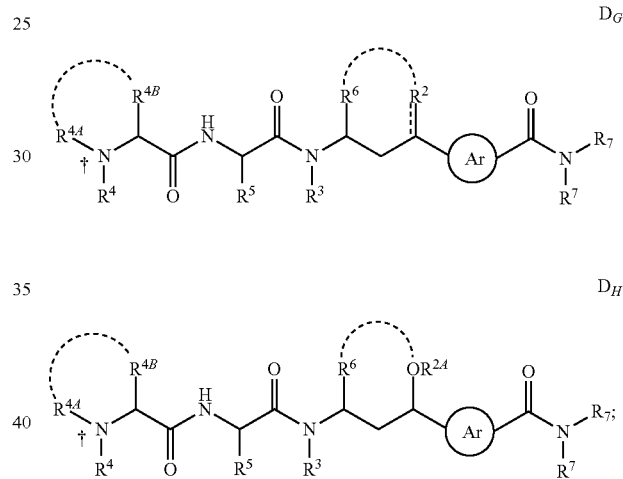

wherein the straight dashed line indicates an optional double bond, the curved dash line indicates optional cyclization, the circled Ar indicates an arylene or heteroarylene that is 1,3-substituted within the tubulysin carbon skeleton and is optionally substituted elsewhere, wherein the arylene or heteroarylene and other variable groups are as defined in the embodiments of the invention.

Naturally-occurring tubulysin compounds have the structure of D$_G$-6.

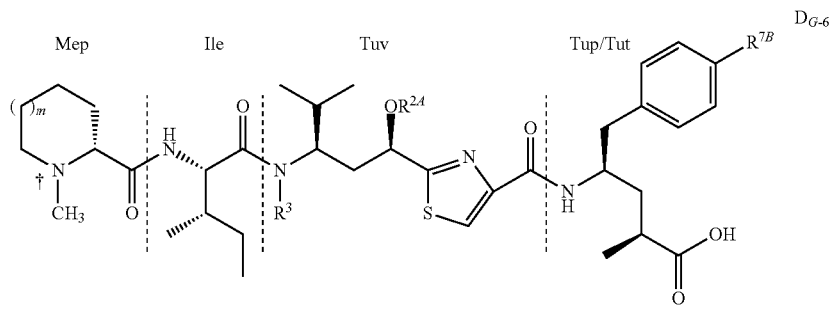

and are conveniently divided into four amino acid subunits, as indicated by the dashed vertical lines, named N-methyl-pipecolinic acid (Mep), isoleucine (Ile), tubuvaline (Tuv), and either tubuphenylalanine (Tup, when $R^{7A}$ is hydrogen) or tubutyrosine (Tut, when $R^{7A}$ is —OH). There are about a dozen naturally occurring tubulysins presently known and are named Tubulysin A-I, Tubulysin U, Tubulysin V and Tubulysin Z, whose structures are indicated by variable groups for structure $D_{G-6}$ defined in embodiments of tubulysin-based quaternized Drug Units.

Pretubulysins generally have the structure $D_G$, $D_{G-6}$, or $D_H$, wherein $R^3$ is —CH$_3$ and $R^{2A}$ is hydrogen, and desmethyl tubulysins have the structure of $D_G$, $D_{G-6}$, or $D_H$ in which $R^3$ is hydrogen and include other tubulysin structures given by the embodiments of tubulysin-based quaternized Drug Units in which $R^3$ is hydrogen, and wherein the other variable groups are as described for tubulysins. Pretubulysins and desmethyl tubulysins are optionally included in the definition of tubulysins.

In structures $D_G$, $D_{G-6}$, $D_H$ and other tubulysin structures described herein in embodiments of tubulysin-based quaternized Drug Units, the indicated (t) nitrogen atom is the site of quaternization when such structures correspond to or are incorporated into an Ligand Drug Conjugate, Drug Linker compound, or precursor thereof as a quaternized tubulysin Drug Unit. Typically, the quaternized moiety of $D^+$ results from covalent attachment of the nitrogen atom of the tertiary amine-containing N-terminal component of a tubulysin compound to the benzylic carbon of a PAB or PAB-type moiety in a self-immolative Spacer Unit.

"Pharmaceutically acceptable salt" as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

A pharmaceutically acceptable salt may involve the inclusion of another molecule such as an acetate ion, a succinate ion or other counterion. The counterion is typically an organic or inorganic moiety that stabilizes the charge introduced on to the parent compound. A pharmaceutically acceptable salt has one or more than one charged atoms in its structure. In instances where multiple charged atoms are part of the pharmaceutically acceptable salt, typically multiple counter ions are present, or a multiple charged counter ion is present. Hence, a pharmaceutically acceptable salt can have one or more charged atoms and one or more counterions. Typically, a quaternized tubulysin Drug Unit is in pharmaceutically acceptable salt form. In those aspects, the quaternized nitrogen of the N-terminal component of the quaternized tubulysin Drug Unit is associated with a pharmaceutically acceptable counteranion and in other aspects, a carboxylic acid of the C-terminal component is also present in ionized form and is associated with a pharmaceutically acceptable countercation.

Typically, a pharmaceutically acceptable salt is selected from those described in P. H. Stahl and C. G. Wermuth, editors, *Handbook of Pharmaceutical Salts: Properties, Selection and Use*, Weinheim/Zürich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

"Antibody" as used herein is used in the broadest sense and specifically covers intact monoclonal antibodies, polyclonal antibodies, monospecific antibodies, multispecific antibodies (e.g., bispecific antibodies), and antigen-binding fragments thereof that exhibit the desired biological activity provided that the antibody fragment has the requisite number of sites for attachment to the desired number of quaternized drug-linker moieties. The native form of an antibody is a tetramer and typically consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs". In some aspects, the constant regions are recognized by and interact with the immune system (see, e.g., Janeway et al., 2001, *Immunol. Biology*, 5th Ed., Garland Publishing, New York) so as to exert an effector function. An antibody includes any isotype (e.g., IgG, IgE, IgM, IgD, and IgA) or subclass thereof (e.g., IgG1, IgG2, IgG3, IgG4, IgA1 and IgA2). The antibody is derivable from any suitable species. In some aspects, the antibody is of human or murine origin. Such antibodies include human, humanized or chimeric antibodies. An antibody or antibody fragment thereof, is an exemplary targeting agent that corresponds to or is incorporated into a Ligand Drug Conjugate of the present invention as an antibody Ligand Unit.

In some aspects, an antibody selectively and specifically binds to an epitope on hyper-proliferating cells or hyper-stimulated mammalian cells, which are exemplary abnormal cells, wherein the epitope is preferentially displayed by or is more characteristic of the abnormal cells in contrast to normal cells, or is preferentially displayed by or is more characteristic of normal cells in the vicinity of abnormal cells in contrast to normal cells not localized to the site of the abnormal cells. In those aspects, the mammalian cells are typically human cells. Other aspects of antibodies incorporated into Ligand Units are described by embodiments for Ligand Drug Conjugates.

"Monoclonal antibody" as used herein refers to an antibody obtained from a population of substantially homogeneous antibodies, i.e., the individual antibodies comprising the population are identical except for possible naturally-occurring mutations that may be present in minor amounts and/or differences in glycosylation patterns. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

"Ligand Drug Conjugate" or "LDC" as the term is used herein refers to a construct comprised of a Ligand Unit (L) incorporating or corresponding to a targeting agent and a quaternized tubulysin Drug Unit ($D^+$) incorporating or corresponding in structure to a tubulysin compound, wherein L and $D^+$ are bonded to each other through a Linker Unit (LU), wherein the Ligand Drug Conjugate selectively binds to a targeted moiety through its targeting Ligand Unit. In some instances, the term Ligand Drug Conjugate is a plurality (i.e., composition) of individual Conjugate compounds differing primarily by the number of $D^+$ Units bonded to each Ligand Unit and/or the location on the Ligand Unit at which the $D^+$ Units are bound. In other instances, the term Ligand Drug Conjugate applies to an individual member or compound of the composition. An Antibody Drug Conjugate, as defined below, is one type of Ligand Drug Conjugate in which its Ligand Unit is that of an antibody or antigen-binding fragment thereof. A Ligand Drug Conjugate has the general formula of $L\text{-}(L_R\text{-}B_b\text{-}(A\text{-}W\text{—}Y\text{-}D^+)_n)_p$, wherein $L_R$ is $L_{SS}/L_S$ or other primary linker, which has an $L_b$-containing moiety, which along with the other variable groups, is defined elsewhere.

"Antibody Drug Conjugate" or "ADC" as the term is used herein refers to a antibody residue or antigen binding fragment thereof, referred to in some aspects as an antibody Ligand Unit, covalently attached to a quaternized tubulysin Drug Unit through an intervening Linker Unit. Oftentimes the term refers to a collection (i.e., population or plurality) of Conjugate compounds having the same $D^+$, Linker Unit and Ligand Unit, with permissible variations in sequences and glycosylation patterns as previously described for monoclonal antibodies or substantially the same antibody Ligand Unit, as typically found for polyclonal antibodies, which in some aspects have variable loading and/or distribution of the quaternized tubulysin drug linker moieties attached to each antibody residue (as, for example, when the number of quaternized tubulysin Drug Units ($D^+$) of any two Antibody Drug Conjugate compounds in a plurality of such compounds is the same but the location of their sites of attachment to the targeting moiety differ). In those instances, an Antibody Drug Conjugate is described by the averaged drug loading of the Conjugate compounds. The average number quaternized Drug Units per antibody Ligand Unit, or antigen-binding fragment thereof, in an Antibody Drug Conjugate composition (i.e., an averaged number for a population of Antibody Drug Conjugate compounds that in some aspects differ primarily by the number of conjugated quaternized tubulysin Drug Units on the antibody Ligand Unit in each of the Antibody Drug Conjugate compounds that are present in that population and/or by their locations). In that context p is a number ranging from about 2 to about 24 or about 2 to about 20 and is typically about 2, about 4, about 8, about 10 or about 12. In other contexts, p represents the number of quaternized tubulysin Drug Units that are covalently bonded to a single antibody Ligand Unit of an Antibody Drug Conjugate within a population of Antibody Drug Conjugate compounds in which the compounds of that population in some aspects primarily differ by the number and/or locations of the conjugated quaternized tubulysin Drug Units. In that context p is designated as p' and is an integer ranging from 1 to 24 or from 1 to 20, typically from 1 to 12 or 1 to 10, and more typically from 1 to 8. In other aspects, essentially all of the available reactive functional groups of an antibody targeting agent form covalent bonds for conjugating to quaternized Drug Units, which provides an antibody Ligand Unit attached to the maximum number of quaternized drug linker moieties, so that the p value of the Antibody Drug Conjugate composition is the same or nearly the same as each p' value for each of the Antibody Drug Conjugate compounds of the composition, so that only minor amounts of Antibody Drug Conjugate compounds with lower p' values are present, if at all, as detected using electrophoresis or an appropriate chromatographic method, such as HIC, reverse phase HPLC or size-exclusion chromatography.

The average number of quaternized tubulysin Drug Units per antibody Ligand Unit in a preparation from a conjugation reaction in some aspects is characterized by conventional chromatographic means as described above in conjunction with mass spectroscopy detection. In other aspects, the quantitative distribution of conjugate compounds in terms of p' values are determined. In those instances, separation, purification, and characterization of homogeneous Antibody Drug Conjugate compounds in which p' is a certain value from an Antibody Drug Conjugate composition from those with other $D^+$ loadings is achievable by means such as an aforementioned chromatographic method.

"Drug Linker compound" as the terms are used herein, unless otherwise stated or implied by context, refers to a compound having a primary linker, an optional secondary linker that is present and a quaternized tubulysin Drug Unit ($D^+$), wherein the primary linker is comprised of a ligand covalent binding precursor ($L_b'$) moiety, which is capable of reacting with a targeting agent to form a covalent bond between $L_b$ and a Ligand Unit that incorporates or corresponds to the targeting agent. A Drug Linker compound has the general formula of $L_R\text{-}(B_b\text{-}(A\text{-}W\text{—}Y\text{-}D^+)_n)_p$, for which the variable groups are defined elsewhere, wherein $L_R$ in some aspects is $L_{SS}$, and is sometimes shown as $L_R'$ and $L_{SS}'$, respectively, to explicitly indicate these as precursors to $L_R$ and $L_{SS}$ in a Ligand Drug Conjugate.

"Selective and binding" and "selectively binds" as the terms are used herein, unless otherwise stated or implied by context, refers to an antibody, an antigen-binding fragment thereof, or an antibody Ligand Unit as the targeting moiety in an Antibody Drug Conjugate that is capable of binding in an immunologically selective and specific manner with its cognate targeted antigen and not with a multitude of other antigens. Typically, the antibody or antigen-binding fragment thereof binds its targeted antigen with an affinity of at least about $1\times10^{-7}$ M, and preferably at about $1\times10^{-8}$ M to $1\times10^{-9}$ M, $1\times10^{-10}$ M, or $1\times10^{-11}$ M and binds to that predetermined antigen with an affinity that is at least two-fold greater than its affinity for binding to a non-specific antigen (e.g., BSA, casein), other than to a closely-related antigen, wherein said affinities are substantially retained when the antibody or antigen-binding fragment thereof corresponds to or is incorporated into a Ligand Drug Conjugate as an antibody Ligand Unit.

"Targeting agent" as used herein, unless otherwise stated or implied by context, refers to an agent that that is capable of selective binding to a targeted moeity and which substantially retains that capability when it is incorporated into a Ligand Drug Conjugate as a Ligand Unit, or when the Ligand Unit of a Ligand Drug Conjugate corresponds in structure to the targeting agent or incorporates the structure of the targeting agent, so that the Ligand Unit is the targeting moiety of the Conjugate. In some aspects, the targeting agent is an antibody or antigen-binding fragment thereof that selectively and specifically binds to an accessible antigen that is characteristic of an abnormal cell or is present on that cell in higher copy number in comparison to normal cells or is an accessible antigen that is particular to the surrounding environment in which these cells are found to an extent that achieves immunoselective cytotoxicity, which should translate to an acceptable therapeutic index. In other aspects, the targeting agent is a receptor ligand that selectively binds to an accessible receptor characteristic of, or in greater abundance on, abnormal cells, or to an accessible receptor that is peculiar to cells of the surrounding environment in which abnormal cells are found. Typically, a targeting agent is an antibody or antigen-binding fragment thereof as defined herein that binds selectively to a targeted moiety of an abnormal mammalian cell, more typically a targeted moiety of an abnormal human cell.

"Targeted moeity" as defined herein is a moeity to be specifically recognized by a targeting agent in unconjugated form or a targeting moeity of a Ligand Drug Conjugate, which is the Conjugate's Ligand Unit that corresponds to or incorporates the targeting agent. In some aspects, a targeted moiety is present on, within, or in the vicinity of abnormal cells and is typically present in greater abundance or copy number on those cells in comparison to normal cells or in greater abundance or copy number in the environment of abnormal cells in comparison to the environment of normal cell that are not in the presence of the abnormal cells to a sufficient degree so as to provide for immunoselective cytotoxicity, which should translate to an acceptable therapeutic index. In some aspects, the targeted moiety is an antigen that is accessible for selective and specific binding by an antibody, which is an exemplary targeting agent that is incorporated as or corresponds to an antibody Ligand Unit in a Ligand Drug Conjugate composition or compound thereof. In other aspects, the targeting moiety is that of a ligand for an extracellularly accessible cell membrane receptor, which may be internalized upon binding of the cognate targeting moiety provided by the Ligand Unit of a Ligand Drug Conjugate or compound thereof that incorporates or corresponds in structure to the receptor ligand, or is capable of passive or facilitative transport of a Ligand Drug Conjugate compound subsequent to binding of the cell-surface receptor. In some of those instances, the targeted moiety is present on abnormal mammalian cells or on mammalian cells characteristic of the environment of such abnormal cells. In other of those instances, the targeted moiety is an antigen of an abnormal mammalian cell, more typically a targeted moiety of an abnormal human cell.

"Antigen" is an entity that is capable of being selective bound to an unconjugated antibody or an antigen-binding fragment thereof or to an Antibody Drug Conjugate comprising an antibody Ligand Unit corresponding to or incorporating that antibody or antigen-binding fragment. In some aspects, the antigen is an extracellularly-accessible cell-surface protein, glycoprotein, or carbohydrate preferentially displayed by abnormal cells in comparison to normal cells that are not localized to the abnormal cells and is more often a cell-surface glycoprotein. In some instances the abnormal cells having the antigen are hyper-proliferating cells in a mammal. In other instances, the abnormal cells having the antigen are hyper-activated immune cells in a mammal. In still other aspects, the specifically bound antigen is present in the particular environment of hyper-proliferating cells or hyper-activated immune cells in a mammal in contrast to the environment typically experienced by normal cells in the absence of such abnormal cells. In still other aspects, the cell-surface antigen is capable of internalization upon selective binding of an Antibody Drug Conjugate (ADC) compound and is associated with nearby cells that are particular to the environment in which hyper-proliferating or hyper-stimulated immune cells are found. An antigen is an exemplary targeted moiety of an Antibody Drug Conjugate, wherein its targeting antibody Ligand Unit corresponds to or incorporates an antibody or antigen-binding fragment thereof that preferentially recognizes a targeted antigen and is therefore capable of selective binding to that antigen.

Antigens associated with cancer cells that are cell-surface accessible to an ADC of the present invention include by way of example and not limitation CD19, CD70, CD30 and CD33.

"Target cells", "targeted cells", or like terms as used herein, unless otherwise stated or implied by context, are the intended cells to which Ligand Drug Conjugate is designed to interact in order to inhibit the proliferation or other unwanted activity of abnormal cells. In some aspects, the targeted cells are hyper-proliferating cells or hyper-activated immune cells, which are exemplary abnormal cells. Typically, those abnormal cells are mammalian cells and more typically are human cells. In other aspects, the targeted cells are within the vicinity of the abnormal cells so that action of the Ligand Drug Conjugate on the nearby cells has an intended effect on the abnormal cells. For example, the nearby cells may be epithelial cells that are characteristic of the abnormal vasculature of a tumor. Targeting of those vascular cells by a Ligand Drug Conjugate will either have a cytotoxic or a cytostatic effect on these cells, which is believed to result in inhibition of nutrient delivery to the nearby abnormal cells of the tumor. Such inhibition will indirectly have a cytotoxic or cytostatic effect on the abnormal cells and may also have a direct cytotoxic or cytostatic effect on the nearby abnormal cells subsequent to release of its quaternized Drug Unit as a tubulysin compound (i.e., bystander effect).

"Ligand Unit" as the term is used herein, unless otherwise stated or implied by context, is a component of a Ligand Drug Conjugate and is the targeting moiety of that Conjugate, which is capable of binding selectively to its cognate targeted moiety, and incorporates or corresponds to the structure of a targeting agent that preferentially recognizes the targeted moiety. A Ligand Unit (L) includes without limitation those from receptor ligands, antibodies to cell-surface antigens, and transporter substrates. In some aspects, the receptor, antigen or transporter to be bound by a Conjugate compound of a Ligand Drug Conjugate composition is present in greater abundance on abnormal cells in contrast to normal cells so as to effect immunoselective cytotoxicity, which should translate to an acceptable therapeutic index. In other aspects, the receptor, antigen or transporter to be bound by a Ligand Drug Conjugate compound of the composition is present in greater abundance on normal cells in the vicinity of abnormal cells in contrast to normal cells that are distant from the site of the abnormal cells, so as to selectively expose the nearby abnormal cells to a tubulysin compound upon release of $D^+$ from that Ligand Drug Conjugate compound. Various aspects of Ligand Units, including antibody Ligand Units, are further described herein and by embodiments of the invention.

"Linker Unit" as the term is used herein, unless otherwise stated or implied by context, refers to an organic moiety in a Ligand Drug Conjugate intervening between and covalently attached to a quaternized tubulysin Drug Unit ($D^+$) and a Ligand Unit (L) as these terms are defined herein. A Linker Unit (LU) is comprised of a primary linker ($L_R$), which is a required component of that Unit, and an optional secondary linker ($L_O$) that is present and intervenes between $L_R$ and $D^+$ within a quaternized drug linker moiety of a Ligand Drug Conjugate compound or between $D^+$ and $L_R$ of a Drug Linker compound, which in the latter instance may be represented as $L_R'$ to explicitly indicate that is a precursor of $L_R$ in a Ligand Drug Conjugate. In some aspects, $L_R$ is comprised of a succinimide ($M^2$) or succinic acid amide ($M^3$) moiety and is sometimes further comprised of a Basic Unit (acyclic or cyclic) within a Linker Unit of a Ligand Drug Conjugate compound when $L_R$ is $L_{SS}$ or $L_S$, and in other aspects, a primary linker is comprised of a maleimide ($M^1$) moiety in a Drug Linker compound, and is sometimes further comprised of a Basic Unit (acyclic or cyclic), either in protected or protonated, when $L_R'$ is $L_{SS}'$. As a Drug Linker compound as described herein is sometimes comprised of a maleimide ($M^1$) moiety, attachment of a targeting agent, which results in a Ligand Unit (L), occurs to such a Drug Linker compound through a sulfur atom of a reactive thiol functional group of the targeting agent by way of Michael addition of that sulfur atom to the maleimide ring system of $M^1$. When the targeting agent is an antibody or antigen-binding fragment thereof, the reactive thiol functional group in some aspects is provided by a cysteine thiol of the antibody resulting from disulfide bond reduction and/or other chemical modification of a native antibody amino acid residue and/or by introduction through genetic engineering. As a result of that addition, a Linker Unit of a Ligand Drug Conjugate compound contains a succinimide ($M^2$) moiety having a thio-substituted succinimide ring system. When the Linker Unit contains a Basic Unit subsequent hydrolysis of that ring system under controlled conditions due to the presence of the acyclic or cyclic Basic Unit as part of a self-stabilizing linker ($L_{SS}$), in which $L_R$ within a Ligand Drug Conjugate is $L_{SS}$, results in a succinic acid-amide ($M^3$) moiety, which is a component of self-stabilized linker ($L_S$), as further described herein. As a result, $L_{SS}$ in a Ligand Drug Conjugate compound is hydrolyzed so that $L_R$ as $L_{SS}$ becomes $L_S$. That hydrolysis is controllable due to the Basic Unit (BU), as further described herein, being in appropriate proximity to the succinimide ring system. If no Basic Unit is present in $L_R$, hydrolysis of the succinimide moeity may still occur, but may do so in an uncontrolled manner.

"Primary linker" as the term is used herein, unless otherwise stated or implied by context, refers to a required component of Linker Unit (LU), which provides the site of attachment to the Ligand Unit for Ligand Drug Conjugates and in a Drug Linker compound is capable of providing that attachment. In some aspects, a primary linker is a self-stabilizing ($L_{SS}$) linker in Ligand Drug Conjugate or Drug Linker compound and in other aspects is a self-stabilized ($L_S$) linker in a Ligand Drug Conjugate, as further described herein. A $L_{SS}$ primary linker in a Drug Linker compound or a Ligand Drug Conjugate is characterized by a maleimide ($M^1$) or succinimide ($M^2$) moiety, respectively, in proximity to a Basic Unit, while a $L_S$ primary linker in a Ligand Drug Conjugate composition or compound thereof is characterized by a succinic acid amide ($M^3$) moiety in proximity to a Basic Unit. An $L_{SS}$ or $L_S$ primary linker of the present invention is also characterized by a $C_1$-$C_{12}$ alkylene moiety bonded to the imide nitrogen of the maleimide or succinimide ring system of $M^1$ or $M^2$ or the amide nitrogen of $M^3$, wherein the alkylene moiety in some aspects is substituted by an acyclic Basic Unit and may be further substituted by optional substituents, or in other aspects incorporates a cyclic Basic Unit that is optionally substituted. A primary linker not containing a Basic Unit may also contain a $C_1$-$C_{12}$ alkylene moiety bonded to the imide nitrogen of the maleimide or succinimide ring system of $M^1$ or $M^2$. Drug Linker compounds having a $L_{SS}$ primary linker are typically represented in general as $L_{SS}$-$L_O$-$D^+$ while Ligand Drug Conjugates having a $L_{SS}$ primary linker are typically represented in general as L-($L_{SS}$-$L_O$-$D^+$)$_p$ and those having a $L_S$ primary linker are typically represented in general as L-($L_S$-$L_O$-$D^+$)$_p$ in which the variable groups are as previously defined herein.

A maleimide ($M^1$) moiety of $L_{SS}$, which is sometimes shown as $L_{SS}'$ to explicitly indicate that it is a precursor to $L_{SS}$ in a Ligand Drug Conjugate in a Drug Linker Compound, or in other $M^1$-containing primary linkers, is capable of reacting with a thiol functional group of a targeting agent to form a thio-substituted succinimide moiety ($M^2$) in primary linker of a Ligand Drug Conjugate, wherein the thio-substituent is a Ligand Unit incorporating or corresponding to the structure of the targeting agent, and wherein the Ligand Unit is bonded to $M^2$ through a sulfur atom from one of the targeting agent's thiol functional groups. As a result of that reaction, the targeting agent becomes covalently bonded to the primary linker as a Ligand Unit. Subsequent hydrolysis of $M^2$ in a $L_{SS}$ primary linker results in a $L_S$ primary linker in which $M^2$ is converted to a succinic acid amide moiety ($M^3$). That linker moiety may exist as a mixture of two regioisomers ($M^{3A}$ and $M^{3B}$), depending on the relative reactivity of the two carbonyl groups of the succinimide ring system to hydrolysis.

"Ligand covalent binding moiety" as the term is used herein, unless otherwise stated or implied by context, refers to a moiety of a Linker Unit (LU) in an Ligand Drug Conjugate that interconnects the Ligand Unit (L) and the remainder of the Linker Unit and is derived from reaction of the corresponding ligand covalent binding precursor ($L_b'$) moiety in a Drug Linker compound with the targeting moiety. For example, when $L_b'$ is comprised of a maleimide moiety ($M^1$), reaction of that moiety with a reactive thiol functional group of a targeting moiety converts $L_b'$ to a ligand covalent binding ($L_b$) moiety so that a thio-substituted succinimide moiety is obtained, wherein its thio-substituent is comprised of a sulfur atom of the Ligand Unit corresponding to or incorporating the targeting moiety. In another example, when $L_b'$ is comprised of an activated carboxylic acid functional group, reaction of that functional group with an epsilon amino group of a lysine in a targeting moiety converts the functional group to an amide, wherein that amide functional group is shared between $L_b$ and the attached Ligand Unit. Other $L_b'$-containing moieties and $L_b$-containing moieties obtained therefrom are described in the embodiments of the invention. In some instances, a targeting moiety is derivitized with a bi-functional molecule to provide an intermediate that is condensed with a $L_b'$ moiety. As a result of that condensation the $L_b$ moiety so formed has atoms attributable to the bi-functional molecule and $L_b'$.

"Ligand covalent binding precursor" is a moiety of a Linker Unit, or substructure thereof used in the preparation of a Linker Unit, that is capable of covalent binding to a targeting moiety during the preparation of an Ligand Drug Conjugate whereupon the ligand binding moiety precursor ($L_b'$) moiety is converted to a ligand covalent binding ($L_b$) moiety. In some aspects, a $L_b'$ moiety typically has a functional group capable of reacting with a nucleophile or electrophile native to an antibody or antigen-binding fragment thereof or is introduced into the antibody or antigen-binding fragment by chemical transformation or genetic engineering. In some aspects, the nucleophile is an N-terminal amino group of a peptide comprising the antibody or antigen-binding fragment or the epsilon amino group of a lysine residue of that peptide. In other aspects, the nucleophile is the sulfur atom of a sulfhydryl group from a cysteine residue introduced by genetic engineering or from chemical reduction of interchain disulfide(s) of an antibody or antigen-binding fragment thereof. In some aspects, the electrophile is an aldehyde introduced by selective oxidation of an antibody's carbohydrate moiety or is a ketone from an unnatural amino acid introduced into an antibody using a genetically engineered tRNA/tRNA synthetase pair. Those and other methods for introducing a reactive functional group to provide for a conjugation site in an antibody are reviewed by Behrens and Liu "Methods for site-specific drug conjugation to antibodies" *mAB* (2014) 6(1): 46-53.

"Secondary linker" as used herein, unless otherwise stated or implied by context, refers to an organic moiety in a Linker Unit (LU), wherein the secondary linker ($L_O$) is an optional component of that Unit that is present and interconnects a quaternized tubulysin Drug Unit to a primary linker ($L_R$), which in some aspects is a self-stabilizing ($L_{SS}$) linker of a Drug Linker compound or a Ligand Drug Conjugate compound, or is a self-stabilized ($L_S$) linker of a Ligand Drug Conjugate compound obtained upon hydrolysis of $L_{SS}$. Typically, $L_R$ is attached to $L_O$ through a heteroatom or functional group shared between the two Linker Unit components in which $L_O$ is further comprised of a self-immolative Spacer Unit (Y) having a PAB or PAB-type moiety, and a Peptide Cleavable Unit. In those aspects, W, Y and $D^+$ are arranged in a linear configuration, as represented by —W—Y-$D^+$, in which the Cleavable Unit W is the Peptide Cleavable Unit and Y bonded to $D^+$ is the PAB or PAB-type self-immolative Spacer Unit. In other aspects, $L_O$ is comprised of a Glucuronide Unit, in which the self-immolative Spacer Unit having the PAB or PAB-type self-immolative moiety is attached to a carbohydrate moiety (Su) through a glycoside cleavable bond in which the carbohydrate moiety and the glycosidic heteroatom (E') that attaches Su to Y is referred to as W'. In those aspects the Cleavable Unit W is a Glucuronide Unit of formula in —Y(W')— and W', Y and $D^+$ are arranged in an orthogonal configuration, as represented by —Y(W')—$D^+$, wherein Y, which is bonded to W' and $D^+$, is the PAB or PAB-type self-immolative Spacer Unit.

In either of those aspects, a secondary linker may be further comprised of a first optional Stretcher Unit (A) and/or a Branching Unit (B) when LU is attached to more than one quaternized Drug Unit. When present, the first optional Stretcher Unit, interconnects $L_R$, which in some aspects is $L_{SS}$ or $L_S$, optionally through intermediacy of B depending on its presence or absence, with the remainder of the secondary linker, or optionally by way of $A_O$, which is an optional second Stretcher Unit, with $D^+$ through —W—Y—, when W is a Peptide Cleavable Unit or when W is a Glucuronide Unit through —Y(W')— of the secondary linker, wherein Y covalently attached to W or W' is a self-immolative Spacer Unit having a PAB or PAB-type moiety. When $L_R$ is $L_{SS}/L_S$ $A_O$ when present is a component of $L_R$, and when $L_R$ is other than $L_{SS}/L_S$ then $A_O$ is a subunit or substituent of A.

Since W as a Peptide Cleavable Unit or W' of a Glucuronide Unit is attached to a self-immolative Spacer Unit, enzymatic action on W/W' results in fragmentation of the self-immolating Spacer Unit with concomitant release of $D^+$ as a tubulysin compound. That fragmentation of the self-immolative Spacer Unit occurs by a 1, 4- or 1,6-elimination of $D^+$ from the Spacer Unit's PAB or PAB-type moiety as described herein.

A secondary linker ($L_O$) bonded to $D^+$ in a Linker Unit as exemplified when only one quaternized tubulysin Drug Unit is attached to LU is typically represented by structure s1 or structure s2:

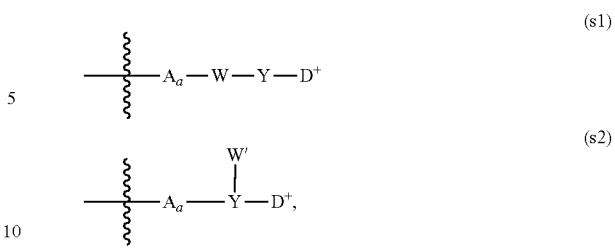

wherein the variable groups are as defined herein. In structure s1, Y is a self-immolative Spacer Unit (Y) as described herein, wherein its PAB or PAB-type moiety is bonded to $D^+$ and W is a Peptide Cleavable Unit. In structure s2, Y is a self-immolative Spacer Unit (Y) as described herein, wherein its PAB or PAB-type moiety is substituted with W' of a Glucuronide Unit and $D^+$, and in a Ligand Drug Conjugate is further substituted with -$L_R$-$A_a$- with $L_R$ bonded to a Ligand Unit (L) or in a Drug Linker compound is further substituted with $L_R'$-$A_a$-.

Typically, secondary linkers bonded to $D^+$ with structure s1 in which subscripts a is 0 or 1, are represented by:

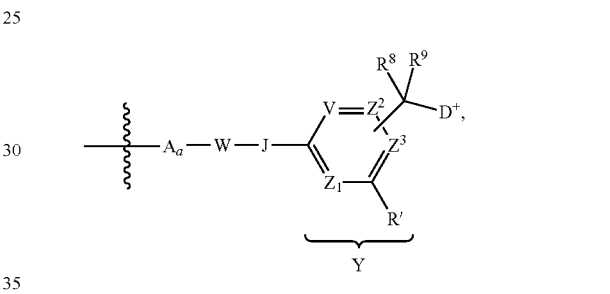

and secondary linkers bonded to $D^+$ with structure s2 in which subscripts a is 0 or 1 are represented by:

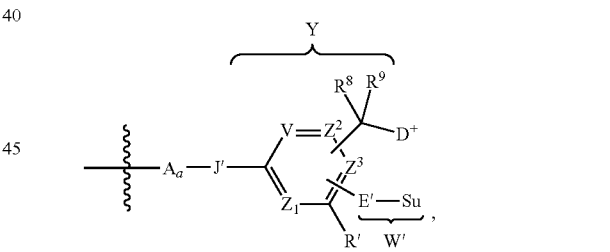

wherein J/J', V, $Z^1$, $Z^2$, $Z^3$, $R^1$, $R^8$ and $R^9$ are as defined in embodiments for PAB or PAB-type self-immolative Spacer Units, and E' and Su are as defined in embodiments for Glucuronide Units of formula —Y(W')—; and wherein the $A_a$-W-J- and —C($R^8$)($R^9$)-$D^+$ substituents on the central (hetero)arylene in a secondary linker of structure s1 are ortho or para to each other or the -E'-Su (i.e., W') and —C($R^S$)($R^9$)-$D^+$ substituents on the central (hetero)arylene in a secondary linker of structure s2 are ortho or para to each other.

"Maleimide moiety" as used herein, unless otherwise stated or implied by context, refers to a component of a primary linker of a Drug Linker compound, which in some aspects is a self-stabilizing linker and is sometimes represented as $L_R'$ or $L_{SS}'$ to explicitly indicated for a Drug Linker compound that it is a precursor to $L_R/L_{SS}$ of a Ligand Drug Conjugate compound. A maleimide moiety ($M^1$) is capable of participating in Michael addition (i.e., 1,4-conjugate addition) by a sulfur atom of a reactive thiol functional group of a targeting agent to provide a thio-substituted succinimide ($M^2$) moiety, wherein the thio substituent is from a Ligand Unit that incorporates or correspond to the structure of the targeting agent as described herein in a Ligand Drug Conjugate composition or compound thereof. An $M^1$ moiety of a Drug Linker compound is attached to the remainder of the primary linker through its imide nitrogen atom. Other than the imide nitrogen atom, an $M^1$ moiety is typically unsubstituted, but may be asymmetrically substituted at the cyclic double bond of its maleimide ring system. Such substitution can result in regiochemically preferred conjugate addition of a sulfur atom of reactive thiol functional group of a targeting agent to the less hindered or more electronically deficient double bonded carbon atom (dependent on the more dominant contribution) of the maleimide ring system. That conjugate addition results in a succinimide ($M^2$) moiety, which is thio-substituted by a Ligand Unit though the sulfur atom from the thiol functional group provided by the targeting agent. When $L_R$ is $L_{SS}$, the component of $L_{SS}$ in a Drug Linker compound that is a substituent of the imide nitrogen of $M^1$ and which attaches $L_{SS}$ to the remainder of the Linker Unit is $A_R$, which is a required Stretcher Unit. In some aspects, $A_R$ is comprised of an optionally substituted $C_1$-$C_4$ alkylene moiety substituted by or incorporating a Basic Unit and optionally in combination with $A_O$, is a optionally substituted $C_1$-$C_{12}$ alkylene that is optionally substituted by [HE], wherein [HE] is a hydrolysis enhancing moiety. In other aspects when $L_R$ in a Drug Linker compound is other than $L_{SS}$, but nonetheless is comprised of a maleimide moiety or some other $L_b'$ moeity, $L_b'$ is attached to an optional first Stretcher Unit of a secondary linker, which in some aspects, optionally in combination with $A_O$, is an optionally substituted $C_1$-$C_{12}$ alkylene optionally substituted by [HE]. Thus, in aspects in which $L_R$ is $L_{SS}$, the $C_1$-$C_{12}$ alkylene moiety is sometimes comprised of a second optional Stretcher Unit ($A_O$) that is present, both of which are components of $L_{SS}$ wherein $A_O$ attaches $L_{SS}$ to the secondary linker at a position that is typically distal to the attachment site of the $C_1$-$C_{12}$ alkylene moiety to the imide nitrogen atom, Thus, in those aspects, a substituent of the $C_1$-$C_{12}$ alkylene moiety of -$A_R$-$A_O$- is an acyclic Basic Unit, so that the primary linker ($L_R$) is a self-stabilizing linker ($L_{SS}$) of a Drug Linker compound, and in other such aspects, the optionally substituted $C_1$-$C_{12}$ alkylene moiety of -$A_R$-$A_O$- incorporates a cyclic Basic Unit. When $L_R$ is other than $L_{SS}$, $A_O$ is a subunit or substituent of a first Stretcher Unit (A), which is an optional component of a secondary linker.

"Succinimide moiety" as used herein, unless otherwise stated or implied by context, refers to a component of one type of primary linker, which in turn is a component of a Linker Unit of a Ligand Drug Conjugate, and results from Michael addition of a sulfur atom of a reactive thiol functional group of a targeting agent to the maleimide ring system of a maleimide moiety ($M^1$) in a Drug Linker compound or a $M^1$-containing precursor thereof. A succinimide ($M^2$) moiety is therefore comprised of a thio-substituted succinimide ring system that has its imide nitrogen atom substituted with the remainder of the primary linker through the optionally substituted $C_1$-$C_{12}$ alkylene moiety, which in some aspects is a component of $A_R$ optionally in combination with $A_O$ as when the primary linker is a self-stabilizing linker. In those aspects the alkylene moiety incorporates a cyclic Basic Unit into $A_R$ or is substituted by an acyclic Basic Unit as described elsewhere, and is optionally substituted with substituent(s) at its succinimide ring system that may have been present on the $M^1$ precursor. In some aspects, those optional substituents on the succinimide ring system in $L_{SS}$ of a Ligand Drug Conjugate compound are not present and in other aspects the $C_1$-$C_{12}$ alkylene moiety of -$A_R$-$A_O$- is optionally substituted by [HE], both of which are components of the $L_{SS}$ primary linker, at a position that is typically distal to its attachment site to the imide nitrogen atom. In turn, the $C_1$-$C_{12}$ alkylene moiety of $A_R$ in optional combination with $A_O$ (i.e., of -$A_R$-$A_O$)— is either covalently attached directly to the secondary linker or indirectly through [HE] of $A_O$.

"Succinic acid-amide moiety" as used herein, unless otherwise stated or implied by context, refers to component of a self-stabilized linker ($L_S$) of a Linker Unit within a Ligand Drug Conjugate and has the structure of a succinic amide hemi-acid residue, which is sometimes referred to as a succinic acid amide, with substitution of its amide nitrogen by another component of $L_S$ wherein that component is an optionally substituted $C_1$-$C_{12}$ alkylene moiety optionally in combination with $A_O$, which in some aspects incorporates cyclic Basic Unit and is optionally substituted by [HE], or in other aspects is substituted by an acyclic Basic Unit and optionally substituted by [HE], wherein the succinic acid amide ($M^3$) moiety has further substitution by L-S—, wherein L is Ligand Unit incorporating or corresponding to a targeting agent and S is a sulfur atom from that targeting agent. A $M^3$ moiety results from the thio-substituted succinimide ring system of a succinimide ($M^2$) moiety in self-stabilizing primary linker having undergone breakage of one of its carbonyl-nitrogen bonds by hydrolysis, which is assisted by the Basic Unit. Thus, a $M^3$ moiety has a free carboxylic acid functional group and an amide functional group whose nitrogen heteroatom is attached to the remainder of the primary linker, and is substituted by L-S— at the carbon that is alpha to that carboxylic acid or amide functional group, depending on the site of hydrolysis of its $M^2$ precursor. Without being bound by theory, it is believed the aforementioned hydrolysis resulting in a $M^3$ moiety provides a Linker Unit (LU) in a Ligand Drug Conjugate that is less likely to suffer premature loss from the Conjugate of its targeting Ligand Unit (L) through elimination of the thio substituent.

When present in a self-stabilizing linker ($L_{SS}$) in a Ligand Drug Conjugate compound, hydrolysis of the succinimide ring system of the thio-substituted succinimide ($M^2$) moiety, which is pH controllable due to the nearby presence of the acyclic or cyclic Basic Unit, can provide regiochemical isomers of succinic acid-amide ($M^3$) moieties in a self-stabilized linker ($L_S$) due to its asymmetric substitution by the thio substituent. The relative amounts of those isomers will be due at least in part to differences in reactivity of the two carbonyl carbons of $M^2$, which can be attributed at least in part to any substituent(s) that were present in the $M^1$ precursor. Hydrolysis is also expected to occur to some extent when $L_R$ having a $M^2$ moiety that does not contain a Basic Unit, but is highly variable in comparison to the controlled hydrolysis provided by the Basic Unit. In those instances, it is the $C_1$-$C_{12}$ alkylene moiety of A from the secondary linker that is attached to the imide nitrogen atom of $M^2$ prior to hydrolysis and to the amide nitrogen atom of $M^3$ subsequent to hydrolysis. If $L_R$ in a Ligand Drug Conjugate is other than $L_{SS}$ and whose $L_b$ component is an unsymmetrical $M^2$ moiety, regiochemical isomers from uncontrolled hydrolysis of its succinimide ring is also expected.

"Self-stabilizing linker" as used herein, unless otherwise stated or implied by context, refers to a $M^2$-containing component in a primary linker of a Linker Unit in a Ligand Drug Conjugate or to a $M^1$-containing component of a Linker Unit in a Drug Linker compound. In a Drug Linker compound that component may be designated as $L_{SS}'$ to indicate that it is a precursor to the $M^2$-containing component of $L_{SS}$ in a Ligand Drug Conjugate, which subsequently undergoes conversion under controlled hydrolysis conditions to the corresponding self-stabilized linker ($L_S$). That hydrolysis is facilitated by the Basic Unit component of $L_{SS}$, such that a Ligand Drug Conjugate initially comprised of $L_{SS}$ becomes more resistant to premature loss of its Ligand Unit by virtue of its Linker Unit (LU) now being comprised of $L_S$. The $L_{SS}$ moiety, in addition to its $M^1$ or $M^2$ moiety, is comprised of $A_R$, which is a required Stretcher Unit, and in some aspects optionally in combination with $A_O$, is comprised of an optionally substituted $C_1$-$C_{12}$ alkylene moiety to which $M^2$ and the remainder of LU are covalently attached, wherein the alkylene moeity incorporates a cyclic Basic Unit and is optionally substituted by [HE] or is substituted by an acyclic Basic Unit and is optionally substituted by [HE].

In the context of the present invention, $L_{SS}$ of a Drug Linker compound, contains a required Stretcher Unit $A_R$ and a maleimide ($M^1$) moiety through which a targeting agent is to be attached as a Ligand Unit. In some aspects, the $C_1$-$C_{12}$ alkylene moiety of $A_R$, optionally in combination with $A_O$ (i.e., of -$A_R$-$A_O$- is attached to the imide nitrogen atom of the maleimide ring system of $M^1$ in a Drug Linker compound and to the remainder of the Linker Unit, the latter of which optionally occurs through $A_O$ of $L_{SS}$. In some of those aspects, $A_O$ consists or is comprised of an optionally substituted electron withdrawing heteroatom or functional group, referred herein as a hydrolysis-enhancing moiety, which in some aspects, in addition to BU, may enhance the hydrolysis rate of the $M^2$ moiety in the corresponding $L_{SS}$ moeity of a Ligand Drug Conjugate compound. After incorporation of the Drug Linker compound into a Ligand Drug Conjugate compound, $L_{SS}$ now contains a succinimide ($M^2$) moiety that is thio-substituted by the Ligand Unit (i.e., Ligand Unit attachment occurs through Michael addition of a sulfur atom of a targeting agent's reactive thiol functional group to the maleimide ring system of $M^1$).

In some aspects, a cyclized Basic unit (cBU) corresponds in structure to an acyclic Basic Unit through formal cyclisation of the basic nitrogen atom of that Unit to a carbon of $A_R$ so that the cyclic Basic Unit structure is incorporated into $A_R$. Typically, the carbon atom of $A_R$ for cyclization is from a branched carbon chain of the $C_1$-$C_{12}$ alkylene moiety of -$A_R$-$A_O$-, designated as $R^2$, wherein that branched carbon atom is attached is to the imide nitrogen atom of $M^1/M^2$, which is some aspects is also the attachment site of BU prior to formal cyclization so as to define an optionally substituted spiro $C_4$-$C_{12}$ heterocyclo. In such constructs, the spiro carbon of that heterocyclo is attached to the maleimide imide nitrogen of $M^1$, and hence to that nitrogen in $M^2$, and is further attached to the remainder of the Linker Unit optionally through $A_O$, which in some aspects is or is comprised of a hydrolysis-enhancing [HE] moiety. In that aspect, a cyclic BU assists in the hydrolysis of the succinimide moiety of $M^2$ to its corresponding ring-opened form(s) represented by $M^3$ in qualitatively similar manner to that of an acyclic Basic Unit, which may also be enhanced by HE.

In some aspects, a $L_{SS}$ moiety in a Drug Linker compound, sometimes shown as $L_{SS}'$ to explicitly indicate that it is a precursor to $L_{SS}$, or a Ligand Drug Conjugate, according to the present invention, is represented by the general formula of $M^1$-$A_R$(BU)-$A_O$- or -$M^2$-$A_R$(BU)-$A_O$-, respectively, wherein $A_R$(BU) is a required Stretcher Unit ($A_R$) incorporating a cyclic Basic Unit or substituted by an acyclic Basic Unit, $M^1$ and $M^2$ are maleimide and succinimide moieties, respectively, and $A_O$ is an second optional Stretcher Unit, which in some aspects consists or is comprised of HE.

Exemplary, but non-limiting $L_{SS}$ structures for some Ligand Drug Conjugates compounds is represented by:

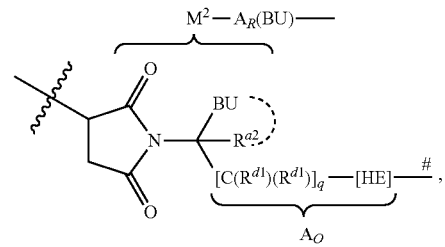

wherein the wavy line indicates the site of covalent attachment to a Ligand Unit, the pound sign (#) indicates the site of covalent attachment to $L_O$, the dotted curved line indicates optional cyclization which is present when BU is a cyclic Basic Unit or is absent when BU is an acyclic Basic Unit, the $[C(R^{d1})R^{d1})]_q$—[HE] moiety is $A_O$ of $L_{SS}$ in which $A_O$ is present, wherein [HE] is an optional hydrolysis-enhancing moiety, subscript q is 0 or an integer ranging from 1 to 6; each $R^{d1}$ is independently selected from the group consisting of hydrogen and optionally substituted $C_1$-$C_6$ alkyl, or two of $R^{d1}$, the carbon atom(s) to which they are attached and any intervening carbon atoms define an optionally substituted $C_3$-$C_8$ carbocyclo, and the remaining $R^{d1}$, if any, are independently hydrogen or optionally substituted $C_1$-$C_6$; and $R^{a2}$ is an optionally substituted $C_1$-$C_8$ alkyl, which in a cyclic Basic Unit along with the carbon atom to which BU and $R^{a2}$ are attached define an optionally substituted spiro $C_4$-$C_{12}$ heterocyclo having a skeletal secondary or tertiary basic nitrogen atom, such that the cyclic Basic Unit is capable of increasing the rate of hydrolysis of the shown succinimide ($M^2$) moiety to provide a succinic acid amide ($M^3$) moiety at a suitable pH in comparison to the corresponding Conjugate in which $R^{a2}$ is hydrogen and BU is replaced by hydrogen, and/or substantially retains the increase in the rate of hydrolysis of the corresponding Conjugate in which in which $R^{a2}$ is hydrogen and BU is an acyclic BU over the aforementioned Conjugate in which $R^{a2}$ is hydrogen and BU is replaced by hydrogen.

Other exemplary $L_{SS}'$ structures, which are present in Drug Linker compounds typically used as intermediates in the preparation of Ligand Drug Conjugate compositions, are represented by:

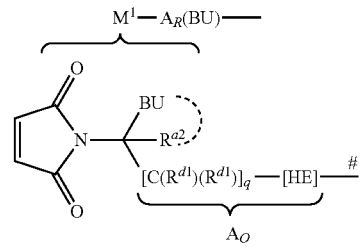

wherein BU and the other variable groups are as defined above for $L_{SS}$ structures in Ligand Drug Conjugates and in the embodiments for that and other exemplary $L_{SS}$ structures. When a Drug Linker compound having a self-stabilizing linker precursor ($L_{SS}'$), which is comprised of a maleimide moiety, is used in the preparation of a Ligand Drug Conjugate, that $L_{SS}'$ moiety is converted into a $L_{SS}$ moiety having a succinimide moiety.

"Self-stabilized linker" is an organic moiety derived from a $M^2$-containing moiety of a self-stabilizing linker ($L_{SS}$) in a Ligand Drug Conjugate that has undergone hydrolysis under controlled conditions so as to provide a corresponding $M^3$-moiety of a self-stabilized linker ($L_S$) wherein that LU component is less likely to reverse the condensation reaction of a targeting moiety with a $M^1$-containing moiety that provided the original $M^2$-containing $L_{SS}$ moiety. In addition to the $M^3$ moiety, a self-stabilized linker ($L_S$) is comprised of $A_R$ incorporating a cyclic Basic Unit or substituted by an acyclic Basic Unit wherein $A_R$, optionally in combination with $A_O$, is covalently attached to $M^3$ and the remainder of the Linker Unit in which $L_S$ is a component. The $M^3$ moiety is obtained from conversion of a succinimide moiety ($M^2$) of $L_{SS}$ in a Ligand Drug Conjugate, wherein the $M^2$ moiety has a thio-substituted succinimide ring system resulting from Michael addition of a sulfur atom of a reactive thiol functional group of a targeting moiety to the maleimide ring system of $M^1$ of a $L_{SS}$ moiety in a Drug Linker compound, wherein that $M^2$-derived moiety has reduced reactivity for elimination of its thio-substituent in comparison to the corresponding substituent in $M^2$. In those aspects, the $M^2$-derived moiety has the structure of a succinic acid-amide ($M^3$) moiety corresponding to $M^2$ wherein $M^2$ has undergone hydrolysis of one of its carbonyl-nitrogen bonds of its succinimide ring system, which is assisted by the basic functional group of BU due to its appropriate proximity as a result of that attachment. The product of that hydrolysis therefore has a carboxylic acid functional group and an amide functional group substituted at its amide nitrogen, which corresponds to the imide nitrogen in the $M^2$-containing $L_{SS}$ precursor to $L_S$, with the remainder of LU. In some aspects, the basic functional group is a primary, secondary or tertiary amine of an acyclic Basic Unit or secondary or tertiary amine of a cyclic Basic Unit. In other aspects, the basic nitrogen of BU is a heteroatom of an optionally substituted basic functional group as in a guanidino moeity. In either aspect, the reactivity of the basic functional group of BU for base-catalyzed hydrolysis is controlled by pH by reducing the protonation state of the basic nitrogen.

Thus, a self-stabilized linker ($L_S$) typically has the structure of an $M^3$ moiety covalently bond $A_R$ incorporating a cyclic Basic Unit or substituted by an acyclic Basic Unit, wherein $A_R$ in turn is covalently bonded to the secondary linker $L_O$. $L_S$ with its $M^3$, $A_R$, $A_O$ and BU components and $L_O$ arranged in the manner so indicated is represented by the formula of -$M^3$-$A_R$(BU)-$A_O$-$L_O$- or -$M^3$-$A_R$(BU)-$A_O$-$L_O$-, wherein BU represents either type of Basic Unit (cyclic or acyclic).

Exemplary non-limiting structures of $L_{SS}$ and $L_S$ moieties with $M^2$ or $M^3$ and $A_R$(BU), $A_O$ and $L_O$ arranged in the manner indicated above in which BU is acyclic is shown by way of example but not limitation by:

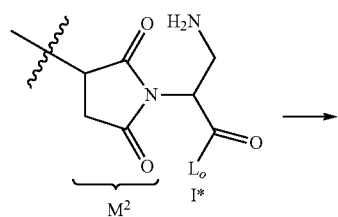

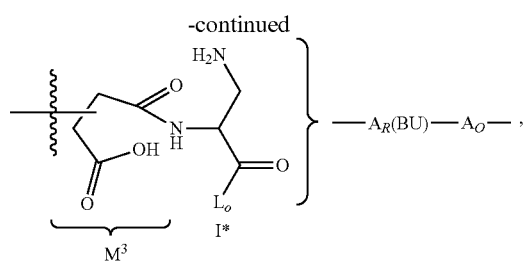

wherein the indicated —CH(CH$_2$NH$_2$)C(=O)— moiety is -$A_R$(BU)-$A_O$-, wherein BU is an acyclic Basic Unit in which $A_R$ in combination with $A_O$ is covalently bonded to the imide or amide nitrogen of $M^2$ or $M^3$, respectively, and is substituted by the acyclic Basic Unit, —CH$_2$NH$_2$, and wherein $A_O$ is [HE], which is bonded to $L_O$, wherein [HE] is —C(=O)—. Those exemplary structures contain a succinimide ($M^2$) moiety or a succinic acid-amide ($M^3$) moiety from succinimide ring hydrolysis of $M^2$ in the conversion of $L_{SS}$ to $L_S$.

Exemplary structures of $L_{SS}$ and $L_S$ moieties with $M^2$ or $M^3$ and $A_R$(BU) and $A_O$ components bonded to $L_O$ in the manner indicated above in which BU is incorporated into $A_R$ as a cyclic Basic Unit is shown by way of example but not limitation by:

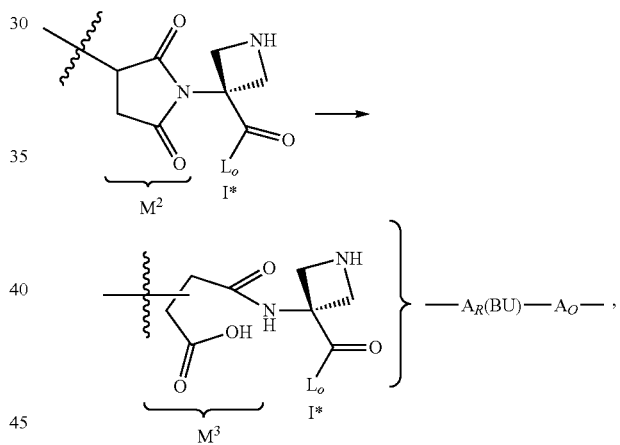

wherein in these -$A_R$(BU)-$A_O$- moieties, BU is a heterocyclo cyclic Basic Unit, the structure of which corresponds to the aminoalkyl of an acyclic Basic Unit in an $A_R$(BU) moiety in which the basic nitrogen of the acyclic Basic Unit has been formally cyclized at least in part back through $R^2$ to the carbon atom that is alpha to the succinimide nitrogen of $M^2$ to which the acyclic Basic Unit is attached. The wavy line in each of the above $L_{SS}$ and $L_S$ structures indicates the site of covalent attachment of a sulfur atom of a Ligand Unit derived from a reactive thiol functional group of a targeting agent upon Michael addition of that sulfur atom to the maleimide ring system of an $M^1$ moiety in a corresponding Drug Linker compound. The asterisk (*) in each of the above structures indicates the site of covalent attachment of a quaternized Drug Unit to the -$L_{SS}$-$L_O$- and -$L_S$-$L_O$- structures of formula -$M^2$/$M^3$-$A_R$(BU)-$A_O$-$L_O$- in which BU is cyclic or acyclic. Since the succinimide ring system of $M^2$ is asymmetrically substituted due to its thio substituent, regiochemical isomers of succinic acid-amide ($M^3$) moieties as defined herein differing in position relative to the liberated carboxylic acid group may result on $M^2$ hydrolysis. In the above structures, the carbonyl functional group attached to $L_O$ exemplifies a hydrolysis enhancer [HE] as defined herein in which [HE] is the indicated $A_O$ component of $L_{SS}$ or $L_S$ that is covalently attached to -$A_R$(BU) and $L_O$.

The -$M^3$-$A_R$(BU)- moieties wherein BU is acyclic or cyclic Basic Unit represent exemplary structures of self-stabilized linker ($L_S$) moieties, so named because these structures are less likely to eliminate the thio substituent of the Ligand Unit, and thus cause loss of that targeting moiety, in comparison to the corresponding $L_{SS}$ moieties of formula $M^2$-$A_R$(BU). Without being bound by theory, it is believed the increased stability results from the greater conformational flexibility in $M^3$ in comparison to $M^2$, which no longer constrains the thio substituent in a conformation favorable for E2 elimination.

"Basic Unit" as used herein, unless otherwise stated or implied by context, refers to an organic moiety within a self-stabilizing linker ($L_{SS}$) moiety, as described herein, which is carried forward into a corresponding $L_S$ moiety by BU participating in base catalyzed hydrolysis of the succinimide ring system within a $M^2$ moiety comprising $L_{SS}$ (i.e., catalyzes addition of a water molecule to one of the succinimide carbonyl-nitrogen bonds). In some aspects, the base-catalyzed hydrolysis is initiated under controlled conditions tolerable by the targeting Ligand Unit attached to $L_{SS}$. In other aspects the base-catalyzed hydrolysis is initiated on contact of the Drug Linker compound comprised of $L_{SS}$ with a targeting agent in which Michael addition of a sulfur atom of a reactive thiol functional group of the targeting agent effectively competes with hydrolysis of the $L_{SS}$ $M^1$ moeity of the Drug Linker compound. Without being bound by theory, the following aspects describe various considerations for design of a suitable Basic Unit. In one such aspect, the basic functional group of an acyclic Basic Unit and its relative position in $L_{SS}$ with respect to its $M^2$ component are selected for the ability of BU to hydrogen bond to a carbonyl group of $M^2$, which effectively increases its electrophilicity and hence its susceptibility to water attack. In another such aspect, those selections are made so that a water molecule, whose nucleophilicity is increased by hydrogen bonding to the basic functional group of BU, is directed to an $M^2$ carbonyl group. In a third such aspect, those selections are made so the basic nitrogen on protonation does not increase the electrophilicity of the succinimide carbonyls by inductive electron withdrawal to an extent that would promote premature hydrolysis requiring compensation from an undesired excess of Drug Linker compound. In a final such aspect, some combination of those mechanistic effects contributes to catalysis for controlled hydrolysis of $L_{SS}$ to $L_S$.

Typically, an acyclic Basic Unit, which may act through one or more of the above mechanistic aspects, is comprised of 1 carbon atom or 2 to 6 contiguous carbon atoms, more typically of 1 carbon atom or 2 or 3 contiguous carbon atoms, wherein the carbon atom(s) connect the basic amino functional group of the acyclic Basic Unit to the remainder of the $L_{SS}$ moiety to which it is attached. In order for that basic amine nitrogen to be in the required proximity to assist in the hydrolysis of a succinimide ($M^2$) moiety to its corresponding ring-opened succinic acid amide ($M^3$) moiety, the amine-bearing carbon chain of an acyclic Basic Unit is typically attached to $A_R$ of $L_{SS}$ at the alpha carbon of that moiety relative to the site of attachment of $A_R$ to the succinimide nitrogen of $M^2$ (and hence to the maleimide nitrogen of its corresponding $M^1$-$A_R$ structure). Typically, that alpha carbon in an acyclic Basic Unit has the (S) stereochemical configuration or the configuration corresponding to that of the alpha carbon of L-amino acids.

As previously described, BU in acyclic form or BU in cyclized form is typically connected to $M^1$ or $M^2$ of $L_{SS}$ or $M^3$ of $L_S$ through an optionally substituted $C_1$-$C_{12}$ alkylene moiety in which that moiety incorporates the cyclized Basic Unit or is substituted by the acyclic Basic Unit and is bonded to the maleimide or succinimide nitrogen of $M^1$ or $M^2$, respectively, or the amide nitrogen of $M^3$. In some aspects, the $C_1$-$C_{12}$ alkylene moiety incorporating the cyclic Basic Unit is covalently bonded to $L_O$ and typically occurs through intermediacy of an ether, ester, carbonate, urea, disulfide, amide carbamate or other functional group, more typically through an ether, amide or carbamate functional group. Likewise, BU in acyclic form is typically connected to $M^1$ or $M^2$ of $L_{SS}$ or $M^3$ of $L_S$ through an optionally substituted $C_1$-$C_{12}$ alkylene moiety of -$A_R$-$A_O$- which is substituted by the acyclic Basic unit at the same carbon of the $C_1$-$C_{12}$ alkylene moiety that is attached to the imino nitrogen atom of the maleimide or succinimide ring system of $M^1$ or $M^2$ or the amide nitrogen of $M^3$ subsequent to hydrolysis of the succinimide ring system of $M^2$.

In some aspects, a cyclic Basic Unit incorporates the structure of an acyclic BU by formally cyclizing an acyclic Basic Unit to $R^{a2}$, which is a branched alkyl moiety of the $C_1$-$C_{12}$ alkylene moiety of -$A_R$-$A_O$- and bonded to the carbon atom alpha to the imide nitrogen atom of $M^1$/$M^2$ or the amide nitrogen atom of $M^3$ as the acyclic Basic Unit, thus forming a spirocyclic ring system so that a cyclic Basic Unit is incorporated into the structure of $A_R$ rather than being a substituent of $A_R$ as when BU is acyclic. In those aspects, the formal cyclization is to the basic amine nitrogen of an acyclic Basic Unit thus providing a cyclic Basic Unit as an optionally substituted symmetrical or asymmetrical spiro $C_4$-$C_{12}$ heterocyclo, depending on the relative carbon chain lengths in the two alpha carbon substituents, in which the basic nitrogen is now a basic skeletal heteroatom. In order for that cyclization to substantially retain the basic properties of the acyclic Basic Unit in a cyclic Basic Unit, the basic nitrogen atom of the acyclic Basic Unit nitrogen should be that of a primary or secondary amine and not a tertiary amine since that would result in a quaternized skeletal nitrogen in the heterocyclo of the cyclic Basic Unit. In that aspect of formal cyclization of an acyclic Basic Unit to a cyclic Basic Unit, in order to substantially retain the ability of the basic nitrogen to assist in hydrolysis of $M^2$ to $M^3$ in conversion of $L_{SS}$ to $L_S$, the resulting structure of the cyclic Basic Unit in these primary linkers will typically have its basic nitrogen located so that no more than three, and typically one or two, intervening carbon atoms are between the basic nitrogen atom and the alpha spiro carbon of the $A_R$ component. Cyclic Basic Units incorporated into $A_R$ and the $L_{SS}$ and $L_S$ moieties having those as components are further described by the embodiments of the invention.

"Hydrolysis-enhancing moeity" as used herein, unless otherwise stated or implied by context, refers to is electron withdrawing group or moiety that is an optional substituent of an $L_{SS}$ moiety and its hydrolysis product $L_S$. A hydrolysis-enhancing [HE] moiety is an optional second Stretcher Unit ($A_O$) or subunit thereof [HE] when present as a substituent of $A_R$-$A_O$- and thus is another component of $L_{SS}$, wherein $A_R$ is bonded to the imide nitrogen of an $M^2$ moiety, so that the electron withdrawing effect of [HE] can increase the electrophilicity of the succinimide carbonyl groups in that moiety for its conversion to a $M^3$ moiety of $L_S$. With $A_R$ incorporating or substituted by a cyclic Basic Unit or an acyclic Basic Unit, respectively, the potential effect of [HE]

on the carbonyl groups of $M^2$ for increasing the hydrolysis rate to $M^3$ by induction and the aforementioned effect(s) of either type of BU, are adjusted so that premature hydrolysis of $M^1$ does not occur to an appreciable extent during preparation of a Ligand Drug Conjugate from a Drug Linker compound comprised of the structure of $M^1$-$A_R$(BU)-[HE]-. Instead, the combined effects of BU and [HE] to promote hydrolysis (i.e., conversion of an -$M^2$-$A_R$(BU)-[HE]-moiety of a Ligand Drug Conjugate compound to its corresponding -$M^3$-$A_R$(BU)-[HE]-moiety) under controlled conditions (as when pH is purposely increased so as to decrease protonation of the Basic Unit) are such that an undue molar excess of Drug Linker compound to compensate for hydrolysis of its $M^1$ moiety is not required. Therefore, Michael addition of the sulfur atom of a reactive thiol functional group of the targeting agent to the maleimide ring system of $M^1$, which provides a targeting Ligand Unit attached to a succinimide ring system of $M^2$, typically occurs at a rate that effectively competes with $M^1$ hydrolysis. Without being bound by theory, it is believed that at low pH, as for example when the basic amine of BU is in the form of a TFA salt, premature hydrolysis of $M^1$ in a Drug Linker product is much slower than when the pH is raised to that suitable for base catalysis using an appropriate buffering agent and that an acceptable molar excess of Drug Linker compound can adequately compensate for any loss due to premature $M^1$ hydrolysis that does occur during the time course for completion or near completion of the Michael addition of a sulfur atom of a targeting agent's reactive thiol functional group to a Drug Linker compound's $M^1$ moiety.

As previously discussed, enhancement of carbonyl hydrolysis by either type of Basic Unit is dependent on the basicity of its functional group and the distance of that basic functional group in relation to the $M^1/M^2$ carbonyl groups. Typically, [HE] is a carbonyl moiety (i.e., ketone or —C(=O)—) or other carbonyl-containing functional group. When $A_O$ is comprised of HE, HE is sometimes located distal to the carbon atom of -$A_R$-$A_O$- that is bonded to $M^2$, or $M^3$ derived therefrom, and that also provides for covalent attachment of $L_{SS}$ or $L_S$ to the secondary linker ($L_O$). Carbonyl-containing functional groups other than ketone include esters, carbamates, carbonates and ureas. When [HE] is a carbonyl-containing functional group other than ketone the carbonyl moiety of that functional group, which is shared with $L_O$, is typically bonded to the remainder of -$A_R$-$A_O$-. In some aspects, the HE moiety may be sufficiently distant from the imide nitrogen to which $A_R$ of -$A_R$-$A_O$- is covalently bonded so that no discernable or minor effect on hydrolytic sensitivity of the succinimide carbonyl-nitrogen bonds of an $M^2$-containing moiety is observable, but instead is driven primarily by BU.

"Stretcher Unit" as used herein, unless otherwise stated or implied by context, refers to an organic moiety in a primary or secondary linker of a Linker Unit that physically separates the targeting Ligand Unit from other intervening components of the Linker Unit that are more proximal to the Drug Unit. An $A_R$ Stretcher Unit is a required component in primary linker ($L_R$) when that linker is a $L_{SS}$ or $L_S$ primary linker since it provides the Basic Unit. The presence of a first optional Stretcher Unit (A) and/or second optional Stretcher Unit ($A_O$) may be required when there is insufficient steric relief from the Ligand Unit provided by an $L_R$, $L_{SS}$ or $L_S$ primary linker absent one or both of those optional Stretcher Units to allow for efficient processing of a Linker Unit in a quaternized drug linker moiety of a Ligand Drug Conjugate for release of its quaternized Drug Unit as a tubulysin compound. Alternatively, or in addition to steric relief, those optional components may be included for synthetic ease in preparing a Drug Linker compound. A first or second optional Stretcher Unit (A or $A_O$) can each be a single unit or can contain multiple subunits. Typically, A or $A_O$ is one distinct unit or has 2 to 4 distinct subunits.

In some aspects, when $L_R$ is $L_{SS}/L_S$, in addition to covalent attachment to $M^1$ of a Drug Linker compound or $M^2/M^3$ of a Ligand Drug Conjugate compound, $A_R$ is bonded to a secondary linker optionally through $A_O$ wherein $A_O$, as a substituent of $A_R$ and is thus a component of $L_{SS}/L_S$, is a carbonyl-containing functional group, which can serve as a Hydrolysis-enhancing (HE) Unit for improving the rate of conversion of $L_{SS}$ to $L_S$, which is catalyzed by an cyclic Basic Unit as incorporated into $A_R$ or by an acyclic Basic Unit as a substituent of $A_R$. In some of those aspects, $A_R$ or $A_R$-$A_O$ is bonded to a secondary linker ($L_O$) through a Branching Unit of $L_O$ in a Ligand Drug Conjugate of general formula L-($L_R$-$B_b$-(A-W—Y-$D^+$)$_n$)$_p$ wherein $L_R$ is $L_{SS}$ or $L_S$, or a Drug Linker compound of general formula $L_R$-$B_b$-($A_a$-W—Y-D)$_n$, wherein $L_R$ is $L_{SS}$, sometimes indicated as $L_R$' and $L_{SS}$', and whose variable groups are define elsewhere, when subscript n is 2 or more, which requires that subscript b is 1. In other aspects, if subscript n is 1, which requires that subscript b is 0, then $A_R$ of $L_{SS}/L_S$ or $L_{SS}$' is bonded to a secondary linker ($L_O$) through an optional second Stretcher Unit ($A_O$) of $L_{SS}/L_S$ or $L_{SS}$', or $A_R$ or $A_O$ of $L_{SS}/L_S$ or $L_{SS}$', is bonded to $L_O$ through a first optional Stretcher Unit (A) of $L_O$, when subscript a is 1, or through W when subscript a is 0 and components W, Y and $D^+$ are arranged linearly (i.e., arranged as —W—Y-$D^+$), wherein W is a Peptide Cleavable Unit. In still other aspects, $A_R$ or $A_O$ of $L_{SS}$ or $L_S$ is bonded to Y in a Glucuronide Unit of formula —Y(W')—, so that W, Y and $D^+$ are arranged orthogonally (i.e., arranged as —Y(W')—$D^+$), when subscript a is 0, or is bonded to A of $L_O$ when subscript a is 1.

In other aspects, $L_R$ is other $L_{SS}/L_S$, but is nonetheless comprised of a $M^1/M^2$ moiety or some other $L_b/L_b$' moiety, so that no $A_R$ component is required; and therefore $L_b$' of a Drug Linker compound or $L_b$ of a Ligand Drug conjugate is attached to A or $A_O$, which is now a subunit of A depending on the absence or presence of $A_O$, respectively. Alternatively, $L_R$ is comprised of $L_b/L_b$' and is attached to W, when W is a Peptide Cleavable Unit or to Y when W is a Glucuronide Unit of formula —Y(W)— when A and $A_O$ are both absent.

In some aspects, A of a secondary linker or $A_O$ of a primary linker, or a subunit of either of these Stretcher Units, has the formula of -$L^P$(PEG)- in which $L^P$ is a Parallel Connecter Unit and PEG is a PEG Unit as defined elsewhere. Thus, some Linker Units in an Ligand Drug Conjugate or Drug Linker compound contain the formula of -$L^P$(PEG)-W—Y—, in which subscript a is 1 and A, or a subunit thereof, in the generalized formula of a Ligand Drug Conjugate or Drug Linker compound is -$L^P$(PEG)-, and wherein W is a Peptide Cleavable Unit, or contain the formula -$L^P$(PEG)-Y(W')— in which subscript a is 1 and A, or a subunit thereof, in the generalized formulae is -$L^P$(PEG)-, wherein —Y(W')— is a Glucuronide Unit.

Typically, when subscript a is 1, a first optional Stretcher Unit (A) is present and has one carbon atom or two to six contiguous carbon atoms that connects A to $A_R$ or to a second optional Stretcher Unit ($A_O$), depending on the absence or presence of $A_O$, respectively, of the primary linker, when subscript b is 0 or to B when subscript b is 1, through one functional group and connects A to W, wherein W is a Peptide Cleavable Unit, or to Y of a Glucuronide Unit, within the secondary linker through another functional group. In some aspects, subscript a is 0, so that no first Stretcher Unit is present, or subscript a is 1 wherein A present as an α-amino acid, a β-amino acid or other amine-containing acid residue so that A is bonded $A_R$, $A_O$ or B, and to W or Y of —Y(W')— through amide functional groups. In other aspects, A is bonded to $A_O$, when $A_O$ is present and consists or is comprised of a Hydrolysis-enhancing Unit [HE].

"Branching Unit" as used herein, unless otherwise stated or implied by context, refers to a tri-functional organic moiety that is an optional component of a Linker Unit (LU). A Branching Unit (B) is present when more than one quaternized tubulysin Drug Units, typically 2, 3 or 4, are attached to a Linker Unit (LU) of a quaternized drug linker moiety in a Ligand Drug Conjugate compound or Drug Linker compound. In a Ligand Drug Conjugate having the afore-described generalized formula, the presence of a Branching Unit is indicated when subscript b of $B_b$ is 1, which occurs when subscript n greater than 1 in that formula. A Branching Unit is at least trifunctional in order to be incorporated into a secondary linker unit ($L_O$). In aspects where n is 1, a Branching Unit is not present, as indicated when subscript b is 0. Drug Linker or Ligand Drug Conjugate compounds with a Branching Unit due to multiple $D^+$ units per LU have Linker Units containing the formula —B-$A_a$-W—Y—, wherein subscripts a is 0 or 1 and W is a Peptide Cleavable Unit, or have Linker Units containing formula —B-$A_a$-Y(W')—, when W is a Glucuronide Unit of formula —Y(W')—, wherein subscript a is 0 or 1. As A can contain formula -$L^P$(PEG)-, Linker Units in those instances can contain formula -$L^P$(PEG)-W—Y— or -$L^P$(PEG)-Y(W')— when subscript b is 0 or formula —B-$L^P$(PEG)-W—Y— or —B-$L^P$(PEG)-Y(W')— when subscript b is 1.

In some aspects, a natural or un-natural amino acid or other amine-containing acid compound having a functionalized side chain serves as a Branching unit. In some aspects B is a lysine, glutamic acid or aspartic acid moiety in the L- or D-configuration in which the epsilon-amino, gamma-carboxylic acid or beta-carboxylic acid functional group, respectively, along with their amino and carboxylic acid termini, interconnects B within the remainder of LU.

"Cleavable Unit" as used herein, unless otherwise stated or implied by context, refers to an organic moiety that provides for a reactive site within a Linker Unit wherein reactivity towards that site is greater within or surrounding an abnormal cell such as a hyper-proliferating cell or hyper-stimulated immune cell in comparison to normal cells that typically are not present at the site or are distant from the site of the abnormal cells such that action upon the reactive site of the Linker Unit. That greater reactivity in some aspects is due to a greater amount of enzymatic or non-enzymatic activity at the site of or within the abnormal cells and occurs to a sufficient extent so as to provide immunologically selective cytotoxicity by preferential exposure of the abnormal cells to a cytotoxic or cytostatic tubulysin compound, upon release of a quaternized tubulysin Drug Unit ($D^+$) from a Ligand Drug Conjugate compound having that Linker Unit. The exposure from release of $D^+$ as a tubulysin compound is initiated by enzymatic or non-enzymatic action on the Linker Unit having that Cleavable Unit. In some aspects of the invention, a Cleavable Unit contains a reactive site cleavable by an enzyme whose activity or abundance is greater within or surrounding the hyper-proliferating, immune-stimulating or other abnormal cells compared to normal cells or within the vicinity of normal cells that are distant from the site of the abnormal cells so as to provide immunologically selective cytotoxicity. In some of those aspects of the invention, the Cleavable Unit is a substrate for a protease so that W is a Peptide Cleavable Unit, which in some aspects is a substrate for a regulatory protease. In other aspects, the Cleavable Unit is a Glucuronide Unit of formula —Y(W')— replacing W in the generalized formula of a Ligand Drug Conjugate or Drug Linker compound, wherein the Glucuronide Unit is a substrate for a glycosidase. In either of those aspects, the protease or glycosidase is sometimes located intracellularly in targeted cells (i.e., the reactive site of the Cleavable Unit is a peptide bond or glycoside bond, respectively, cleavable by the protease or glycosidase), or the peptide or glycoside bond of the Cleavable Unit is capable of selective cleavage by an intracellular regulatory protease, hydrolase or glycosidase in comparison to serum proteases, hydrolases, or glycosidases. In some of those aspects, the reactive site is more likely operated upon enzymatically subsequent to cellular internalization of a Ligand Drug Conjugate compound into a targeted abnormal cell.

Functional groups that provide for cleavable bonds include, by way of example and not limitation, carboxylic or amino groups that form an amide bond, as in peptide bonds that are susceptible to enzymatic cleavage by proteases produced or excreted preferentially by abnormal cells in comparison to normal cells or by a regulatory protease within a targeted cell. Other functional groups that provide for cleavable bonds are found in sugars or carbohydrates having a glycosidic linkage that are substrates for glycosides, which sometimes may be produced preferentially by abnormal cells in comparison to normal cells. Alternatively, the protease or glycosidase enzyme required for processing of the Linker Unit to release a quaternized tubulysin Drug Unit as a tubulysin compound need not be produced preferentially by abnormal cells in comparison to normal cells provided the processing enzyme is not excreted by normal cells to an extent that would cause undesired side effects from premature release of $D^+$ as the tubulysin compound. In other instances, the required protease or glycosidase enzyme may be excreted, but to avoid undesired premature release of drug, some aspects of the invention typically require the processing enzyme be excreted in the vicinity of abnormal cells and remain localized to that enviroment, whether produced by abnormal cells or nearby normal cells in response to the abnormal enviroment caused by the abnormal cells. In that respect, W as a Peptide Cleavable Unit or W' of a Glucuronide Unit is selected to be preferentially acted upon by a protease or glycosidase, respectively, in or within the enviroment of abnormal cells in contrast to freely circulating enzymes. In those instances, a Ligand Drug Conjugate compound is less likely to release $D^+$ as a tubulysin compound in the vicinity of unintended normal cells, nor would it be internalized to any appreciable extent into normal cells that do intracellularly produce but do not excrete the enzyme intended to be acted upon by the internalized Ligand Drug Conjugate compound to any appreciable extent since such cells are less likely to display a targeted moiety required for entry by that compound or have sufficient copy number of that targeted moeity.

In some aspects, W in the generalized formula of a Ligand Drug Conjugate or Drug Linker compound is a Peptide Cleavable Unit comprised of an amino acid residue or is comprised or consists of one or more sequences of amino acids that provide a substrate for a protease present within abnormal cells or a protease localized to the environment of these abnormal cells. Thus, W may be comprised or consist of a dipeptide, tripeptide, tetrapeptide, pentapeptide, hexapeptide, heptapeptide, octapeptide, nonapeptide, decapeptide, undecapeptide or dodecapeptide moiety incorporated into a Linker Unit through an amide bond to a PAB or PAB-type moiety of a self-immolative Spacer Unit (Y) wherein the peptide provides a recognition sequence for that protease. In some of those aspects, the protease is a intracellular protease as further described herein that acts upon the Peptide Cleavable Unit of a Ligand Drug Conjugate compound that has been internalized into a targeted cell.

In other aspects, W in the generalized Ligand Drug Conjugate of Drug Linker compound formulae is replaced by —Y(W')—, which is referred to as a Glucuronide Unit, wherein W' is a carbohydrate moiety (Su) attached to a PAB or PAB-type moiety of the Glucuronide Unit's self-immolative Spacer Unit (Y) by a glycosidic bond through an optionally substituted heteroatom (E') that is cleavable by a glycosidase preferentially produced by abnormal cells, or is found in such cells to which an Ligand Drug Conjugate compound having that Spacer Unit and carbohydrate moiety has selective entry due to the presence of the targeted moiety on the abnormal cells.

"Natural amino acid" as used herein, unless otherwise stated or implied by context, refers to a naturally occurring amino acid, namely, arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine or a residue thereof, in the L or D-configuration, unless otherwise specified or implied by context.

"Un-natural amino acid" as used herein, unless otherwise stated or implied by context, refers to an alpha-amino-containing acid or residue thereof, which has the basic structure of a natural amino acid, but has a side chain group attached to the alpha carbon that is not present in natural amino acids.

"Non-classical amino acid" as used herein, unless otherwise stated or implied by context, refers to an amine-containing acid compound that does not have its amine substituent bonded to the carbon alpha to the carboxylic acid and therefore is not an alpha-amino acid. Non-classical amino acids include β-amino acids in which a methylene is inserted between the carboxylic acid and amino functional groups in a natural amino acid or an un-natural amino acid.

"Peptide" as used herein, unless otherwise stated or implied by context, refers to a polymer of two or more amino acids wherein carboxylic acid group of one amino acid forms an amide bond with the alpha-amino group of the next amino acid in the peptide sequence. Methods for preparing amide bonds in polypeptides are additionally provided in the definition of amide. Peptides may be comprised of naturally occurring amino acids in the L- or D-configuration or unnatural or non-classical amino acids.

"Protease" as defined herein refers to a protein capable of enzymatic cleavage of a carbonyl-nitrogen bond such as an amide bond typically found in a peptide. Proteases are classified into major six classes: serine proteases, threonine proteases, cysteine proteases, glutamic acid proteases, aspartic acid proteases and metalloproteases so named for the catalytic residue in the active site that is primarily responsible for cleaving the carbonyl-nitrogen bond of its substrate. Proteases are characterized by various specificities, which are dependent of identities of the residues at the N-terminal and/or C-terminal side of the carbonyl-nitrogen bond and various distributions.

When W is a Peptide Cleavable Unit comprised of amide or other carbonyl-nitrogen containing functional group cleavable by a protease, the site of that cleavage is typically limited to those recognized by proteases that are found in hyper-proliferating cells or hyper-stimulated immune cells or within nominally normal cells particular to the environment in which hyper-proliferating cells or hyper-stimulated immune cells are present. In those instances, the protease is not necessarily required to be preferentially present or found in greater abundance in the cells targeted by a Ligand Drug Conjugate since the Conjugate will have poorer access to those cells that do not preferentially have the targeting moiety. Other times, the protease is preferentially excreted by abnormal cells or by nominally normal cells in the environment in which those abnormal cells are found in comparison to normal cells in the periphery, which are in their typical environment in which abnormal cells are not present. Thus, in those instances where the protease is excreted, the protease is necessarily required to be preferentially present or found in greater abundance in the vicinity of cells targeted by the Conjugate in comparison to that of distant normal cells.

When incorporated into an Ligand Drug Conjugate, a peptide that comprises W as a Peptide Cleavable Unit will present a recognition sequence to a protease that cleaves a carbonyl-nitrogen bond in W resulting in fragmentation of the Linker Unit to cause release of an tertiary amine-containing drug from $D^+$. Sometimes, the recognition sequence is selectively recognized by an intracellular protease present in abnormal cells to which the Conjugate has preferred access in comparison to normal cells due to targeting of the abnormal cells, or is preferentially produced by abnormal cells in comparison to normal cells, for the purpose of selectively delivering the drug to the desired site of action. Usually the peptide is resistant to circulating proteases in order to minimize premature expulsion of $D^+$ in the form of a tubulysin compound and thus minimize unwanted systemic exposure to that compound. Typically, the peptide will have one or more unnatural or non-classical amino acids in its sequence in order to have that resistance. Oftentimes, the amide bond that is specifically cleaved by a protease produced by an abnormal cell is an anilide wherein the nitrogen of that anilide is a nascent electron-donating heteroatom (i.e., J) of a self-immolative moiety of a self-immolative Spacer Unit whose structure are described elsewhere. Thus, protease action on such a peptide sequence in W results in release of $D^+$ as a tubulysin compound from the linker fragment by 1,4- or 1,6-elimination involving the (hetero)arylene component of the self-immolative moiety.

Regulatory proteases are typically located intracellularly and are required for the regulation of cellular activities that sometimes becomes aberrant or dysregulated in abnormal cells. In some instances, when W is directed to a protease having preferential distribution intracellularly, that protease is a regulatory protease, which is involved in cellular maintenance or proliferation. In some instances, those proteases include lysosomal proteases or cathepsins. Cathepsins include the serine proteases, Cathepsin A, Cathepsin G, aspartic acid proteases Cathepsin D, Cathepsin E and the cysteine proteases, Cathepsin B, Cathepsin C, Cathepsin F, Cathepsin H, Cathepsin K, Cathepsin L1, Cathepsin L2, Cathepsin O, Cathepsin S, Cathepsin W and Cathepsin Z. Recognition sequences for lysosomal proteases that are cysteine proteases for incorporation into a Peptide Cleavable Unit are described by Turk, V. et al. *Biochem. Biophys. Acta* (2012) 1824: 66-88.

In other instances, when W is a Peptide Cleavable Unit directed to a protease that is preferentially distributed extracellularly in the vicinity of hyper-proliferating or hyper-stimulated immune cells due to preferential excretion by such cells or by neighboring cells whose excretion is peculiar to the environment of hyper-proliferating or hyper-stimulated immune cells, that protease is usually a metalloprotease. Typically, those proteases are involved in tissue remodeling, which aids in the invasiveness of hyper-proliferating cells or undesired accumulation of hyper-activated immune cells that results in further recruit of such cells.

"Spacer Unit" as used herein, unless otherwise stated or implied by context, refers to a component in a secondary linker ($L_O$) within a Linker Unit of a Ligand Drug Conjugate or Drug Linker compound that is covalently bonded to a quaternized Tubulysin Drug Unit ($D^+$), and in some aspects is also covalently bonded to a first optional Stretcher Unit (A) if subscript b is 0 in the generalized Ligand Drug Conjugate of Drug Linker compound or to a Branching Unit (B) if subscript b is 1 in any one of these formulae or to a second optional Stretcher Unit ($A_O$), if A and B are absent (i.e., subscripts a and b are both 0), or to $A_R$ in a $L_{SS}/L_S$-containing Linker Unit if none of these other Linker Unit components are present. In some aspects, Y is covalently bonded to W and $D^+$, wherein W is a Peptide Cleavable Unit and Y is capable self-immolation so that Y is a self-immolative Spacer Unit. In other aspects, Y is a component of a Glucuronide Unit of formula —Y(W')—, wherein Y bonded to W' is a self-immolative Spacer Unit in order for $D^+$ to be released as a tubulysin compound subsequent to cleavage of the glycosidic bond between W' and Y.

Typically, in one configuration W, Y, and $D^+$ are arranged linearly with $D^+$ bonded to Y in the generalized Ligand Drug Conjugate of Drug Linker compound, wherein W is a Peptide Cleavable Unit, so that protease action upon W initiates release $D^+$ as a tubulysin compound. Typically, in another configuration in which a Ligand Drug Conjugate or Drug Linker compound contains a Glucuronide Unit of formula —Y(W')—, in which W is replaced by that Unit within a secondary linker ($L_O$) in the generalized Ligand Drug Conjugate of Drug Linker compound formulae, wherein W' of the Glucuronide Unit and $D^+$ are covalently bonded to Y, wherein Y is a self-immolative Spacer Unit, and Y in turn is also bonded to $A/A_R$, B, $A_O$ or $L_R$, depending on the presence or absence of A, B and/or $A_O$, so that W' is orthogonal to the remainder of $L_O$. As before, glycosidase action is followed by self-immolation of Y to release $D^+$ as a free cytotoxic or cytostatic drug tubulysin compound. In either configuration, Y may also serve to separate the cleavage site of the Peptide Cleavable Unit or Glucuronide from $D^+$ to avoid steric interactions from that Unit that would interfere with cleavage of W/W'.

Typically, a self-immolative Spacer Unit is comprised or consists of a PAB or PAB-type moiety bonded to a quaternized tubulysin Drug Unit ($D^+$) as defined herein so that enzymatic processing of the Peptide Cleavable Unit or Glucuronide activates the self-immolative PAB or PAB-type moiety for self-destruction thus initiating release of the quaternized tubulysin Drug Unit as tubulysin compound. In some aspects, a PAB or PAB-type moiety of a self-immolative Spacer Unit is covalently bonded to $D^+$ and to W as a Peptide Cleavable Unit through an amide (or anilide) functional group cleavable by a protease, whereas in other aspects the PAB or PAB-type moiety is covalently bonded to $D^+$ and to W' of a Glucuronide Unit through a glycosidic bond cleavable by a glycosidase.

In either of those aspects, a quaternized tubulysin Drug Unit is directly attached to the PAB or PAB-type moiety of the self-immolative Spacer Unit through a quaternized skeletal nitrogen atom of its N-terminal component. In some aspects, the quaternized nitrogen in the N-terminal component of the quaternized tubulysin Drug Unit is that of a saturated 5- or 6-membered heterocyclic ring system such as an N-alkyl-pipecolic acid residue.

In some of the above aspects, the PAB or PAB-type moiety of a self-immolative Spacer Unit (Y) is attached to a quaternized tubulysin Drug Unit ($D^+$) and to W by an amide or anilide functional group, enzymatic action upon which results in release of $D^+$ due to spontaneous self-destruction of the PAB or PAB-type moiety of Y to provide a tubulysin compound. In other aspects, the PAB or PAB-type moiety of a self-immolative Spacer Unit (Y) is attached to a quaternized tubulysin Drug Unit ($D^+$) and W' of a Glucuronide Unit through a glycosidic bond so that cleavage of that bond initiates release of $D^+$ due to spontaneous self-destruction of the PAB or PAB-type moiety of Y to provide a tubulysin compound.

"Self-immolating moiety" as used herein refers to a bifunctional moiety within a Spacer Unit (Y) wherein the self-immolative moiety is covalently attached to $D^+$ through a quaternized skeletal nitrogen of a saturated nitrogen-containing heterocyclic component of that quaternized Drug Unit, wherein that component corresponds to a tubulysin N-terminal component. and is also covalently attached to an amino acid residue of W wherein W is a Peptide Cleavable Unit through an optionally substituted heteroatom (J), or to a optionally substituted heteroatom glycosidic heteroatom (E'), bonded to the carbohydrate moiety (Su) of W' of a Glucuronide Unit of formula —Y(W')— so that the self-immolative moiety incorporates these quaternized drug linker components into a normally stable tripartite molecule unless activated, where such substitution of J or E' is permitted and consistent with the electron-donating properties required for self-immolation as described herein on activation.

On activation, the covalent bond to W in which W is a Peptide Cleavable Unit or the glycosidic bond of W' in a Glucuronide Unit of formula —Y(W')— replacing W is cleaved so that $D^+$ spontaneously separates from the tripartite molecule by self-destruction of the PAB or PAB-type moiety of the self-immolative Spacer Unit resulting in release of $D^+$ as a tubulysin compound, which no longer has a quaternized nitrogen. In either of those aspects, self-destruction of Y occurs in some instances after cellular internalization of a Ligand Drug Conjugate compound comprised of a quaternized tubulysin Drug Unit ($D^+$) and a Linker Unit having a self-immolative Spacer Unit in which its PAB or PAB-type moiety is bonded $D^+$.

In some aspects, a component of a PAB or PAB-type moiety of a self-immolative Spacer Unit intervening between $D^+$ and the optionally substituted heteroatom J of Y, wherein J is bonded to W as a Peptide Cleavable Unit has the formula of —$C_6$-$C_{24}$ arylene-C($R^9$)($R^9$)—, —$C_5$-$C_{24}$ heteroarylene-C($R^9$)($R^9$)—, —$C_6$-$C_{24}$ arylene-C($R^9$)=C($R^9$)— or —$C_5$-$C_{24}$ heteroarylene-C($R^9$)=C($R^9$)—, optionally substituted, wherein $R^9$ independently selected, is as described by the embodiments of the invention. Typically, the intervening component is $C_6$-$C_{10}$ arylene-$CH_2$— or $C_5$-$C_{10}$ heteroarylene-$CH_2$—, in which the (hetero)arylene is optionally substituted.

In other aspects, a component of a PAB or PAB-type moiety of a self-immolative Spacer Unit (Y) in a Glucuronide Unit of formula —Y(W')— replacing W and intervening between $D^+$ and the optionally substituted heteroatom E' in W' has the formula of —$C_6$-$C_{24}$ arylene-C($R^9$)($R^9$)—, —$C_5$-$C_{24}$ heteroarylene-C($R^9$)($R^9$)—, —$C_6$-$C_{24}$ arylene-C($R^9$)=C($R^9$)— or —$C_5$-$C_{24}$ heteroarylene-C($R^9$)=C($R^9$)—, optionally substituted and typically is $C_6$-$C_{10}$ arylene-$CH_2$— or $C_5$-$C_{10}$ heteroarylene-$CH_2$—, wherein $R^9$, independently selected, is as described by the embodiments of the invention, the (hetero)arylene of which is also substituted with $L_R$-$A_a$- in a Drug Linker compound, or -$L_R$-$A_a$- in a Ligand Drug Conjugate compound, having a Glucuronide-based Linker Unit and is otherwise optionally substituted, wherein A is a first optional Stretcher Unit, subscript a is 0 or 1 and $L_R$ is a primary linker. In those aspects -$L_R$-$A_a$- is bonded to the (hetero)arylene component of the PAB or PAB-type moiety through an optionally substituted heteroatom (J') or functional group comprised of J', which is independently selected from E'.

In either aspect, the intervening component of the PAB or PAB-type moiety of a self-immolative Spacer Unit is capable of undergoing fragmentation to form a iminoquinone methide or related structure by 1,4 or 1,6-elimination with concomitant release of $D^+$ on cleavage of the protease cleavable bond between J and W or on cleavage of the glycosidase cleavable bond of W'. In some aspects, a self-immolative Spacer Unit having the aforementioned central (hetero)arylene component bonded to J, or to W' and -$L_R$-$A_a$-, is exemplified by an optionally substituted β-aminobenzyl alcohol (PAB) moiety, ortho or para-aminobenzylacetals, or other aromatic compounds that are electronically similar to the PAB group (i.e., PAB-type) such as 2-aminoimidazol-5-methanol derivatives (see, e.g., Hay et al., 1999, *Bioorg. Med. Chem. Lett.* 9:2237) or those in which the phenyl group of the β-aminobenzyl alcohol (PAB) moiety is replaced by a heteroarylene.

In a Glucuronide Unit, the intervening (hetero)arylene component to which W' and —C($R^9$)($R^9$)-$D^+$ or —C($R^9$)=C($R^9$)-$D^+$ are bound is sometimes substituted with an electron withdrawing group, which sometimes can increase the rate of glycosidic cleavage, but may decrease the rate of fragmentation of the self-immolative moeity Spacer Unit for releasing $D^+$ as a tubulysin compound due to destabilization of the quinone-methide intermediate produced as an obligatory by-product of that fragmentation.

Without being bound by theory, an aromatic carbon of the central arylene or heteroarylene group of a PAB or PAB-type moeity of a self-immolative Spacer Unit in a Peptide Cleavable-based Linker Unit is substituted by J, wherein the electron-donating heteroatom of J is attached to the cleavage site of W in a Peptide Cleavable-based Linker Unit so that the electron-donating capacity of that heteroatom is attenuated (i.e., EDG ability is masked by incorporation of a PAB or PAB-type moiety of a Self-immolative Spacer Unit into the Peptide Cleavable-based Linker Unit). The other required substituent of the hetero(arylene) is an optionally substituted benzylic carbon that is attached to the quaternized nitrogen atom of the quaternized tubulysin Drug Unit ($D^+$), wherein the benzylic carbon is attached to another aromatic carbon atom of the central (hetero)arylene, wherein the aromatic carbon bearing the attenuated electron-donating heteroatom is adjacent to (i.e., 1,2-relationship), or two additional positions removed (i.e., 1,4-relationship) from that other aromatic carbon atom.

Likewise, in a Glucuronide-based Linker Unit, the central (hetero)arylene group of a PAB or PAB-type moeity of its self-immolative Spacer Unit is substituted by W' through a glycosidic bond wherein the electron-donating ability of the optionally substituted heteroatom (E') of that bond is attenuated (i.e., EDG ability is masked by incorporation of the PAB or PAB-type moiety of a Self-immolative Spacer Unit into a Glucuronide-based Linker Unit). The other required substituents of the hetero(arylene) are (1) the remainder of the Linker Unit of formula $L_R$-$A_a$- in a Drug Linker compound or -$L_R$-$A_a$- in Ligand Drug Conjugate compound is attached to a second aromatic carbon atom of the central (hetero)arylene and (2) a benzylic carbon that is attached to the quaternized nitrogen atom of a quaternized tubulysin Drug Unit ($D^+$), wherein the benzylic carbon is also attached to a third aromatic carbon atom of the central (hetero)arylene, wherein the aromatic carbon bearing the attenuated electron-donating heteroatom is adjacent to (i.e., 1,2-relationship), or two additional positions removed (i.e., 1,4-relationship) from that third aromatic carbon atom.

In either type of Linker Unit, the EDG heteroatom is chosen so that upon processing of the cleavage site of W as a Peptide Cleavable Unit or W' of a Glucuronide Unit replacing W, the electron-donating capacity of the masked heteroatom is restored thus triggering a 1,4- or 1,6-elimination to expel -$D^+$ as a tubulysin compound from the benzylic substituent. Exemplary, but non-limiting, self-immolative moieties and self-immolative Spacer Unit having those self-immolative moieties are exemplified by the embodiments of the invention.

"Glycosidase" as used herein, unless otherwise stated or implied by context, refers to a protein capable of enzymatic cleavage of a glycosidic bond. Typically, the glycosidic bond to be cleaved is present in a Glucuronide Unit as the Cleavable Unit of Ligand Drug Conjugate or Drug Linker compound. Sometimes the glycosidase acting upon a Ligand Drug Conjugate is present intracellularly in hyper-proliferating cells, hyper-activated immune cells or other abnormal cells to which the Ligand Drug Conjugate has preferential access in comparison to normal cells, which is attributable to the targeting capability of its Ligand Unit. Sometimes the glycosidase is more specific to the abnormal or cells or is preferentially excreted by abnormal or cells in comparison to normal cells or is present in greater amount in the vicinity of abnormal cells in comparison to amounts of the glycosidase typically found in serum of an intended subject to whom the Ligand Drug Conjugate is to be administered. Typically, the glycosidic bond within a Glucuronide Unit, which has the formula of —W'(Y)—, connects the anomeric carbon of a carbohydrate moiety (Su) to a self-immolative Stretcher Unit (Y) through an optionally substituted heteroatom (E') so that W' is Su-E'- and is acted upon by a glycosidase. In some aspects E', which forms the glycosidic bond to the carbohydrate moiety (Su), is a phenolic oxygen atom of a self-immolating moiety in a self-immolative Stretcher Unit (Y) such that glycosidic cleavage of that bond triggers 1,4- or 1,6-elimination of $D^+$ as a tubulysin compound.

In some aspects, in which W is a Glucuronide Unit, which has the formula of —Y(W')— Drug Linker compounds having that Cleavable Unit are represented by formula $L_R$-$B_b$-($A_a$-Y(W')—$D^+$)$_n$ including $L_{SS}$-$B_b$-($A_a$-Y(W')—$D^+$)$_n$ in which $L_{SS}$ is $M^1$-$A_R$(BU)-$A_O$- and Ligand Drug Conjugates are represented by L-($L_R$-$B_b$-($A_a$-Y(W')—$D^+$)$_n$)$_p$ including L-($L_{SS}$-$B_b$-($A_a$-Y(W')—$D^+$)$_n$)$_p$ or L-($L_S$-$B_b$-($A_a$-Y(W')—$D^+$)$_n$)$_p$, in which $L_{SS}$ is $M^2$-$A_R$(BU)-$A_O$ and $L_S$ is $M^3$-$A_R$(BU)-$A_O$-, wherein $A_O$ is an second optionally Stretcher Unit, which in some aspects serves as least in part as Hydrolysis-enhancing [HE] Unit and A is a first optionally Stretcher Unit, wherein in some aspects A or a subunit thereof has the formula of -$L^P$(PEG)-, wherein -$L^P$ and PEG are as defined herein for parallel connector units and PEG Units, respectively; BU represents an acyclic or cyclic Basic Unit, and subscripts a and b are independently 0 or 1, and subscript n is 1, 2, 3 or 4, wherein B is a Branching Unit, and is present when subscript n is 2, 3 or 4 so that subscript b is 1 and wherein A is a first Stretcher Unit, when subscript a is 1.

In some of those aspects, —Y(W')— is of the formula (Su-O')—Y—, wherein Su is a carbohydrate moiety, Y is a self-immolative Spacer Unit having a PAB or PAB-type self-immolative moiety with glycosidic bonding to Su, wherein O' as E' represents the oxygen atom of the glycosidic bond cleavable by a glycosidase, wherein a quaternized nitrogen atom of a quaternized tubulysin Drug ($D^+$) Unit is bonded directly to the self-immolative moiety of Y, and wherein Su-O'— is attached to the optionally substituted (hetero)arylene of the self-immolative moiety of Y, and $D^+$ is attached to that (hetero)arylene through an optionally substituted benzylic carbon such that self-immolative release of $D^+$ is initiated, thereby providing a tubulysin compound. Although such —Y(W')— moieties are referred to as Glucuronide Units, Su of W' is not limited to a glucuronic acid residue.

Typically, a Glucuronide Unit having the formula of (Su-O'—Y)— (in which —O'— represents the oxygen of the glycosidic bond and Su is a carbohydrate moiety) is represented by a structure described herein for a self-immolating Spacer Unit (Y) in which E' bonded to the central (hetero)arylene moiety of a PAB or PAB-type moiety of Y is an oxygen atom with that heteroatom bonded to the carbohydrate moiety (Su) through that moiety's anomeric carbon atom.

In some aspects, such moieties attached to $D^+$ include those of formula -(Su-O')—Y-$D^+$ having the structure of:

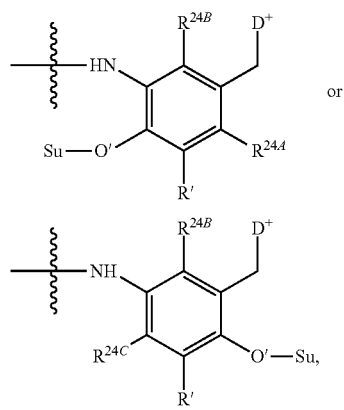

wherein $R^{24A}$, $R^{24B}$ and $R^{24C}$ are independently selected from the group consisting of hydrogen, $C_1$-$C_6$ alkyl, $C_1$-$C_6$ alkoxy, other EDGs, halogen, nitro and other EWGs or $R^{24A}$ and R' in the left-hand structure or $R^{24C}$ and R' in the right-hand structure together with the aromatic carbons to which they are attached define an benzo-fused $C_5$-$C_6$ carbocycle, and are selected so that the electron donating ability of the phenolic —OH released from the glycosidic bond by enzymatic action of a glycosidase, the sensitivity to selective cleavage by the glycosidase, and the stability of the iminoquinone methide intermediate resulting from fragmentation by 1,4- or 1,6-elimination are balanced with the leaving ability of $D^+$ in order for a suitably efficient release of $D^+$ as a tubulysin compound to occur. The (Su-O')—Y— moieties in the above structures are representative Glucuronide Units of formula —Y(W')—. When the glycosidic bond is to a glucuronic acid and the glycosidase capable of enzymatic cleavage of that glycosidic bond is a glucuronidase.

In some of those aspects -(Su-O')—Y-$D^+$ has the structure of:

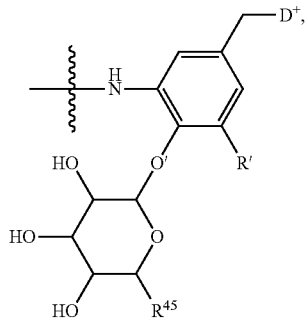

wherein $D^+$ corresponds to or incorporates a tubulysin compound; $R^{45}$ is —OH or —$CO_2H$. Further descriptions of those and other Glucuronide Units are provided by the embodiments of the invention.

"Carbohydrate moiety" as used herein, unless otherwise stated or implied by context, refers to a monovalent radical of a monosaccharide having the empirical formula of $C_m(H_2O)_n$, wherein n is equal to m, containing an aldehyde moiety in its hemiacetal form or a derivative thereof in which a $CH_2OH$ moiety within that formula has been oxidized to a carboxylic acid (e.g., glucuronic acid from oxidation of the $CH_2OH$ group in glucose). Typically, a carbohydrate moiety (Su) is a monovalent radical of cyclic hexose, such as a pyranose, or a cyclic pentose, such as a furanose. Usually, the pyranose is a glucuronide or hexose in the β-D conformation. In some instances, the pyranose is a β-D-glucuronide moiety (i.e., β-D-glucuronic acid linked to the self-immolative moiety of a self-immolative Spacer Unit via a glycosidic bond that is cleavable by β-glucuronidase). Sometimes, the carbohydrate moiety is unsubstituted (e.g., is a naturally occurring cyclic hexose or cyclic pentose). Other times, the carbohydrate moiety can be a β-D-glucuronide derivative, e.g., glucuronic acid in which one or more, typically 1 or 2 of its hydroxyl moieties are independently replaced with moieties selected from the group consisting of halogen and $C_1$-$C_4$ alkoxy.

"PEG Unit" as used herein refers to a group comprising a polyethylene glycol moiety (PEG) having a repetition of ethylene glycol subunits having the formula of

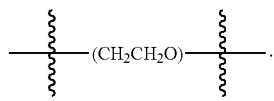

PEGs include polydisperse PEGs, monodisperse PEGs and discrete PEGs. Polydisperse PEGs are a heterogeneous mixture of sizes and molecular weights whereas monodisperse PEGs are typically purified from heterogeneous mixtures and are therefore provide a single chain length and molecular weight. Discrete PEGs are compounds that are synthesized in step-wise fashion and not via a polymerization process. Discrete PEGs provide a single molecule with defined and specified chain length.

A PEG Unit comprises at least 2 subunits, at least 3 subunits, at least 4 subunits, at least 5 subunits, least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. Some PEG Units comprise up to 72 subunit.

"PEG Capping Unit" as used herein is an organic moiety or functional group that terminates the free and untethered end of a PEG Unit and in some aspects is other than hydrogen so as to protect or reduced the chemical reactivity of the untethered end. In those aspects a PEG Capping Unit is methoxy, ethoxy, or other $C_1$-$C_6$ ether, or is —$CH_2$—$CO_2H$, or other suitable moiety. The ether, —$CH_2$—$CO_2H$, —$CH_2CH_2CO_2H$, or other suitable organic moiety thus acts as a cap for the terminal PEG subunit of the PEG Unit.

"Intracellularly cleaved", "intracellular cleavage" and like terms used herein refer to a metabolic process or reaction within a targeted cell occurring upon a Ligand Drug Conjugate or the like, whereby covalent attachment through its Linker Unit between the quaternized tubulysin Drug Unit and the Ligand Unit of the Conjugate is broken, resulting in release of $D^+$ as a tubulysin compound within the targeted cell.

"Hematological malignancy" as used herein, unless otherwise stated or implied by context, refers to a blood cell tumor that originates from cells of lymphoid or myeloid origin and is synonymous with the term "liquid tumor". Hematological malignancies may be categorized as indolent, moderately aggressive or highly aggressive.

"Lymphoma" as used herein, unless otherwise stated or implied by context, refers to is hematological malignancy that usually develops from hyper-proliferating cells of lymphoid origin. Lymphomas are sometimes classified into two major types: Hodgkin lymphoma (HL) and non-Hodgkin lymphoma (NHL). Lymphomas may also be classified according to the normal cell type that most resemble the cancer cells in accordance with phenotypic, molecular or cytogenic markers. Lymphoma subtypes under that classification include without limitation mature B-cell neoplasms, mature T cell and natural killer (NK) cell neoplasms, Hodgkin lymphoma and immunodeficiency-associated lymphoproliferative disorders. Lymphoma subtypes include precursor T-cell lymphoblastic lymphoma (sometimes referred to as a lymphoblastic leukemia since the T-cell lymphoblasts are produced in the bone marrow), follicular lymphoma, diffuse large B cell lymphoma, mantle cell lymphoma, B-cell chronic lymphocytic lymphoma (sometimes referred to as a leukemia due to peripheral blood involvement), MALT lymphoma, Burkitt's lymphoma, mycosis fungoides and its more aggressive variant Sezary's disease, peripheral T-cell lymphomas not otherwise specified, nodular sclerosis of Hodgkin lymphoma, and mixed-cellularity subtype of Hodgkin lymphoma.

"Leukemia" as used herein, unless otherwise stated or implied by context, refers to a hematological malignancy that usually develops from hyper-proliferating cells of myeloid origin, and include without limitation, acute lymphoblastic leukemia (ALL), acute myelogenous leukemia (AML), chronic lymphocytic leukemia (CLL), chronic myelogenous leukemia (CML) and acute monocyctic leukemia (AMoL). Other leukemias include hairy cell leukemia (HCL), T-cell lymphatic leukemia (T-PLL), large granular lymphocytic leukemia and adult T-cell leukemia.

"Hyper-proliferating cells" as used herein, unless otherwise stated or implied by context, refer to abnormal cells that are characterized by unwanted cellular proliferation or an abnormally high rate or persistent state of cell division or other cellular activity that is unrelated or uncoordinated with that of the surrounding normal tissues. In some aspects, hyper-proliferating cells are hyper-proliferating mammalian cells. In other aspects, hyper-proliferating cells are hyper-stimulated immune cells as defined herein whose persistent state of cell division or activation occurs after the cessation of the stimulus that may have initially evoked the change in their cell division. In other aspects, the hyper-proliferating cells are transformed normal cells or cancer cells and their uncontrolled and progressive state of cell proliferation may result in a tumor that is benign, potentially malignant (premalignant) or frankly malignant. Hyperproliferation conditions resulting from transformed normal cells or cancer cells include, but are not limited to, those characterized as a precancer, hyperplasia, dysplasia, adenoma, sarcoma, blastoma, carcinoma, lymphoma, leukemia or papilloma. Precancers are usually defined as lesions that exhibit histological changes and are associated with an increased risk of cancer development and sometimes have some, but not all, of the molecular and phenotypic properties that characterize the cancer. Hormone associated or hormone sensitive precancers include without limitation, prostatic intraepithelial neoplasia (PIN), particularly high-grade PIN (HGPIN), atypical small acinar proliferation (ASAP), cervical dysplasia and ductal carcinoma in situ. Hyperplasias generally refers to the proliferation of cells within an organ or tissue beyond that which is ordinarily seen that may result in the gross enlargement of an organ or in the formation of a benign tumor or growth. Hyperplasias include, but are not limited to, endometrial hyperplasia (endometriosis), benign prostatic hyperplasia and ductal hyperplasia.

"Normal cells" as used herein, unless otherwise stated or implied by context, refer to cells undergoing coordinated cell division related to maintenance of cellular integrity of normal tissue or replenishment of circulating lymphatic or blood cells that is required by regulated cellular turnover, or tissue repair necessitated by injury, or to a regulated immune or inflammatory response resulting from pathogen exposure or other cellular insult, where the provoked cell division or immune response terminates on completion of the necessary maintenance, replenishment or pathogen clearance. Normal cells include normally proliferating cells, normal quiescent cells and normally activated immune cells. Normal cells include normal quiescent cells, which are noncancerous cells in their resting $G_o$ state and have not been stimulated by stress or a mitogen or are immune cells that are normally inactive or have not been activated by pro-inflammatory cytokine exposure.

"Abnormal cells" as used herein, unless otherwise stated or implied by context, refer to unwanted cells that are responsible for promoting or perpetuating a disease state to which a Ligand Drug Conjugate is intended to prevent or treat. Abnormal cells include hyper-proliferating cells and hyper-stimulated immune cells as these term are define elsewhere. Abnormal cells may also refer to nominally normal cells that are in the environment of other abnormal cells, but which nonetheless support the proliferation and/or survival of these other abnormal cells, such as tumor cells, so that targeting the nominally normal cells indirectly inhibits the proliferation and/or survival of the tumor cells.

"Hyper-stimulated immune cells" as used herein, unless otherwise stated or implied by context, refer to cells involved in innate or adaptive immunity characterized by an abnormally persistent proliferation or inappropriate state of stimulation that occurs after the cessation of the stimulus that may have initially evoked the change in proliferation or stimulation or that occurs in the absence of any external insult. Oftentimes, the persistent proliferation or inappropriate state of stimulation results in a chronic state of inflammation characteristic of a disease state or condition. In some instances, the stimulus that may have initially evoked the change in proliferation or stimulation is not attributable to an external insult but is internally derived, as in an autoimmune disease. In some aspects, a hyper-stimulated immune cell is a pro-inflammatory immune cell that has been hyper-activated through chronic pro-inflammatory cytokine exposure.

In some aspects of the invention, a Ligand Drug Conjugate compound of a Ligand Drug Conjugate composition binds to an antigen preferentially displayed by pro-inflammatory immune cells that are abnormally proliferating or are inappropriately or persistently activated. Those immune cells include classically activated macrophages or Type 1 T helper (Th1) cells, which produce interferon-gamma (INF-γ), interleukin-2 (IL-2), interleukin-10 (IL-10), and tumor necrosis factor-beta (TNF-β), which are cytokines that are involved in macrophage and $CD8^+$ T cell activation.

"Bioavailability" unless otherwise stated or implied by context, refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

"Subject" unless otherwise stated or implied by context, refers to a human, non-human primate or mammal having a hyper-proliferation, inflammatory or immune disorder or other disorder attributable to abnormal cells or is prone to such a disorder who would benefit from administering an effective amount of a Ligand Drug Conjugate. Non-limiting examples of a subject include human, rat, mouse, guinea pig, monkey, pig, goat, cow, horse, dog, cat, bird and fowl. Typically, the subject is a human, non-human primate, rat, mouse or dog.

"Carrier" unless otherwise stated or implied by context refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a subject, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The present compositions, if desired, can also contain minor amounts of wetting or emulsifying agents, or pH buffering agents.

"Salt form" as used herein, unless otherwise indicated by context, refers to a charged compound in ionic association with a countercation(s) and/or counteranions so as to form an overall neutral species. In some aspects, a salt form of a compound occurs through interaction of the parent compound's basic or acid functional group with an external acid or base, respectively. In other aspects the charged atom of the compound that is associated with a counteranion is permanent in the sense that spontaneous disassociation to a neural species cannot occur without altering the structural integrity of the parent compound as when a nitrogen atom is quaternized. Accordingly, a salt form of a compound may involve a quaternized nitrogen atom within that compound and/or a protonated form of a basic functional group and/or ionized carboxylic acid of that compound each of which is in ionic association with a counteranion. In some aspects a salt form may result from interaction of a basic functional group and an ionized acid functional group within the same compound or involve inclusion of a negatively charged molecule such as an acetate ion, a succinate ion or other counteranion. Thus, a compound in salt form may have more than one charged atom in its structure. In instances where multiple charged atoms of the parent compound are part of the salt form, that salt from can have multiple counter ions so that a salt form of a compound may have one or more charged atoms and/or one or more counterions. The counterion may be any charged organic or inorganic moiety that stabilizes an opposite charge on the parent compound.

A protonated salt form of a compound is typically obtained when a basic functional group of a compound, such as a primary, secondary or tertiary amine or other basic amine functional group interacts with an organic or inorganic acid of suitable pKa for protonation of the basic functional group, or when an acid functional group of a compound with a suitable $pK_a$, such as a carboxylic acid, interacts with a hydroxide salt, such as NaOH or KOH, or an organic base of suitable strength, such as triethylamine, for deprotonation of the acid functional group. In some aspects, a compound in salt form contains at least one basic amine functional group, and accordingly acid addition salts can be formed with this amine group, which includes the basic amine functional group of a cyclic or acyclic Basic Unit. A suitable salt form in the context of a Drug Linker compound is one that does not unduly interfere with the condensation reaction between a targeting agent and the Drug Linker compound that is intended to provide a Ligand drug Conjugate.

"Pharmaceutically acceptable salt" as used herein, unless otherwise indicated by context, refers to a salt form of a compound in which its counterion is acceptable for administration of the salt form to an intended subject and include inorganic and organic countercations and counteranions. Exemplary pharmaceutically acceptable counteranions for basic amine functional groups, such as those in cyclic or acyclic Basic Units, include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, mesylate, besylate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

Typically, a pharmaceutically acceptable salt is selected from those described in P. H. Stahl and C. G. Wermuth, editors, *Handbook of Pharmaceutical Salts: Properties, Selection and Use*, Weinheim/Ziirich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability as when in a lyophilized formulation under accelerated conditions (i.e., for determining degradation or solid-state changes when stored at 40° C. and 75% relative humidity).

"Inhibit", "inhibition of" and like terms, unless otherwise stated or implied by context, means to reduce by a measurable amount, or to prevent entirely an undesired activity or outcome. In some aspects, the undesired outcome or activity is related to abnormal cells and includes hyper-proliferation, or hyper-stimulation or other dysregulated cellular activity underlying a disease state. Inhibition of such a dysregulated cellular activity by a Ligand Drug Conjugate is typically determined relative to untreated cells (sham treated with vehicle) in a suitable test system as in cell culture (in vitro) or in a xenograft model (in vivo). Typically, a Ligand Drug Conjugate that targets an antigen that is not present or has low copy number on the abnormal cells of interest or is genetically engineered to not recognize any known antigen for use as a negative control.

"Treat", "treatment," and like terms, unless otherwise indicated by context, refer to a therapeutic treatment, including prophylactic measures to prevent relapse, wherein the object is to inhibit or slow down (lessen) an undesired physiological change or disorder, such as the development or spread of cancer or tissue damage from chronic inflammation. Typically, beneficial or desired clinical benefits of such therapeutic treatments include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival or quality of life as compared to expected survival or quality of life if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor, inhibiting replication of tumor cells or cancer cells, inhibiting dissemination of tumor cells or cancer cell, lessening of overall tumor burden or decreasing the number of cancerous cells, or ameliorating one or more symptoms associated with cancer.

"Therapeutically effective amount" unless otherwise stated or implied by context, refers to an amount of tubulysin compound or Ligand Drug Conjugate having a quaternized tubulysin Drug Unit effective to treat a disease or disorder in a mammal. In the case of cancer, the therapeutically effective amount of the Tubulysin compound or Ligand Drug Conjugate may reduce the number of cancer cells, reduce tumor size, inhibit (i.e., slow to some extent and preferably stop) cancer cell infiltration into peripheral organs, inhibit (i.e., slow to some extent and preferably stop) tumor metastasis, inhibit, to some extent, tumor growth, and/or relieve to some extent one or more of the symptoms associated with the cancer. To the extent the tubulysin compound or Ligand Drug Conjugate may inhibit growth and/or kill existing cancer cells, it may be cytostatic or cytotoxic. For cancer therapy, efficacy can, for example, be measured by assessing the time to disease progression (TTP) determining the response rate (RR) and/or overall survival (OS).

In the case of immune disorders resulting from hyper-stimulated immune cells, a therapeutically effective amount of the drug may reduce the number of hyper-stimulated immune cells, the extent of their stimulation and/or infiltration into otherwise normal tissue and/or relieve to some extent one or more of the symptoms associated with a dysregulated immune system due to hyper-stimulated immune cells. For immune disorders due to hyper-stimulated immune cells, efficacy can, for example, be measured by assessing one or more inflammatory surrogates, including one or more cytokines levels such as those for IL-1β, TNFα, INFγ and MCP-1, or numbers of classically activated macrophages.

In some aspects of the invention, a Ligand Drug Conjugate compound associates with an antigen on the surface of a targeted cell (i.e., an abnormal cell such as a hyper-proliferating cell or a hyper-stimulated immune cell), and the Conjugate compound is then taken up inside the targeted cell through receptor-mediated endocytosis. Once inside the cell, one or more Cleavage Units within a Linker Unit of the Conjugate are cleaved, resulting in release of the quaternized tubulysin Drug Unit ($D^+$) as a tubulysin compound. The compound so released is then free to migrate within the cytosol and induce cytotoxic or cytostatic activities, or in the case of hyper-stimulated immune cells may alternatively inhibit pro-inflammatory signal transduction. In another aspect of the invention, the quaternized tubulysin Drug Unit ($D^+$) is released from a Ligand Drug Conjugate compound outside the targeted cell but within the vicinity of the targeted cell so that the resulting tubulysin compound from that release is able to subsequently penetrate the cell rather than being prematurely released at distal sites.

2. Embodiments

A number of embodiments of the invention are described below followed by a more detailed discussion of the components, e.g., groups, reagents, and steps that are useful in the processes of the present invention. Any of the selected embodiments for the components of the processes can apply to each and every aspect of the invention as described herein or they may relate to a single aspect. The selected embodiments may be combined together in any combination appropriate for preparing a tubulysin compound or Intermediate thereof and for preparing a Ligand Drug Conjugate, Drug Linker compound or Intermediate thereof having a quaternized tubulysin Drug Unit, incorporating or corresponding to the tubulysin compound.

2.1 Tubuvaline Intermediates 2.1.1 Embodiment Group 1

In a first group of embodiments, methods are provided for preparing a mixture of two enantiomeric tubuvaline intermediates, each optionally in salt form, represented by Formula AB:

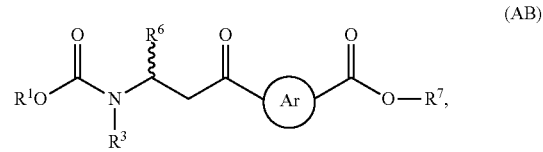

(AB)

or a composition comprised or consisting essentially of that mixture, wherein the circled Ar is a 1,3-phenylene or a 5- or 6-membered nitrogen-containing 1,3-heteroarylene optionally substituted at the remaining positions; $R^1$ is phenyl, t-butyl, 9-fluorenyl or allyl, optionally substituted, or other moiety so that $R^1$—OC(=O)— is a suitable nitrogen protecting group, in particular $R^1$—OC(=O)— is BOC; $R^3$ is optionally substituted saturated $C_1$-$C_8$ alkyl, optionally substituted unsaturated $C_3$-$C_8$ alkyl, optionally substituted $C_3$-$C_8$ carbocyclyl, or optionally substituted $C_3$-$C_8$ heteroalkyl; $R^6$ is optionally substituted saturated $C_1$-$C_8$ alkyl or optionally substituted unsaturated $C_3$-$C_8$ alkyl; and $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moiety so that $R^7$—O— provides for a suitable carboxylic acid protecting group, the method comprising the step of: contacting a tubuvaline intermediate, optionally in salt form, of Formula A:

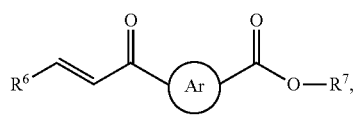

(A)

with a carbamate compound of Formula B having the structure of $R^3NHC(O)OR^1$, wherein the variable groups of Formulae A and B are as defined for Formula AB, in a suitable polar aprotic solvent in the presence of a suitable transition metal (II) or transition metal (III) catalyst, in particular, one comprising a transition metal selected from the group consisting of Cu(II), Zn(II) and Yb(III), so as to form the enantiomeric Formula AB mixture or composition thereof.

In context of the method, a suitable polar, aprotic solvent allows for sufficient solubilization of the Formula A tubuvaline intermediates, the Formula B carbamate compound, and the transition metal catalyst to allow for the carbamate aza-Michael conjugated addition of the Formula B carbamate compound to the Formula A tubuvaline intermediate, which provides the enantiomeric mixture of Formula AB tubuvaline intermediates. Without being bound by theory, a preferred counter anion of the transition metal comprising that catalyst contributes to its solubilization while binding weakly enough to the transition (II) or transition (III) metal to allow for complexation to the Formula A tubuvaline intermediates and/or Formula B carbamate compound for activation so as to promote the conjugate addition to form the enantiomeric mixture of Formula AB tubuvaline intermediates, or composition thereof. For that purpose, a preferred counteranion of a transition metal (II) or transition (III) metal comprising the catalyst is -OTf, —SbF$_5$ or —Cl, more preferably -OTf. Accordingly, a preferred transition metal catalyst is comprised of Cu(OTf)$_2$ or Yb(OTf)$_3$ with Cu(OTf)$_2$ more preferred. A preferred polar, apolar solvent will not unduly interfere with that complexation by competing off the transition metal from the reactant(s) due to its own interaction with the transition metal. For that purpose, a preferred polar, aprotic solvent is dichloromethane (CH$_2$Cl$_2$). In preferred embodiments, $R^3$ is methyl, ethyl or propyl and $R^6$ is a unsubstituted saturated $C_1$-$C_6$ alkyl, in particular, methyl, ethyl or isopropyl. In preferred embodiments, the carboxylic acid protecting group provided by —OR$^7$ is removable by a hydrolysis agent under conditions that would not result to any appreciable extent in removal of the $R^1$—OC(=O)— nitrogen protecting group. In other embodiments, $R^1$ is selected so that the $R^1$—OC(=O)— nitrogen protecting group can be subsequently removed when desired under acid conditions, by a weakly nucleophillic basic amine or in the presence of a Pd or Pt catalyst without appreciable or undesired loss of other functional and/or protecting group(s), which may be present in, or subsequently introduced, into compounds, or intermediates thereof, prepared by, or involved in, other methods of the invention.

In some embodiments, the methods further include the step of separating the two enantiomers, each optionally in salt form, represented by Formula AB to obtain the enantiomer having the (R)-configuration at the carbon atom substituted by $R^6$, which is sometimes indicated as (R)-Formula AB, substantially or essentially free of the other enantiomer, which is sometimes indicated as (S)-Formula AB. In other embodiments, an enantiomeric mixture of Formula AB tubuvaline intermediates, or compositing thereof, is carried forward in subsequent step(s) in methods described herein for preparing a tubuvaline compound.

In any one of the foregoing embodiments, the circled Ar moiety of the Formula A and Formula AB tubuvaline intermediates is a $C_5$ 1,3-heteroarylene, optionally in salt form and optionally substituted at the remaining positions, including, but without limitation, a $C_5$ 1,3-heteroarylene related to thiazole, isoxazole, pyrazole or imidazole as the parent heterocycle, preferably thiazole or oxazole, more preferably thiazole. Accordingly, other embodiments provided herein are methods for preparing a mixture of Formula AB tubuvaline intermediates represented by the structure of

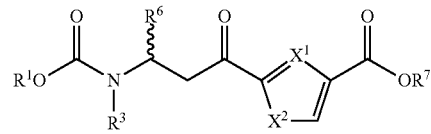

or a composition comprised or consisting essential of these intermediates, each optionally in salt form, by a carbamate aza-Michael conjugate addition to a Formula A tubuvaline intermediate having the structure of:

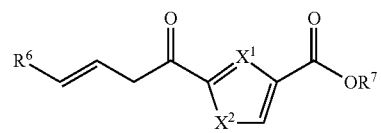

optionally in salt form, wherein in each one of these structures $X^1$ is =N— and $X^2$ is S, O, or N($R^{X2}$)—, or $X^1$ is =C($R^{X1}$)— and $X^2$ is N$R^{X2}$, wherein $R^{X1}$ and $R^{X2}$ are independently selected from the group consisting of —H and optionally substituted $C_1$-$C_4$ alkyl, preferably from the group consisting of —H, —CH$_3$ and —CH$_2$CH$_3$, by a Formula B carbamate compound having the structure of $R^3NHC(O)OR^1$; wherein the variable groups retain their previous meanings from Formula A and Formula B. In preferred embodiments, the circled Aryl is thizaol-1,3-di-yl.

In more preferred embodiments, the Formula A tubuvaline intermediate and the Formula B carbamate compound have the structures of:

and

-continued

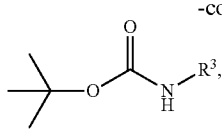

respectively, so that the Formula AB composition obtained from the transition metal catalyzed carbamate aza-Michael reaction is comprised or consists essentially of a mixture of enantiomers represented by the structure of:

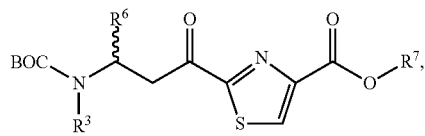

each optionally in salt form, wherein $R^3$, $R^6$ and $R^7$ are as previously defined for Formula A and Formula B, and are preferably independently $C_1$-$C_4$ saturated alkyl.

In particularly preferred embodiments, the Formula AB composition so prepared is comprised or consists essentially of a mixture of enantiomers represented by the structure of:

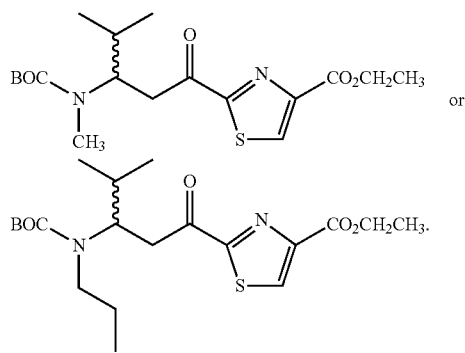

2.2 Tubuvaline Compounds

2.2.1 Embodiment Group 2

In a second group of embodiments, methods are provided for preparing a tubuvaline compound having the structure of:

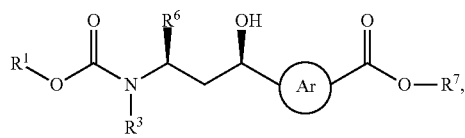

or a composition comprised or consists essentially of that compound, optionally in salt form, which has the (1R,3R)-configuration, sometimes indicated as (R,R)-Formula 1a, in which $R^6$ and the hydroxyl functional group are both in the R-configuration, wherein: the circled Ar is a 1,3-phenylene or a 5- or 6-membered nitrogen-containing 1,3-heteroarylene, optionally substituted at the remaining positions; $R^1$ is phenyl, t-butyl, 9-fluorenyl or allyl, optionally substituted, or other moeity so that $R^1$—OC(=O)— is a suitable nitrogen protecting group; $R^3$ is optionally substituted saturated $C_1$-$C_8$ alkyl, optionally substituted unsaturated $C_3$-$C_8$ alkyl, optionally substituted $C_3$-$C_8$ carbocyclyl or optionally substituted $C_3$-$C_8$ heteroalkyl; $R^6$ is optionally substituted saturated $C_1$-$C_8$ alkyl or optionally substituted unsaturated $C_3$-$C_8$ alkyl; and $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moeity so that $R^7$—O— provides for a suitable carboxylic acid protecting group, the method comprising the steps of:

(a) contacting a tubuvaline intermediate of Formula A:

(A)

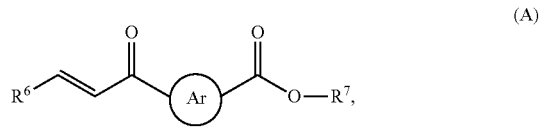

with a carbamate compound of Formula B having the structure of $R^3NHC(O)OR^1$, in a suitable polar, aprotic solvent in the presence of a suitable transition metal (II) or transition metal (III) catalyst, in particular, one comprising a transition metal selected from the group consisting of Cu(II), Zn(II) and Yb(III), so as to form an enantiomeric mixture of tubuvaline intermediates, each optionally in salt form, or a composition comprised or consisting essentially of that mixture, represented by Formula AB:

(AB)

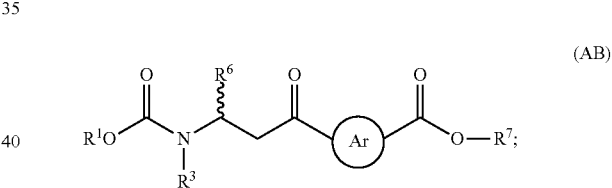

and (b) contacting the enantiomeric Formula AB tubuvaline intermediates, or composition comprised or consisting essentially of these intermediates or salts thereof, with a suitable reducing agent, in particular, a chiral reducing agent, so as to form a mixture of two tubuvaline diastereomers, each optionally in salt form, or a composition comprising or consisting essentially of that mixture, represented by the structure of Formula R-1a:

(R-1a)

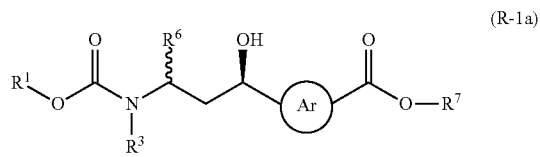

said structure indicating that the hydroxyl functional group is in the R-configuration, and wherein remaining variable groups of Formulae A, B, AB and R-1a are as defined for (R,R)-Formula 1a.

A suitable reducing agent will comprise a hydrogen donor typically used for ketone reduction, preferably one compatible with ester, amide and carbamate functional groups that are desired to be maintained. For that purpose, a suitable reducing agent will preferably be a boron hydrogen donor, including but not limited to hydroboranes and borohydride alkali metal salts, more preferably the boron hydrogen donor is $BH_3$, preferably complexed with a ligand. Due to introduction of a new chiral center as a result of the ketone reduction, a composition containing a mixture of two diastereomers and their enantiomeric impurities is generally expected and will thus be comprised of variable amounts of the (R,R)-Formula 1a diastereomer relative to the total amount of the optical isomers in the composition. Thus, in more preferred embodiments, a chiral ligand is chosen for complexation with $BH_3$ so as to predominately provide a diastereomeric mixture, or composition thereof, represented by (1R,3R)- and (1R,3S)-Formula 1a, which is sometimes indicated as (R,R)- and (R,S)-Formula 1a, respectively. For that purpose, particularly preferred chiral ligands, which are commonly referred to as (S)-(−)-CBS ligands, for complexation with $BH_3$ have the structure of:

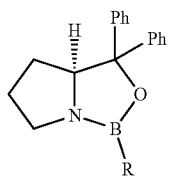

wherein R is —H, $C_1$-$C_6$ saturated alkyl or optionally substituted phenyl, preferably methyl, butyl, phenyl, 4-methylphenyl, 4-fluorophenyl, 4-tri-fluoromethyl-phenyl, 3,5-difluorophenyl, 3,4,5-trifluorophenl or 2,4,6-trifluorophenyl, with methyl especially preferred. Methods for selecting the appropriate (S)-(−)-CBS ligand for achieving reduction with the desired stereochemical outcome for the carbon atom to which the resulting hydroxyl functional group is attached is taught in general by Korenaga, T. et al. *J.C.S. Chem. Comm.* (2010) 46: 8624-8626.

Step (b) is preferably conducted in toluene or a weakly coordinating polar, aprotic solvent such as $CH_2Cl_2$, THF or dioxane, or a mixture of $CH_2Cl_2$/THF or $CH_2Cl_2$/dioxane, by admixing a solution of $BH_3$—$SMe_2$ with solution of (S)-(−)-CBS ligand at a temperature between about −10° C. to about 4° C., preferably about −4° C. or about 0° C., followed by about 5 min. to about 30 min., preferably about 15 min. or about 10 min., so as to form the desired chiral reducing agent then cooling the chiral reducing agent to between about −20° C. to about −50° C., preferably about −40° C., whereupon a solution of the Formula AB tubuvaline intermediate mixture is added while substantially maintaining the original temperature of the chiral reducing agent, followed by stirring of the resulting reaction mixture until consumption of the enantiomeric Formula AB tubuvaline intermediates is substantially or essentially complete. Preferably, a molar excess of between about 5% to about 10% of the chiral reducing agent is used to achieve that consumption.

Preferred substituents for variable groups in Formula A and Formula B, and thus of Formula AB and Formula R-1a, and other preferred reagents of the method are as described for the afore-described first group of embodiments.

In some of the embodiments, the method further includes the step of separating the Formula AB enantiomers to obtain the enantiomer, optionally in salt form, having the (R)-configuration at the carbon atom substituted by $R^6$, which is indicated as (R)-Formula AB, substantially or essentially free of the other enantiomer, which is indicated as (S)-Formula AB. In other embodiments, an enantiomer mixture, or composition thereof, of Formula AB tubuvaline intermediates is carried forward into step (b) and the Formula R-1a tubuvaline intermediate mixture, or composition thereof, resulting therefrom contains the diastereomer having the (1R,3R)-configuration, which is sometimes indicated as (R,R)-Formula 1a, in which the carbon atom substituted by $R^6$ is in the (R)-configuration and the carbon atom substituted by —OH is in the (R)-configuration, and is separated from the diastereomer having the (1R,3S)-configuration, which is sometimes indicated as (R,S)-Formula 1a and in which the carbon atom substituted by $R^6$ is in the (S)-configuration and the carbon atom substituted by —OH is in the (R)-configuration to provide a composition in which the (R,R)-Formula 1a diastereomer is the predominate optical isomer. In those embodiments, the major optical isomer impurity, if optical impurity(ies) are present in the composition, is preferably the enantiomer of that diastereomer, sometimes indicated as (S,S)-Formula 1a whose variable groups are the same as for (R,R)-Formula 1a and having the structure of:

(S,S-1a)

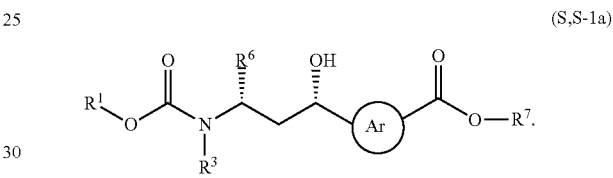

In preferred embodiments, chiral reduction of a composition comprised or consisting essentially of an enantiomeric mixture of tubuvaline intermediates, which is represented by Formula AB, of step (b) is conducted so as to provide a composition comprised or consisting essentially of a diastereomeric mixture of the (R,R)- and (R,S)-Formula 1a tubuvaline compounds, in particular one having 10% w/w or less, 5% w/w or less or 3% w/w or less combined weight of their respective (S,S)- and (S,R)-Formula 1a enantiomers of the two diastereomers in comparison to the combined amounts of the (S,S)-, (S,R)-, (R,R)- and (R,S)-Formula 1a optical isomers. In other preferred embodiments, separation of the two diastereomers following chiral reduction of step (b) of the enantiomeric mixture represented by Formula AB, or the composition comprised or consisting essentially of that mixture, sometimes indicated as step (b'), provides a composition comprised or consisting essentially of the desired (R,R)-Formula 1a tubuvaline diastereomer in diastereomeric excess (d.e.) of at least 80%, 90%, 95% or 97% relative to the (R,S)-Formula 1a diastereomeric optical impurity or is substantially or essentially free of that diastereomer and having no more than about 5% w/w, about 3% w/w of the other Formula 1a optical impurities, or the composition of the desired (R,R)-Formula 1a tubuvaline diastereomer has about 1.5% w/w of the (S,S)-Formula 1a enantiomeric optical impurity and less than a combined weight of about 3% w/w, about 1% w/w or about 0.5% w/w of the other optical impurities, which have the structures of (S,R)- and (R,S)-Formula 1a, relative to the total amount of the optical isomers in the composition.

In especially preferred embodiments, diastereomeric separation by chromatography in step (b') following chiral reduction of step (b) provides a composition comprised or consisting essentially of the desired (R,R)-Formula 1a tubuvaline diastereomer, no more than about 3% w/w or about 1.5% w/w of its enantiomeric optical impurity, which has the structure of (S,S)-Formula 1a and is related in structure to Formula R-1a in which $R^6$ in the S-configuration and the stereochemistry of its hydroxyl group is inverted to the S-configuration, relative to the total amount of optical isomers present in the composition, and is essentially free of the other optical impurities, which have the structures of (S,R)- and (R,S)-Formula 1a.

In any one of the foregoing second group of embodiments, the circled Ar moiety of the Formula A and Formula AB tubuvaline intermediates and the Formula R-1a tubuvaline compound is a $C_{58}$ heteroarylene, optionally in salt form, including without limitation a $C_5$ heteroarylene related to thiazole, isoxazole, pyrazole or imidazole as the parent heterocycle, preferably thiazole or isoxazole, more preferably thiazole. Accordingly, preferred embodiments provided herein are methods for preparing a (R,R)-Formula 1a tubuvaline compound, optionally in salt form, or a composition comprised or consisting essentially of that compound, having the structure of:

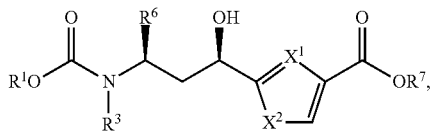

which is prepared from an enantiomeric mixture of Formula AB tubuvaline intermediates, or a composition comprised or consisting essential of these enantiomers, each optionally in salt form, represented by the structure of:

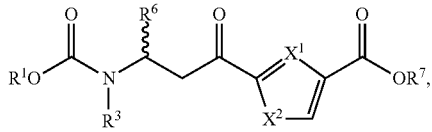

which in turn is prepared from a transition metal catalyzed aza-Michael conjugate addition to a Formula A tubuvaline intermediate, optionally in salt form, having the structure of:

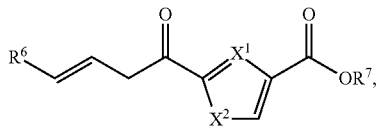

wherein in each one of these structures $X^1$ is =N— and $X^2$ is S, O, or $N(R^{X2})$, or $X^1$ is =$C(R^{X1})$— and $X^2$ is $NR^{X2}$, wherein $R^{X1}$ and $R^{X2}$ are independently selected from the group consisting of —H and optionally substituted $C_1$-$C_4$ alkyl, preferably from the group consisting of —H, —$CH_3$ and —$CH_2CH_3$, by a carbamate compound of Formula B having the structure of $R^3NHC(O)OR^1$; and wherein remaining variable groups retain their previous meanings from Formulae A, B and AB, and R-1a an optical isomers thereof. In preferred embodiments, the circled Aryl is thizaol-1,3-di-yl.

In more preferred embodiments, the Formula A tubuvaline intermediate and the Formula B carbamate compound have the structures of:

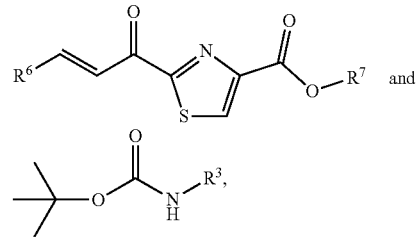

respectively, so that the Formula AB composition from the transition metal catalyzed carbamate aza-Michael reaction of step (a) is a mixture of enantiomers represented by the structure of:

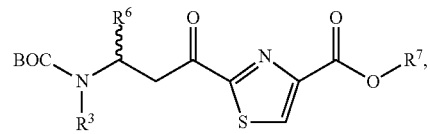

and the composition from chiral reduction of step (b) is comprised or consists essentially of a mixture of two diastereomers represented by the structure of Formula R-1a:

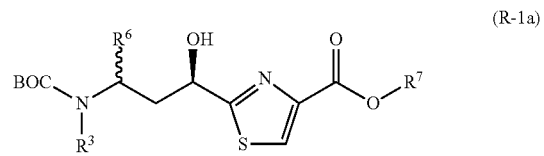

(R-1a)

in which the (R,R)- and (R,S)-Formula 1a tubuvaline diastereomers together are the predominate optical isomers, and wherein $R^3$, $R^6$ and $R^7$ are as previously defined and are preferably independently selected $C_1$-$C_4$ saturated alkyl.

After separation of the diastereomers obtained from step (b) a composition is obtained having the (R,R)-Formula 1a diastereomer as the predominate optical isomer with the major optical isomer impurity, if optical impurity(ies) are present, preferably being its enantiomer, which is the (S,S)-Formula 1a optical isomer having the structure of:

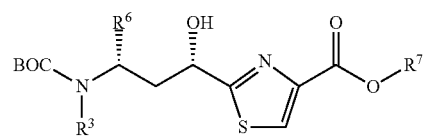

In particularly preferred embodiments, the Formula AB composition from step (a) is comprised or consists essentially of a mixture of enantiomers, or a composition comprised or consisting essentially of that mixture, represented by the structure of:

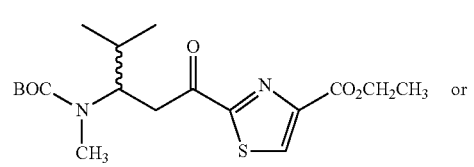

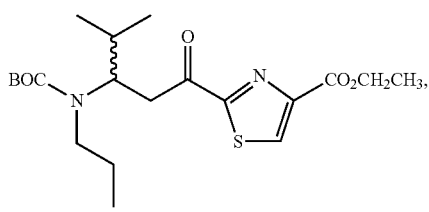

and the Formula R-1a diastereomeric composition from step (b), without prior separation of the Formula AB enantiomeric precursors, is comprised or consists essentially of a mixture of two tubuvaline diastereomeric compounds represented by the structure of:

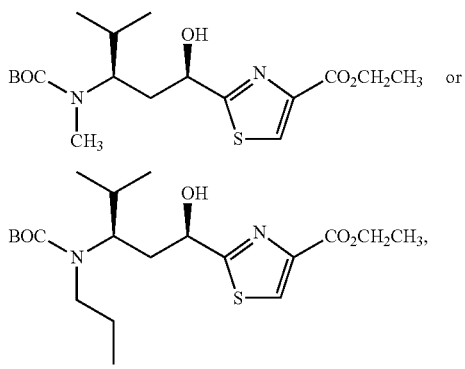

and its corresponding (R,S)-diastereomer having the structure of:

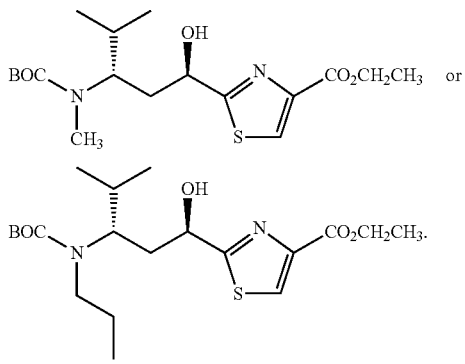

In other particularly preferred embodiments, separation of the diastereomers from the composition obtained from step (b) is performed, wherein the (R,R)-diastereomer, which is ethyl 2-((1R,3R)-3-((tert-butoxycarbonyl)(methyl)-amino)-1-hydroxy-4-methylpentyl)thiazole-4-carboxylate or ethyl 2-((1R,3R)-3-((tert-butoxycarbonyl)-(propyl) amino)-1-hydroxy-4-methylpentyl)thiazole-4-carboxylate, provides the (R,R)-diastereomer or composition thereof substantially or essentially free of its corresponding (R,S)-diastereomer in which the (S,S)-enantiomer of the corresponding (R,R)-diastereomer, if optical impurity(ies) are present, is preferably the major optical isomer impurity, which has the structure of:

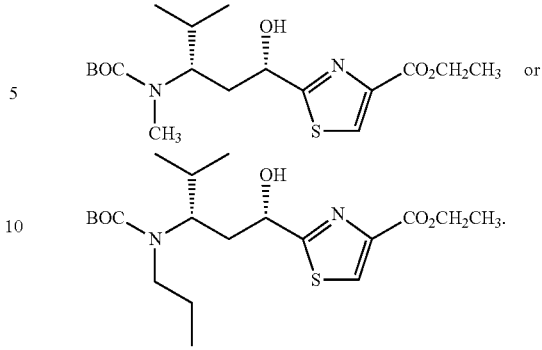

In especially preferred embodiments, the composition from chiral reduction of step (b) prior to separation of the (R,R)- and (R,S)-diastereomers has no more than about 5%, about 3%, about 1.5% or about 1% w/w of the (S,S)-Formula 1a optical impurity and less than about 5%, about 3%, about 1.5% or about 1% w/w of the other optical impurity, which has the structure of (S,R)-Formula 1a, in comparison to the total amount of the optical isomers in the composition in which the predominate optical isomers are ethyl 2-((1R,3R)- and 2((1R,3S)-3-((tert-butoxycarbonyl)(methyl)amino)-1-hydroxy-4-methylpentyl)thiazole-4-carboxylate or ethyl 2-((1R,3R)- and 2-((1R,3S)-3-((tert-butoxycarbonyl)(propyl)amino)-1-hydroxy-4-methylpentyl) thiazole-4-carboxylate.

In other especially preferred embodiments, chiral reduction followed by separation of the (R,R)- and (R,S)-Formula 1a diastereomers by chromatography provides a composition essentially consisting of the desired (R,R)-Formula 1a diastereomer and no more than a combined amount of the (R,S)-Formula 1a diastereomeric impurity and the other optical impurities, which have the structures of (S,S)-Formula 1a and (S,R)-Formula 1a, of about 3% or about 1.5% w/w in comparison to the total amount of the optical isomers of the composition in which the predominate optical isomer is ethyl 2-((1R,3R)-3-((tert-butoxycarbonyl)-(methyl)-amino)-1-hydroxy-4-methylpentyl)-thiazole-4-carboxylate or ethyl 2-((1R,3R)- or 2-((1R,3R)-3-((tert-butoxycarbonyl)-(propyl)amino)-1-hydroxy-4-methylpentyl)-thiazole-4-carboxylate, or is essentially free of the (R,S)- and (S,R)-Formula 1a optical impurities.

2.2.2 Embodiment Group 3

In a third group of embodiments, methods are provided for preparing a Formula 2 tubuvaline compound with the (1R,2R)-configuration having the structure of:

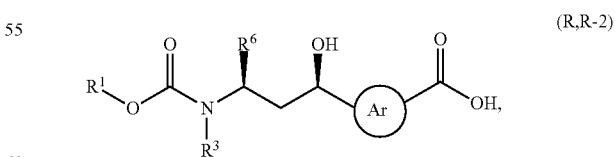

(R,R-2)

optionally in salt form, sometimes indicated as (R,R)-Formula 2, or a composition comprised or consisting essentially of that intermediate, wherein: the circled Ar is a 1,3-phenylene or a 5- or 6-membered nitrogen-containing 1,3-heteroarylene, optionally substituted at the remaining positions; $R^1$ is phenyl, t-butyl, 9-fluorenyl or allyl, optionally substituted, or other moiety so that R¹—OC(=O)— is a suitable nitrogen protecting group; R³ is optionally substituted saturated $C_1$-$C_8$ alkyl, optionally substituted unsaturated $C_3$-$C_8$ alkyl, optionally substituted $C_3$-$C_8$ carbocyclyl or optionally substituted $C_3$-$C_8$ heteroalkyl; and R⁶ is optionally substituted saturated $C_1$-$C_8$ alkyl, or optionally substituted unsaturated $C_3$-$C_8$ alkyl, the method comprising the steps of:

(a) contacting a tubuvaline intermediate of Formula A:

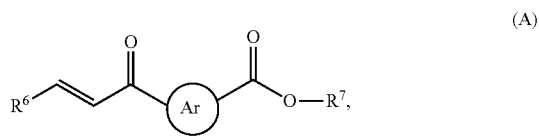

(A)

or a composition comprised or consisting essentially of that intermediate, optionally in salt form, wherein R⁷ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moiety so that R⁷—O— provides for a suitable carboxylic acid protecting group, with a carbamate compound of Formula B having the structure of R³NHC(O)OR¹, in a suitable polar, aprotic solvent in the presence of a suitable transition metal (II) or transition metal (III) catalyst, in particular, one comprising a transition metal selected from the group consisting of Cu(II), Zn(II) and Yb(III), so as to form a an enantiomeric mixture of tubuvaline intermediates, each optionally in salt form, or composition comprised or consisting essentially of that mixture, represented by Formula AB:

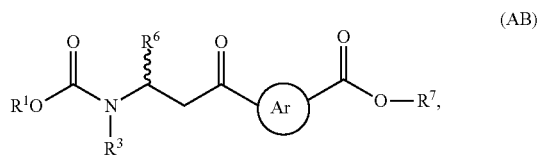

(AB)

(b) contacting the enantiomeric Formula AB tubuvaline intermediates, or a composition comprised or consisting essentially of these intermediates, each optionally in salt form, with a suitable reducing agent, in particular, a chiral reducing agent, so that the Formula R-1a composition from chiral reduction of step (b) is comprised or consists essentially of a mixture of two tubuvaline diastereomeric compounds, each optionally in salt form, represented by the structure of:

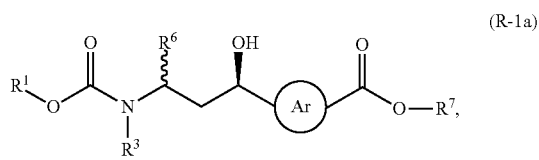

(R-1a)

in which the (1R,3R)- and (1R,3S)-Formula 1a tubuvaline diastereomers, sometimes indicated as (R,R)- and (R,S)-Formula 1a, together are the predominate optical isomers; and (c) contacting the Formula 1a tubuvaline diastereomers, or composition comprised or consisting essentially of these diastereomers, each optionally in salt form, with a suitable hydrolysis agent so as to form a mixture of Formula R-2 tubuvaline diastereomers represented by the structure of:

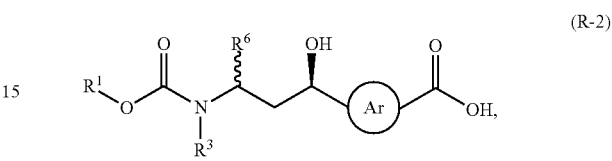

(R-2)

or composition comprised or consisting essentially of these diastereomers, each optionally in salt form, wherein the (1R,3R)- and (1R,3S) Formula 2 tubuvaline diastereomers, sometimes indicated as (R,R)- and (R,S)-Formula 2, together are the predominate optical isomers, and wherein the remaining variable group(s) of Formulae A, B, and AB and Formula R-1a and optical isomers thereof are as defined for (R,R)-Formula 2.

In more preferred embodiments, a suitable hydrolysis agent is one capable of removing the carboxylic acid protecting group provided by —OR⁷ under conditions that would not result to any appreciable extent in removal of the R¹—OC(=O)— nitrogen atom protecting group, such as a solution of an alkali metal hydroxide salt, including but not limited to LiOH monohydrate in water at between about −10° C. to about 10° C., preferably about −4° C. to about 5° C., more preferably at about 0° C. For those preferred embodiments, R⁷ is preferably methyl or ethyl.

Other preferred substituents for variable groups in Formula A and Formula B, and thus of Formula AB, and Formula R-1a, (R,R)-Formula 2 and corresponding optical isomers thereof, and other preferred reagents and conditions for the method are as described for the first and second group of embodiments.

In some of the embodiments, the method further includes the step of separating the enantiomers of Formula AB to obtain the enantiomer having the (R)-configuration at the carbon atom substituted by R⁶, which is sometimes indicated as (R)-Formula AB, substantially or essentially free of the other enantiomer, which is indicated as (S)-Formula AB.

In preferred embodiments, an enantiomeric mixture of Formula AB tubuvaline intermediates or composition thereof is carried forward into step (b) and the Formula R-1a tubuvaline compounds resulting therefrom containing the diastereomer having the (1R,3R)-configuration, which is sometimes indicated as (R,R)-Formula 1a and in which the carbon atom substituted by R⁶ is in the (R)-configuration and the carbon atom substituted by —OH is in the (R)-configuration, is separated from the diastereomer having the (1R,3S)-configuration, which is sometimes indicated as (R,S)-Formula 1a and in which the carbon atom substituted by R⁶ is in the (S)-configuration and the carbon atom substituted by —OH is in the (R)-configuration. In preferred embodiments, that separation, sometimes indicated as step (b'), provides a composition having the (R,R)-Formula 1a tubuvaline compound in diastereomeric excess (d.e.) of at least about 85%, about 90%, about 95% or about 97% relative to its diastereomer having the structure (R,S)-Formula 1a, or is substantially or essentially free of the (R,S)-Formula 1a diastereomer. In other preferred embodiments, the composition from diastereomeric separation has the (R,R)-Formula 1a tubuvaline compound in diastereomeric excess (d.e.) of at least about 95% or about 97% relative to the (R,S)-Formula 1a diastereomer or is substantially or essentially free of the (R,S)-Formula 1a diastereomer and, if optical impurity(ies) are present, preferably has the (S,S)-Formula 1a optical isomer, which is the enantiomer of the predominate optical isomer (R,R)-Formula 1a, as the major optical impurity.

In other embodiments, separation of diastereomers is delayed until after step (c) to provide the (R,R)-Formula 2 tubuvaline compound in d.e. of at least about 85%, about 90%, about 95% or about 97% relative to the diastereomer having the structure of (R,S)-Formula 2 or is essentially free of that diastereomer, wherein that delayed separation is sometimes indicated as step (c'). In preferred embodiments, the composition from diastereomeric separation has the (R,R)-Formula 2 tubuvaline intermediate in diastereomeric excess (d.e.) of at least about 95% or about 97% relative to the (R,S)-Formula 2 diastereomer or is substantially or essentially free of that diastereomer and has the (S,S)-Formula 2 optical isomer as the major optical impurity, if optical impurity(ies) are present, which is the enantiomer of the predominate optical isomer that has the structure of (R,R)-Formula 2.

In more preferred embodiments, chiral reduction of step (b) of the Formula AB enantiomers is conducted so as to provide a composition comprised or consisting essentially of a diastereomeric mixture of the (R,R)-Formula 1a and (R,S)-Formula 1a tubuvaline compounds having a total weight no more than about 10% or less, about 5% or less or about 3% or less of their respective (1S,3S)-Formula 1a and (1S,3R)-Formula 1a enantiomers, sometimes referred to as (S,S)- and (S,R)-Formula 1a, respectively, relative to the total weight of the Formula 1a optical isomers of the composition. In other preferred embodiments, in absence of separating diastereomers following step (b), or in absence of that separation following step (b) and step (c) in combination with the chiral reduction of step (b), provides a composition comprised or consisting essentially of (R,R)- and (R,S)-Formula 1a or (R,R)- and (R,S)-Formula 2 diastereomers and no more than about 5% w/w, about 3% w/w or about 1.5% w/w of the enantiomeric (S,S)-Formula 1a or (S,S)-Formula 2 optical impurity and no more than about 5% w/w, about 3% w/w or about 1.5% w/w of the other (R,S)-Formula 1a or (R,S)-Formula 2 optical impurity relative to the total weight of the optical isomers of the composition, in which the (R,R)- and (R,S)-Formula 1a diastereomers together or the (R,R)- and (R,S)-Formula 2 diastereomers together are the predominate optical isomers.

In other preferred embodiments separation of diastereomers following step (b) chiral reduction or following step (b) chiral reduction and step (c) hydrolysis is conducted to provide a composition of (R,R)-Formula 1a or (R,R)-Formula 2 optical isomers having less than a combined weight of about 3% w/w, about 1% w/w or about 0.5% w/w of the other (S,R)- and (R,S)-Formula 1a or (S,R)- and (R,S)-Formula 2 optical impurities relative to the total weight of the optical isomers of the composition in which (R,R)-Formula 1a or (R,R)-Formula 2 is the predominate optical isomer.

In particularly preferred embodiments, the diastereomeric mixture in the Formula R-1a composition obtained after chiral reduction of step (b), and in absence of diastereomeric separation, is substantially or essentially retained in the Formula R-2 composition, which is obtained from the hydrolysis of step (c), whereupon the (R,R)- and (S,R)-Formula 2 diastereomers are separated to provide a composition comprised or consisting essentially of the (R,R)-Formula 2 tubuvaline compound substantially or essentially free of the corresponding (R,S)-Formula 2 diastereomer.

In other particularly preferred embodiments, the Formula R-1a composition obtained from chiral reduction of step (b) is followed by separation of the diastereomers, sometimes indicated as step (b') to provide a composition comprised or consisting essentially of the (R,R)-Formula 1a diastereomer that is substantially or essentially free of the corresponding (R,S)-Formula 1a diastereomer, and the (R,R)-Formula 2 diastereomer subsequently obtained from the hydrolysis of step (c) substantially or essentially retains that diastereomeric purity.

In especially preferred embodiments, separation of the diastereomers by chromatography in step (b') following chiral reduction of step (b) is conducted to provide a composition having the desired (R,R)-Formula 1a tubuvaline diastereomer, no more than about 5%, about 3%, or about 1.5% w/w of its enantiomeric optical impurity, which has the structure of (S,S)-Formula 1a, in comparison to the total weight of the Formula 1a optical isomers that are present, and is essentially free of the other (S,R)- and (R,S)-Formula 1a optical impurities, wherein the relative amounts of the (S,S)-, (S,R)- and (R,S)-Formula 1a optical impurities in the composition are essentially retained in the Formula R-2 composition that is obtained from the hydrolysis of step (c).

In any one of the foregoing third group of embodiments, the circled Ar moeity of the Formula A and Formula AB tubuvaline intermediates and the (R,R)-Formula 1a and (R,R)-Formula 2 tubuvaline compounds and optical isomers thereof, each optionally in salt form, is a $C_5$ heteroarylene, including without limitation a $C_5$ heteroarylene related to thiazole, isoxazole, pyrazole or imidazole as the parent heterocycle. Accordingly, other embodiments provided herein are methods for preparing a (R,R)-Formula 2 tubuvaline compound, or a composition comprised or consisting of that compound, optionally in salt form, having the structure of:

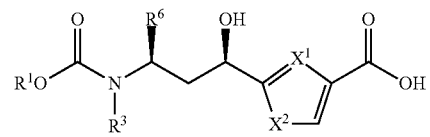

which is prepared from a mixture of tubuvaline diastereomers, or a composition comprised or consisting essentially of these diastereomers, each optionally in salt form, represented by the structure of:

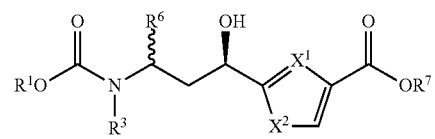

in which the diastereomeric (R,R)-Formula 1a and (R,S)-Formula 1a tubuvaline compounds are the predominate optical isomers, which in turn is prepared from an enantiomeric mixture of Formula AB tubuvaline intermediates, or a composition comprised or consisting essentially of these intermediates, each optionally in salt form, represented by the structure of:

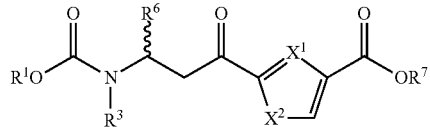

which in turn is prepared by a transition metal catalyzed aza-Michael conjugate addition to a Formula A tubuvaline intermediate, optionally in salt form, having the structure of:

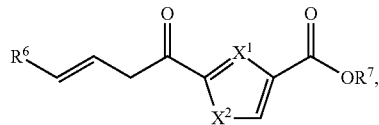

wherein in each one of these structures $X^1$ is =N— and $X^2$ is S, O, or $N(R^{X2})$—, or $X^1$ is $=C(R^{X1})$— and $X^2$ is $NR^{X2}$, wherein $R^{X1}$ and $R^{X2}$ are independently selected from the group consisting of —H and optionally substituted $C_1$-$C_4$ alkyl, preferably from the group consisting of —H, —CH$_3$ and —CH$_2$CH$_3$, by a carbamate compound of Formula B having the structure of $R^3NHC(O)OR^1$; and wherein remaining variable groups retain their previous meanings from Formulae A, B, AB, and Formula R-1a, and (R,R)-Formula 2 and corresponding optical isomers thereof. In preferred embodiments, the circled Aryl is thizaol-1,3-di-yl.

In more preferred embodiments, the Formula A tubuvaline intermediate and the Formula B carbamate compound has the structures of:

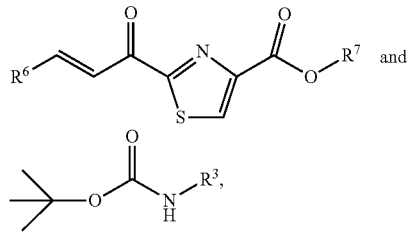

respectively, so that the Formula AB composition from the transition metal catalyzed carbamate aza-Michael reaction of step (a) is comprised or consists essentially of a mixture of enantiomeric tubuvaline intermediates represented by the structure of:

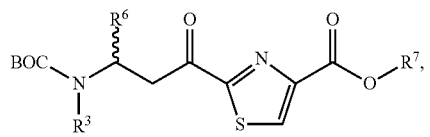

each optionally in salt form, and the Formula R-1a composition from chiral reduction of step (b) is comprised or consists essentially of a mixture of two diastereomers represented by the structure of:

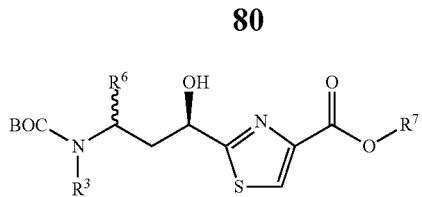

each optionally in salt form, wherein the (R,R)-Formula 1a and (R,S)-Formula 1a diastereomers together are the predominate optical isomers, and the Formula R-2 composition from hydrolysis of step (c) is comprised or consists essentially of a mixture of two diastereomers represented by the structure of:

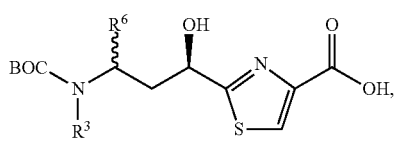

each optionally in salt form, wherein the (R,R)-Formula 2 and (R,S)-Formula 2 diastereomers together are the predominate optical isomers, and wherein $R^3$, $R^6$ and $R^7$ are as previously defined and are preferably independently selected $C_1$-$C_4$ saturated alkyl.

In particularly preferred embodiments, the Formula AB tubuvaline intermediate composition from step (a) is comprised or consists essentially of a mixture of enantiomers represented by the structure of:

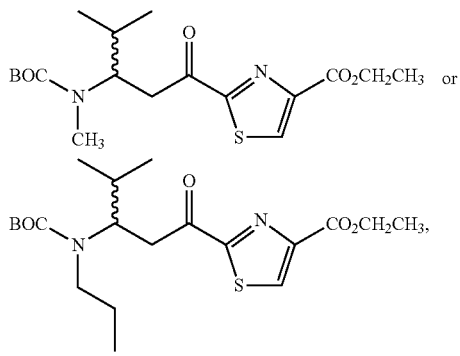

and the Formula R-1a composition from step (b) in absence of diastereomer separation of step (b') is comprised or consists essentially of a mixture of (R,R)-Formula 1a and (R,S)-Formula 1a diastereomers as the predominate optical isomers having the structures of:

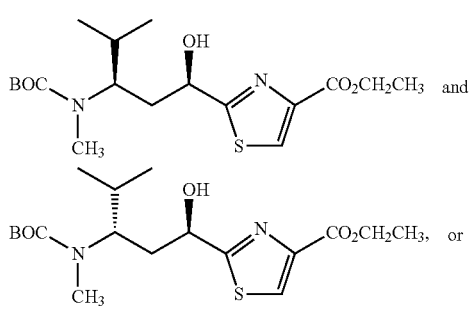

-continued

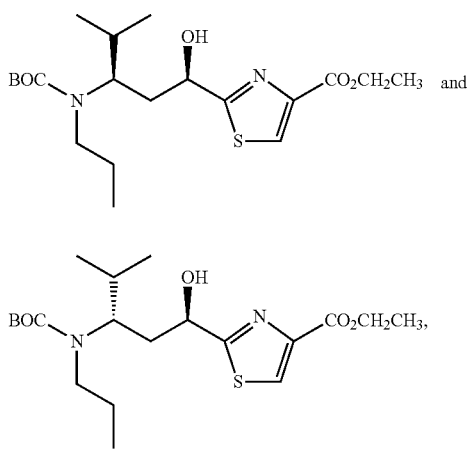

and and the Formula R-2 composition after step (c) in absence of diastereomeric separation of step (b') following step (b) and absence of diastereomeric separation of step (c') following step (c) is comprised or consists essentially of a mixture of (R,R)-Formula 2 and (R,S)-Formula 2 diastereomers, each optionally in salt form, as the predominate optical isomers having the structure of:

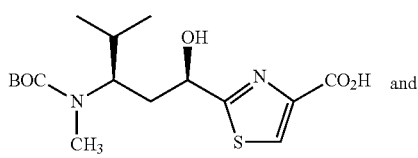 and

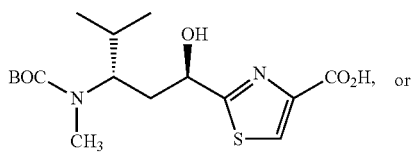 or

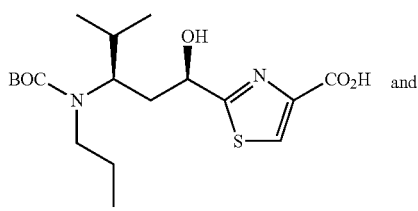 and

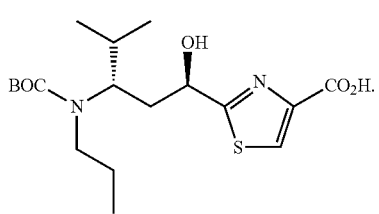

In other particularly preferred embodiments, separation of the (R,R)- and (R,S)-Formula 1a diastereomers by step (b') is conducted to provide a composition comprised or consisting essentially of the (R,R)-Formula 1a diastereomer as the predominate optical isomer having the structure of:

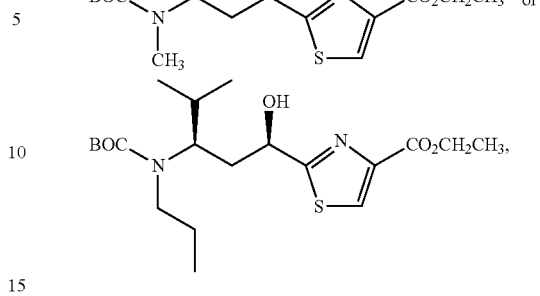 or and if optical impurity(ies) are present, preferably having the enantiomer of that predominate diastereomer as the major optical isomer impurity, wherein that enantiomer has the structure of:

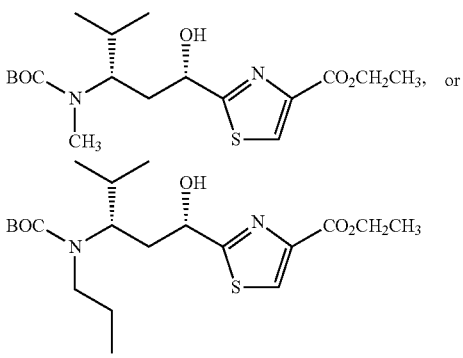

and the Formula 2 composition after step (c) hydrolysis of the (R,R)-Formula 1a diastereomer or composition thereof obtained from step (b') separation of the diastereomeric products from step (b) provides a composition comprised or consisting essentially of the (R,R)-Formula 2 diastereomer, optionally in salt form, as the predominate optical isomer having the structure of:

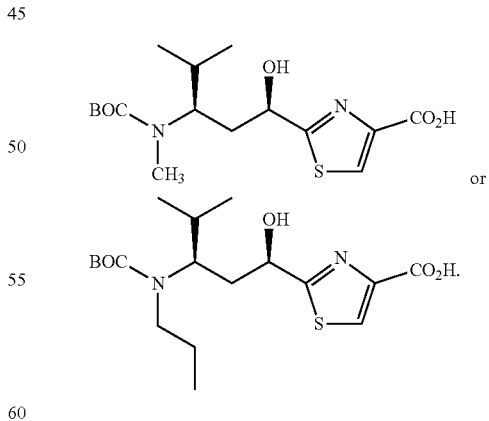

2.2.3 Embodiment Group 4

In a fourth group of embodiments, methods are provided for preparing a tubuvaline compound of Formula 2a in the (1R,3R)-configuration having the structure of:

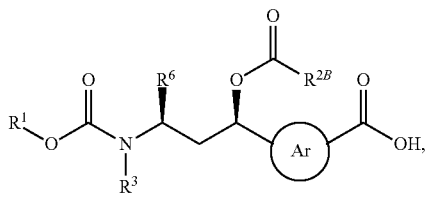

(R,R)-2a optionally in salt form, which is sometimes indicated as (R,R)-Formula 2a, or a composition comprised or consisting essentially of that compound, optionally in salt form, wherein: the circled Ar is a 1,3-phenylene or a 5- or 6-membered nitrogen-containing 1,3-heteroarylene, optionally substituted at the remaining positions;

$R^{2B}$ is optionally substituted saturated $C_1$-$C_8$ alkyl, optionally substituted unsaturated $C_3$-$C_8$ alkyl, optionally substituted $C_2$-$C_8$ alkenyl or optionally substituted $C_2$-$C_8$ alkynyl; $R^1$ is phenyl, t-butyl, 9-fluorenyl or allyl, optionally substituted, or other moiety so that $R^1$—OC(=O)— is a suitable nitrogen protecting group; $R^3$ is optionally substituted saturated $C_1$-$C_8$ alkyl, optionally substituted unsaturated $C_3$-$C_8$ alkyl, optionally substituted $C_3$-$C_8$ carbocyclyl or optionally substituted $C_3$-$C_8$ heteroalkyl; and $R^6$ is optionally substituted saturated $C_1$-$C_8$ alkyl or optionally substituted unsaturated $C_{13}$-$C_8$ alkyl, the method comprising the steps of: (a) contacting a tubuvaline intermediate of Formula A:

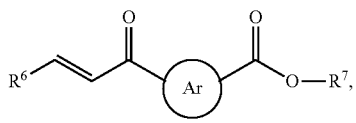

(A)

optionally in salt form, wherein $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moiety so that $R^7$—O— provides for a suitable carboxylic acid protecting group, with a carbamate compound of Formula B having the structure of $R^3NHC(O)OR^1$, in a suitable polar, aprotic solvent in the presence of a suitable transition metal (II) or transition metal (III) catalyst, in particular, one comprising a transition metal selected from the group consisting of Cu(II), Zn(II) and Yb(III), so as to form an enantiomeric mixture of two tubuvaline intermediates, represented by Formula AB:

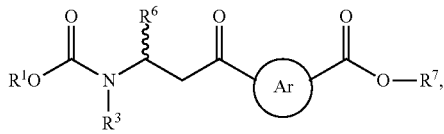

(AB)

or a composition comprised or consisting essentially of these intermediates, each optionally in salt form;

(b) contacting the enantiomeric Formula AB tubuvaline intermediates, or a composition comprised or consisting essentially of these intermediates, or salts thereof, with a suitable reducing agent, so as to form a diastereomeric mixture of tubuvaline compounds represented by the structure of Formula R-1a:

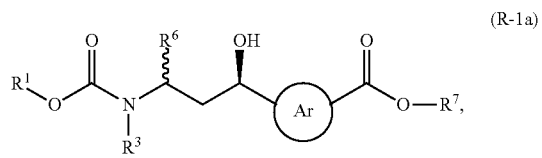

(R-1a)

or a composition comprised or consisting essentially of these diastereomers, each optionally in salt form; and in particular a chiral reducing agent that provides the composition comprised of these diastereomers in which the (1R,3R)- and (1R,3S)-Formula 1a tubuvaline diastereomers, sometimes indicated as (R,R)- and (R,S)-Formula 1a, together are the predominate optical isomers, wherein (R,R)-Formula 1a has the structure of:

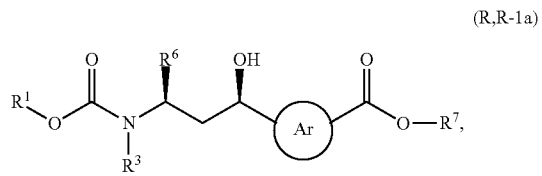

(R,R-1a)

and wherein (R,S)-Formula 1a has the structure of:

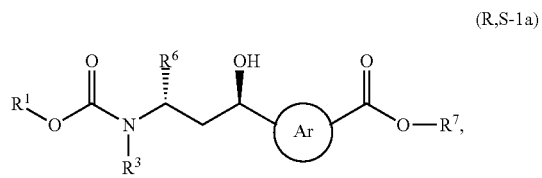

(R,S-1a)

(b') optionally separating the diastereomers from step (b) to obtain the diastereomer, (R,R)-Formula 1a, optionally in salt form, or a composition comprised or consisting essentially of that diastereomer, optionally in salt form, that is substantially or essentially free of the other diastereomer, which is (R,S)-Formula 1a;

(c) contacting the Formula R-1a tubuvaline compound, optionally in salt form, or composition thereof, from step (b) with a suitable hydrolysis agent so as to form a diastereomeric mixture of tubuvaline compounds represented by the structure of Formula

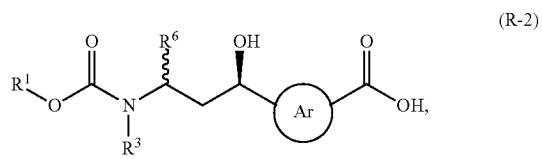

(R-2)

and (c') optionally separating the diastereomers from step (c), or contacting the (R,R)-Formula 1a tubuvaline compound, optionally in salt form, or composition thereof, obtained from step (b') with a suitable hydrolysis agent, so that steps (b') and (c) or steps (b) and (c') provide the corresponding diastereomer having the structure of:

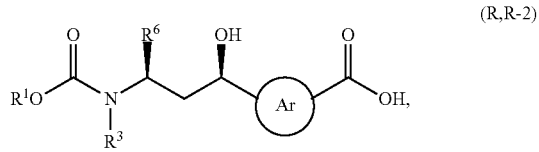

(R,R-2)

optionally in salt form, which has the (1R,3R)-configuration, sometimes indicated as (R,R)-Formula 2, or a composition comprised or consisting essentially of that diastereomer, or salt thereof, in which (R,R)-Formula 2 is the predominate optical isomer, wherein the optical purity of the corresponding composition of (R,R)-Formula 1a, from step (b') is substantially or essentially retained by the (R,R)-Formula 2 composition; and (d) contacting the Formula R-2 composition from steps (c) with a suitable acylating agent so as to form a Formula R-2a composition, or contacting a tubuvaline compound, or a composition comprised or consisting essentially of the diastereomer, represented by (R,R)-Formula 2a, optionally in salt form, from steps (b') and (c) or steps (b) and (c') with a suitable acylating agent wherein the optical purity of the corresponding (R,R)-Formula 1a from step (b') or the optical purity of (R,R)-Formula 2 optical isomer from steps (b') and (c) or steps (b) and (c') is substantially or essentially retained by the (R,R)-Formula 2a composition, wherein the remaining variable groups of Formulae A, B, AB and Formula R-1a and (R,R)-Formula 2 and optical isomers thereof are as defined for (R,R)-Formula 2a, and in absence of diastereomeric separations of steps (c') and (d');

and (d') optionally in absence of the diastereomeric separations of step (b') and (c') separating the Formula R-2a diastereomers to provide (R,R)-Formula 2a, optionally in salt form, or a composition comprised or consisting essentially of that compound, as the predominate optical isomer.

In preferred embodiments, the acylating agent of step (d) has the structure of $R^{2B}C(O)Cl$ or $[R^{2B}C(O)]_2O$, wherein $R^{2B}$ is saturated $C_1$-$C_6$ alkyl, unsaturated $C_3$-$C_8$ alkyl, $C_2$-$C_8$ alkenyl or $C_2$-$C_4$ alkynyl. In those preferred embodiments, $R^{2B}$ is more preferably a branched chain, optionally substituted $C_3$-$C_8$ saturated or unsaturated alkyl, preferably unsubstituted, including but not limited to —$CH(CH_3)_2$, —$CH_2CH(CH_3)_2$, —$CH_2C(CH_3)_3$, —$CH=C(CH_3)_2$ and —$CH_2$—$C(CH_3)=CH_2$.

In other preferred embodiments, $R^{2B}$ in Formula 2a is —$CH_3$, —$CH_2CH_3$, —$CH_2CH_2CH_3$, —$CH_2CH=CH_2$, —$CH_2CH(CH_3)_2$, —$CH_2C(CH_3)_3$, —$CH_2C(CH_3)=CH_2$, —$CH=CH_2$ or —$CHC\equiv CH$, in particular —$CH_3$.

Substituents preferred for other variable groups in Formula A and Formula B, and thus of Formula AB and Formula R-1a, (R,R)-Formula 2 and (R,R)-Formula 2a and corresponding optical isomers thereof, and other preferred reagents and conditions for the method are as described for the first, second and third group of embodiments.

In more preferred embodiments, chiral reduction in step (b) of the Formula AB enantiomers is conducted so as to provide a composition comprising or consisting essentially of a diastereomeric mixture of (R,R)-Formula 1a and (R,S)-Formula 1a tubuvaline compounds, each optionally in salt form, in particular one having about 10% w/w, about 5% w/w, about 3% w/w or less or 1.5% w/w by weight of their respective (S,S)- and (S,R)-Formula 1a enantiomers in comparison to the total amount of the Formula 1a optical isomers of the composition. In other preferred embodiments, the diastereomer separation of step (b') provides a composition having the diastereomer of structure (R,R)-Formula 1a in at least about 90% d.e. at least about 95% d.e. or at least about 97% d.e in relation to the diastereomer having the structure of (R,S)-Formula 1a or is substantially or essentially free of the (R,S)-Formula 1a diastereomer. In other more preferred embodiments, the diastereomeric excess in the (R,R)-Formula 1a composition obtained subsequent to step (b') is substantially or essentially retained in the (R,R)-Formula 2a composition obtained from the hydrolysis and acylation steps of step (c) and step (d), respectively.

In particularly preferred embodiments, the diastereomer separation of step (b') provides a composition having the (R,R)-Formula 1a diastereomer in at least about 90% to about 95% d.e. or at least about 97% d.e in relation to the (R,S)-Formula 1a diastereomer and having (S,S)-Formula 1a, which is the enantiomer of the predominate diastereomer, which has the structure of (R,R)-Formula 1a, as the major optical impurity In other embodiments, the diastereomeric separation of step (b') is replaced by diastereomeric separation after step (c) or step (d), sometimes indicated as step (c') and step (d'), respectively, to provide the (R,R)-Formula 2 or (R,R)-Formula 2a optical isomer, optionally in salt form, or a composition thereof, substantially or essentially free of its corresponding (R,S)-Formula 2a or (R,S)-Formula 2a diastereomer.

In any one of the foregoing fourth group of embodiments, the circled Ar moiety of the Formula A and Formula AB tubuvaline intermediates and the (R,R)-Formula 1a, (R,R)-Formula 2 and (R,R)-Formula 2a tubuvaline compounds and optical isomers thereof, each optionally in salt form, is a $C_5$ heteroarylene, including without limitation a $C_5$ heteroarylene related to thiazole, isoxazole, pyrazole or imidazole as the parent heterocycle. Accordingly, other embodiments provided herein are methods for preparing a (R,R)-Formula 2a tubuvaline compound, or a composition comprised or consisting essentially of that compound, optionally in salt form, having the structure of:

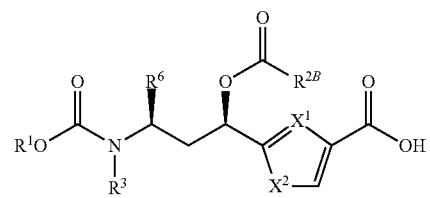

by acylation of a (R,R)-Formula 2 tubuvaline compound, optionally in salt form, having the structure of:

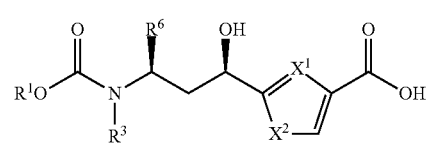

or a composition thereof substantially or essentially free of its corresponding (R,S)-diastereomer, optionally in salt form, which in turn is obtained by separation of a mixture of two Formula R-1a tubuvaline diastereomers represented by the structure of:

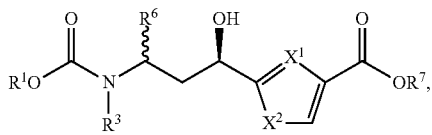

or a composition comprised or consisting essentially of these diastereomers, or salts thereof, which is followed by hydrolysis of the diastereomer, (R,R)-Formula 1a, or composition thereof that is substantially or essentially free of the other diastereomer, which is (R,S)-Formula 1a, optionally in salt form, which in turn is prepared from an enantiomeric mixture of two Formula AB tubuvaline intermediates represented by the structure of:

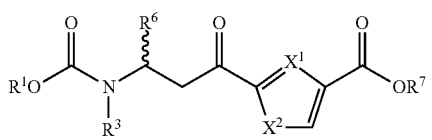

or a composition comprised or consisting essentially of these intermediates, each optionally in salt form, which in turn is prepared from a carbamate aza-Michael conjugate addition of a carbamate compound of Formula B having the structure of $R^3NHC(O)OR^1$, to a Formula A tubuvaline intermediate, optionally in salt form, having the structure of:

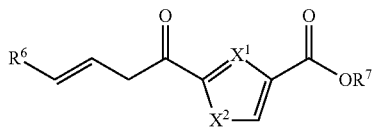

wherein in each one of these structures $X^1$ is =N— and $X^2$ is S, O, or $N(R^{X2})$—, or $X^1$ is =$C(R^{X1})$— and $X^2$ is $NR^{X2}$, wherein $R^{X1}$ and $R^{X2}$ are independently selected from the group consisting of —H and optionally substituted $C_1$-$C_4$ alkyl, preferably from the group consisting of —H, —$CH_3$ and —$CH_2CH_3$, and the remaining variable groups of Formulae A, B and AB, and (R,R)-Formula 1a, (R,R)-Formula 2 and (R,R)-Formula 2a and corresponding optical isomers thereof retain their previous meanings given by (R,R)-Formula 2a. In preferred embodiments, the circled Aryl is thizaol-1,3-di-yl.

In more preferred embodiments, the Formula A tubuvaline intermediate and the Formula B carbamate compound have the structures of:

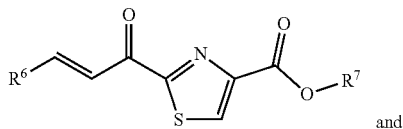

and

-continued

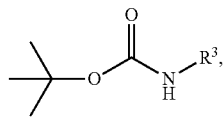

respectively, so that the Formula AB composition from the transition metal catalyzed carbamate aza-Michael reaction of step (a) is comprised or consists essentially of a mixture of two Formula AB enantiomers represented by the structure of:

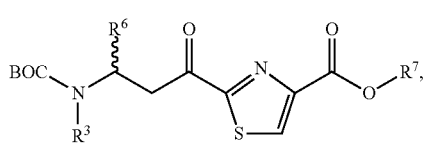

and the Formula R-1a composition from chiral reduction of step (b) is comprised or consists essentially of a mixture of two Formula R-1a diastereomers represented by the structure of:

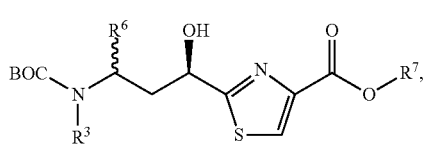

and the Formula R-2 composition from hydrolysis of step (c) is comprised or consists essentially of a mixture of two diastereomers, each optionally in salt form, represented by the structure of:

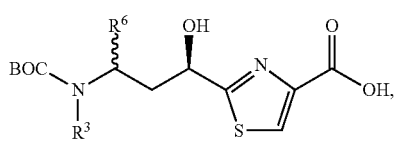

or the Formula R-1a composition from chiral reduction of step (b) is followed by separation of the diastereomers of step (b') to provide a composition comprising or consisting essentially of the diastereomer, (R,R)-Formula 1a, optionally in salt form, as the predominate optical isomer having the structure of:

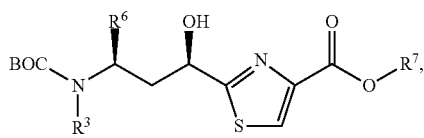

or a composition comprised or consists essentially of that diastereomer substantially or essentially free of its corresponding (R,S)-Formula 1a diastereomer, optionally in salt form, which has the structure of:

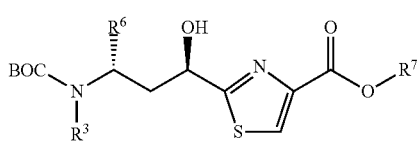

and the composition from hydrolysis of step (c) following step (b') provides a composition comprising or consisting essentially of the diastereomer, (R,R)-Formula 2, optionally in salt form, as the predominate optical isomer having the structure of:

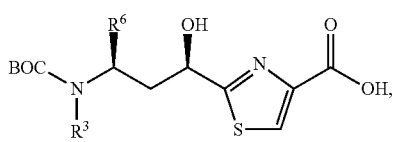

or a composition comprised or consists essentially of that diastereomer substantially or essentially free of its corresponding (R,S)-Formula 2 diastereomer, optionally in salt form, which has the structure of:

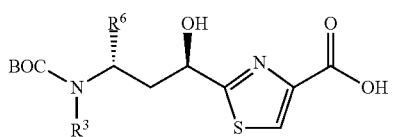

and the composition from acylation of step (d) following step (b) chiral reduction and step (c) hydrolysis in absence of diastereomeric separation of step (b') is comprised or consists essentially of a mixture of two diastereomers, each optionally in salt form, represented by the structure of:

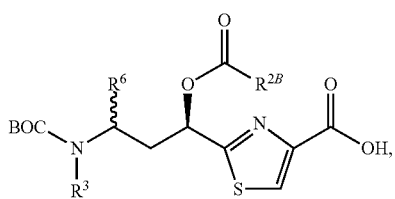

or the composition from acylation of step (d) following step (b) chiral reduction, step (b') diastereomer separation and step (c) hydrolysis has the (R,R)-Formula 2a diastereomer as the predominate optical isomer, optionally in salt form, having the structure of:

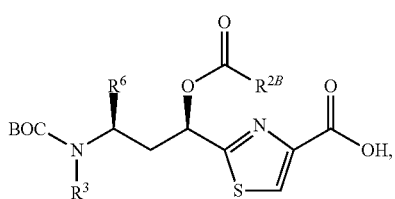

or that composition is comprised or consists essentially of that diastereomer substantially or essentially free of its corresponding (R,S)-Formula 2a diastereomer, optionally in salt form, which has the structure of:

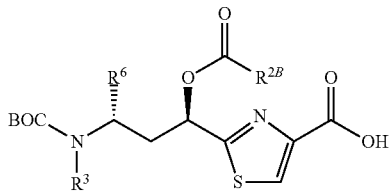

wherein the variable groups of Formulae A, B, AB, Formula R-1a, Formula R-2, and (R,R)-Formula 2 and corresponding optical isomer thereof retain their previous meanings from (R,R)-Formula 2a, for which $R^3$, $R^6$ and $R^7$ are preferably independently selected $C_1$-$C_4$ saturated alkyl.

In particularly preferred embodiments, the Formula AB tubuvaline intermediate composition from step (a) is comprised or consists essentially of a mixture of enantiomers represented by the structure of:

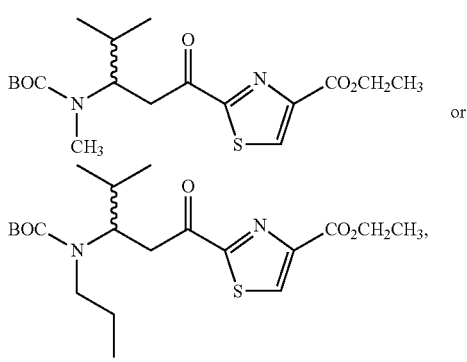

and the Formula R-1a tubuvaline compound composition from step (b) chiral reduction and step (b') diastereomer separation is comprised or consists essentially of the diastereomer, (R,R)-Formula 1a, as the predominate optical isomer having the structure of:

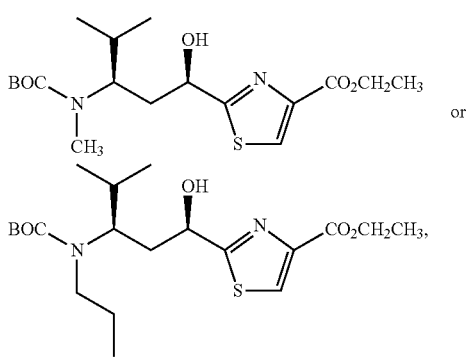

or is comprised or consists essentially of the (R,R)-Formula 1a diastereomer essentially free of its corresponding (R,S)-Formula 1a diastereomer, and the enantiomer of that corresponding diastereomer, (S,R)-Formula 1a, which have the structures of

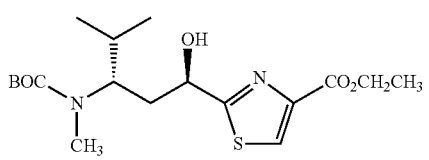

or

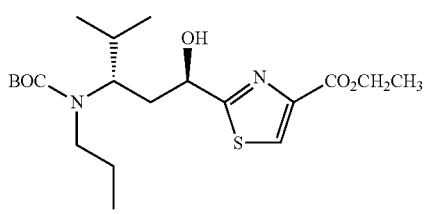

and

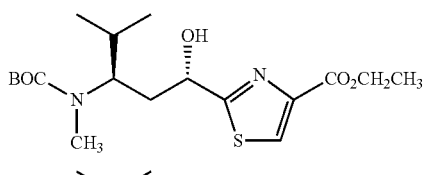

or

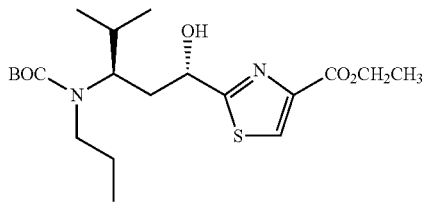

respectively, and if optical impurity(ies) are present, having the (S,S)-Formula 1a optical isomer as the major optical impurity, which has the structure of:

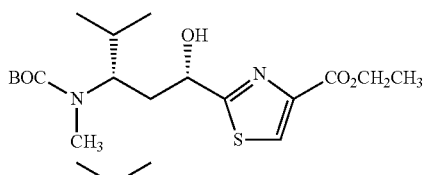

or

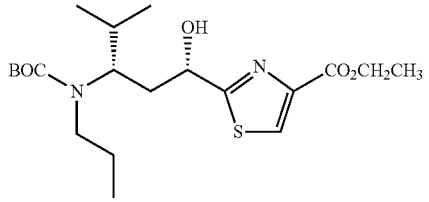

and the tubuvaline composition from step (c) hydrolysis, following step (b) chiral reduction and step (b') diastereomer separation is comprised or consists essentially of the (R,R)-Formula 2 tubuvaline compound, optionally in salt form, as the predominate optical isomer having the structure of:

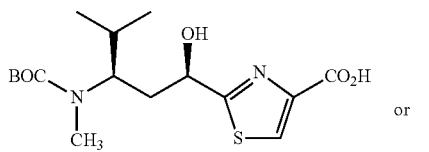

or

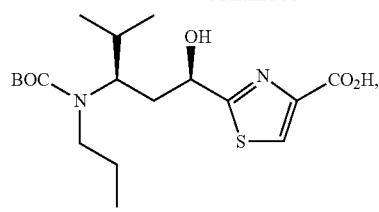

(BOC-Desacetyl-Tubuvaline)

or is comprised or consists essentially of the (R,R)-Formula 2 diastereomer substantially or essentially free of its corresponding (R,S)-Formula 2 diastereomer, optionally in salt form, which has the structure of:

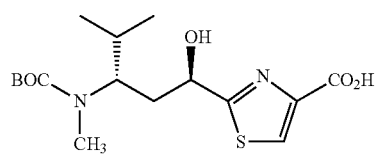

or

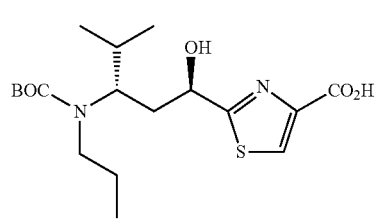

and is substantially or essentially free of the enantiomer of that corresponding diastereomer, which is (S,R)-Formula 2, optionally in salt form, and which has the structure of:

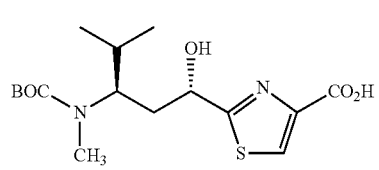

or

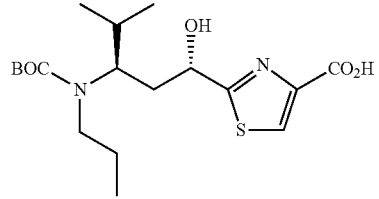

and if optical impurity(ies) are present, having the (S,S)-Formula 2 optical isomer, optionally in salt form, as the major optical impurity, which has the structure of:

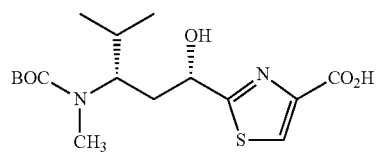

or

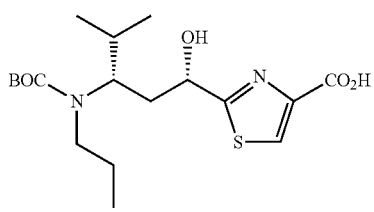

and the Formula R-2a tubuvaline composition from step (d) acylation following step (b) chiral reduction, step (b') diastereomer separation and step (c) hydrolysis is comprised or consists essentially of the (R,R)-Formula 2a diastereomer, optionally in salt form, as the predominate optical isomer having the structure of:

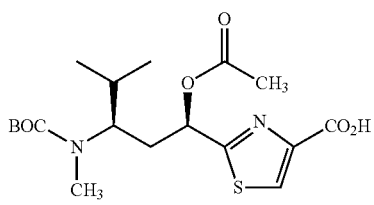

or

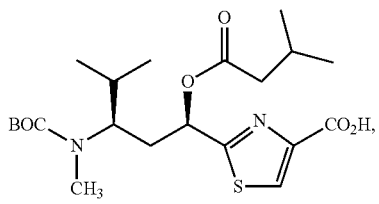

(BOC-Tubuvaline)

or is comprised or consists essentially of the (R,R)-Formula 2a diastereomer substantially or essentially free of its corresponding (R,S)-Formula 2a diastereomer, optionally in salt form, which has the structure of:

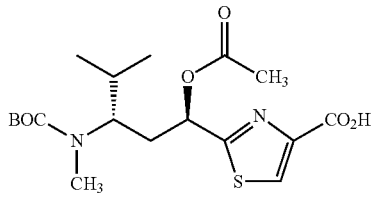

or

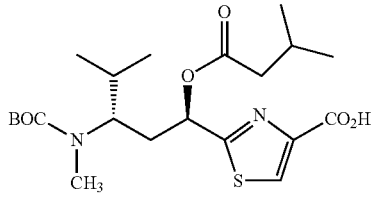

and is substantially or essentially free of the enantiomer of that corresponding diastereomer, which is (S,R)-Formula 2a, optionally in salt form, and which has the structure of:

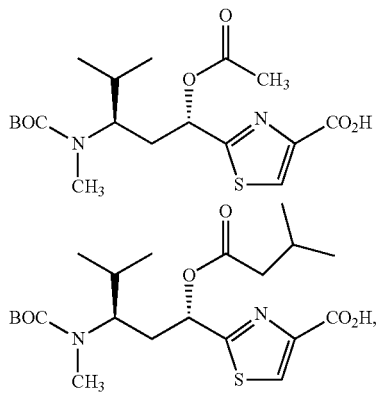

and if optical impurity(ies) are present, preferably having the (S,S)-Formula 2a optical isomer, optionally in salt form, as the major optical impurity, which has the structure of:

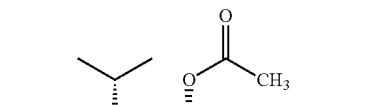

or

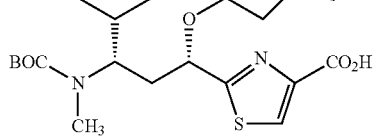

2.2.4 Embodiment Group 5

In a fifth group of embodiments, methods are provided for preparing a tubuvaline compound of Formula 2b with the (1R,3R)-configuration having the structure of:

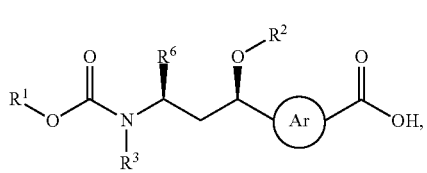

(R,R)-2b optionally in salt form, sometimes indicated as (R,R)-Formula 2b, or a composition comprised or consisting essentially of that compound, wherein: the circled Ar is a phenylene or a 5- or 6-membered nitrogen-containing heteroarylene, optionally substituted at the remaining positions; $R^1$ is phenyl, t-butyl, 9-fluorenyl or allyl, optionally substituted, or other moeity so that $R^1$—OC(=O)— is a suitable protecting group; $R^2$ is optionally substituted saturated $C_1$-$C_8$ alkyl, optionally substituted unsaturated $C_3$-$C_6$ alkyl or $R^2$ is $R^{2A}$ wherein $R^{2A}$ is —$CH_2R^{2C}$, wherein $R^{2C}$ is optionally substituted $C_1$-$C_8$ ether or optionally substituted $C_2$-$C_8$ ether; and $R^3$ is optionally substituted saturated $C_1$-$C_8$ alkyl, optionally substituted unsaturated $C_3$-$C_8$ alkyl, optionally substituted $C_3$-$C_8$ carbocyclyl or optionally substituted $C_3$-$C_8$ heteroalkyl; and $R^6$ is optionally substituted saturated $C_1$-$C_8$ alkyl or optionally substituted unsaturated $C_2$-$C_8$ alkyl, the method comprising the steps of:

(a) contacting a tubuvaline intermediate of Formula A:

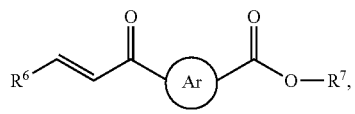

(A)

optionally in salt form, wherein $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moeity so that $R^7$—O— provides a suitable carboxylic acid protecting group, with a carbamate compound of Formula B having the structure of $R^3NHC(O)OR^1$, in a suitable polar, aprotic solvent in the presence of a suitable transition metal (II) or transition metal (III) catalyst, in particular, one comprising a transition metal selected from the group consisting of Cu(II), Zn(II) and Yb(III) catalysts, so as to form an enantiomeric mixture of tubuvaline intermediates, each optionally in salt form, or a composition comprised or consisting essentially of these intermediates represented by the structure of Formula AB:

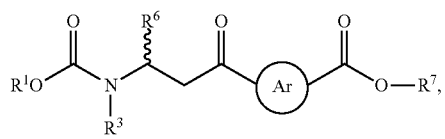

(AB)

(b) contacting the optical isomer mixture of Formula AB tubuvaline intermediates, or the composition comprised or consisting essentially of these intermediates, obtained from steps (a) and (b) with a suitable reducing agent that provides a composition comprised of a diastereomeric mixture of (R,R)-Formula 1a and (R,S)-Formula 1a tubuvaline compounds represented by the structure of Formula R-1a:

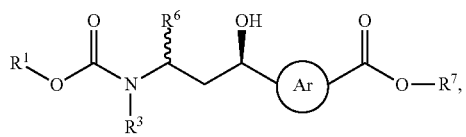

(R-1a)

in particular a chiral reducing agent that provides the composition comprised of these diastereomers in which the (1R,3R)- and (1R,3S)-Formula 1a tubuvaline diastereomers, sometimes indicated as (R,R)- and (R,S)-Formula 1a, are the predominate optical isomers, wherein (R,R)-Formula 1a has the structure of:

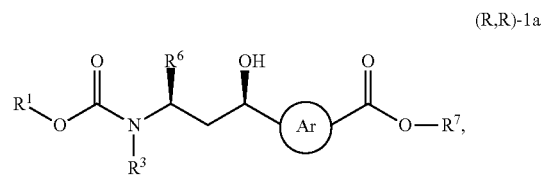

(R,R)-1a and wherein (R,S)-Formula 1a has the structure of:

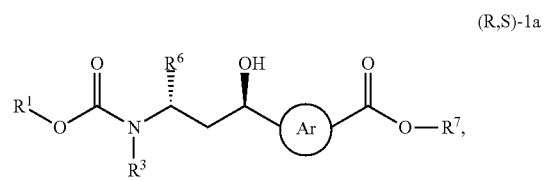

(R,S)-1a (b') optionally separating the diastereomers from step (c) to obtain the diastereomer, (R,R)-Formula 1a, optionally in salt form, or a composition comprised or consisting essentially of that diastereomer, or salt thereof, as the predominate optical isomer and is substantially or essentially free of the other diastereomer, which is (R,S)-Formula 1a;

(e) contacting the diastereomeric Formula R-1a tubuvaline compounds, or a composition comprised or consisting essentially of these compounds, each optionally in salt form, with a suitable alkylating agent so as to form a mixture of diastereomeric tubuvaline compounds each optionally in salt form, or a composition comprised or consisting essentially of that mixture, represented by the structure of Formula R-1b:

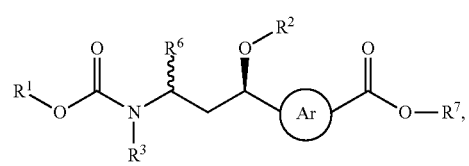

(R-1b)

or contacting the (R,R)-Formula 1a compound, or composition thereof in which the (R,R)-Formula 1a tubuvaline compound is the predominate optical isomer resulting from chromatography of step (c') with a suitable alkylating agent, so as to form the corresponding diastereomer having the structure of:

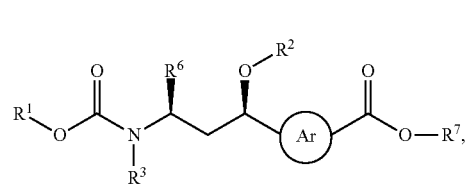

(R,R-1b)

optionally in salt form, which has the (1R,3R)-configuration, sometimes indicated as (R,R)-Formula 1b (as shown), or a composition comprised or consisting essentially of that diastereomer, or salt thereof, in which (R,R)-Formula 1b is the predominate optical isomer, wherein the optical purity of the corresponding composition of (R,R)-

Formula 1a, from step (c') is substantially or essentially retained by the (R,R)-Formula 1b composition; and and (e') optionally in absence of the diastereomeric separations of step (c') separating the Formula R-1b diastereomers to provide (R,R)-Formula 1b, optionally in salt form, or a composition comprised or consisting essentially of that compound, as the predominate optical isomer (f) contacting the diastereomeric Formula R-1b tubuvaline compounds, or composition thereof, from step (c) with a suitable hydrolysis agent so as to form a mixture of diastereomeric tubuvaline compounds, or composition comprised or consisting essentially of these diastereomers, each of which is optionally in salt form, represented by Formula R-2b having the structure of:

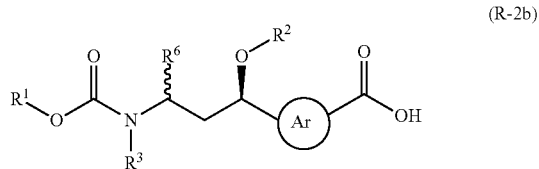

(R-2b)

or contacting the (R,R)-Formula 1b compound or composition thereof in which the (R,R)-Formula 1b compound is the predominate optical isomer resulting from chromatography of step (c') or (e'), preferably after step (c'), to provide the corresponding diastereomer, (R,R)-Formula 2b, or composition thereof in as the predominate optical isomer diastereomer, which has the structure of;

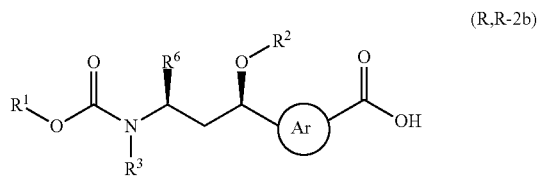

(R,R-2b)

and (f') optionally in absence of the diastereomeric separations of steps (c') and (e') separating the Formula R-2b diastereomers to provide (R,R)-Formula 1b, optionally in salt form, or a composition comprised or consisting essentially of that compound, as the predominate optical isomer, wherein variable group(s) of Formulae A, B and AB and Formula R-1a and (R,R)-Formula 1b and corresponding optical isomers thereof are as defined for (R,R)-Formula 2b.

In preferred embodiments, the alkylating agent for step (c) has the structure of $R^2X$, wherein $R^2$ is saturated $C_1$-$C_8$ alkyl or unsaturated $C_3$-$C_8$ alkyl, or $R^2X$ is $R^{24}X$ having the formula of $R^{2C}CCH_2X$, wherein $R^{2C}$ is saturated $C_1$-$C_8$ ether or unsaturated $C_2$-$C_8$ ether; and X is Br, I, -OTs, -OMs or other suitable leaving group.

In other preferred embodiments, $—OR^2$ in the optical isomers of Formula 2b is $—OCH_3$, $—OCH_2CH_3$, $—OCH_2CH_2CH_3$, $—OCH_2CH=CH_2$ or $—OCH_2—O—CH_3$, in particular $—OCH_2CH_3$.

In preferred embodiments, chiral reduction of step (b) of the enantiomeric Formula AB mixture is conducted so as to provide a composition having a combined amount of (R,R)-Formula 1a and (R,S)-Formula 1a diastereomers of at least about 80% w/w or at least about 90% w/w in relation to the total weight of the optical isomers of the composition, and more particularly a composition of at least about a combined 90% w/w of (R,R)-Formula 1a and (R,S)-Formula 1a diastereomers additionally having about 10% w/w or less, about 5% w/w or less, about 3% w/w or less or about 1.5% w/w or less combined weight of the respective (S,S)- and (S,R)-Formula 1a enantiomers of these diastereomers in relation to the total weight of the Formula 1a optical isomers of the composition, or additionally having about 5% w/w or less, about 3% w/w or less or about 1.5% w/w or less of the (S,S)-Formula 1a optical impurity in relation to the total weight of the optical isomers of the composition and is essentially free of the (S,R)-Formula 1a optical isomer.

In other preferred embodiments, separation of the diastereomers subsequent to step (b) chiral reduction, step (e) alkylation or step (f) hydrolysis in combination with provides a composition having the (R,R)-Formula 1a, (R,R)-Formula 1b, or (R,R)-Formula 2b compound, in at least about 90% d.e. at least about 95% d.e. or at least about 97% d.e with respect to the corresponding (R,S)-diastereomer, or a composition that is essentially free of that (R,S)-diastereomer. In more preferred embodiments the composition so provided has the (R,R)-Formula 1a, (R,R)-Formula 1b or (R,R)-Formula 2b tubuvaline compound in at least about 95% d.e. or at least about 97% d.e with respect to the corresponding (R,S)-diastereomer and having the (S,S)-Formula 1a, (S,S)-Formula 1b, or (S,S)-Formula 2b optical isomer, which is the respective enantiomer of the predominate diastereomer, as the major optical impurity, or a composition that is essentially free of that (R,S)-diastereomer. In particularly preferred embodiments, the diastereomeric excess in the Formula R-1a composition subsequent to step (b) and optional diastereomer separation thereafter is substantially or essentially retained in the R-2b composition obtained from the alkylation and hydrolysis steps of step (e) and step (f), respectively.

In any one of the foregoing fifth group of embodiments, the circled Ar moiety of the Formula A and Formula AB tubuvaline intermediates and the Formulae R-1a, Formula R-1b, and Formula R-2b compositions and (R,R)-Formula 2b tubuvaline compounds and optical isomers thereof, each optionally in salt form, is a $C_5$ heteroarylene, including without limitation a $C_5$ heteroarylene related to thiazole, isoxazole, pyrazole or imidazole as the parent heterocycle. Accordingly, other embodiments provided herein are methods for preparing a (R,R)-Formula 2b tubuvaline compound having the structure of:

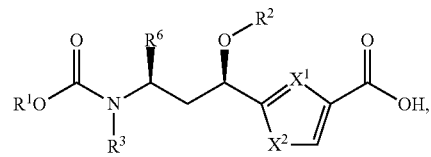

or a composition comprised or consisting essentially of that compound optionally in salt form, which is prepared from a diastereomeric mixture of Formula R-1b tubuvaline compounds represented by the structure:

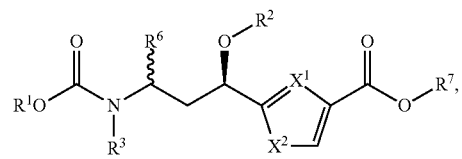

or a composition comprised or consisting essentially of these diastereomers, each in optionally in salt form, which in turn is prepared from a diastereomeric mixture of Formula R-1a tubuvaline compounds represented by the structure:

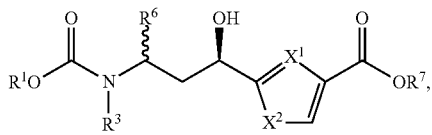

or a composition comprised or consisting essentially of these diastereomers, each optionally in salt form, which in turn is prepared from a Formula AB enantiomeric mixture of two tubuvaline intermediates represented by,

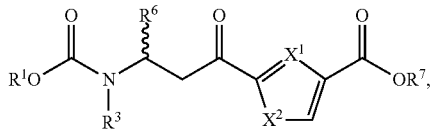

or a composition comprised or consisting essentially of these intermediates, each optionally in salt form, which in turn is prepared from a Formula A tubuvaline intermediate having the structure of:

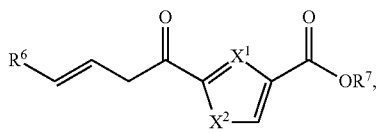

optionally in salt form, wherein in each one of these tubuvaline intermediate structures $X^1$ is =N— and $X^2$ is S, O, or $N(R^{X2})$—, or $X^1$ is =C($R^{X1}$)— and $X^2$ is $NR^{X2}$, wherein $R^{X1}$ and $R^{X2}$ are independently selected from the group consisting of —H and optionally substituted $C_1$-$C_4$ alkyl, preferably from the group consisting of —H, —$CH_3$ and —$CH_2CH_3$; and remaining variable groups retain their previous meanings from Formulae A, B and AB, and Formula R-1a, (R,R)-Formula 2 and (R,R)-Formula 2b and corresponding optical isomers thereof. In preferred embodiments, the circled Aryl is thizaol-1,3-di-yl.

In more preferred embodiments, the Formula A tubuvaline intermediate and the Formula B carbamate compound have the structures of:

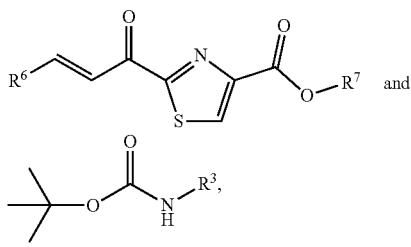

respectively, so that the Formula AB intermediate composition from the transition metal catalyzed carbamate aza-Michael reaction of step (a) is comprised or consists essentially of a mixture of two enantiomers represented by the structure of:

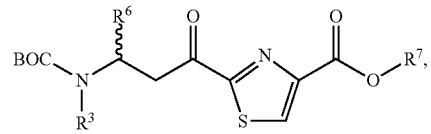

and the Formula R-1a tubuvaline composition from chiral reduction of step (b) is comprised or consists essentially of a mixture of two diastereomers represented by the structure of:

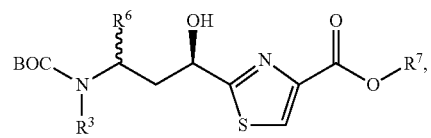

or the Formula R-1a tubuvaline composition from chiral reduction of step (b) is followed by separation of the predominate diastereomers of step (b') to provide the (R,R)-Formula 1a tubuvaline compound or composition thereof as the predominate optical isomer, wherein the (R,R)-Formula 1a tubuvaline compound has the structure of:

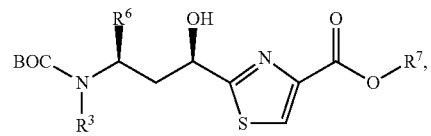

or the (R,R)-Formula 1a diastereomer or composition thereof is essentially free of the corresponding (R,S)-diastereomer having the structure of:

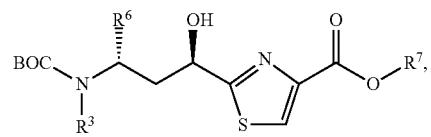

and if optical impurity(ies) are present, preferably has the (S,S)-Formula 1a optical isomer as the major optical impurity, which has the structure of:

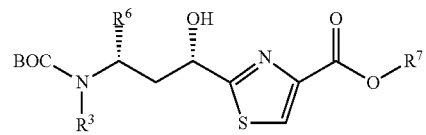

and the Formula R-1b tubuvaline composition from alkylation of step (e) is comprised or consists essentially of a mixture of two diastereomers represented by the structure of:

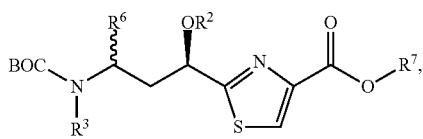

or after diastereomeric separation of step (b) or (e') is comprised or consists essentially of (R,R)-Formula 1b tubuvaline compound or composition thereof as the predominate diastereomer in relation to the other optical isomers, wherein the (R,R)-Formula 1b diastereomer has the structure of:

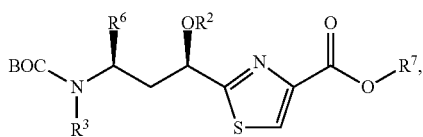

or the (R,R)-Formula 1b diastereomer or composition thereof is essentially free of the corresponding (R,S)-diastereomer having the structure of:

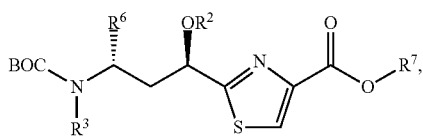

and if optical impurity(ies) are present, preferably has the (S,S)-Formula 1b optical isomer as the major optical impurity having the structure of:

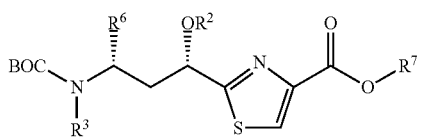

and the Formula R-2b tubuvaline composition from hydrolysis of step (f) is comprised or consists essentially of a mixture of two diastereomers represented by the structure of:

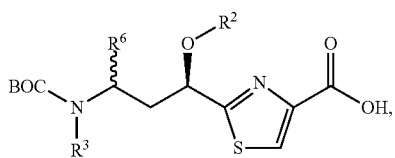

each optionally in salt form, in which the (R,R)-Formula 2b diastereomer is the predominate optical isomer, wherein the (R,R)-Formula 2b diastereomer, optionally in salt form, has the structure of:

or the composition from hydrolysis of step (f) after diastereomer separation of step (b'), step (e') or step (f') is comprised or consists essentially of the (R,R)-Formula 2b diastereomer, optionally in salt form, and is essentially free of the (R,S)-Formula 2b diastereomer, optionally in salt form, which has the structure of:

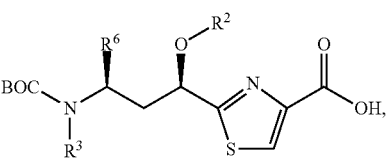

and if optical impurity(ies) are present, preferably has the (S,S)-Formula 2b optical isomer as the major optical impurity, optionally in salt form, which has the structure of:

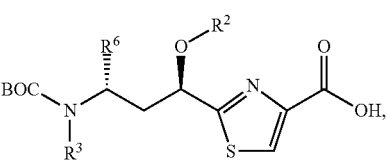

wherein $R^3$, $R^6$ and $R^7$ are as previously defined and are preferably independently selected $C_1$-$C_4$ saturated alkyl.

In particularly preferred embodiments, the Formula AB intermediate composition from step (a) is comprised or consists essentially of a mixture of two enantiomers represented by the structure of:

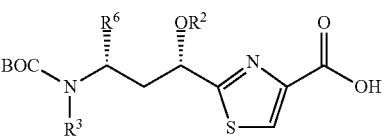

or

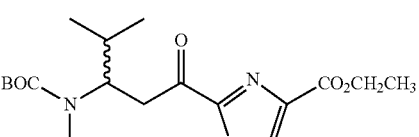

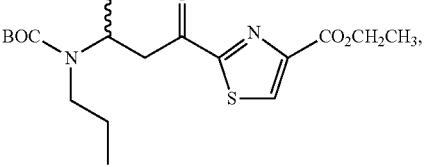

and the Formula R-1a compound composition from that step is followed by separation of the (R,R)- and (R,S)-Formula 1a diastereomers so obtained by chromatography to provide a composition comprised or consisting essentially of the (R,R)-Formula 1a diastereomer as the predominate optical isomer, which has the structure of:

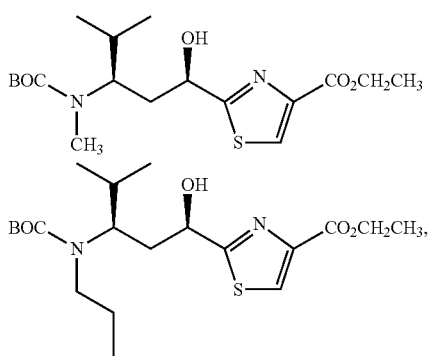

(BOC-Desacetyl-Tubuval-OEt)

or is comprised or consists essentially of that diastereomer and is essentially free of the corresponding (R,S)-Formula 1a diastereomer, which has the structure of:

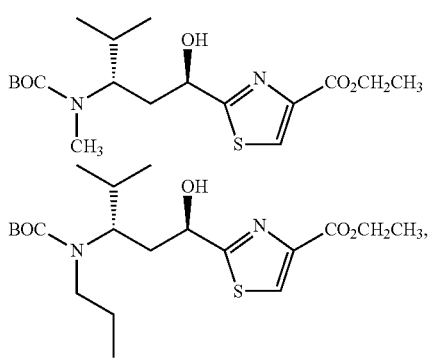

and is essentially free of the enantiomer of that corresponding diastereomer, which is (S,R)-Formula 1a having the structure of:

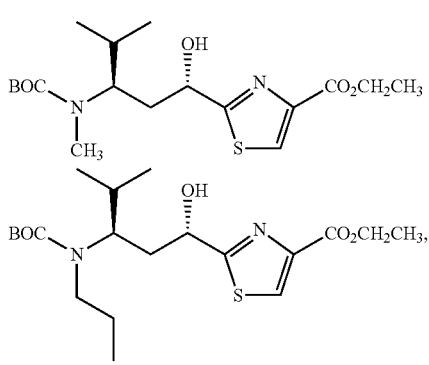

and if optical impurity(ies) are present, preferably has the (S,S)-Formula 1a optical isomer as the major optical impurity, which has the structure of:

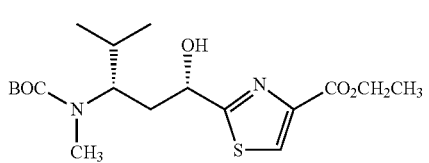

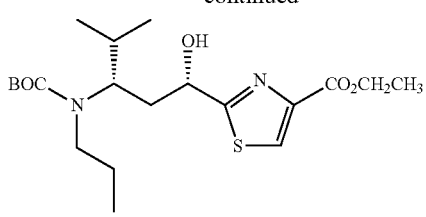

and the Formula R-1b tubuvaline composition from alkylation of step (e) subsequent to said step (b') chromatographic separation of the product of step (b) is comprised or consists of the (R,R)-Formula 1b compound as the predominate optical isomer, which has the structure of:

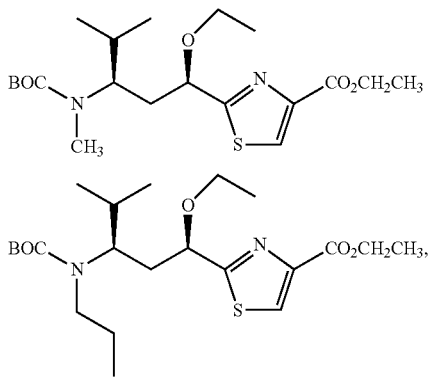

or is comprised or consists essentially of that diastereomer and is substantially or essentially free of the corresponding diastereomer, (R,S)-Formula 1b, which has the structure of:

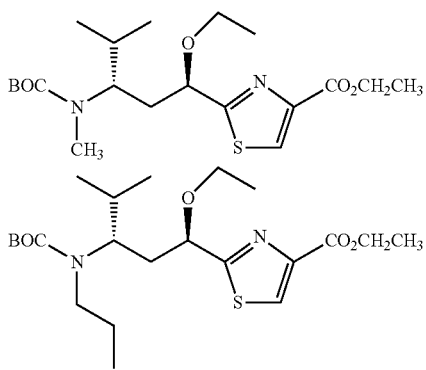

and is essentially free of the enantiomer of that corresponding diastereomer, which is (S,R)-Formula 1b having the structure of:

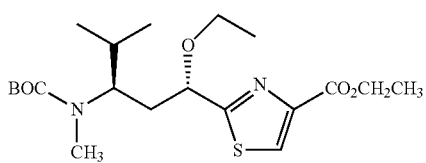

-continued

[Structure: BOC-N(propyl)-CH(iPr)-CH2-CH(OEt)-thiazole-CO2CH2CH3]

and if optical impurity(ies) are present, preferably has (S,S)-Formula 1a optical isomer as the major optical impurity, which has the structure of:

[Structure: BOC-N(CH3)-CH(iPr)-CH2-CH(OEt)-thiazole-CO2CH2CH3]

or

[Structure: BOC-N(propyl)-CH(iPr)-CH2-CH(OEt)-thiazole-CO2CH2CH3]

and the Formula R-2b tubuvaline composition from hydrolysis of step (f) contains the (R,R)-Formula 2b compound, optionally in salt form, as the predominate optical isomer, which has the structure of:

[Structure: BOC-N(CH3)-CH(iPr)-CH2-CH(OEt)-thiazole-CO2H]

or

[Structure: BOC-N(propyl)-CH(iPr)-CH2-CH(OEt)-thiazole-CO2H]

or is comprised or consists essentially of that diastereomer and is substantially or essentially free of the corresponding (R,S)-Formula 2b diastereomer, optionally in salt form, which has the structure of:

[Structure: BOC-N(CH3)-CH(iPr)-CH2-CH(OEt)-thiazole-CO2H]

or

-continued

[Structure: BOC-N(propyl)-CH(iPr)-CH2-CH(OEt)-thiazole-CO2H]

and is essentially free of the enantiomer of that corresponding diastereomer, which is (S,R)-Formula 2b having the structure of:

[Structure: BOC-N(CH3)-CH(iPr)-CH2-CH(OEt)-thiazole-CO2H]    or

[Structure: BOC-N(propyl)-CH(iPr)-CH2-CH(OEt)-thiazole-CO2H], and if optical impurity(ies) are present, preferably has the (S,S)-Formula 2b optical isomer as the major optical impurity, optionally in salt form, which has the structure of:

[Structure: BOC-N(CH3)-CH(iPr)-CH2-CH(OEt)-thiazole-CO2H]    or

[Structure: BOC-N(propyl)-CH(iPr)-CH2-CH(OEt)-thiazole-CO2H].

2.3 Tubulysin Compounds 2.3.1 Embodiment Group 6

In another group of embodiments, provided herein are methods for preparing a tubulysin compound, optionally in salt form, of (R,R)-Formula T1:

(R,R-T1)

[Structure: $R^{4B}$-N($R^4$)-CH($R^{4A}$)-C(O)-NH-CH($R^5$)-C(O)-N($R^3$)-CH($R^6$)-CH($OR^2$)-Ar-C(O)-N($R^T$)$_2$], or a composition comprising or consisting essentially of that compound as the predominate optical isomer in which $R^6$ and —$OR^2$ are in the (R)-configuration as shown, and optionally having (S,S)-Formula T1 as an optical impurity, optionally in salt form, which has the structure of:

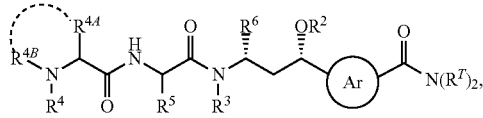
(S,S-T1)

or a composition comprising or consisting essentially of (R,R)-Formula T1, substantially or essentially free of the optical isomer, (R,S)-Formula 1a, optionally in salt form, which has the structure of:

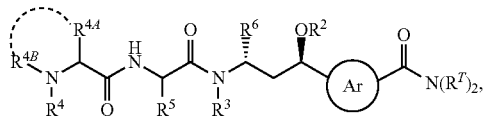
(R,S-T1)

and substantially or essentially free of the optical isomer, (S,R)-Formula T1, optionally in salt form, which has the structure:

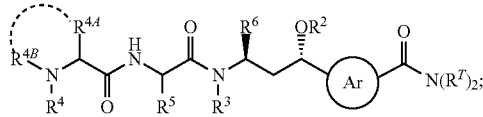
(S,R-T1)

and if optical impurity(ies) are present, having (S,S)-Formula T1 as the major optical impurity, wherein:

the curved dashed line indicates optional cyclization;

$R^2$ is hydrogen, optionally substituted saturated $C_1$-$C_6$ alkyl, or optionally substituted unsaturated $C_3$-$C_8$ alkyl, or $R^2$ is $R^{2A}$, wherein $R^{2A}$ is —$CH_2OR^{2C}$ or —$C(O)R^{2B}$, wherein $R^{2B}$ is saturated $C_1$-$C_6$ alkyl, unsaturated $C_3$-$C_8$ alkyl, $C_2$-$C_8$ alkenyl or $C_2$-$C_4$ alkynyl, optionally substituted; and $R^{2C}$ is saturated $C_1$-$C_8$ alkyl or unsaturated $C_3$-$C_8$ alkyl, optionally substituted;

and the circled Ar moiety represents a 5-membered nitrogen-containing heteroarylene, wherein the indicated substituents attached thereto are in a 1,3-relationship with each other with optional substitution at the remaining positions;

$R^3$ is an optionally substituted $C_1$-$C_6$ alkyl;

$R^4$, $R^5$, and $R^6$ are optionally substituted $C_1$-$C_6$ alkyl;

$R^{4A}$ is hydrogen or optionally substituted $C_1$-$C_6$ alkyl;

$R^{4B}$ is optionally substituted $C_1$-$C_6$ alkyl, or both together with the nitrogen to which they are attached, as indicated by the curved dashed line, define a optionally substituted 5-, 6-, 7-, or 8-membered nitrogen-containing heterocyclyl, in particular a 6-membered nitrogen-containing heterocyclyl; and one $R^T$ is hydrogen or optionally substituted $C_1$-$C_6$ alkyl; and the other is optionally substituted $C_1$-$C_6$ alkyl, or optionally substituted $C_3$-$C_6$ heteroalkyl, wherein each optionally substituted $C_1$-$C_6$ alkyl is independently selected, wherein the tubulysin compound incorporates a tubuvaline compound, prepared by any one of the foregoing methods, in particular:

the method comprising the steps of:

(a) contacting a tubuvaline intermediate of Formula A:

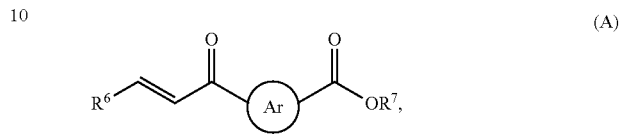
(A)

wherein $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moiety so that $R^7$—O— provides for a suitable carboxylic acid protecting group and the remaining variable groups are as defined for Formula T1, with a carbamate compound of Formula B:

$R^3NHC(O)OR^1$ (B), 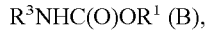

wherein $R^1$ is phenyl, t-butyl, 9-fluorenyl or allyl, optionally substituted, or other moiety so that $R^1$—OC(=O)— is a suitable amine protecting group and $R^3$ is as defined for Formula T1, in a suitable solvent in the presence of a suitable transition metal (II) catalyst, preferably selected from the group consisting of Cu(II) catalysts and Pd(II) catalysts, so as to provide a an enantiomeric mixture of tubuvaline intermediates, each optionally in salt form, or a composition comprising or consisting essentially of that mixture represented by Formula AB:

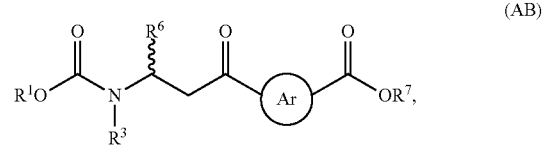
(AB)

wherein, the variable groups retain their meanings from Formula A and Formula B (b) contacting the Formula AB enantiomeric mixture or composition thereof with a suitable reducing agent wherein said reducing agent contacting provides a diastereomeric mixture of tubuvaline compounds, each optionally in salt form, or a composition comprising or consisting essentially of that mixture, represented by Formula R-1a:

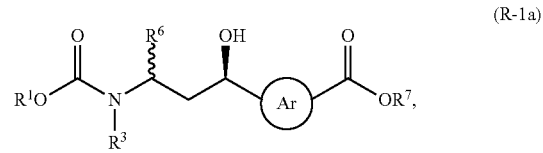
(R-1a)

and (b') separating the diastereomers to provide the diastereomer, (R,R)-Formula 1a, optionally in salt form, or a composition comprising or consisting essentially of that diastereomer, or salt thereof, as the predominate optical isomer, which has the structure of:

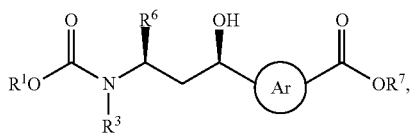

(R,R-1a)

and optionally having the corresponding enantiomer, which is (S,S)-Formula 1a, optionally in salt form, as an optical impurity, and which has the structure of:

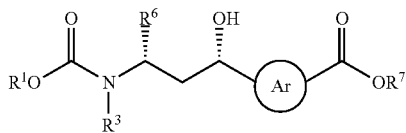

(S,S-1a)

or, a composition comprising or consisting essentially of (R,R)-Formula 1a, or salt thereof, substantially or essentially free of the corresponding diastereomer, which is (R,S)-Formula 1a, optionally in salt form, and which has the structure of:

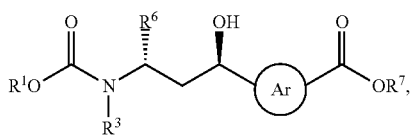

(R,S-1a)

and substantially or essentially free its enantiomer, which is (S,R)-Formula 1a, optionally in salt form, and which has the structure of:

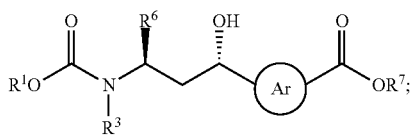

(S,R-1a)

and if optical isomer impurity(ies) are present, having (S,S)-Formula 1a, or salt thereof, as the major optical impurity;

(c) contacting the optical isomer, (R,R)-Formula 1a, optionally in salt form, or the composition thereof, with a suitable hydrolysis agent, wherein said hydrolysis agent contacting provides the diastereomer, (R,R)-Formula 2, optionally in salt form, as the predominate optical isomer having the structure of:

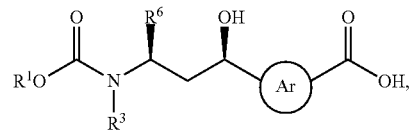

(R,R-2)

and optionally having as an optical impurity the corresponding enantiomer, which is (S,S)-Formula 2, optionally in salt form, and which has the structure of:

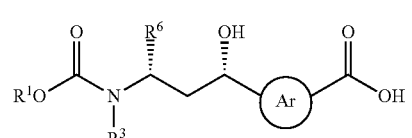

(S,S-2)

or a composition comprising or consisting essentially of (R,R)-Formula 2, or salt thereof, substantially or essentially free of the corresponding diastereomer, (R,S)-Formula 2, optionally in salt form, which has the structure of:

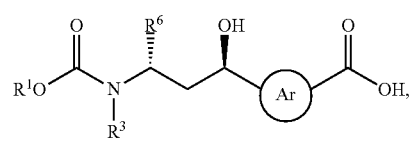

(R,S-2)

and substantially or essentially free of its enantiomer, which is (S,R)-Formula 2, optionally in salt form, and which has the structure of:

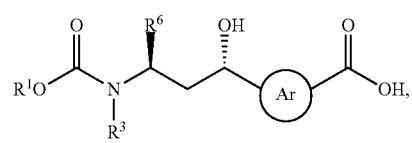

(S,R-2)

and if optical isomer impurity(ies) are present, having (S,S)-Formula 2, or salt thereof, as the major optical impurity; and wherein the variable groups of the optical isomers of Formula 1a and Formula 2 retain their meanings from Formula AB and optionally;

and for tubulysin compounds in which $R^2$ is $R^{2A}$, wherein $R^{2A}$ is $-C(O)R^{2B}$, the method further comprising the steps of:

(d) contacting the diastereomer, (R,R)-Formula 2, optionally in salt form, or the composition thereof, with a suitable acylating agent, wherein said acylating agent contacting provides the diastereomer, (R,R)-Formula 2a, optionally in salt form, as the predominate optical isomer having the structure of:

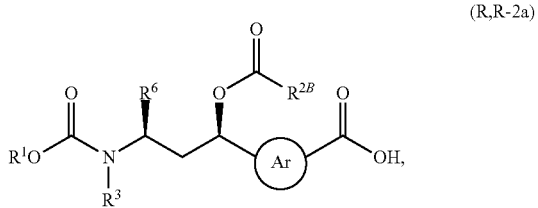
(R,R-2a)

and optionally having as an optical impurity the corresponding enantiomer, which is (S,S)-Formula 2a, optionally in salt form, and which has the structure of:

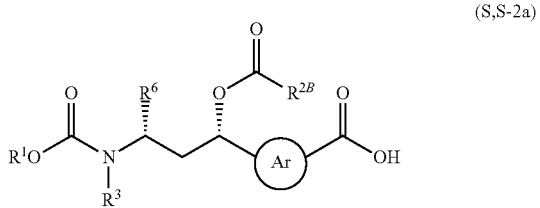
(S,S-2a)

or a composition comprising or consisting essentially of (R,R)-Formula 2a, optionally in salt form, substantially or essentially free of the corresponding diastereomer, (R,S)-Formula 2a, or salt thereof, which has the structure of:

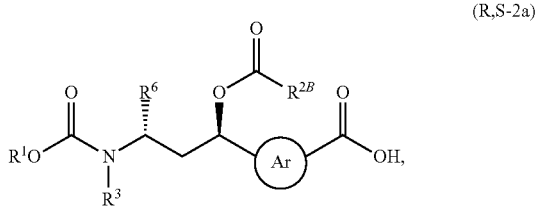
(R,S-2a)

and substantially or essentially free of its enantiomer, which is (S,R)-Formula 2a, optionally in salt form, and which has the structure of:

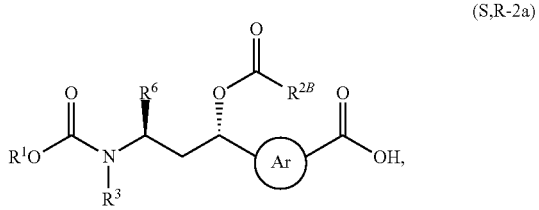
(S,R-2a)

and if optical isomer impurity(ies) are present, having (S,S)-Formula 2a, or salt thereof, as the major optical impurity, wherein $R^{2B}$ in (R,R)-Formula 2a and optical isomers thereof is as defined for (R,R)-Formula T1, and wherein the remaining variable groups retain their meanings from their respective Formula 1a optical isomers;

wherein incorporation of (R,R)-Formula 2 or (R,R)-Formula 2a, into a (R,R)-Formula T1 tubulysin compound, provides that compound, optionally in salt form, in which $R^2$ is —H or $R^2$ is $R^{2A}$, respectively, wherein $R^{2A}$ is —C(O)$R^{2B}$, wherein $R^{2B}$ is as previously defined for (R,R)-Formula T1; and for tubulysin compounds in which $R^2$ is optionally substituted saturated $C_1$-$C_6$ alkyl, or optionally substituted unsaturated $C_3$-$C_8$ alkyl, or $R^2$ is $R^{2A}$, wherein $R^{2A}$ is —CH$_2$O$R^{2C}$ step (c'), which provides the optical isomer, (R,R)-Formula 1a, or salt thereof, in purified form, is followed by the steps of:

(e) contacting the optical isomer, (R,R)-Formula 1a, optionally in salt form, or composition thereof, with a suitable alkylating agent, wherein said alkylating agent contacting provides a tubuvaline compound diastereomer, optionally in salt form, having the structure of (R,R)-Formula 1b:

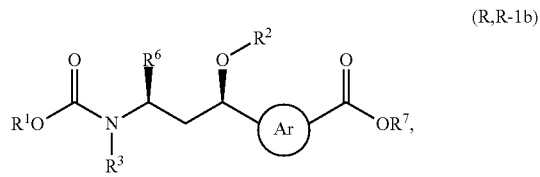
(R,R-1b)

or a composition comprising or consisting essentially of that diastereomer, or salt thereof, as the predominate optical isomer, and optionally having as an optical impurity, the corresponding enantiomer, which is (S,S)-Formula 1b, optionally in salt form, and which has the structure of:

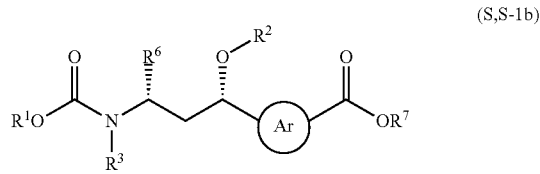
(S,S-1b)

or a composition comprising or consisting essentially of (R,R)-Formula 1b, or salt thereof, substantially or essentially free of the corresponding diastereomer, which is (R,S)-Formula 1b, optionally in salt form, and which has the structure of:

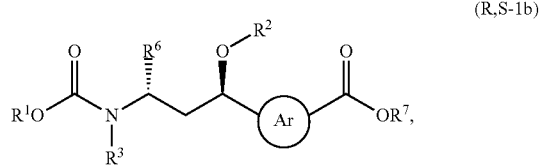
(R,S-1b)

and substantially or essentially free of its corresponding enantiomer, which is (S,R)-Formula 1b, optionally in salt form, and which has the structure of:

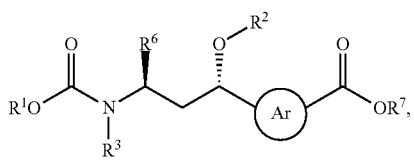
(S,R-1b)

and optionally having (S,S)-Formula 1b, or salt thereof, as the major optical isomer impurity, or a (R,R)-Formula 1b composition substantially retaining the optical purity of the (R,R)-Formula 1a composition obtained from step (b'), wherein $R^2$ is optionally substituted saturated $C_1$-$C_6$ alkyl, or optionally substituted unsaturated $C_3$-$C_8$ alkyl, or $R^2$ is $R^{2A}$, wherein $R^{2A}$ is —$CH_2OR^{2C}$ wherein $R^{2C}$ is as previously defined for their respective Formula T1 optical isomers; and wherein the remaining variable groups of (R,R)-Formula 1b and optical isomers thereof retain their meanings from their respective Formula 1a optical isomers; and (f) contacting the (R,R)-Formula 1b tubuvaline compound, optionally in salt form, or a composition thereof, with a suitable hydrolysis agent, wherein said hydrolysis agent contacting provides a tubuvaline compound, optionally in salt form, having the structure of (R,R)-Formula 2b:

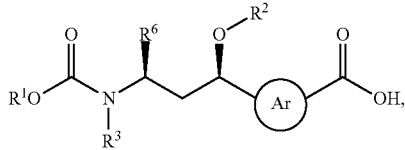
(R,R-2b)

or a composition comprising or consisting essentially of that optical isomer, or salt thereof, as the predominate optical isomer, and optionally having as an optical impurity, optionally in salt form, the corresponding enantiomer, which is (S,S)-Formula 2b, and which has the structure of:

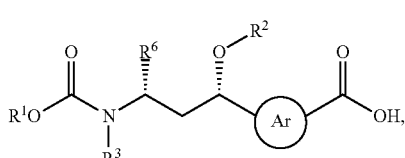
(S,S-2b)

or a composition comprising or consisting essentially of (R,R)-Formula 2b, or salt thereof, substantially or essentially free of the corresponding diastereomer, which is (R,S)-Formula 2b, optionally in salt form, and which has the structure of:

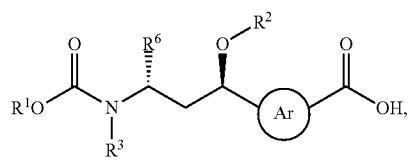
(R,S-2b)

and substantially or essentially free of its corresponding enantiomer, which is (S,R)-Formula 2b, optionally in salt form, and which has the structure of:

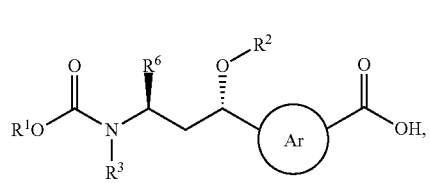
(S,R-2b)

and if optical isomer impurity(ies) are present having (S,S)-Formula 2b, or salt thereof as the major optical isomer impurity, or provides the (R,R)-Formula 2b composition substantially retaining the optical purity of the (R,R)-Formula 1a composition obtained from step (b') or the (R,R)-Formula 1b composition obtained from step (e), wherein incorporation of (R,R)-Formula 2b into a (R,R)-Formula T1 tubulysin compound provides that compound or composition thereof in which $R^2$ is optionally substituted saturated $C_1$-$C_6$ alkyl, or optionally substituted unsaturated $C_3$-$C_8$ alkyl, or $R^2$ is $R^{2A}$, wherein $R^{2A}$ is —$CH_2OR^{2C}$, with $R^{2C}$ as previously defined for (R,R)-Formula 1b, wherein the remaining variable groups retaining their meanings from their respective Formula 1a optical isomers.

Suitable acylating and alkylating reagents in step (d) or step (e), respectively, in methods for preparing (R,R)-Formula 2a and (R,R)-Formula 2b tubuvaline compounds and compositions thereof include the reagents as previously described for preparation of compositions comprising or consisting essentially of a diastereomeric mixture represented by Formula R-2a of "Embodiment Group 4" or by Formula R-2b of "Embodiment Group 5", respectively.

In some embodiments, methods for preparing tubulysin compounds of (R,R)-Formula T1 further comprises the steps of:

(g) contacting a tubuvaline compound, or salt thereof, of (R,R)-Formula 2, (R,R)-Formula 2a, (R,R)-Formula 2b, or composition thereof, with a compound of Formula C having the structure of $HN(R^T)_2$, or salt thereof, wherein $R^T$ are as previously defined for (R,R)-Formula T1, in the presence of a first coupling agent and optionally in the presence of a first suitable hindered base, or contacting the Formula C compound, optionally in the presence of a first hindered base, with an activated ester of the tubuvaline compound to form, optionally in salt form, with a tubulysin intermediate of (R,R)-Formula 3v having the structure of:

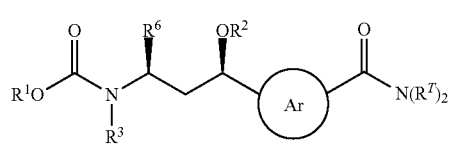
(R,R-3v)

or a composition comprising or consisting essentially of that intermediate, or salt thereof, as the predominate optical isomer, and optionally having as an optical impurity, optionally in salt form, (S,S)-Formula 3v, which has the structure of:

(S,S-3v)

or a composition comprising or consisting essentially of (R,R)-Formula 3v substantially or essentially free of (R,S)-Formula 3v, optionally in salt form, which has the structure of:

(R,S-3v)

and substantially or essentially free of (S,R)-Formula 3, optionally in salt form, which has the structure of:

(S,R-3v)

and if optical isomer impurity(ies) are present, having (S,S)-Formula 3v, or salt thereof as the major optical isomer impurity, or substantially retaining the optical purity of the tubuvaline compound prior to said first coupling agent or activated ester contacting; and (h) contacting the tubulysin intermediate of (R,R)-Formula 3v, optionally in salt form, or composition thereof, with a suitable deprotecting agent to form a tubulysin intermediate of (R,R)-Formula 4v:

(R,R-4v)

optionally in salt form, or a composition comprised or consisting essentially of that intermediate, or salt thereof, as the predominate optical isomer, and optionally having as an optical impurity (S,S)-Formula 4v, optionally in salt form, which has the structure of:

(S,S-4v)

or a composition comprised or consisting essentially of (R,R)-Formula 4v substantially or essentially free of (R,S)-Formula 4v, optionally in salt form, which has the structure of:

(R,S-4v)

and substantially or essentially free (S,R)-Formula 4v, optionally in salt form, which has the structure of:

(S,R-4v)

and if optical isomer impurity(ies) are present, having (S,S)-Formula 4v, or salt thereof, as the major optical impurity, or or a (R,R)-Formula 4v composition substantially retaining the optical purity of the tubuvaline composition of (R,R)-Formula 2, (R,R)-Formula 2a, or (R,R)-Formula 2b prior to step (g); and wherein the variable groups of the optical isomers of Formula 3 and Formula 4v retain their meanings from Formula C and their respective Formula 1a, Formula 2a or Formula 2b and optical isomers; and wherein incorporation of (R,R)-Formula 4v, into a (R,R)-Formula T1 tubulysin compound, provides that compound in which $R^2$ is hydrogen, optionally substituted saturated $C_1$-$C_6$ alkyl, or optionally substituted unsaturated $C_3$-$C_8$ alkyl, or $R^2$ is $R^{2A}$, wherein $R^{2A}$ is —$CH_2OR^{2C}$, or —$C(O)R^{2B}$ wherein $R^{2B}$ and $R^{2C}$ are as defined by (R,R)-Formula T1.

In some embodiments, acylation of step (d) is delayed until completion of step (g), in which $R^2$ in (R,R)-Formula 3v is hydrogen, which defines (R,R)-Formula 3, to provide (R,R)-Formula 3a.

2.3.2 Embodiment Group 7

In a further group of embodiments, provided herein are methods for preparing a tubulysin compound of desacyl (R,R)-Formula T1A or (R,R)-Formula T1A, either optionally in salt form, having the structure of:

(desacyl R,R-T1A)

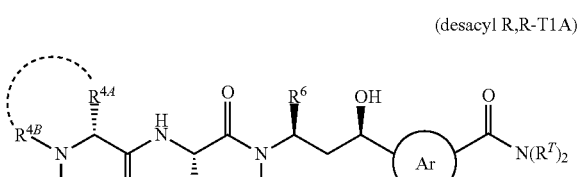

(R,R-T1A)

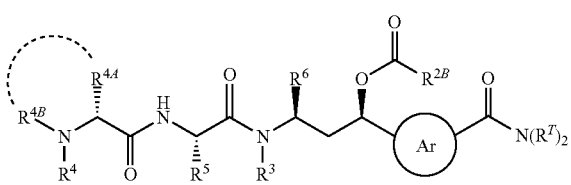

respectively, or a composition comprising or consisting essentially of either compound, or salt thereof, as the predominate optical isomer in which $R^6$ and —OH or —C(=O)$R^{2B}$ are in the (R)-configuration as shown, and optionally having desacyl (S,S)-Formula T1A or (S,S)-Formula T1A as an optical impurity, optionally in salt form, which have the structures of:

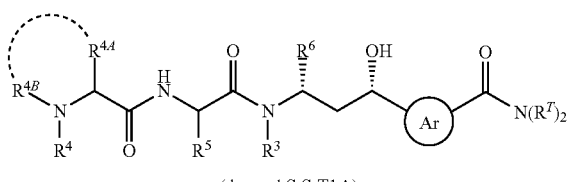

(desacyl S,S-T1A)

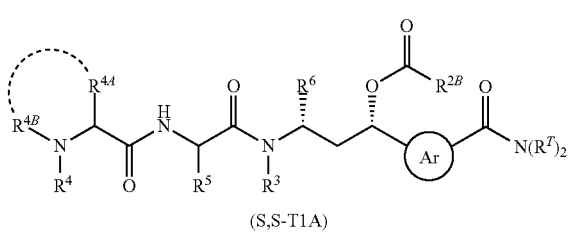

(S,S-T1A)

respectively, or a composition comprising or consisting essentially of desacyl (R,R)-Formula T1A, essentially or substantially free of the optical isomer, desacyl (R,S)-Formula T1A, optionally in salt form, which has the structure of:

(desacyl R,S-T1A)

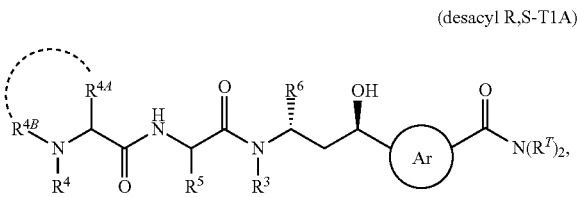

and substantially or essentially free of the optical isomer, desacyl (S,R)-Formula T1A, optionally in salt form, which has the structure of:

(desacyl S,R-T1A)

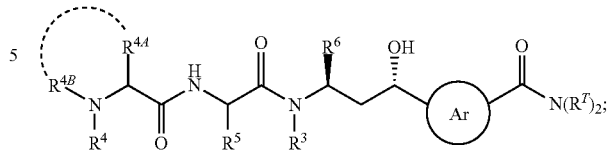

and if optical impurity(ies) are present having desacyl (S,S)-Formula T1A, or salt thereof, as the major optical impurity, or a composition comprising or consisting essentially of (R,R)-Formula T1A, substantially or essentially free of the optical isomer, (R,S)-Formula T1A, optionally in salt form, which has the structure of:

(R,S-T1A)

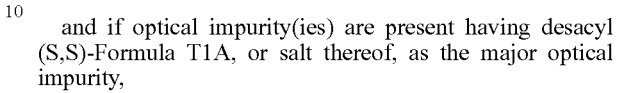
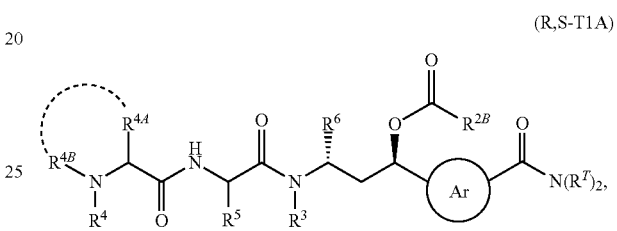

and substantially or essentially free of the optical isomer, (S,R)-Formula T1A, optionally in salt form, which has the structure of:

(S,R-T1A)

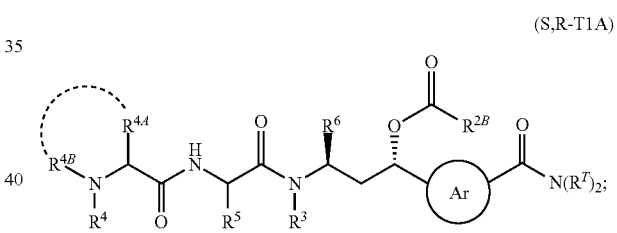

and if optical impurity(ies) are present having (S,S)-Formula T1A, or salt thereof, as the major optical impurity, wherein:

the curved dashed line indicates optional cyclization;

$R^{2B}$ is saturated $C_1$-$C_6$ alkyl, unsaturated $C_3$-$C_8$ alkyl, $C_2$-$C_8$ alkenyl or $C_2$-$C_4$ alkynyl, optionally substituted; and the circled Ar moeity represents a 5-membered nitrogen-containing heteroarylene, wherein the indicated substituents attached thereto are in a 1,3-relationship with each other with optional substitution at the remaining positions;

$R^3$ is an optionally substituted $C_1$-$C_6$ alkyl;

$R^4$, $R^5$, and $R^6$ are optionally substituted $C_1$-$C_6$ alkyl;

$R^{4A}$ is hydrogen or optionally substituted $C_1$-$C_6$ alkyl;

$R^{4B}$ is optionally substituted $C_1$-$C_6$ alkyl, or $R^{4A}$ and $R^{4B}$ together with the atoms to which they are attached, as indicated by the curved dashed line, define a optionally substituted 5-, 6-, 7-, or 8-membered nitrogen-containing heterocyclyl, preferably a 6-membered nitrogen-containing heterocyclyl;

one $R^T$ is hydrogen or optionally substituted $C_1$-$C_6$ alkyl; and the other is optionally substituted $C_1$-$C_6$ alkyl or optionally substituted $C_3$-$C_6$ heteroalkyl, wherein each optionally substituted $C_1$-$C_6$ alkyl is independently selected, wherein the tubulysin compound of desacetyl (R,R)-Formula T1A and (R,R)-Formula T1A incorporates a tubuvaline compound prepared by any one of the foregoing methods of "Embodiment Group 3" or "Embodiment Group 4", respectively, in particular, the method comprising the steps of:
(a) contacting a tubuvaline intermediate of Formula A:

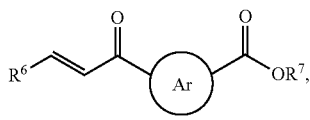
(A)

with a carbamate compound of Formula B:

R³NHC(O)OR¹ (B), in a suitable solvent in the presence of a suitable transition metal (II) catalyst, preferably selected from the group consisting of Cu(II) catalysts and Pd(II) catalysts, to form a enantiomeric mixture of tubuvaline intermediates represented by Formula AB:

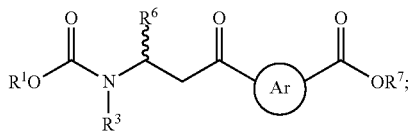
(AB)

each optionally in salt form, wherein the variable groups retain their meanings from Formula A and Formula B, or a composition comprising or consisting essentially of that mixture;

(b) contacting the enantiomeric mixture, or composition thereof, of Formula AB with a suitable reducing agent wherein said reducing agent contacting results in formation of a diastereomeric mixture, or a composition comprising or consisting essentially of that mixture, represented by Formula R-1a:

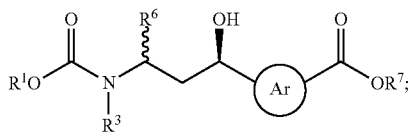
(R-1a)

(b') separating the diastereomers to provide the (R,R)-Formula 1a diastereomer, optionally in salt form, or a composition comprising or consisting essentially of that diastereomer, or salt thereof, as the predominate optical isomer, which has the structure of:

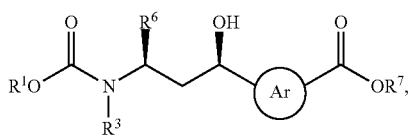
(R,R-1a)

and having its corresponding enantiomer, which is (S,S)-Formula 1a, optionally in salt form, as an optical impurity, and which has the structure of:

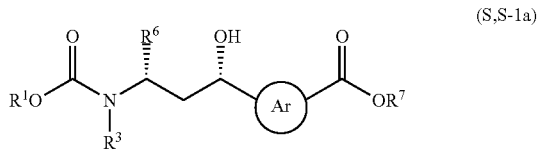
(S,S-1a)

or a composition comprising or consisting essentially of (R,R)-Formula 1a, or salt thereof, substantially or essentially free of the corresponding diastereomer, which is (R,S)-Formula 1a, optionally in salt form, and which has the structure of:

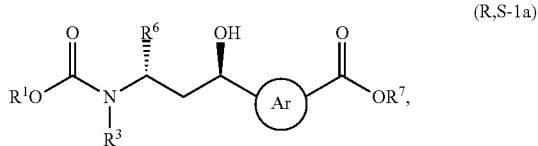
(R,S-1a)

and substantially or essentially free of its corresponding enantiomer, (S,R)-Formula 1a, optionally in salt form, which has the structure of:

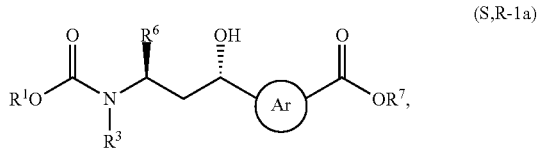
(S,R-1a)

and if optical isomer impurity(ies) are present having (S,S)-Formula 1a as the major optical impurity; and wherein the variable groups of the Formula 1a optical isomers retain their meanings from Formula AB;

(c) contacting (R,R)-Formula 1a or composition thereof with a suitable hydrolysis agent, wherein said hydrolysis agent contacting results in formation of (R,R)-Formula 2, optionally in salt form, having the structure of:

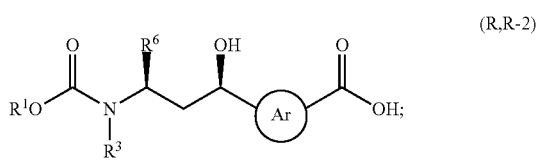
(R,R-2)

or a composition comprising or consisting essentially of (R,R)-Formula 2, or salt thereof, as the predominate optical isomer, and having its corresponding enantiomer, which is (S,S)-Formula 2, as an optical impurity, optionally in salt form, which has the structure of:

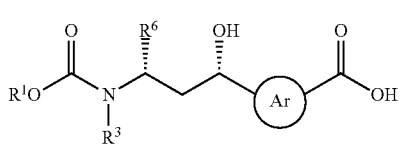
(S,S-2)

or a composition comprising or consisting essentially of (R,R)-Formula 2 substantially or essentially free of (R,S)-Formula 2, optionally in salt form, which has the structure of

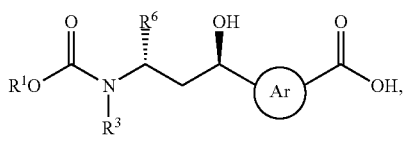
(R,S-2)

and substantially or essentially free of its corresponding enantiomer, which is (S,R)-Formula 2, optionally in salt form, which has the structure of:

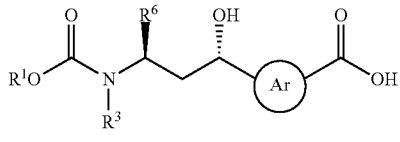
(S,R-2)

and if optical impurity(ies) are present, having (S,S)-Formula 2, or salt thereof, as the major optical impurity, or substantially retaining the optical purity of the composition of (R,R)-Formula 1a obtained from step (b'); and wherein the variable groups retain their meanings from their respective Formula 1a optical isomers;

(d) contacting (R,R)-Formula 2, optionally in salt form, or the composition thereof, with a suitable acylating agent, wherein said acylating agent contacting provides (R,R)-Formula 2a as the predominate optical isomer, which has the structure of:

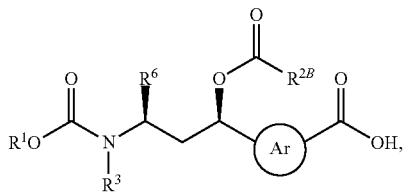
(R,R-2a)

optionally having as an optical impurity its corresponding enantiomer, which is (S,S)-Formula 2a, optionally in salt form, and which has the structure of:

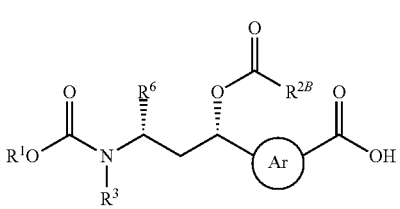
(S,S-2a)

or a composition comprising or consisting essentially of (R,R)-Formula 2a, optionally in salt form, substantially or essentially free of its corresponding diastereomer, which is (R,S)-Formula 2a, optionally in salt form, and which has the structure of:

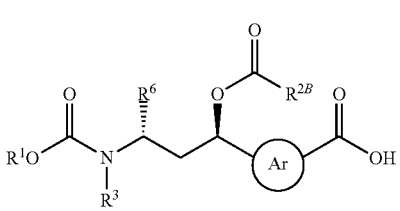
(R,S-2a)

and substantially or essentially free of its corresponding enantiomer, which is (S,R)-Formula 2a, optionally in salt form, and which has the structure of:

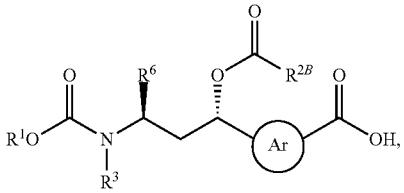
(S,R-2a)

and if other optical impurity(ies) are present having (S,S)-Formula 2a as the major optical impurity, or a composition of (R,R)-Formula 2a substantially retaining the optical purity of (R,R)-Formula 1a obtained from step (b') or (R,R)-Formula 2 obtained from step (c); and wherein $R^{2B}$ is as defined for (R,R)-Formula T1A, and wherein the remaining variable groups retain their meaning from their respective Formula 1a optical isomers, (g) contacting (R,R)-Formula 2a, optionally in salt form or composition thereof with a compound of Formula C having the structure of $HN(R^T)_2$, or salt thereof, wherein each $R^T$ is a defined for (R,R)-Formula T1A, in the presence of a first coupling agent and optionally in the presence of a first suitable hindered base, or contacting the Formula C compound with an activated ester of (R,R)-Formula 2a, optionally in the presence of a first suitable hindered base, wherein said first coupling agent or activated ester contacting provides (R,R)-Formula 3a, optionally in salt form, having the structure of:

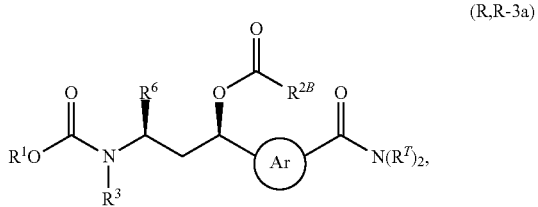
(R,R-3a)

or a composition comprising or consisting essentially of (R,R)-Formula 3a, optionally in salt form, as the predominate optical isomer, optionally having (S,S)-Formula 3a, optionally in salt form, as an optical impurity, which has the structure of:

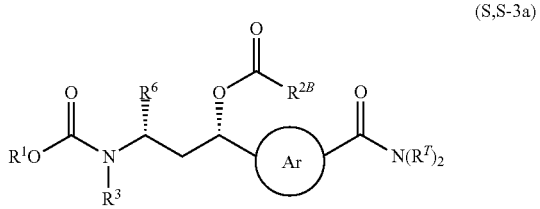
(S,S-3a)

or a composition comprising or consisting essentially of (R,R)-Formula 3a, or salt thereof, substantially or essentially free of (R,S)-Formula 3a, optionally in salt form, and which has the structure of:

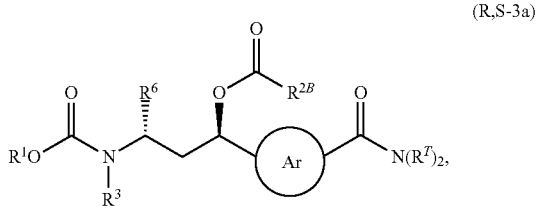
(R,S-3a)

and substantially or essentially free of (S,R)-Formula 3a, optionally in salt form, and which has the structure of:

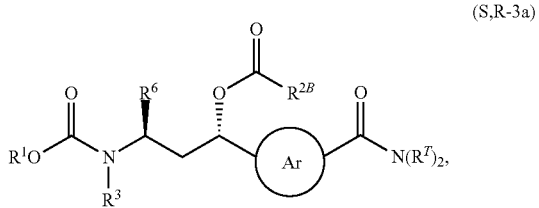
(S,R-3a)

and if other optical impurity(ies) are present having (S,S)-Formula 3a, optionally in salt form, as the major optical isomer impurity, or a composition of (R,R)-Formula 3a substantially retaining the optical purity of the composition of (R,R)-Formula 1a obtained from step (b'), (R,R)-Formula 2 obtained from step (c) or (R,R)-Formula 2a obtained from step (d); and wherein the variable groups of (R,R)-Formula 3a and optical isomers thereof retain their meanings from their respective Formula 1a optical isomers, or step (d) is followed by:

(g') contacting (R,R)-Formula 2, optionally in salt form, or composition thereof, with a compound of Formula C having the structure of $HN(R^T)_2$, or salt thereof, wherein each $R^T$ is a defined for (R,R)-Formula T1A, in the presence of a first coupling agent and optionally in the presence of a first suitable hindered base, or contacting the Formula C compound with an activated ester of (R,R)-Formula 2 with, optionally in the presence of a first suitable hindered base, wherein said first coupling agent or activated ester contacting provides (R,R)-Formula 3, optionally in salt form, having the structure of:

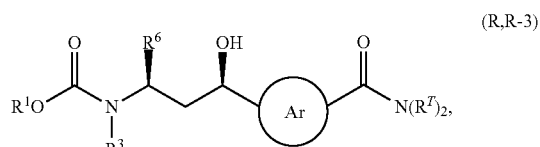
(R,R-3)

or a composition comprising or consisting essentially of (R,R)-Formula 3, optionally in salt form, as the predominate optical isomer, optionally having (S,S)-Formula 3, optionally in salt form, as an optical impurity, which has the structure of:

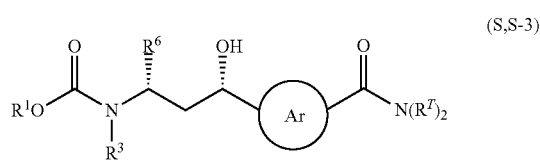
(S,S-3)

or a composition comprising or consisting essentially of (R,R)-Formula 3 or salt thereof substantially or essentially free of (R,S)-Formula 3, optionally in salt form, which has the structure of:

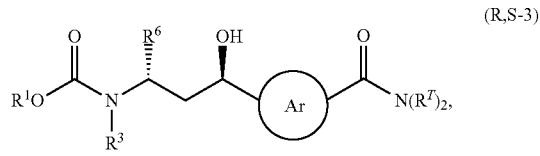
(R,S-3)

and is substantially or essentially free of (S,R)-Formula 3, optionally in salt form, which has the structure of:

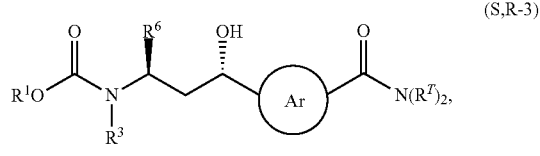
(S,R-3)

and if other optical impurity(ies) are present having (S,S)-Formula 3, optionally in salt form, as the major optical isomer impurity, or a composition of (R,R)-Formula 3 substantially retaining the optical purity of the composition of (R,R)-Formula 1a obtained from step (b'), or (R,R)-Formula 2 obtained from step (c); and wherein the variable groups of (R,R)-Formula 3 and optical isomers thereof retain their meanings from their respective Formula 1a optical isomers; and wherein step (g) is followed by (h) contacting (R,R)-Formula 3a, optionally in salt form, or composition thereof with a suitable deprotecting agent, wherein said deprotecting agent contacting provides (R,R)-Formula 4a, optionally in salt form, having the structure of:

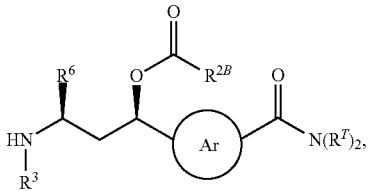
(R,R-4a)

or a composition comprising or consisting essentially of (R,R)-Formula 4a or salt thereof as the predominate optical isomer, optionally having as an optical impurity (S,S)-Formula 4a, optionally in salt form, which has the structure of:

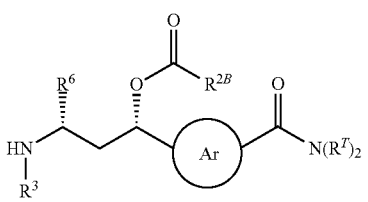
(S,S-4a)

or a composition comprising or consisting essentially of (R,R)-Formula 4a, substantially or essentially free of (R,S)-Formula 4a, optionally in salt form, which has the structure of:

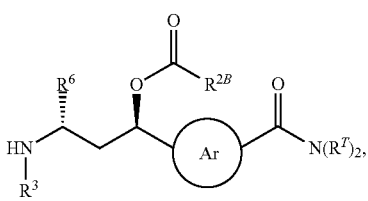
(R,S-4a)

and substantially or essentially free of (S,R)-Formula 4a, optionally in salt form, which has the structure of:

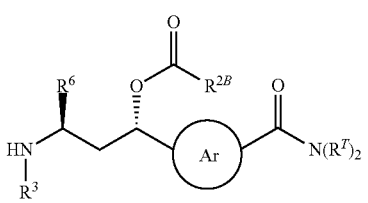
(S,R-4a)

and if optical impurity(ies) are present having (S,S)-Formula 4a, optionally in salt form, as the major optical isomer impurity, or a composition of (R,R)-Formula 4a substantially retaining the optical purity of the composition of (R,R)-Formula 1a obtained from step (b'), (R,R)-Formula 2a obtained from step (c), or (R,R)-Formula 3a from obtained step (g); and wherein the variable groups of the (R,R)-Formula 4a and optical isomers thereof retain their meanings from their respective Formula 1a optical isomers and the variable groups of the Formula 3a and Formula 4a optical isomers retain their meanings from Formula C and their respective Formula 2a optical isomers, or wherein step (g') is followed by step (h')

(h') contacting (R,R)-Formula 3, optionally in salt form, or composition thereof with a suitable deprotecting agent, wherein said deprotecting agent contacting provides (R,R)-Formula 4, optionally in salt form, having the structure of:

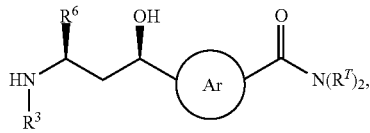
(R,R-4)

or a composition comprising or consisting essentially of (R,R)-Formula 4, or salt thereof, as the predominate optical isomer, optionally having as an optical impurity (S,S)-Formula 4, optionally in salt form, which has the structure of:

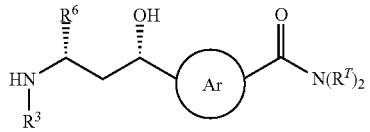
(S,S-4)

or a composition comprising or consisting essentially of (R,R)-Formula 4, substantially or essentially free of (R,S)-Formula 4, optionally in salt form, which has the structure of:

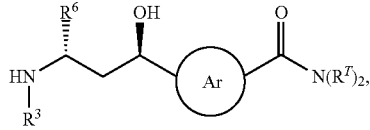
(R,S-4)

and substantially or essentially free of (S,R)-Formula 4, optionally in salt form, and which has the structure of:

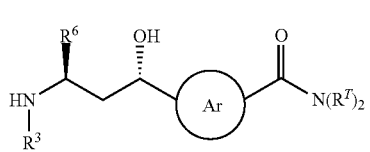
(S,R-4)

and if optical isomer impurity(ies) are present having (S,S)-Formula 4a=, optionally in salt form, as the major optical isomer impurity, or a composition of (R,R)-Formula 4 substantially retaining the optical purity of the composition of (R,R)-Formula 1a obtained from step (b'), (R,R)-Formula 2 obtained from step (c), or (R,R)-Formula 3 from obtained step (g'); and wherein the variable groups of the (R,R)-Formula 4 and optical isomers thereof retain their meanings from their respective Formula 1a optical isomers and the variable groups of the Formula 3 and Formula 4 optical isomers retain their meanings from Formula C and their respective Formula 2 optical isomers; and wherein step (h) or (h') is followed by (i):

(i) contacting (R,R)-Formula 4 or (R,R)-Formula 4a, optionally in salt form, or composition thereof, in the presence of a second coupling agent, and optionally in the presence of a second suitable hindered base, with a protected amino acid, optionally in salt form, of Formula S-D2, or contacting with an activated ester thereof, optionally in the presence of a second suitable hindered base, wherein the Formula S-D2 protected amino acid has the structure of:

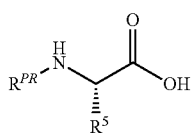

(S-D2)

wherein $R^{PR}$ is an amino protecting group, wherein said second coupling agent or said protected amino acid activated ester contacting of step (i) provides a protected tubulysin intermediate, (R,R)-Formula 5 or (R,R)-Formula 5a, either optionally in salt form, or a composition thereof, that on deprotection provides a deprotected tubulysin intermediate, optionally in salt form, of (R,R)-Formula 6 or (R,R)-Formula 6a having the structure of:

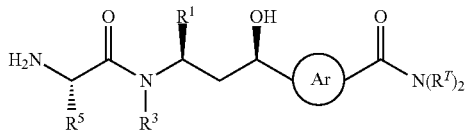

(R,R-6)

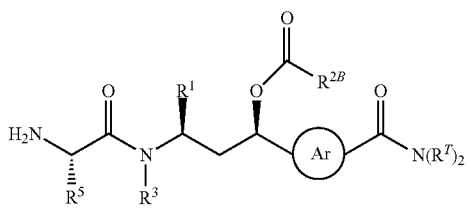

(R,R-6a)

wherein the variable group meanings of (R,R)-Formula 5 and (R,R)-Formula 6 or (R,R)-Formula 5a and (R,R)-Formula 6a and their corresponding optical isomers are retained from their respective Formula 4 or Formula 4a optical isomers and are as defined for the respective Formula T1A optical isomers, or provides a composition comprising or consisting essentially of (R,R)-Formula 6 or (R,R)-Formula 6a, either in optionally in salt form, as the predominate optical isomer, optionally having as the major optical impurity, (S,S)-Formula 6 or (S,S)-Formula 6a, either in optionally in salt form, and which has the structure of:

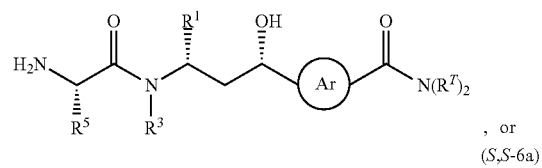

(S,S-6)

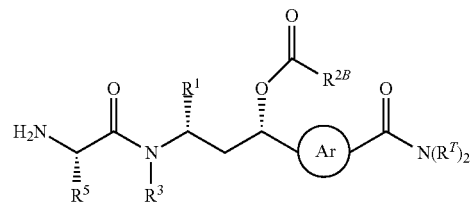

(S,S-6a)

or a composition comprising or consisting essentially of (R,R)-Formula 6, or salt thereof, or (R,R)-Formula 6a, or salt thereof, substantially or essentially free of (R,S)-Formula 6a or (R,S)-Formula 6a, either optionally in salt form, which has the structure of:

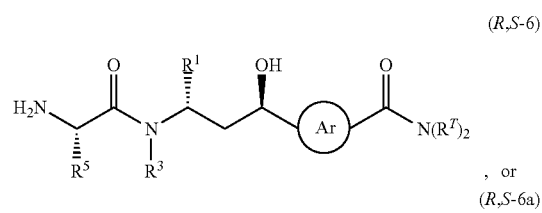

(R,S-6)

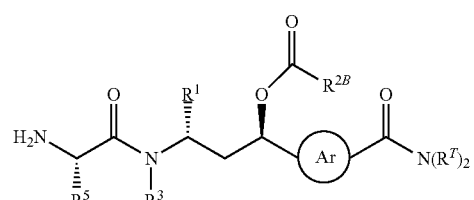

(R,S-6a)

and substantially or essentially free of (S,R)-Formula 6 or (S,R)-Formula 6a, optionally in salt form, and which has the structure of:

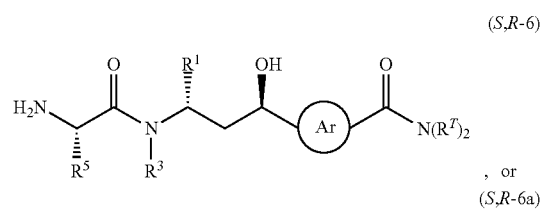

(S,R-6)

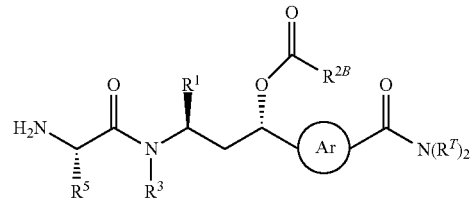

(S,R-6a)

and if optical isomer impurity(ies) are present having (S,S)-Formula 6a or (S,S)-Formula 6a, either optionally in salt form, as the major optical impurity, or step (h) or step (h') is followed by step (i'):

(i') contacting (R,R)-Formula 4 or (R,R)-Formula 4a, optionally in salt form, or composition thereof, in the presence of a second coupling agent, and optionally in the presence of a second suitable hindered base, with a (R,S)-D1-D2 dipeptide, optionally in salt form, or contacting with an activated ester thereof, optionally in the presence of a second suitable hindered base, wherein the dipeptide has the structure of:

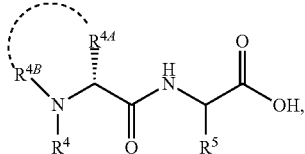

(R,S-D1-D2)

wherein the variable groups of the protected amino acid or dipeptide are as defined for (R,R)-Formula T1A; and wherein said second coupling agent contacting or said dipeptide activated ester contacting of step (i) with (R,R)-Formula 4a, optionally in salt form, or composition thereof, provides the tubulysin compound (R,R)-Formula T1A, optionally in salt form, or the composition thereof, or with (R,R)-Formula 4 provides desacetyl (R,R)-Formula T1A that on acylation provides the (R,R)-Formula T1A tubulysin compound or composition.

In some preferred embodiments step (i') provides a composition comprising (R,R)-Formula T1A, or step (i) provides a composition comprising (R,R)-Formula 6 or (R,R)-Formula 6a wherein the composition substantially retains the optical purity of the composition of (R,R)-Formula 1a obtained from step (b'), (R,R)-Formula 2 obtained from step (c), (R,R)-Formula 2a obtained from step (d), (R,R)-Formula 3a obtained from step (g) or (R,R)-Formula 3a obtained from step (g'), (R,R)-Formula 4a obtained from step (h) or (R,R)-Formula 4 obtained from step (h') or (R,R)-Formula 5a obtained from step (i).

In some of those embodiments providing the tubulysin intermediate of (R,R)-(R,R)-Formula 6 or (R,R)-Formula 6a, either optionally in salt form, or composition thereof, the tubulysin compound of desacetyl (R,R)-Formula T1A or (R,R)-Formula T1A, either optionally in salt form, or composition thereof, is obtained from contacting the tubulysin intermediate or composition thereof, with an amine-containing acid of formula R-D1, or salt thereof, having the structure of:

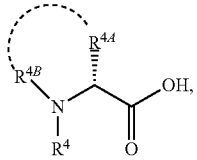

(R-D1)

in the presence of a third coupling agent and optionally in the presence of a third suitable hindered based, or by contacting the tubulysin intermediate with an activated ester of the amine-containing acid, optionally in the presence of a third suitable hindered based, wherein the variable groups are as defined for (R,R)-Formula T1A, wherein said third coupling agent providing desacetyl (R,R)-Formula T1A in some embodiments is followed by acylation to provides the (R,R)-Formula T1A tubulysin compound, optionally in salt form or composition thereof, wherein in preferred embodiments the optical purity of the (R,R)-Formula 6, or (R,R)-Formula 6a composition is substantially or essentially retained by the (R,R)-Formula T1A composition so obtained.

Preferred embodiments for the tubuvaline intermediates of Formula A, Formula AB, and tubuvaline compounds of (R,R)-Formulae 1a, 2 and 2a and optical isomers thereof are as previously described for "Embodiment Group 4".

Accordingly, in preferred embodiments for tubulysin intermediates of (R,R)-Formulae 3a, 4a, 5a and 6a, and optical isomers thereof, obtained from steps (g), (h) and (i), respectively, and tubulysin intermediates of (R,R)-Formulae 3, 4, 5 and 6, and optical isomers thereof, obtained from steps (g'), (h') and (i) and for the tubulysin compound of desacyl (R,R)-Formula T1A and (R,R)-Formula T1A and optical isomers thereof obtained from steps (g), (h) and (i') or (g'), (h') and (i') the circled Ar moeity is a $C_5$ heteroarylene, optionally in salt form, including without limitation a $C_5$ heteroarylene related to thiazole, isoxazole, pyrazole or imidazole as the parent heterocycle.

Thus, one preferred embodiment provides a method for preparing a (R,R)-(R,R)-Formula 6 or Formula 6a tubulysin intermediate, either optionally in salt form, having the structure of:

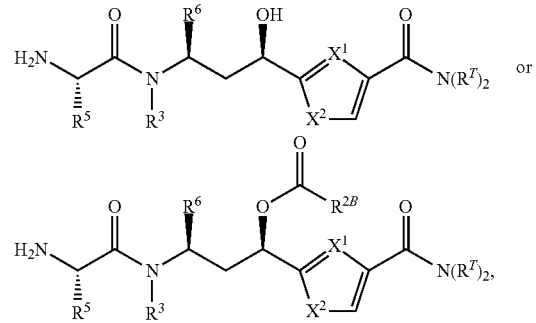

respectively, or a composition comprised or consisting essentially of (R,R)-Formula 6 as the predominate optical isomer, or a composition comprised of (R,R)-Formula 6 essentially free of the optical impurities of (R,S)-Formula 6 and (S,R)-Formula 6, each optionally is salt form, which have the structures of:

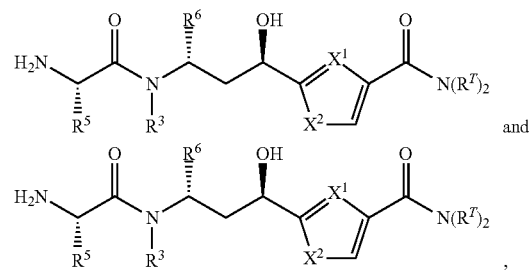

respectively, and if other optical isomer impurity(ies) are present having (S,S)-Formula 6 as the major optical impurity, optionally in salt form, which has the structure of:

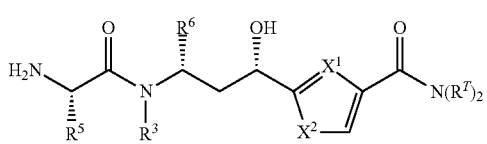

or a composition comprised or consisting essentially of (R,R)-Formula 6a as the predominate optical isomer, or a composition comprised of (R,R)-Formula 6a essentially free of the optical impurities of (R,S)-Formula 6a and (S,R)-Formula 6a, each optionally is salt form, which have the structures of:

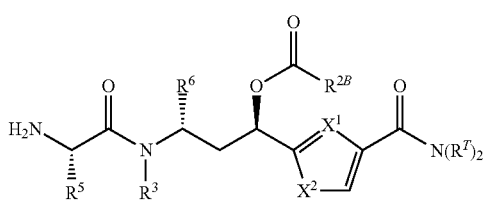

respectively, and if other optical isomer impurity(ies) are present having (S,S)-Formula 6a as the major optical impurity, optionally in salt form, which has the structure of:

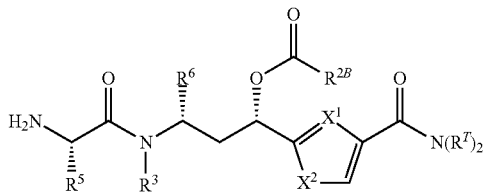

wherein the method further comprises the step of deprotection of (R,R)-Formula 5 or Formula 5a, either optionally in salt form, having the structure of:

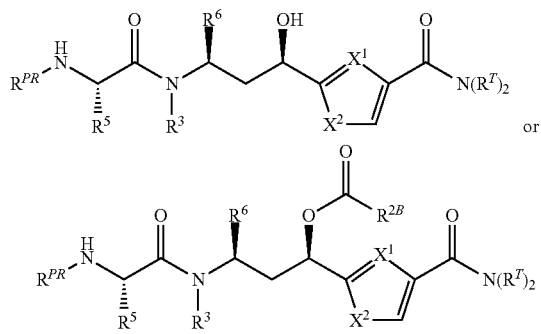

respectively, or composition comprising or consisting essentially of (R,R)-Formula 5, or salt thereof, as the predominate optical isomer, or a composition comprised or consisting essentially of (R,R)-Formula 5 essentially free of the optical impurities of (R,S)-Formula 5 and (S,R)-Formula 5, which have the structures of:

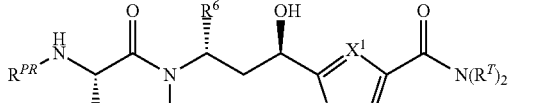

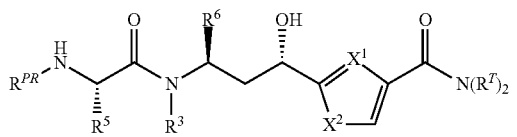

respectively, each optionally in salt form, and if optical impurity(ies) are present having (S,S)-Formula 5 as the major optical impurity, optionally in salt form, which has the structure of:

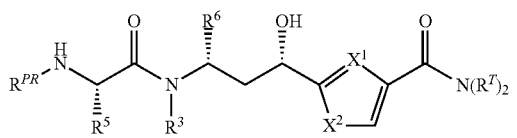

or composition comprising or consisting essentially of (R,R)-Formula 5a, or salt thereof, as the predominate optical isomer, or a composition comprised or consisting essentially of (R,R)-Formula 5a essentially free of the optical impurities of (R,S)-Formula 5a and (S,R)-Formula 5a, which have the structures of:

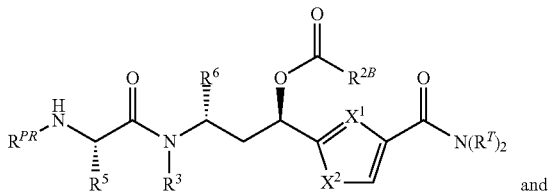

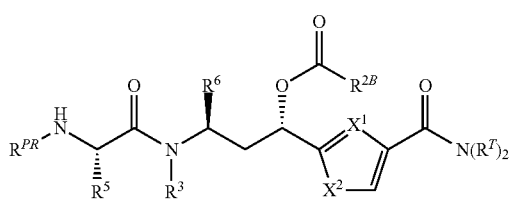

respectively, each optionally in salt form, and if optical impurity(ies) are present having (S,S)-Formula 5a as the major optical impurity, optionally in salt form, which has the structure of:

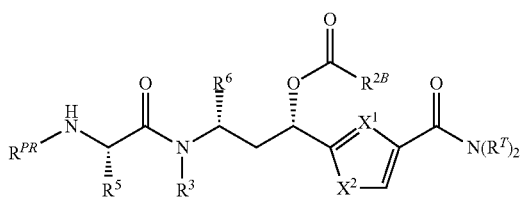

and wherein $R^{PR}$ is a suitable amino protecting group and meanings of the remaining variable groups of (R,R)-Formula 5, (R,R)-Formula 6, (R,R)-Formula 5a, (R,R)-Formula 6a, and optical isomers thereof, are retained from the corresponding (R,R)-Formula 4 and (R,R)-Formula 4a optical isomers described herein and are as previously defined in this embodiment group.

In another preferred embodiment a method is provided for preparing a (R,R)-Formula T1A tubulysin compound or a desacyl (R,R)-Formula T1A tubulysin compound that provides (R,R)-Formula T1A on acylation, optionally in salt form, wherein desacyl (R,R)-Formula T1A tubulysin and (R,R)-Formula T1A has the structure of:

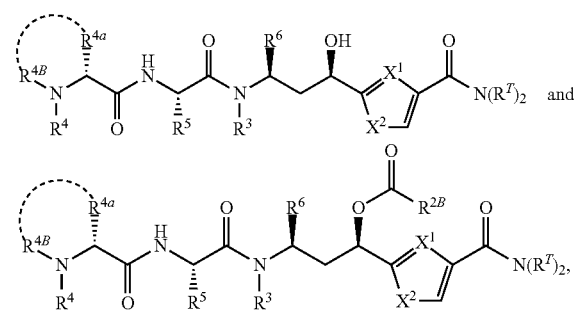

or a method is provided for preparing a composition comprising or consisting essentially of desacyl (R,R)-Formula T1A, optionally in salt form, as the predominate optical isomer or a composition comprising or consisting essentially of desacyl (R,R)-Formula T1A, or salt thereof, essentially free of the optical impurities of desacyl (R,S)-Formula T1A and desacyl (S,R)-Formula T1A, which have the structures of:

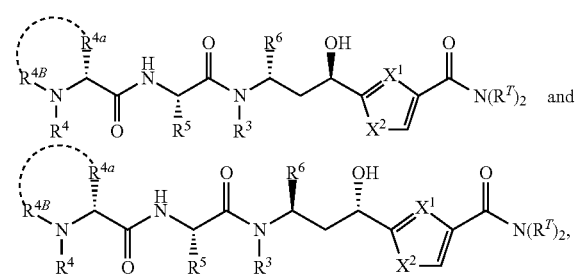

respectively respectively, each optionally in salt form, and if optical isomer impurity(ies) are present having desacyl (S,S)-Formula T1A, optionally in salt form, as the major optical impurity, which has the structure of:

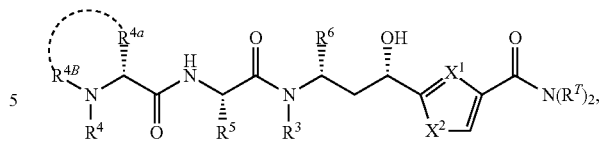

or a composition comprising or consisting essentially of (R,R)-Formula T1A, optionally in salt form, as the predominate optical isomer or a composition comprising or consisting essentially of (R,R)-Formula T1A, or salt thereof, essentially free of the optical impurities of (R,S)-Formula T1A and (S,R)-Formula T1A, which have the structures of:

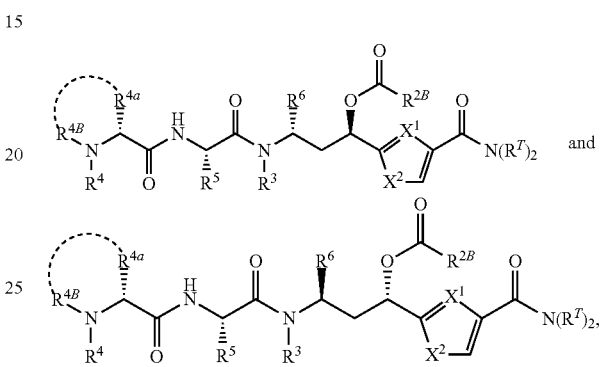

respectively respectively, each optionally in salt form, and if optical isomer impurity(ies) are present having (S,S)-Formula T1A, optionally in salt form, as the major optical impurity, which has the structure of:

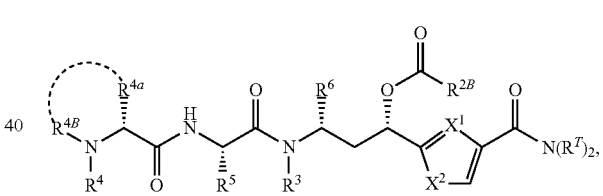

wherein the desacyl (R,R)-Formula T1A or (R,R)-Formula T1A tubulysin compound, either optionally in salt form, or composition thereof, is prepared by contacting the (R,R)-Formula 6 or (R,R)-Formula 6a tubulysin intermediate, optionally in salt form, or composition thereof, in the presence of a third coupling agent, and optionally in the presence of a third suitable hindered base, with an amine-containing acid, optionally in salt form, having the structure of Formula R-D1:

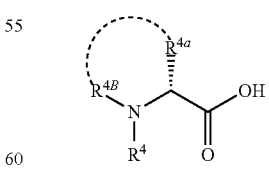

or contacting the (R,R)-Formula 6 or (R,R)-Formula 6a tubulysin intermediate, or composition thereof, with the activated ester thereof, optionally in the presence of a third suitable hindered base, wherein Formula R-D1 is preferably D-N-methyl-pipecolic acid, optionally in salt form, or an activated ester thereof, or desacyl (R,R)-Formula T1A is prepared by contacting a (R,R)-Formula 4 tubulysin intermediate, optionally in salt form, having the structure of:

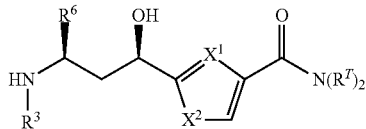

or a composition thereof comprising or consisting essentially of (R,R)-Formula 4, or salt thereof, as the predominate optical isomer, or a composition of (R,R)-Formula 4 essentially free of the optical isomer impurities of (R,S)-Formula 4 and (S,R)-Formula 4, which have the structures of:

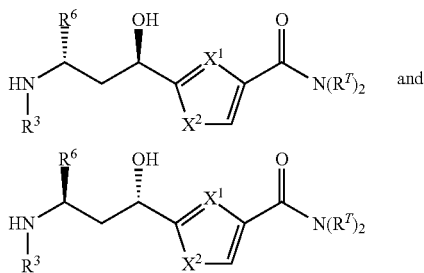

respectively, each optionally in salt form, and if optical impurity(ies) are present having (S,S)-Formula 4 as the major optical impurity, optionally in salt form, which has the structure of:

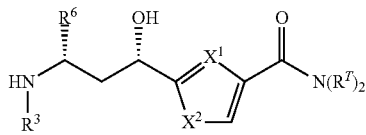

in the presence of a second coupling agent, and optionally in the presence of a second suitable hindered base, with (R,S)-D1-D2 dipeptide having the structure of:

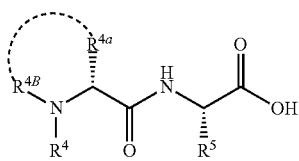

optionally in salt form, or contacting (R,R)-Formula 4, optionally in salt form, or composition thereof with an activated ester of the dipeptide, optionally in the presence of a second suitable hindered base, and wherein (R,R)-Formula T1A is prepared by contacting a (R,R)-Formula 4a tubulysin intermediate, optionally in salt form, of having the structure of:

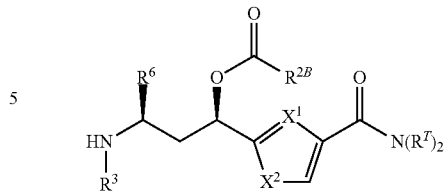

respectively, or a composition thereof comprising or consisting essentially of (R,R)-Formula 4a, or salt thereof, as the predominate optical isomer, or a composition of (R,R)-Formula 4a essentially free of the optical isomer impurities of (R,S)-Formula 4a and (S,R)-Formula 4a, which have the structures of:

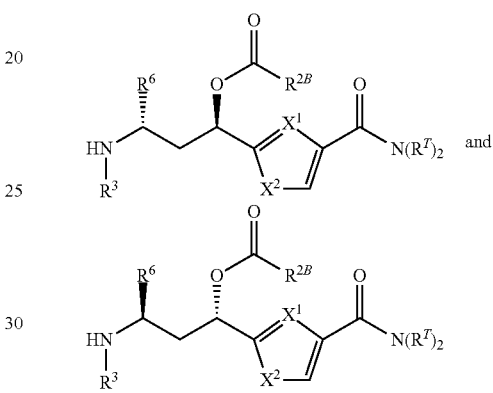

each optionally in salt form, and if other optical impurity (ies) are present having (S,S)-Formula 4a as the major optical impurity, optionally in salt form, which has the structure of:

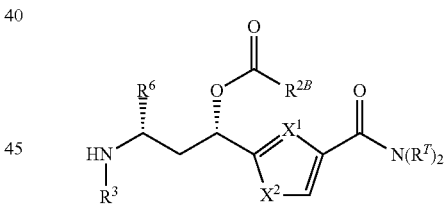

in the presence of a second coupling agent and optionally in the presence of a second suitable hindered base, with the (R,S)-D1-D2 dipeptide, or salt thereof, or by contacting (R,R)-Formula 4a, optionally in salt form, or composition thereof with an activated ester of the dipeptide, optionally in the presence of a second suitable hindered base, wherein (R,R)-Formula 4, or composition thereof, is prepared by deprotection of the (R,R)-Formula 3 tubulysin intermediate, optionally in salt form, having the structure of:

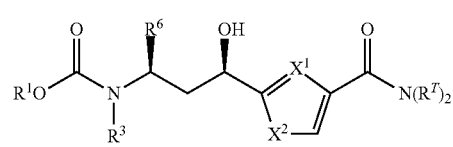

respectively, or by deprotection of a composition comprising or consisting essentially of (R,R)-Formula 3, essentially free of (R,S)-Formula 3 and (S,R)-Formula 3, each optionally in salt form, and which have the structures of:

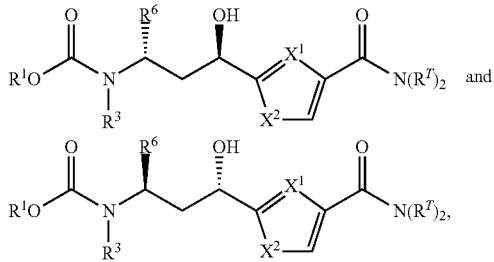

respectively, and if optical isomer impurity(ies) are present having (S,S)-Formula 3 as the major optical impurity, optionally in salt form, which has the structure of:

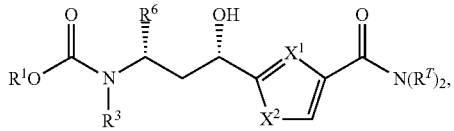

and wherein (R,R)-Formula 4a, or composition thereof, is prepared by deprotection of (R,R)-Formula 3a, or a composition comprising or consisting essentially of (R,R)-Formula 3a, essentially free of (R,S)-Formula 3a, and (S,R)-Formula 3a, each optionally in salt form, which have the structures of:

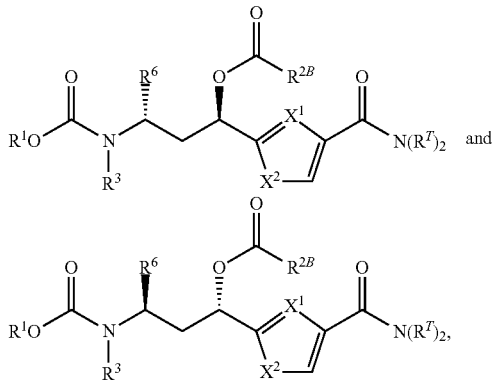

respectively, and if optical isomer impurity(ies) are present having (S,S)-Formula 3a as the major optical impurity, optionally in salt form, which has the structure of:

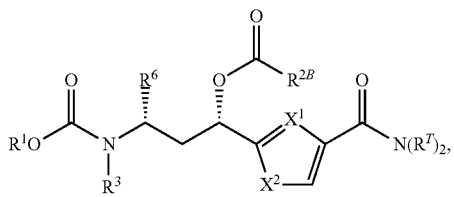

and wherein (R,R)-Formula 3 or (R,R)-Formula 3a, or composition thereof, is in turn prepared by contacting, in the presence of a first coupling agent, and optionally in the presence of a first suitable hindered base, a compound of Formula C having the structure of $HN(R^T)_2$ or a salt thereof, with a (R,R)-Formula 2 or (R,R)-Formula 2a tubuvaline compound, optionally in salt form, or contacting the Formula C compound with an activated ester of the respective tubuvaline compound, optionally in the presence of a first suitable hindered base, wherein (R,R)-Formula 2 and (R,R)-Formula 2a, each optionally in salt form, have the structures of:

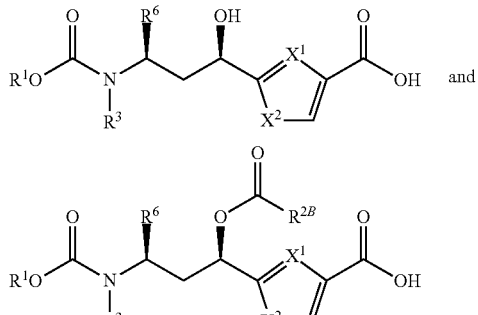

or (R,R)-Formula 3 in turn is prepared by said Formula C contacting with a composition comprised or consisting essentially of (R,R)-Formula 2, or salt thereof, as the predominate optical isomer, wherein the composition is essentially free of the optical impurities, optionally in salt form, of (R,S)-Formula 2 and (S,R)-Formula 2, which have the structures of:

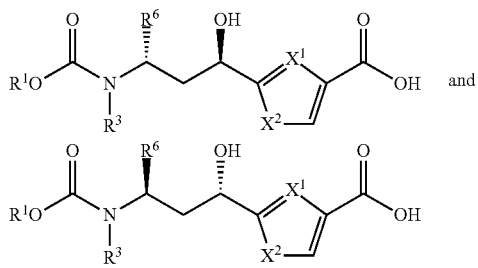

respectively, and if optical isomer impurity(ies) are present having (S,S)-Formula 2a, optionally in salt form, as the major optical isomer impurity, which has the structure of:

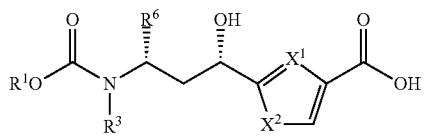

and (R,R)-Formula 3a, or composition thereof, in turn is prepared by said Formula C contacting with a composition comprised or consisting essentially of (R,R)-Formula 2a, or salt thereof, as the predominate optical isomer, wherein the composition is essentially free of the optical impurities, each optionally in salt form, of (R,S)-Formula 2a and (S,R)-Formula 2a, which have the structures of:

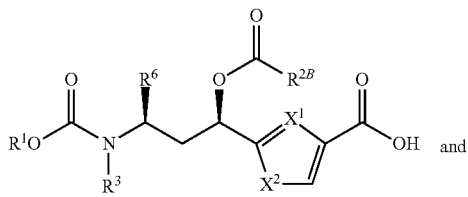

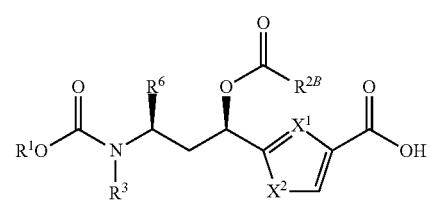

respectively, and if optical impurity(ies) are present having (S,S)-Formula 2a, optionally in salt form, as the major optical isomer impurity, which has the structure of:

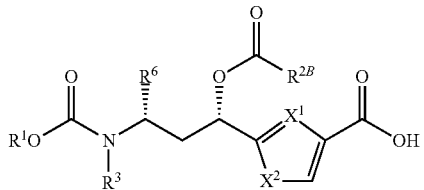

wherein the (R,R)-Formula 2 and (R,R)-Formula 2a tubuvaline compounds are prepared according to a method of "Embodiment Group 3" and "Embodiment Group 4", respectively; and wherein in each one of these tubulysin and tubuvaline structures and intermediates thereof $X^1$ is =N— and $X^2$ is S, O, or N($R^{X2}$)—, or $X^1$ is =C($R^{X1}$)— and $X^2$ is N$R^{X2}$, wherein $R^{X1}$ and $R^{X2}$ are independently selected from the group consisting of —H and optionally substituted $C_1$-$C_4$ alkyl, preferably from the group consisting of —H, —$CH_3$ and —$CH_2CH_3$. In preferred embodiments, the circled Aryl is thizaol-1,3-di-yl.

In more preferred embodiments, the Formula 2a tubuvaline composition is comprised or consists essentially of (R,R)-Formula 2a, optionally in salt form, as the predominate optical isomer, the structure of which is:

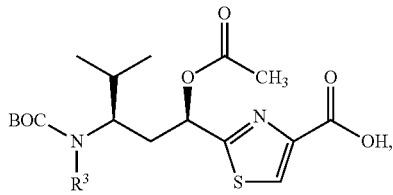

and having (S,S)-Formula 2a, optionally in salt form, as the major optical impurity, the structure of which is:

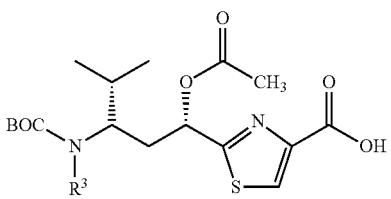

and is essentially free of the optical isomer impurities of (R,S)-Formula 2a and (S,R)-Formula 2a, each optionally in salt form, the structures of which are:

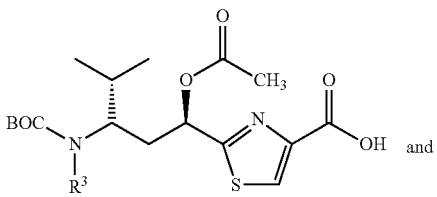

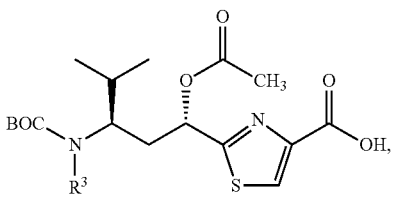

respectively, so that the said first coupling agent contacting provides the Formula 3a composition comprised or consisting essentially of (R,R)-Formula 3a, optionally in salt, as the predominate optical isomer, the structure of which is:

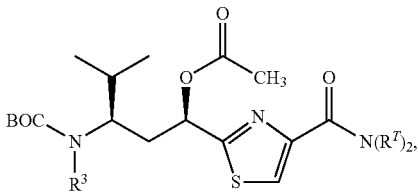

and having (S,S)-Formula 3a, optionally in salt form, as the major optical impurity, if such impurity(ies) are present, the structure of which is:

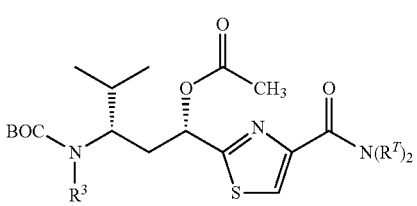

and is essentially free of the optical impurities of (R,S)-Formula 3a and (S,R)-Formula 3a, each optionally in salt form, the structures of which are:

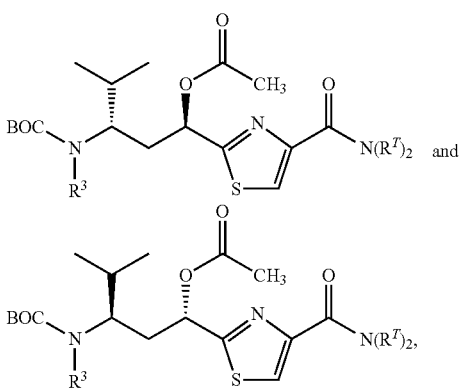

respectively, and the composition of Formula 4a from deprotection of the Formula 3a composition is comprised or consists essentially of (R,R)-Formula 4a, optionally in salt form, as the predominate optical isomer, having the structure of:

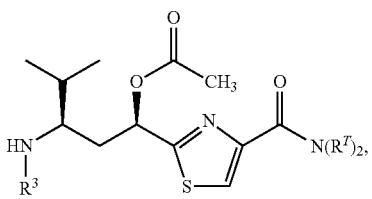

and having (S,S)-Formula 4a, optionally in salt form, as the major optical impurity, if such impurity(ies) are present, the structure of which is:

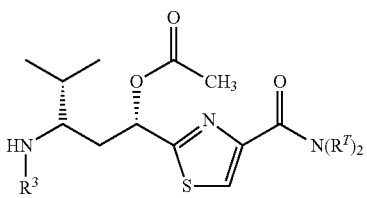

and is essentially free of the optical isomer impurities of (R,S)-Formula 4a and (S,R)-Formula 4a, each optionally in salt form, the structures of which are:

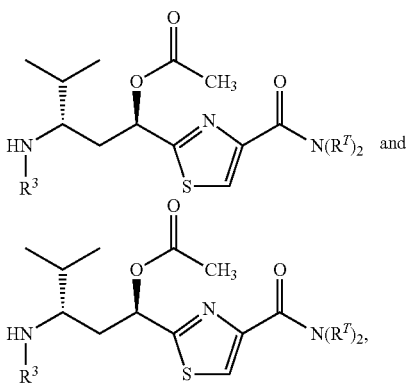

respectively.

2.3.3 Embodiment Group 8

In a further group of embodiments, provided herein are methods for preparing a tubulysin compound of (R,R)-Formula T1A, optionally in salt form, having the structure of:

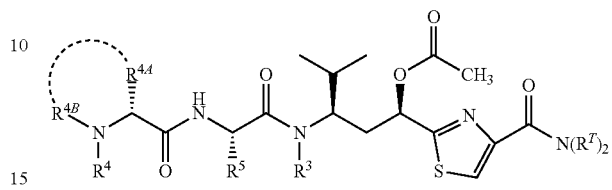

or a composition comprising or consisting essentially of that tubulysin compound, or salt thereof, wherein (R,R)-Formula T1A is the predominate optical isomer and optionally having (S,S)-Formula T1A as an optical impurity, optionally in salt form, the structure of which is:

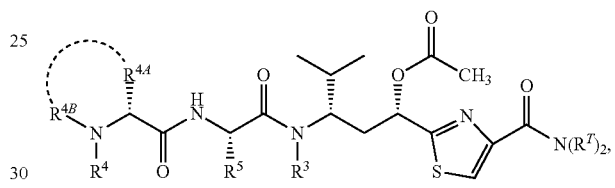

and is substantially or essentially free of the (R,S)-Formula T1A optical impurity, optionally in salt form, which has the structure of:

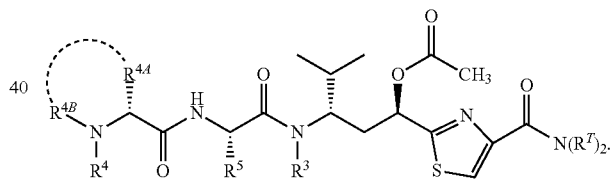

and is substantially or essentially free of the (S,R)-Formula T1A optical impurity, optionally in salt form, which has the structure of:

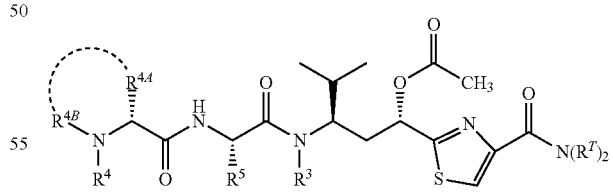

wherein:

the curved dashed line indicates optional cyclization;

$R^{2B}$ is saturated $C_1$-$C_6$ alkyl, unsaturated $C_3$-$C_8$ alkyl, $C_2$-$C_8$ alkenyl or $C_2$-$C_4$ alkynyl, optionally substituted; and $R^3$ is optionally substituted $C_1$-$C_6$ alkyl, in particular methyl, ethyl or propyl;

$R^4$ and $R^5$ are independently optionally substituted $C_1$-$C_6$ alkyl;

$R^{4A}$ is hydrogen or optionally substituted $C_1$-$C_6$ alkyl;

$R^{4B}$ is optionally substituted $C_1$-$C_6$ alkyl, or $R^{4A}$ and $R^{4B}$ together with the atoms to which they are attached, as indicated by the curved dashed line, define a optionally substituted 5-, 6-, 7-, or 8-membered nitrogen-containing heterocyclyl, preferably a 6-membered nitrogen-containing heterocyclyl;

one $R^T$ is hydrogen or optionally substituted $C_1$-$C_6$ alkyl; and the other is optionally substituted $C_1$-$C_6$ alkyl or optionally substituted $C_3$-$C_6$ heteroalkyl, wherein each optionally substituted $C_1$-$C_6$ alkyl is independently selected, wherein the tubulysin compound of (R,R)-Formula T1A incorporates a tubuvaline compound, prepared by any one of the foregoing methods of "Embodiment Group 4", in particular, the method comprising the steps of:

(a) contacting a tubuvaline intermediate of Formula A having the structure of:

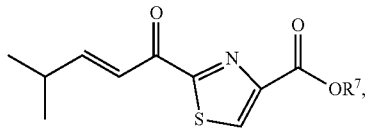

with a carbamate compound of Formula B having the structure of:

in a suitable solvent in the presence of a suitable transition metal (II) catalyst, preferably selected from the group consisting of Cu(II) catalysts and Pd(II) catalysts, to form an enantiomeric mixture of tubuvaline intermediates represented by Formula AB having the structure of:

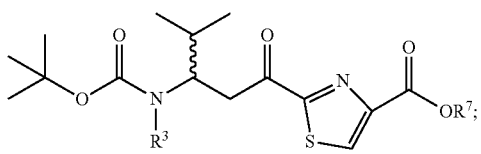

wherein, the variable groups retain their meanings from Formula A and Formula B, or a composition comprising or consisting essentially of that mixture;

(b) contacting the enantiomeric mixture, or composition thereof, of Formula AB with a suitable reducing agent, wherein said reducing agent contacting results in formation of a diastereomeric mixture of tubuvaline compounds, each optionally in salt form, or a composition comprising or consisting essentially of that mixture, represented by Formula R-1a having the structure of:

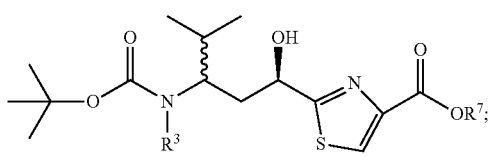

(b') separating the diastereomers of the mixture to provide the diastereomer, (R,R)-Formula 1a, optionally in salt form, or a composition comprising or consisting essentially of that diastereomer, or salt thereof, as the predominate optical isomer, which has the structure of:

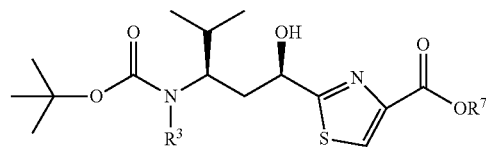

and optionally having as an optical impurity (S,S)-Formula 1a, optionally in salt form, the structure of which is:

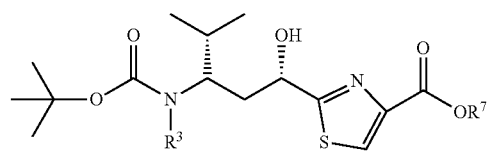

or a composition of (R,R)-Formula 1a or its salt form, essentially free of the corresponding diastereomer, which is (R,S)-Formula 1a, optionally in salt form, which has the structure of:

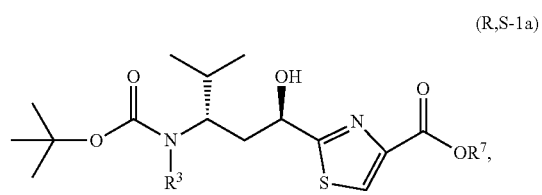

(R,S-1a)

and essentially free of its enantiomer, which is (S,R)-Formula 1a, optionally in salt form, and which has the structure of:

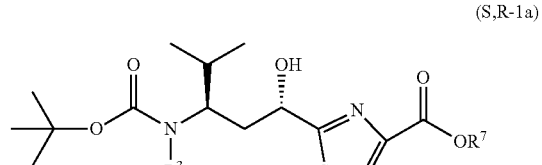

(S,R-1a)

and if optical impurity(ies) are present, preferably having (S,S)-Formula 1a, optionally in salt form, as the major optical isomer impurity, wherein the variable groups of (R,R)-Formula 1a and optical isomers thereof retain their meanings from Formula AB; (c) contacting (R,R)-Formula 1a, optionally in salt form, or composition thereof with a suitable hydrolysis agent, wherein said hydrolysis agent contacting provides the corresponding diastereomer, which is (R,R)-Formula 2, optionally in salt form, which has the structure of:

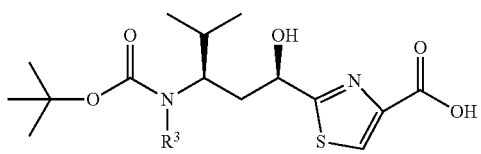

or a composition comprising or consisting essentially of that diastereomer, or salt thereof, as the predominate optical isomer and optionally having as an optical impurity, its corresponding enantiomer, which is (S,S)-Formula 2, optionally in salt form, and which has the structure of:

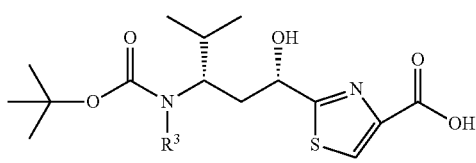

or a composition comprising (R,R)-Formula 2 or salt thereof, essentially free of the diastereomer, (R,S)-Formula 2, optionally in salt form, which has the structure of:

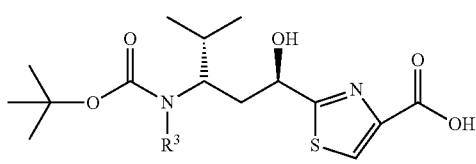

and essentially free of its enantiomer, which is (S,R)-Formula 2, optionally in salt form, and which has the structure of:

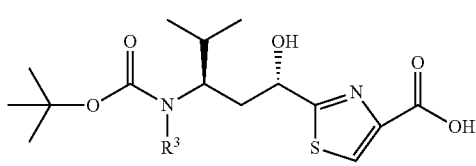

and if optical impurity(ies) are present, preferably having (S,S)-Formula 2, optionally in salt form, as the major optical isomer impurity, wherein variable groups of (R,R)-Formula 2 and optical isomers thereof retain their meanings from (R,R)-Formula 1a;

(d) contacting the (R,R)-Formula 2 diastereomer, optionally in salt form, or the composition thereof, with a suitable acetylating agent, wherein said acetylating agent contacting provides the diastereomer, (R,R)-Formula 2a, optionally in salt form, as the predominate optical isomer, which has the structure of:

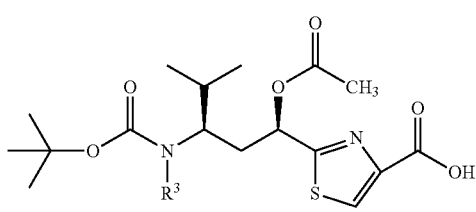

or a composition comprising or consisting essentially of (R,R)-Formula 2a, or salt thereof, as the predominate optical isomer and if optical impurity(ies) are present having the (S,S)-Formula 2a as the major optical impurity, optionally in salt form, which has the structure of:

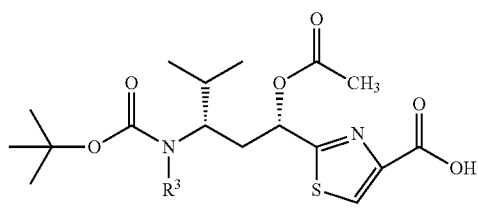

or a composition comprising or consisting essentially of (R,R)-Formula 2a, or salt thereof, essentially free of (R,S)-Formula 2a, optionally in salt form, which has the structure of:

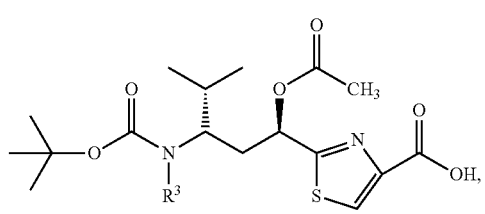

and essentially free its corresponding enantiomer, which is (S,R)-Formula 2a, optionally in salt form, and which has the structure of:

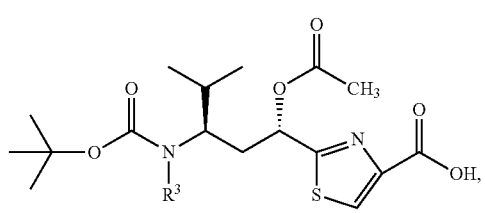

and if optical impurity(ies) are present preferably having (S,S)-Formula 2a, optionally in salt form, as the major optical impurity, wherein the variable groups of (R,R)-Formula 2a and optical isomers thereof, retain their meaning from (R,R)-Formula 1a; and wherein said incorporation of (R,R)-Formula 2a provides the (R,R)-Formula T1A tubulysin compound, optionally in salt form, or composition thereof.

In preferred embodiments for that incorporation, step (d) is followed by the steps of:

(g) contacting the (R,R)-Formula 2a diastereomer or composition thereof, optionally in salt form, with a compound of Formula C having the structure of $HN(R^T)_2$, optionally in salt form, wherein, each $R^T$ is a defined for (R,R)-Formula T1A, in the presence of a first coupling agent and optionally in the presence of a first hindered base or contacting the Formula C compound, optionally in the presence of a first hindered base, with an activated ester of the (R,R)-Formula 2a diastereomer, or salt thereof, to provide (R,R)-Formula 3a as the predominate optical isomer, optionally in salt form, having the structure of:

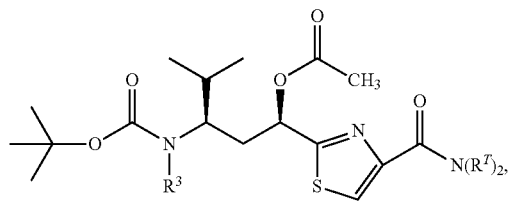

or a composition comprising or consisting essentially of (R,R)-Formula 3a, as the predominate optical isomer and optionally having (S,S)-Formula 3a, optionally in salt form, as an optical impurity, which has the structure of:

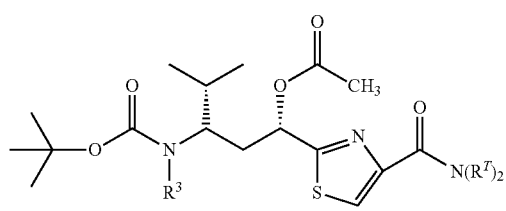

or a composition comprising or consisting essentially of (R,R)-Formula 3a, or salt thereof, essentially free of the (R,S)-Formula 3a, optionally in salt form, which has the structure of:

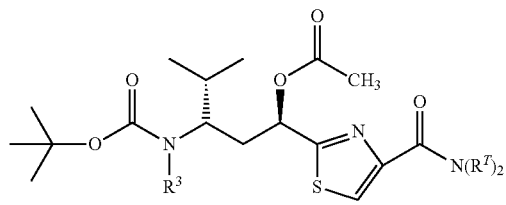

and essentially free of (S,R)-Formula 3a, optionally in salt form, which has the structure of:

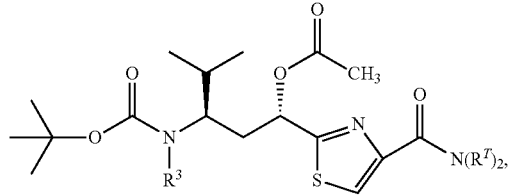

and if optical impurity(ies) are present, having (S,S)-Formula 2, optionally in salt form, as the major optical impurity;

(h) contacting (R,R)-Formula 3, optionally in salt form, or composition thereof, with a suitable deprotecting agent to form (R,R)-Formula 4, optionally in salt form, having the structure of:

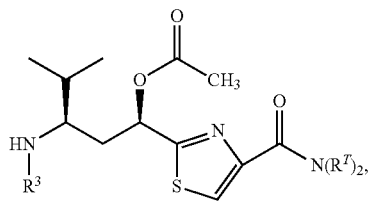

or a composition comprising or consisting essentially of (R,R)-Formula 4a as the predominate optical isomer and optionally having (S,S)-Formula 4a, optionally in salt form, as an optical impurity, which has the structure of:

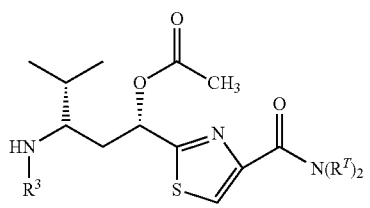

or a composition comprising or consisting essentially of (R,R)-Formula 4a essentially free of (R,S)-Formula 4a, optionally in salt form, which has the structure of:

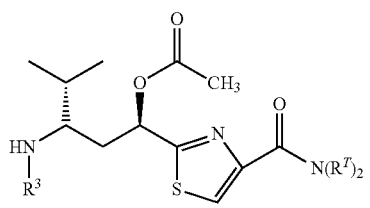

and essentially free of (S,R)-Formula 4a, optionally in salt form, which has the structure of:

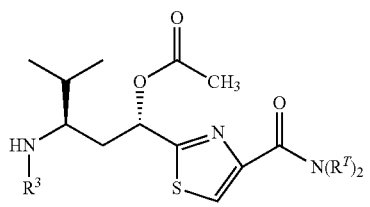

and if optical impurity(ies) are present, preferably (S,S)-Formula 2, optionally in salt form, as the major optical impurity; and wherein the variable groups of (R,R)-Formula 3a and (R,R)-Formula 4a and optical isomers thereof retain their meanings from Formula C and (R,R)-Formula 2a and corresponding optical isomers thereof; and (i) contacting (R,R)-Formula 4a, optionally in salt form, or composition thereof, in the presence of a second coupling agent and optionally in the presence of a second hindered base, with a (R,S)-D1-D2 dipeptide, optionally in salt form, having the structure of:

(R,S-D1-D2)

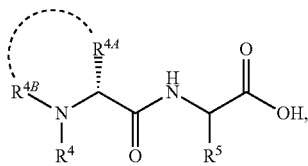

or contacting that diastereomer or composition with an activated ester of the dipeptide, optionally in the presence of a second hindered base, wherein the variable groups of the dipeptide are as defined for (R,R)-Formula T1A; and wherein said second coupling agent or said dipeptide activated ester contacting provides the (R,R)-Formula T1A tubulysin compound, optionally in salt form, or composition thereof.

From those more preferred embodiments particularly preferred embodiments prepare a (R,R)-Formula T1A tubulysin compound, optionally in salt form, having the structure of:

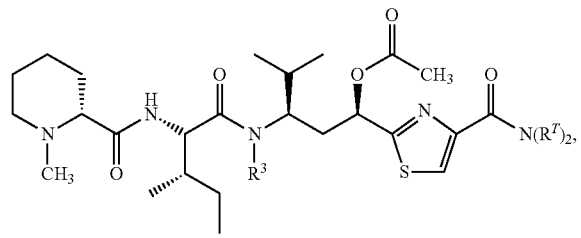

wherein $R^3$ is methyl, ethyl, or propyl; one $R^T$ is hydrogen and the other is optionally substituted $C_1$-$C_6$ alkyl, or particularly preferred embodiments prepare a composition comprising (R,R)-Formula T1A, optionally in salt form, as the predominate optical isomer and having (S,S)-Formula T1A as an optical impurity, optionally in salt form, having the structure of:

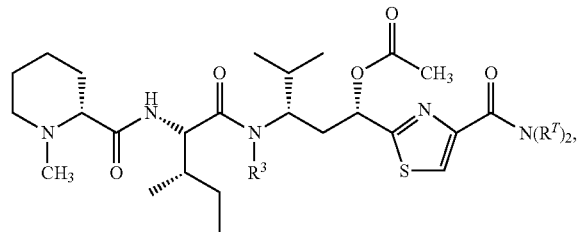

or salt thereof, and/or is essentially free optical impurities (R,S)-Formula T1A and (S,R)-Formula T1A, each optionally in salt form, which have the structures of:

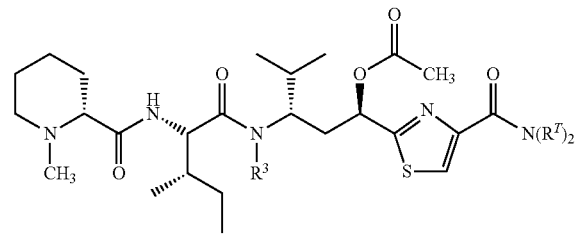

and

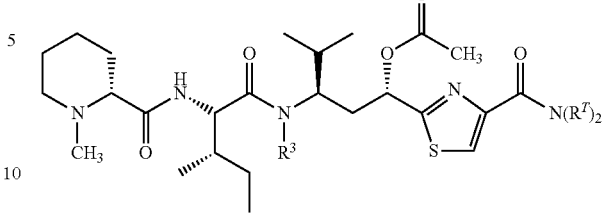

respectively, wherein the (R,R)-Formula T1A tubulysin compound, optionally in salt form, or composition thereof, is prepared by contacting a (R,R)-Formula 4a tubulysin intermediate, optionally in salt form, or a composition thereof in which (R,R)-Formula 4a, optionally in salt form, is the predominate optical isomer having the structure of:

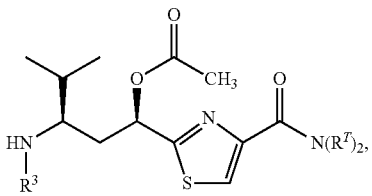

and having (S,S)-Formula 4a as the major optical impurity, if such impurities are present, optionally in salt form, which has the structure of:

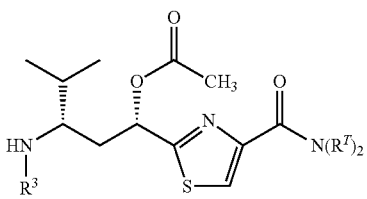

and/or is essentially free of the optical isomer impurities, (R,S)-Formula 4a and (R,S)-Formula 4a, each optionally in salt form, and having the structures of:

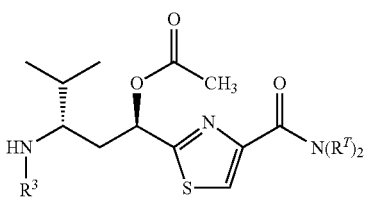

and

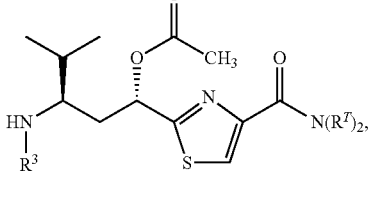

respectively, in the presence of a second coupling agent, and optionally in the presence of a second hindered base, with the dipeptide, D-N-methyl-pipecolyl-isoleucine-OH, optionally in salt form, which has the structure of:

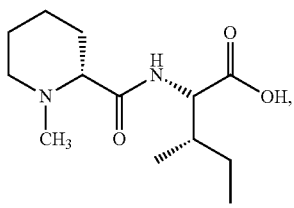

or an activated ester thereof, optionally in the presence of a second hindered base, wherein the (R,R)-Formula 4a composition is prepared as previously described.

For more particularly preferred embodiments, in any one of (R,R)-Formulae 2a-4a, and (R,R)-Formula T1A, and optical isomers thereof, $R_3$ is —$CH_3$.

2.3.4 Embodiment Group 9

In a further group of embodiments, provided herein are methods for preparing a tubulysin compound of (R,R)-Formula T1B, optionally in salt form, or a composition comprising or consisting essentially of that tubulysin compound, or salt thereof, having the structure of:

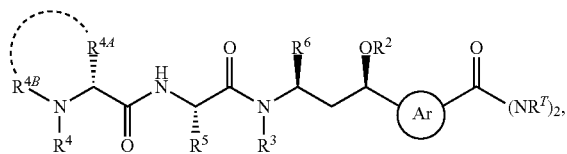
(R,R-T1B)

or a composition thereof in which (R,R)-Formula T1B or its salt form is the predominate optical isomer and having an optical isomer impurity, optionally in salt form, of (S,S)-Formula T1B, which has the structure of:

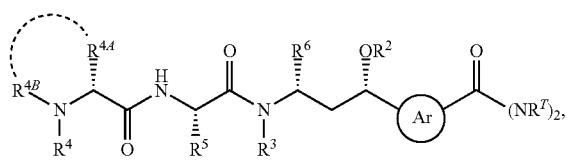
(S,S-T1B)

and is substantially or essentially free of the optical isomer impurities of (R,S)-Formula T1B and (S,R)-Formula T1B, each optionally in salt form, which have the structures of:

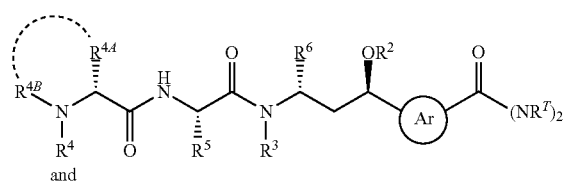
(R,S-T1B)
and

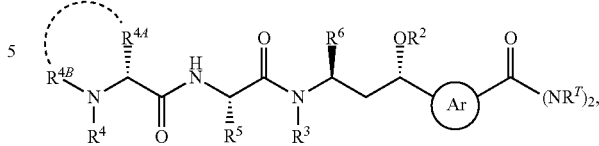
(S,R-T1B)

respectively, wherein:

the curved dashed line indicates optional cyclization;

$R^2$ is optionally substituted saturated $C_1$-$C_6$ alkyl, or optionally substituted unsaturated $C_3$-$C_8$ alkyl, or $R^2$ is $R^{2A}$, wherein $R^{2A}$ is —$CH_2OR^{2C}$, wherein $R^{2C}$ is saturated $C_1$-$C_8$ alkyl or unsaturated $C_3$-$C_8$ alkyl, optionally substituted;

the circled Ar represents a 5-membered heteroarylene, wherein the indicated required substituents to that heteroarylene are in a 1,3-relationship with each other with optional substitution at the remaining positions;

$R^3$ is an optionally substituted $C_1$-$C_6$ alkyl, in particular, methyl ethyl or propyl;

$R^4$, $R^5$, and $R^6$ are independently optionally substituted $C_1$-$C_6$ alkyl;

$R^{4A}$ is hydrogen or optionally substituted $C_1$-$C_6$ alkyl;

$R^{4B}$ is optionally substituted $C_1$-$C_6$ alkyl, or $R^{4A}$ and $R^{4B}$ together with the atoms to which they are attached, as indicated by the curved dashed line, define a optionally substituted 5-, 6-, 7-, or 8-membered nitrogen-containing heterocyclyl, preferably a 6-membered nitrogen-containing heterocyclyl; and one $R^T$ is hydrogen or optionally substituted alkyl; and the other is optionally substituted $C_1$-$C_6$ alkyl or optionally substituted $C_3$-$C_6$ heteroalkyl, wherein each optionally substituted $C_1$-$C_6$ alkyl is independently selected, wherein the tubulysin compound incorporates a tubuvaline compound prepared by any one of the foregoing methods of "Embodiment Group 5", in particular:

the method comprising the steps of:
(a) contacting a tubuvaline intermediate of Formula A:

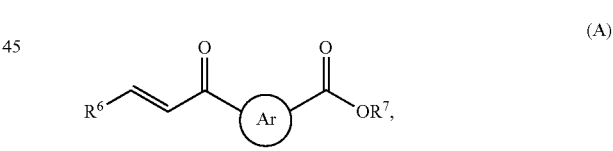
(A)

with a carbamate compound of Formula B:

$R^3NHC(O)OR^1$ (B), in a suitable solvent in the presence of a suitable transition metal (II) catalyst, preferably selected from the group consisting of Cu(II) catalysts and Pd(II) catalysts, to form a enantiomeric mixture of tubuvaline compounds, each optionally in salt form, represented by Formula AB:

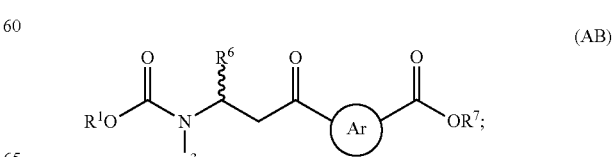
(AB)

wherein, the variable groups retain their meanings from Formula A and Formula B, or a composition comprising or consisting essentially of that mixture;

(b) contacting the enantiomeric mixture, or composition thereof, of Formula AB with a suitable reducing agent wherein said reducing agent contacting results in formation of a diastereomeric mixture, or a composition comprising or consisting essentially of that mixture, represented by Formula R-1a:

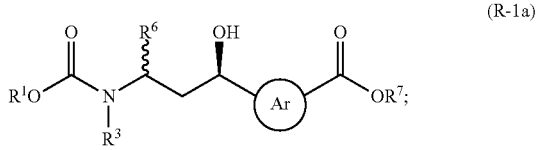

(R-1a)

(b') separating the diastereomers, each optionally in salt form, to provide the (R,R)-Formula 1a tubuvaline compound, or a composition comprising or consisting essentially of that compound or salt thereof, as the predominate optical isomer having the structure of:

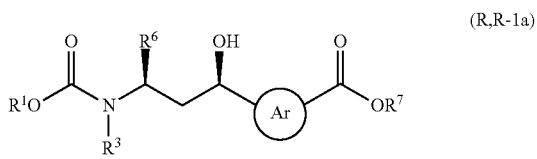

(R,R-1a)

and optionally having as an optical impurity, (S,S)-Formula 1a, optionally in salt form, which has the structure of:

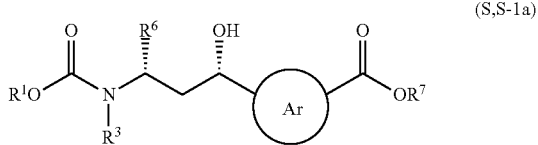

(S,S-1a)

or a composition of (R,R)-Formula 1a substantially or essentially free of (R,S)-Formula 1a, optionally in salt form, which has the structure of:

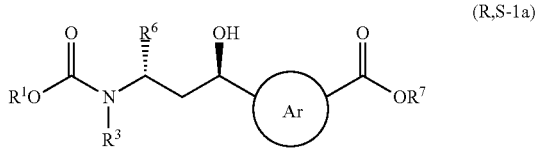

(R,S-1a)

and substantially or essentially free of (S,R)-Formula 1a, optionally in salt form, which has the structure of:

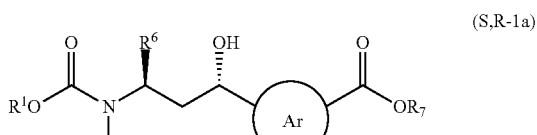

(S,R-1a)

and if optical impurity(ies) are present, having (S,S)-Formula 1a as the major optical impurity, wherein the variable groups of (R,R)-Formula 1a and optical isomers thereof retain their meanings from Formula AB;

(e) contacting the (R,R)-Formula 1a tubuvaline compound, optionally in salt form, or the composition comprising or consisting essentially of that compound, or salt thereof, with a suitable alkylating agent so as to form the (R,R)-Formula 1b tubuvaline compound, optionally in salt form, or a composition comprised or consisting essentially of that compound having the structure of:

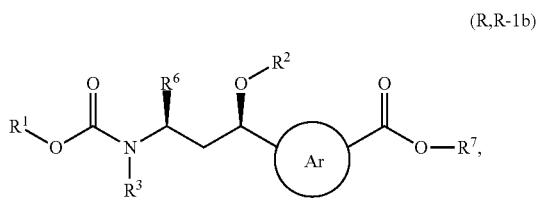

(R,R-1b)

and optionally having as an optical impurity (S,S)-Formula 1b, optionally in salt form, and which has the structure of:

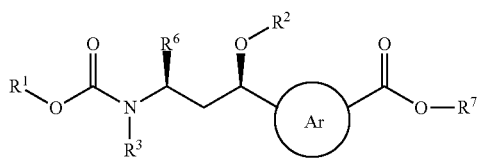

or a composition of (R,R)-Formula 1b substantially or essentially free of (R,S)-Formula 1b, optionally in salt form, having the structure of:

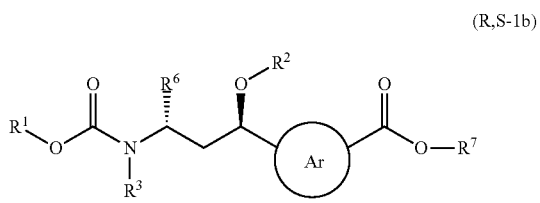

(R,S-1b)

and substantially or essentially free of (S,R)-Formula 1b, optionally in salt form, which has the structure of:

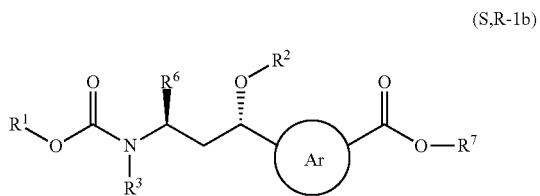

(S,R-1b)

and if optical impurity(ies) are present, having (S,S)-Formula 1b as the major optical impurity, wherein $R^2$ in (R,R)-Formula 1b and optical isomers thereof are as defined for (R,R)-Formula T1B and corresponding optical isomers thereof and the remaining variable groups are as defined in (R,R)-Formula 1a and corresponding optical isomers thereof (f) contacting the (R,R)-Formula 1b tubuvaline compound, optionally in salt form, or composition thereof, with a suitable hydrolysis agent so as to form (R,R)-Formula 2b, optionally in salt form, or composition comprised or consisting essentially of that optical isomer, which has the structure of:

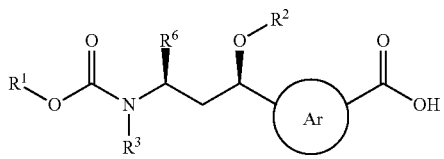
(R,R-2b)

and optionally having as an optical impurity (S,S)-Formula 2b, optionally in salt form, which has the structure of:

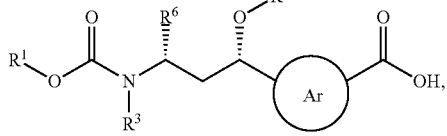
(S,S-2b)

or a composition of (R,R)-Formula 2b substantially or essentially free of (R,S)-Formula 2b, optionally in salt form, and which has the structure of:

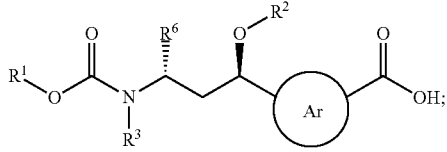

and substantially or essentially free of (S,R)-Formula 2b, optionally in salt form, and which has the structure of:

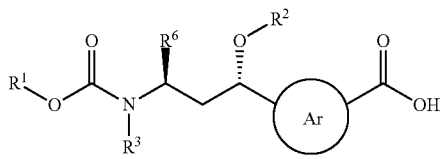
(S,R-2b)

and if optical impurity(ies) are present, having (S,S)-Formula 2b as the major optical impurity, (g) contacting the (R,R)-Formula 2b diastereomer or composition thereof with a compound of Formula C having the structure of $HN(R^T)_2$ in the presence of a first coupling agent and optionally in the presence of a first hindered base, or contacting the Formula C compound an activated ester the (R,R)-Formula 2b diastereomer, optionally in the presence of a first hindered base to form the tubulysin intermediate, (R,R)-Formula 3b, opt

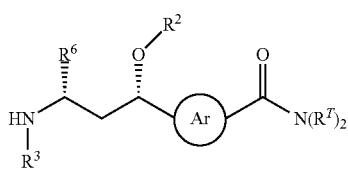
(S,S-4b)

or a composition of (R,R)-Formula 4b, substantially or essentially free (R,S)-Formula 4b, optionally in salt form, having the structure of:

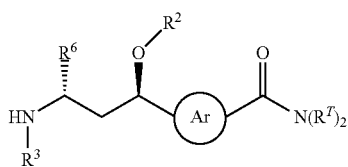
(R,S-4b)

and substantially or essentially free of (S,R)-Formula 4b, optionally in salt form, and which has the structure of:

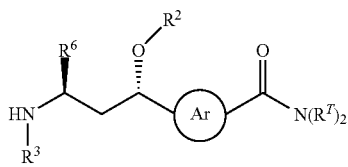
(S,R-4b)

wherein, the variable groups of (R,R)-Formula 3b and (R,R)-Formula 4b, and optical isomers thereof, retain their meanings from Formula C and (R,R)-Formula 2b and corresponding optical isomers thereof;

(i) contacting (R,R)-Formula 4b, optionally in salt form, or composition thereof, in the presence of a second coupling agent, and optionally in the presence of a second suitable hindered base, with a protected amino acid, optionally in salt form, of Formula S-D2, or contacting with an activated ester thereof, optionally in the presence of a second suitable hindered base, wherein the Formula S-D2 protected amino acid has the structure of:

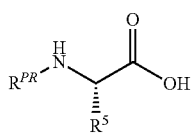
(S-D2)

wherein $R^{PR}$ is an amino protecting group, wherein said second coupling agent or said protected amino acid activated ester contacting provides a protected tubulysin intermediate, (R,R)-Formula 5b, optionally in salt form, or a composition thereof, that on deprotection provides a deprotected tubulysin intermediate, optionally in salt form, of (R,R)-Formula 6b having the structure of:

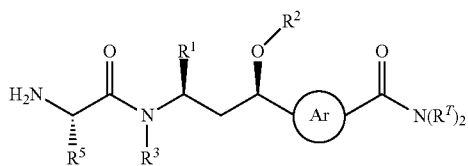
(R,R-6b)

wherein the variable group meanings of (R,R)-Formula 5b and (R,R)-Formula 6b and their corresponding optical isomers are retained from their respective Formula 4b and are as defined for the respective Formula T1B optical isomers, or provides a composition comprising or consisting essentially of (R,R)-Formula 6a, optionally in salt form, as the predominate optical isomer, optionally having as the major optical impurity, (S,S)-Formula 6b, optionally in salt form, and has the structure of:

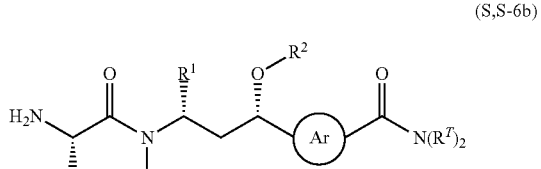
(S,S-6b)

or a composition comprising or consisting essentially of (R,R)-Formula 6b, or salt thereof, substantially or essentially free of the diastereomer, (R,S)-Formula 6b, optionally in salt form, and which has the structure of:

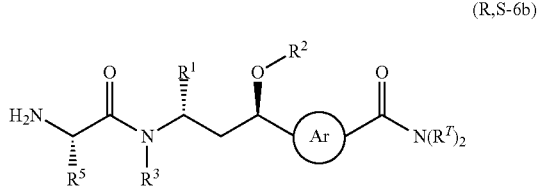
(R,S-6b)

and (S,R)-Formula 6b, optionally in salt form, and which has the structure of:

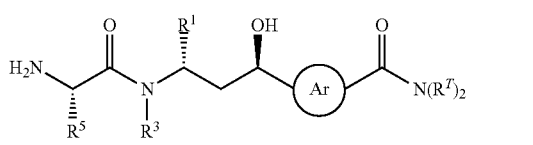
(S,R-6b)

and if optical isomer impurity(ies) are present having (S,S)-Formula 6b, optionally in salt form, as the major optical impurity, or step (h) is followed by step (i'):

(i') contacting (R,R)-Formula 4b, optionally in salt form, or composition thereof, in the presence of a second coupling agent and optionally in the presence of a second hindered base, with a (R,S)-D1-D2 dipeptide, optionally in salt form, having the structure of:

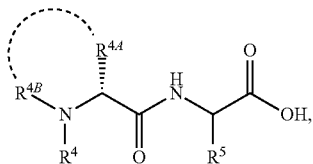

(R,S-D1-D2)

or contacting (R,R)-Formula 4b or composition thereof with an activated ester of the dipeptide, optionally in the presence of a second hindered base, wherein the variable groups of the dipeptide are as defined for (R,R)-Formula T1B; and wherein said second coupling agent contacting with dipeptide or said dipeptide activated ester contacting provides the (R,R)-Formula T1B tubulysin compound, optionally in salt form, or composition thereof.

In some preferred embodiments, step (i') provides a composition comprising or consisting essentially of (R,R)-Formula T1B, or step (i) provides a composition comprising or consisting essentially of (R,R)-Formula 6b, wherein the composition substantially retains the optical purity of the composition of (R,R)-Formula 1a obtained from step (b'), (R,R)-Formula 1b obtained from step (c), (R,R)-Formula 2b obtained from step (d), (R,R)-Formula 3b obtained from step (g), (R,R)-Formula 4b obtained from step (h) or (R,R)-Formula 5a obtained from step (i).

In some of those embodiments providing the tubulysin intermediate of (R,R)-(R,R)-Formula 6b, optionally in salt form, or composition thereof, the tubulysin compound of (R,R)-Formula T1B, optionally in salt form, or composition thereof, is obtained from contacting the tubulysin intermediate or composition thereof, with an amine-containing acid of formula R-D1, or salt thereof, having the structure of:

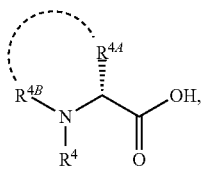

(R-D1)

in the presence of a third coupling agent and optionally in the presence of a third suitable hindered based, or by contacting the tubulysin intermediate with an activated ester of the amine-containing acid, optionally in the presence of a third suitable hindered based, wherein the variable groups are as defined for (R,R)-Formula T1B, wherein in preferred embodiments the optical purity of the composition of (R,R)-Formula 6b is substantially or essentially retained by the (R,R)-Formula T1A composition so obtained.

Preferred embodiments for the tubuvaline intermediates of Formula A and Formula AB, and the tubuvaline compounds of Formula R-1a, Formula R-1b and (R,R)-Formula 2b, and optical isomers thereof, are as previously described for "Embodiment Group 5".

Accordingly, in preferred embodiments for tubulysin intermediates of (R,R)-Formula 3b, (R,R)-Formula 4b, (R,R)-Formula 5b and (R,R)-Formula 6b, and optical isomers thereof, in steps (g)-(i) and for the tubulysin compound of Formula T1B of step (i') the circled Ar moeity is a $C_5$ heteroarylene, optionally in salt form, including without limitation a $C_5$ heteroarylene related to thiazole, isoxazole, pyrazole or imidazole as the parent heterocycle.

Thus, one preferred embodiment provides a method for preparing a (R,R)-Formula 6b tubulysin intermediate, optionally in salt form, having the structure of:

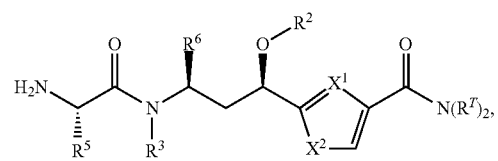

or a composition thereof in which (R,R)-Formula 6b is the predominate optical isomer, and if optical impurities are present, having (S,S)-Formula 6b, optionally in salt form, as the major optical impurity, which has the structure of:

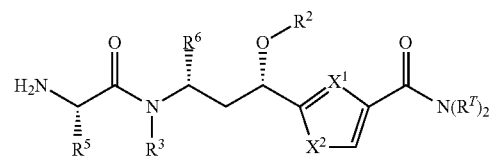

and/or is essentially free of the (R,S)-Formula 6b and (S,R)-Formula 6b optical impurities, each optionally in salt form, having the structure of:

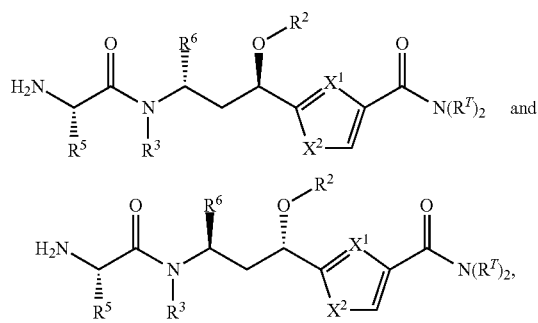

respectively, wherein the method further comprises the step of deprotection of (R,R)-Formula 5b, optionally in salt form, having the structure of:

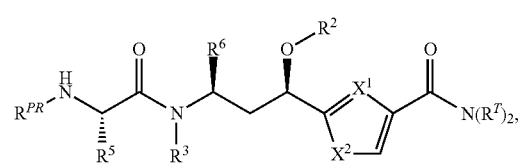

or composition thereof in which (R,R)-Formula 5b is the predominate optical isomer, and/or is essentially free of the (R,S)-Formula 5b and (S,R)-Formula 5b optical impurities, optionally in salt forms, having the structures of:

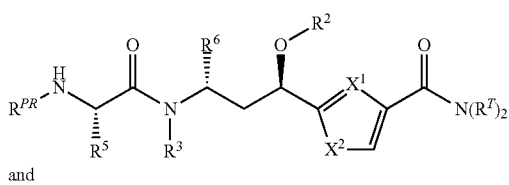

and

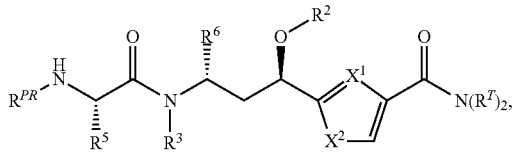

respectively, wherein $R^{PR}$ is a suitable amino protecting group and meanings of the remaining variable groups of (R,R)-Formula 5b and (R,R)-Formula 6b and optical isomers thereof are retained from the corresponding optical isomers of Formula 4b described herein and are as previously defined in this embodiment group.

In another preferred embodiment a method is provided for preparing a tubulysin compound of (R,R)-Formula T1B, optionally in salt form, having the structure of:

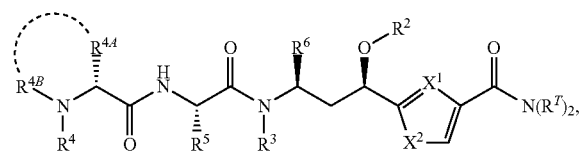

or a composition thereof in which (R,R)-Formula T1B is the predominate optical isomer and if optical impurities are present, having (S,S)-Formula T1A as the major optical impurity having the structure of:

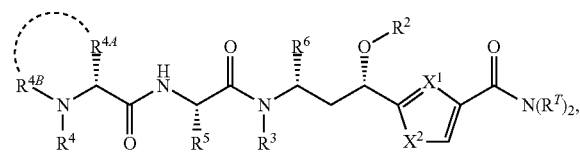

or salt thereof, and is essentially free of the (R,S)-Formula T1B and (S,R)-Formula T1B optical isomer impurities, each optionally in salt form, having the structures of:

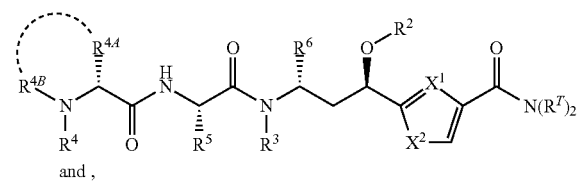

and,

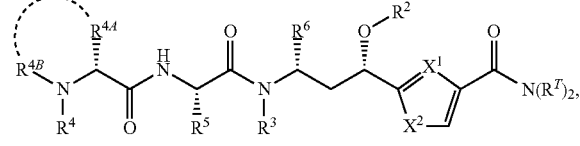

respectively, wherein the (R,R)-Formula T1B tubulysin compound, or composition thereof, is prepared by contacting the (R,R)-Formula 6b tubulysin intermediate, optionally in salt form, or composition thereof, in the presence of a third coupling agent with an amine-containing acid, optionally in salt form, having the structure of Formula R-D1:

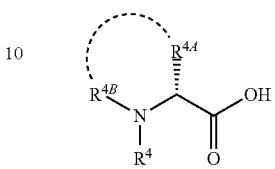

or contacting the (R,R)-Formula 6b tubulysin intermediate, or composition thereof, with the activated ester of that amine-containing acid, wherein Formula R-D1 is preferably D-N-methyl-pipecolic acid, optionally in salt form, or an activated ester thereof, or (R,R)-Formula T1B is prepared by contacting a tubulysin intermediate, optionally in salt form, of (R,R)-Formula 4b having the structure of:

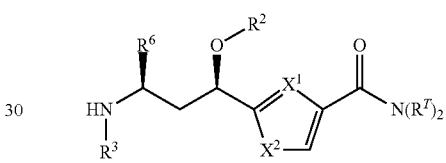

or a composition thereof wherein (R,R)-Formula 4b is the predominate optical isomer, and if optical impurities are present, having (S,S)-Formula 4b, optionally in salt form, as the optical impurity having the structure of:

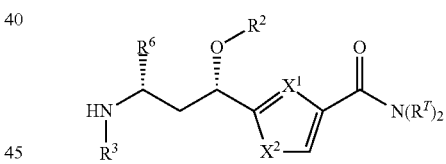

and/or is essentially free of (R,S)-Formula 4b (S,R)-Formula 4b optical isomer impurities, optionally in salt forms, having the structures of:

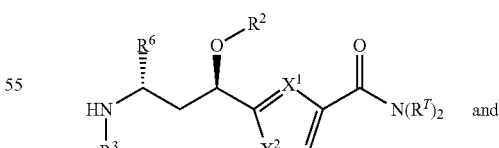 and

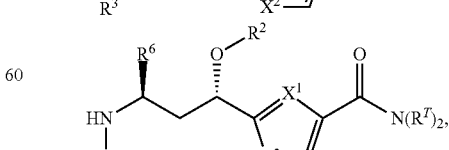

respectively, in the presence of a second coupling agent with a dipeptide of (R,S)-D1-D2 having the structure of:

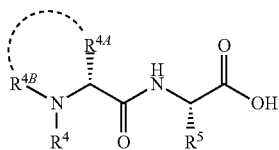

optionally in salt form, or contacting (R,R)-Formula 4b with an activated ester of the dipeptide, wherein (R,R)-Formula 5b, or a composition thereof is prepared from the afore-mentioned (R,R)-Formula 4b compound or composition thereof, wherein (R,R)-Formula 4b, or the composition thereof is prepared by deprotection of (R,R)-Formula 3b, optionally in salt form, having the structure of:

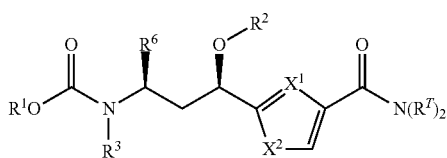

or a composition thereof in which (R,R)-Formula 3b is the predominate optical isomer, and if optical impurities are present having (S,S)-Formula 3b as the major optical impurity having the structure of:

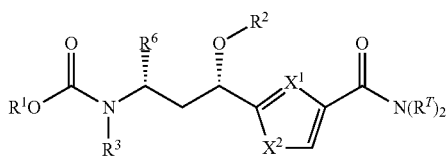

and/or is essentially free of the (R,S)-Formula 3a and (R,S)-Formula 3a optical impurities, optionally in salt forms, having the structures of:

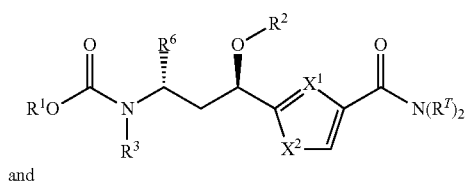

which in turn is prepared by contacting, in the presence of a first coupling agent, a compound of Formula C having the structure of $HN(R^T)_2$, wherein each $R^T$ is a defined for Formula T1B, or salt thereof, with a tubuvaline compound of (R,R)-Formula 2b, optionally in salt form, or contacting the Formula C compound with an activated ester of the tubuvaline compound, wherein (R,R)-Formula 2b has the structure of:

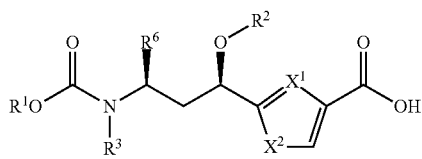

or with a composition thereof in which (R,R)-Formula 2b is the predominate optical isomer having its enantiomer (S,S)-Formula 2b as the major optical isomer impurity, optionally in salt form, having the structure of:

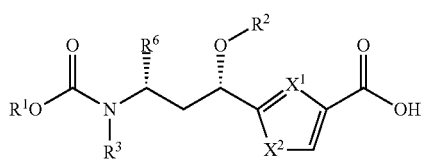

and/or is essentially free of the (R,S)-Formula 2b and (S,R)-Formula 2b optical isomer impurities, each optionally in salt form, having the structures of:

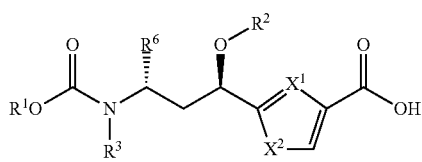

and

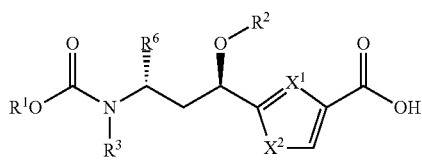

respectively, wherein the (R,R)-Formula 2b tubuvaline compound is prepared according to a method of "Embodiment Group 5"; and wherein in each one of these tubulysin and tubuvaline structures and intermediates thereof $X^1$ is =N— and $X^2$ is S, O, or $N(R^{X2})$—, or $X^1$ is =$C(R^{X1})$— and $X^2$ is $NR^{X2}$, wherein $R^{X1}$ and $R^{X2}$ are independently selected from the group consisting of —H and optionally substituted $C_1$-$C_4$ alkyl, preferably from the group consisting of —H, —$CH_3$ and —$CH_2CH_3$. In preferred embodiments, the circled Aryl is thizaol-1,3-di-yl.

In more preferred embodiments, the Formula 2b composition is comprised or consists essentially of (R,R)-Formula 2b, optionally in salt form, as the predominate optical isomer having the structure of:

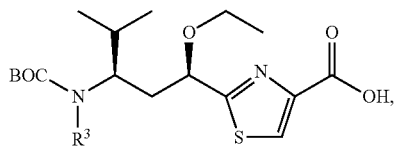

and having (S,S)-Formula 2b as the major optical isomer impurity, optionally in salt form, having the structure of:

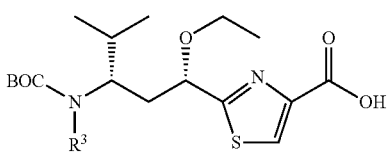

and is essentially free of the optical isomer impurities of (R,S)-Formula 2b and (S,R)-Formula 2b, optionally in salt forms, having the structures of:

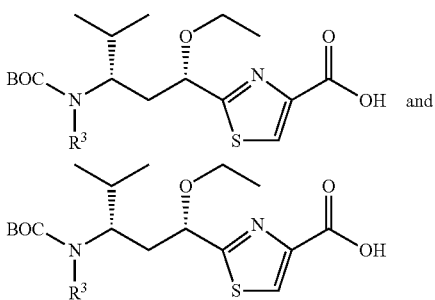

so that said first coupling agent or activated ester contacting provides a Formula 3b composition having (R,R)-Formula 3b as the predominate optical isomer having the structure of:

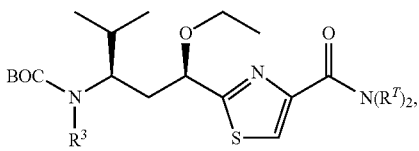

and having (S,S)-Formula 3b as the major optical isomer impurity, and is essentially free of (R,S)-Formula 3b and (S,R)-Formula 3b optical impurities having the structures of:

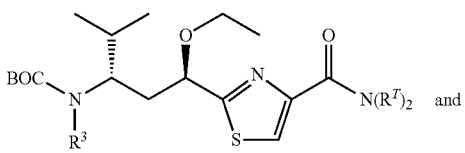

respectively, and the Formula 4b composition from deprotection of the Formula 3b or composition is comprised or consists essentially of (R,R)-Formula 4b, optionally in salt form, as the major optical isomer having the structure of:

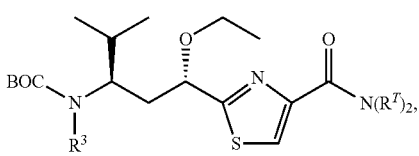

and having (S,S)-Formula 4b as the major optical isomer impurity, optionally in salt form, having the structure of:

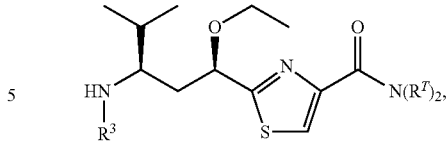

and/or is essentially free of the (R,S)-Formula 4b and (S,R)-Formula 4b optical isomer impurities, optionally in salt forms, having the structures of:

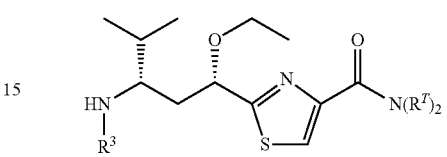

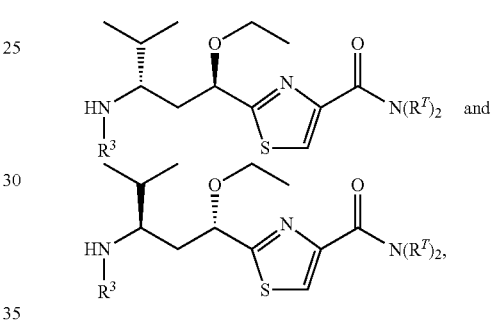

respectively.

From those preferred embodiments, particularly preferred embodiments prepare a (R,R)-Formula T1B tubulysin compound, optionally in salt form, having the structure of:

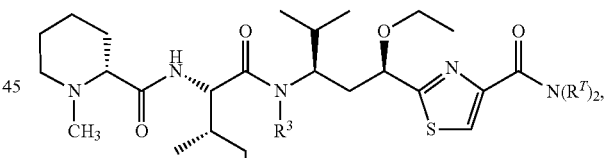

wherein $R^3$ is methyl, ethyl, or propyl; one $R^T$ is hydrogen and the other is optionally substituted $C_1$-$C_6$ alkyl, or a composition thereof in which (R,R)-Formula T1B is the predominate optical isomer and if optical impurities are present having (S,S)-Formula T1B as an optical impurity having the structure of:

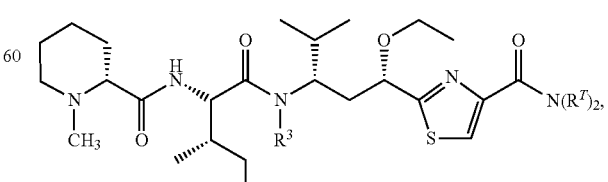

or salt thereof, and/or is essentially free of optical impurities (R,S)-Formula T1B and (R,S)-Formula T1B, optionally in salt forms, having the structures of:

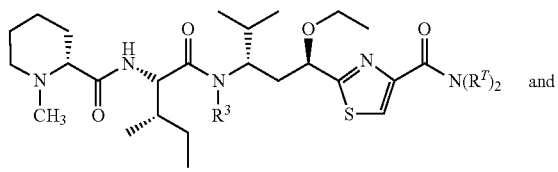

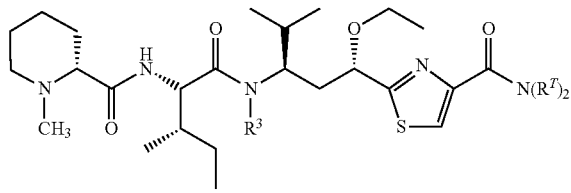

respectively, wherein the (R,R)-Formula T1B tubulysin compound or composition thereof is prepared by contacting (R,R)-Formula 6b, optionally in salt form having the structure of:

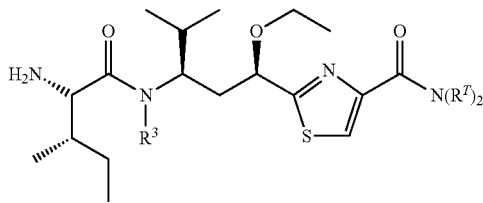

or composition thereof, in which (R,R)-Formula 6b is the predominate optical isomer and if optical impurities are present having (S,S)-Formula 6b, optionally in salt form, as an optical impurity with the structure of:

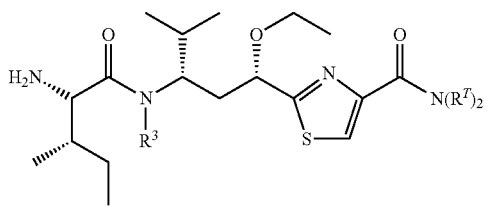

and/or is essentially free of optical impurities (R,S)-Formula 6b and (R,S)-Formula 6b, optionally in salt forms, having the structures of:

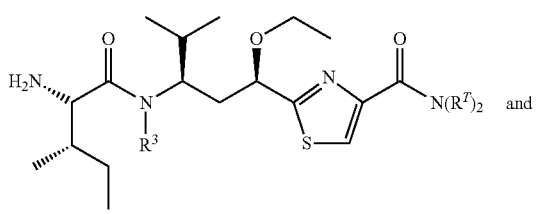

-continued

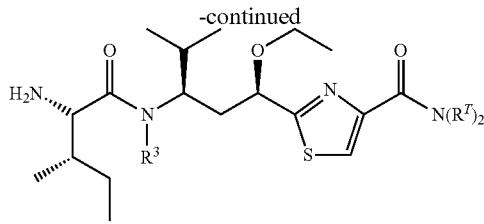

with D-N-methyl-pipecolic acid in the presence of a third coupling agent, or contacting the (R,R)-Formula 6b tubulysin intermediate or composition thereof with an activated ester of D-N-methyl-pipecolic acid, wherein the (R,R)-Formula 6b tubulysin intermediate or composition thereof is prepared by deprotecting (R,R)-Formula 5b, optionally in salt form, having the structure of:

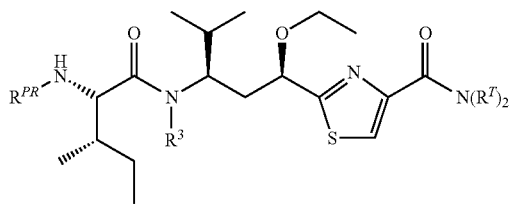

or composition thereof, in which (R,R)-Formula 5b is the predominate optical isomer and if optical impurities are present having (S,S)-Formula 5b, optionally in salt form, as an optical impurity with the structure of:

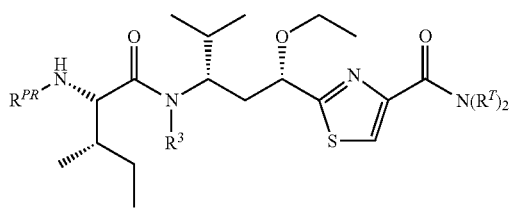

and/or is essentially free of optical impurities (R,S)-Formula 5b and (R,S)-Formula 5b, optionally in salt forms, having the structures of:

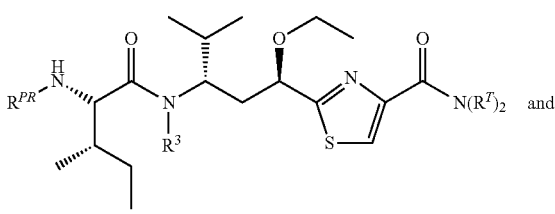

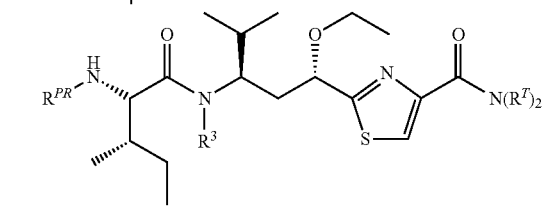

respectively, wherein the (R,R)-Formula 5b tubulysin intermediate or composition thereof is prepared from contacting the (R,R)-Formula 4b tubuvaline compound, or composition thereof, as previously described with suitably N-protected-Ile-OH in the presence of a first coupling agent or by contacting with an activated ester of that N-protected amino acid, or (R,R)-Formula T1B or the composition thereof is prepared by contacting the (R,R)-Formula 4b tubuvaline, or a composition thereof, as previously described, in the presence of a second coupling agent with the dipeptide, D-N-methyl-pipecolyl-isoleucine-OH, optionally in salt form, which has the structure of:

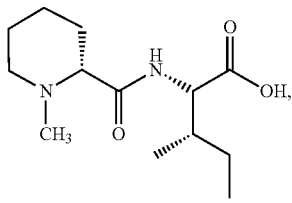

or contacting the (R,R)-Formula 4b tubuvaline or composition thereof with an activated ester of the dipeptide.

For particularly preferred embodiments, the (R,R)-Formula 2b tubuvaline or composition thereof is prepared according to an embodiment of "Embodiment Group 5" and in other particularly preferred embodiments of "Embodiment Group 9" for any one of Formulae 2b-6b, and Formula T1B, $R_3$ is —$CH_3$ or —$CH_2CH_2CH_3$.

In any one of the methods described above, suitable first, second and third coupling agents are coupling agents independently selected from the group consisting of N-(β-Dimethylaminopropyl)-N'-ethylcarbodiimide hydrochloride (EDC. HCl), 2-ethoxy-1-ethoxycarbonyl-1,2-dihydroquinoline (EEDQ), (1-Cyano-2-ethoxy-2-oxoethylidenaminooxy) dimethylamino-morpholino-carbenium hexafluorophosphate (COMU), N-(β-Dimethylaminopropyl)-N'-ethylcarbodiimide hydrochloride/N-Hydroxysuccinimide, O-(7-Azabenzotriazol-1-yl)-N,N,N',N'-tetramethyluronium hexafluorophosphate (HATU), Diphenyl phosphoryl azide (DPPA), Chloro-N,N,N',N'-bis(tetramethylene)formamidinium tetrafluoroborate, Fluoro-N,N,N',N'-bis(tetramethylene)formamidinium hexafluorophosphate, N,N'-Dicyclohexylcarbodiimide, N-(β-Dimethylaminopropyl)-N'-ethylcarbodiimide hydrochloride, 1,1'-Carbonyldiimidazole, 2-Chloro-1,3-dimethylimidazolidinium tetrafluoroborate, (Benzotriazol-1-yloxy)tripyrrolidinophosphonium hexafluorophosphate, O-(7-Azabenzotriazol-1-yl)-N,N,N',N'-tetramethyluronium hexafluorophosphate, 2-Chloro-1-methylpyridinium iodide, and Propylphosphonic anhydride. Preferably, the coupling agent is independently selected from the group consisting of HATU and COMU.

Preferably, in any one of the Group Embodiments and methods therein, $R^1$ is t-Bu and the deprotecting agent is an acid selected from the group consisting of hydrochloric acid and trifluoroacetic acid, and more preferably, the deprotecting agent is trifluoroacetic acid.

Particularly preferred —$N(R^T)_2$ moieties for any one of the embodiments of "Embodiment Group 6", "Embodiment Group 7", "Embodiment group 8" or "Embodiment group 9", are those in which one $R^T$ is hydrogen and the other is a saturated $C_1$-$C_6$ alkyl or unsaturated $C_3$-$C_6$ alkyl substituted by a carboxylic acid functional group and an optionally substituted phenyl or optionally substituted $C_5$-$C_6$-heteroaryl Accordingly in particularly preferred embodiments of "Embodiment Group 6", "Embodiment Group 7", "Embodiment group 8" or "Embodiment group 9", the methods therein are used to prepare a (R,R)-Formula T1 tubulysin compound, optionally in salt form, having the structure of:

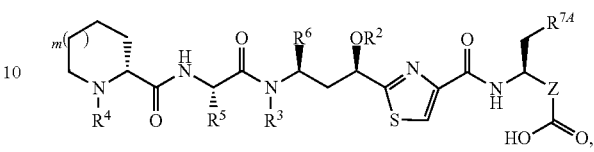

or a composition comprising or consisting essentially thereof in which the (R,R)-Formula T1 tubulysin compound is the predominate optical isomer and if optical impurities are present having the major optical impurity, or salt thereof, of (S,S)-Formula T, the structure of which is:

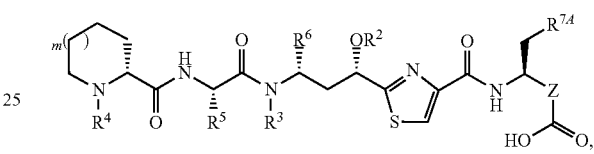

having identical variable group meanings as for the predominate optical isomer of (R,R)-Formula T1, wherein subscript m is 0 or 1; $R^2$ is saturated $C_1$-$C_6$ alkyl or $R^2$ is $R^{2A}$, wherein $R^{2A}$ is —$C(O)R^{2B}$, wherein $R^{2B}$ is saturated $C_1$-$C_6$ alkyl or $C_3$-$C_8$ unsaturated alkyl; $R^3$, $R^4$ and $R^5$ are independently optionally substituted $C_1$-$C_6$ alkyl; Z is an optionally substituted $C_1$-$C_4$ alkylene or an optionally substituted $C_2$-$C_6$ alkenylene; and $R^{7A}$ is optionally substituted phenyl or optionally substituted $C_5$-$C_6$-heteroaryl.

In certain of those particularly preferred embodiments, the methods of the present invention are used to prepare a (R,R)-Formula T1 tubulysin compound, optionally in salt form, having the structure of:

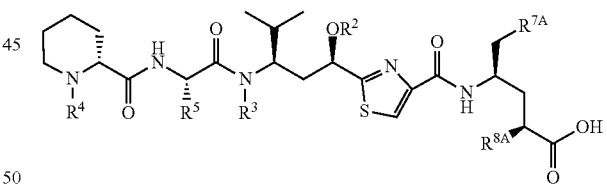

or a composition comprising or consisting essentially thereof in which the (R,R)-Formula T1 tubulysin compound is the predominate optical isomer and if optical impurities are present having the major optical impurity, or salt thereof, of (S,S)-Formula T1, the structure of which is;

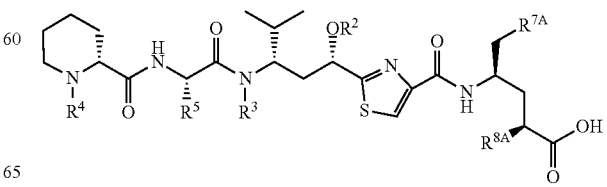

wherein $R^{7A}$ is optionally substituted phenyl; and $R^8$ is hydrogen or $C_1$-$C_4$ alkyl with the remaining variable groups as previously indicated.

In other of those particularly preferred embodiments, the methods of the present invention are used to prepare a (R,R)-Formula T1 tubulysin compound, optionally in salt form, having the structure of:

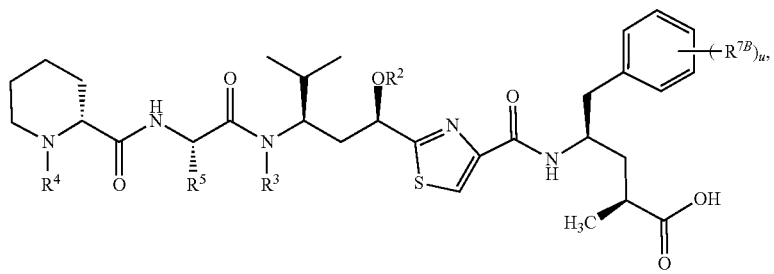

or a composition comprising or consisting essentially thereof in which the (R,R)-Formula T1 tubulysin compound is the predominate optical isomer and if optical impurities are present having the major optical impurity, or salt thereof, of (S,S)-Formula T1, the structure of which is:

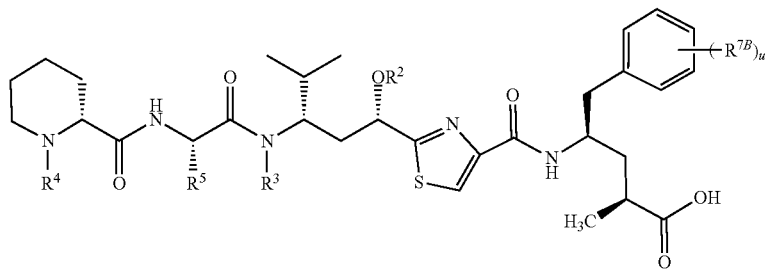

wherein subscript u, indicating the number of $R^{7B}$ substituents, is 0, 1, 2 or 3; each $R^{7B}$, when present, is an independently selected O-linked substituent.

In more particularly preferred embodiments, the methods of the present invention are used to prepare a (R,R)-Formula T1 tubulysin compound, optionally in salt form, having the structure of:

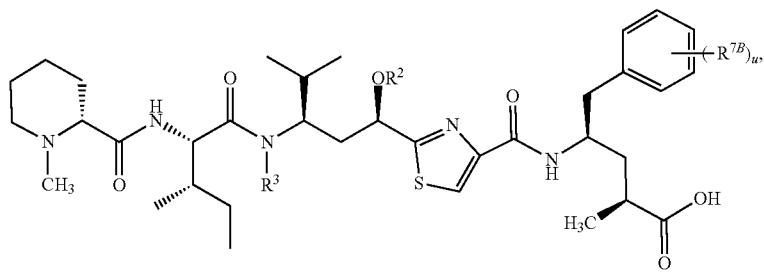

or a composition comprising or consisting essentially thereof in which the (R,R)-Formula T1 tubulysin compound is the predominate optical isomer and if optical impurities are present having the major optical impurity, or salt thereof, of (S,S)-Formula T1, the structure of which is:

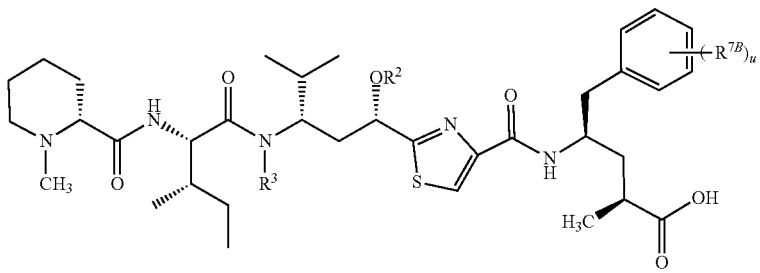

wherein subscript u is 0, 1 or 2; $R^3$ is methyl, ethyl, propyl, —$CH_2$—OC(O)$R^{3A}$, —$CH_2CH(R^{3B})C(O)R^{3A}$ or —CH($R^{3B}$)C(O)NH$R^{3A}$, wherein $R^{3A}$ is $C_1$-$C_6$ alkyl and $R^{3B}$ is H or $C_1$-$C_6$ alkyl, independently selected from $R^{3A}$; and each $R^{7B}$, when present, independently is —OH or —OCH$_3$.

In other particularly preferred embodiments, the methods of the present invention are used to prepare a (R,R)-Formula T1 tubulysin compound, optionally in salt form, having the structure of:

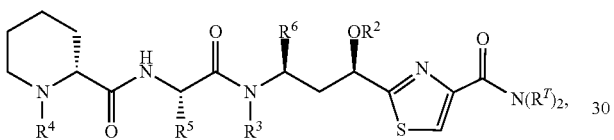

or a composition comprising or consisting essentially thereof in which the (R,R)-Formula T1 tubulysin compound is the predominate optical isomer and if optical impurities are present having the major optical impurity, or salt thereof, of (S,S)-Formula T1, the structure of which is:

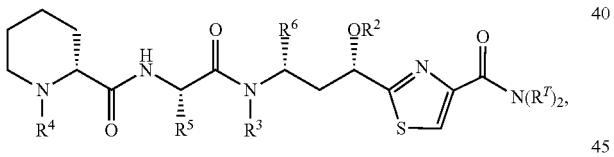

wherein $R^2$ is unsaturated $C_1$-$C_6$ alkyl or $R^2$ is $R^{2A}$, wherein $R^{2A}$ is —C(O)$R^{2B}$, wherein $R^{2B}$ is saturated $C_1$-$C_6$ alkyl or $C_3$-$C_8$ unsaturated alkyl; $R^3$ is $C_1$-$C_6$ alkyl; $R^4$ is methyl; $R^5$ and $R^6$ are alkyl side chain residues of natural or un-natural hydrophobic amino acids, preferably of natural amino acids; and the —N($R^T$)$_2$ moiety is —NH($C_1$-$C_6$ alkyl), optionally substituted by —CO$_2$H, or an ester thereof, or by an optionally substituted phenyl, or is —N($C_1$-$C_6$ alkyl)$_2$, wherein one and only one $C_1$-$C_6$ alkyl is optionally substituted by —CO$_2$H, or an ester thereof, or by an optionally substituted phenyl, in particular —NH(CH$_3$), —NHCH$_2$CH$_2$Ph, and —NHCH$_2$—CO$_2$H, —NHCH$_2$CH$_2$CO$_2$H and —NHCH$_2$CH$_2$CH$_2$CO$_2$H, or the —N($R^T$)$_2$ moiety has the structure of:

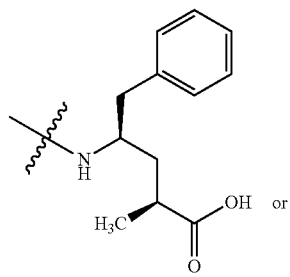

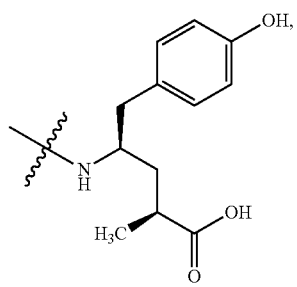

or a salt thereof.

In any one of the embodiments of (R,R)-Formula T1 and (S,S)-Formula T1 $R^2$ is —CH$_2$—CH=CH$_2$.

In especially preferred embodiments, the (R,R)-Formula T1 and (S,S)-Formula T1 tubulysin compounds have the structures of:

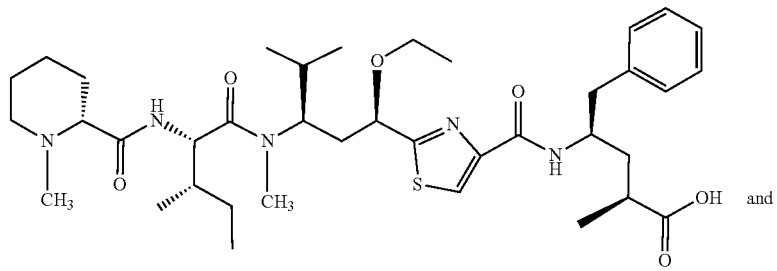

-continued

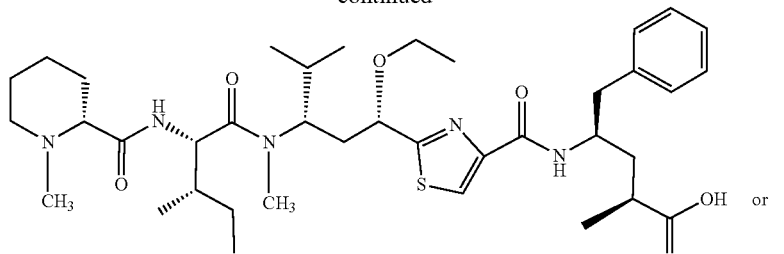

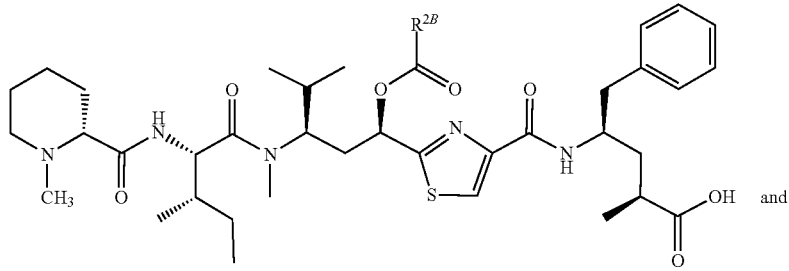

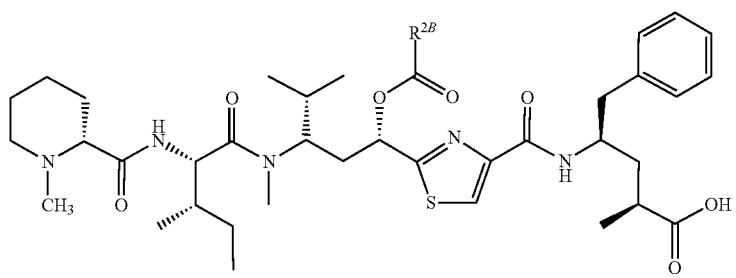

wherein $R^{2B}$ is —CH$_3$, —CH$_2$CH$_3$, —CH$_2$CH$_2$CH$_3$, —CH(CH$_3$)$_2$, —CH$_2$CH(CH$_3$)$_2$ or —CH$_2$C(CH$_3$)$_3$, in particular —CH$_3$.

3.1 Numbered Embodiments

The following numbered embodiments describes various non-limiting aspects of the invention, 1. A method for preparing a tubuvaline intermediate of Formula AB:

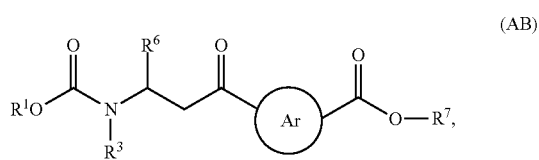

(AB)

or as an enantiomeric mixture, or a composition comprised or consisting essentially of that intermediate or enantiomeric mixture, optionally in salt form, wherein the circled Ar is a 1,3-phenylene or a 5- or 6-membered nitrogen-containing 1,3-heteroarylene, optionally substituted at the remaining positions; $R^1$ is phenyl, t-butyl, 9-fluorenyl or allyl, optionally substituted, or other moeity so that $R^1$—OC(=O)— is a suitable nitrogen protecting group; $R^3$ is optionally substituted saturated C$_1$-C$_8$ alkyl, optionally substituted unsaturated C$_3$-C$_8$ alkyl or optionally substituted C$_3$-C$_8$ heteroalkyl; $R^6$ is optionally substituted C$_1$-C$_8$ alkyl; and $R^7$ is optionally substituted saturated C$_1$-C$_{20}$ alkyl, optionally substituted unsaturated C$_3$-C$_{20}$ alkyl optionally substituted C$_3$-C$_{20}$ heteroalkyl, optionally substituted C$_2$-C$_{20}$ alkenyl, optionally substituted C$_3$-C$_{20}$ heteroalkenyl, optionally substituted C$_2$-C$_{20}$ alkynyl, optionally substituted C$_3$-C$_{20}$ heteroalkynyl, optionally substituted C$_6$-C$_{24}$ aryl, optionally substituted C$_5$-C$_{24}$ heteroaryl, optionally substituted C$_3$-C$_{20}$ heterocyclyl, or other moeity so that $R^7$—O— provides for a suitable carboxylic acid protecting group, the method comprising the step of:

(a) contacting a compound of Formula A:

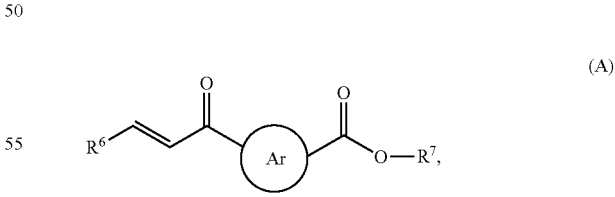

(A)

with a compound of Formula B: $R^3$NHC(O)OR$^1$ (B), wherein the variable groups of Formulae A and B are as defined for Formula AB, in a suitable polar, aprotic solvent in the presence of a suitable transition metal (II) or transition metal (III) catalyst, in particular, one comprising a transition metal selected from the group consisting of Cu(II), Zn(II) and Yb(III), so as to form the Formula AB tubuvaline intermediate or composition.

2. A method for preparing a tubuvaline compound of (R,R)-Formula 1a:

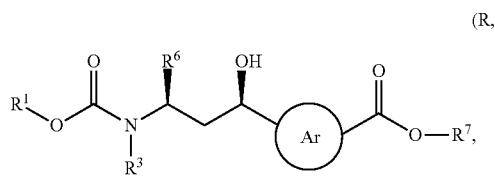

(R,R-1a)

or a composition comprised or consisting essentially of that compound, optionally in salt form, wherein: the circled Ar is a 1,3-phenylene or a 5- or 6-membered nitrogen-containing 1,3-heteroarylene, optionally substituted at the remaining positions; $R^1$ is phenyl, t-butyl, 9-fluorenyl or allyl, optionally substituted, or other moiety so that $R^1$—OC(=O)— is a suitable nitrogen protecting group; $R^3$ is optionally substituted saturated $C_1$-$C_8$ alkyl, optionally substituted unsaturated $C_3$-$C_8$ alkyl or optionally substituted $C_3$-$C_8$ heteroalkyl; $R^6$ is optionally substituted $C_1$-$C_8$ alkyl; and $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moiety so that $R^7$—O— provides for a suitable carboxylic acid protecting group, the method comprising the steps of:

(a) contacting a tubuvaline intermediate of Formula A:

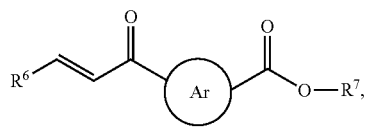

(A)

with a carbamate compound of Formula B: $R^3$NHC(O)OR$^1$ (B), in a suitable polar aprotic solvent in the presence of a suitable transition metal (II) or transition metal (III) catalyst, in particular, one comprising a transition metal selected from the group consisting of Cu(II), Zn(II) and Yb(III), so as to form a tubuvaline intermediate, optionally in salt form, of Formula AB:

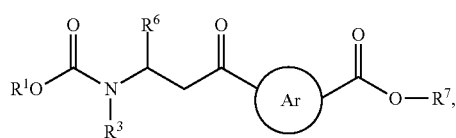

(AB)

as an enantiomeric mixture, or a composition comprised or consisting essentially of that intermediate or enantiomeric mixture; and (b) contacting the Formula AB tubuvaline intermediate or composition, with a suitable reducing agent, in particular, a chiral reducing agent, so as to form the (R,R)-Formula 1a tubuvaline compound, optionally in salt form or composition, wherein the variable groups of Formulae A, B and AB are as defined for (R,R)-Formula 1a.

3. The method of embodiment 2, wherein the method further comprises the step of separating from the tubuvaline composition, the diastereomer of the Formula 1a tubuvaline compound having inverted stereochemistry of the carbon atom to which $R^6$ is attached so as to obtain:

a purified tubuvaline composition comprised or consisting essentially of the (R,R)-Formula 1a tubuvaline compound and no more than about 10% w/w of the Formula 1a diastereomer relative to the (R,R)-Formula 1a tubuvaline compound, in particular, no more than about 5% w/w, more particularly, no more that about 1.5% w/w, or is essentially free of the diastereomer as determined by chiral HPLC.

4. A method for preparing a tubuvaline compound of (R,R)-Formula 2:

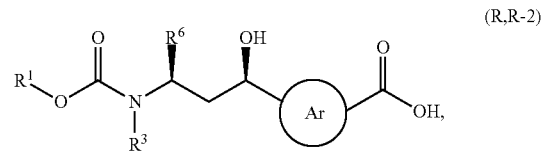

(R,R-2)

or a composition comprised or consisting essentially of that compound, optionally in salt form, wherein: the circled Ar is a 1,3-phenylene or a 5- or 6-membered nitrogen-containing 1,3-heteroarylene, optionally substituted at the remaining positions; $R^1$ is phenyl, t-butyl, 9-fluorenyl or allyl, optionally substituted, or other moiety so that $R^1$—OC(=O)— is a suitable nitrogen protecting group; $R^3$ is optionally substituted saturated $C_1$-$C_8$ alkyl, optionally substituted unsaturated $C_3$-$C_6$ alkyl or optionally substituted $C_3$-$C_6$ heteroalkyl; and $R^6$ is optionally substituted $C_1$-$C_8$ alkyl, the method comprising the steps of:

(a) contacting a compound of Formula A:

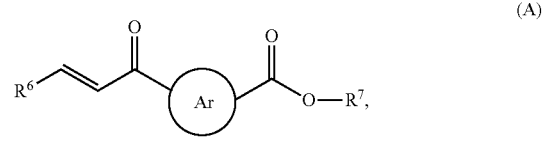

(A)

wherein $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moiety so that $R^7$—O— provides for a suitable carboxylic acid protecting group, with a compound of Formula B: $R^3$NHC(O)OR$^1$ (B), in a suitable polar, aprotic solvent in the presence of a suitable transition metal (II) or transition metal (III) catalyst, in particular, one comprising a transition metal selected from the group consisting of Cu(II), Zn(II) and Yb(III), so as to form a tubuvaline intermediate of Formula AB:

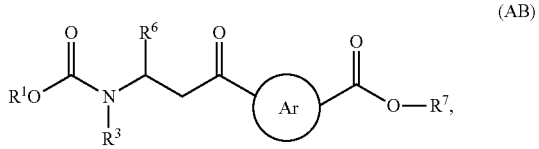

or as an enantiomeric mixture, or a composition comprised or consisting essentially of that intermediate or enantiomeric mixture, optionally in salt form;

(b) contacting the Formula AB tubuvaline intermediate, optionally in salt form, or composition, with a suitable reducing agent, in particular a chiral reducing agent, so as to form a tubuvaline compound of (R,R)-Formula 1a

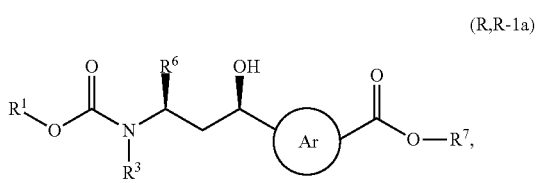

or a composition comprised or consisting essentially of that compound, optionally in salt form; and (c) contacting the (R,R)-Formula 1a tubuvaline compound or composition, with a suitable hydrolysis agent so as to form the Formula 2 tubuvaline composition or compound, optionally in salt form, wherein the variable groups of Formulae A, B, AB and (R,R)-Formula 1a are as defined for (R,R)-Formula 2.

5. The method of embodiment 4, wherein the method further comprises the step of separating from the tubuvaline composition the diastereomer of the Formula 1a or Formula 2 tubuvaline compound having inverted stereochemistry of the carbon atom to which $R^6$ is attached so as to obtain: a purified tubuvaline composition comprised or consisting essentially of the (R,R)-Formula 1a or (R,R)-Formula 2 tubuvaline compound, optionally in salt form, and no more than about 10% w/w of the diastereomer relative to the (R,R)-Formula 1a or (R,R)-Formula 2 tubuvaline compound, in particular, no more than about 5% w/w, more particularly, no more that about 1.5% w/w, or is essentially free of the diastereomer as determined by chiral HPLC.

6. A method for preparing a tubuvaline compound of (R,R)-Formula 2a:

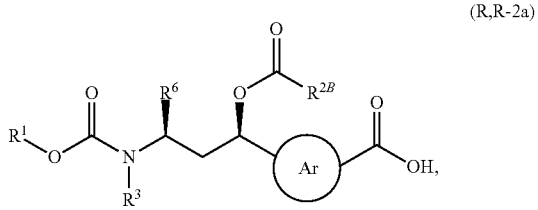

or a composition comprised or consisting essentially of that compound, optionally in salt form, wherein: the circled Ar is a 1,3-phenylene or a 5- or 6-membered nitrogen-containing 1,3-heteroarylene, optionally substituted at the remaining positions; $R^{2B}$ is optionally substituted saturated $C_1$-$C_8$ alkyl, optionally substituted unsaturated $C_3$-$C_8$ alkyl, optionally substituted $C_2$-$C_8$ alkenyl or optionally substituted $C_2$-$C_8$ alkynyl; $R^1$ is phenyl, t-butyl, 9-fluorenyl or allyl, optionally substituted, or other moeity so that $R^1$—OC(=O)— is a suitable nitrogen protecting group; $R^3$ is optionally substituted saturated $C_1$-$C_8$ alkyl, optionally substituted unsaturated $C_3$-$C_8$ alkyl or optionally substituted $C_3$-$C_8$ heteroalkyl; and $R^6$ is optionally substituted $C_1$-$C_8$ alkyl, the method comprising the steps of:

(a) contacting a compound of Formula A:

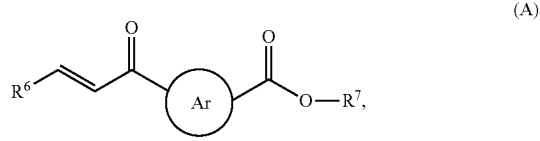

wherein $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moeity so that $R^7$—O— provides a suitable carboxylic acid protecting group, with a compound of Formula B: $R^3NHC(O)OR^1$ (B), in a suitable polar, aprotic solvent in the presence of a suitable transition metal (II) or transition metal (III) catalyst, in particular, one comprising a transition metal selected from the group consisting of Cu(II), Zn(II) and Yb(III), so as to form a tubuvaline intermediate, optionally in salt form, of Formula AB:

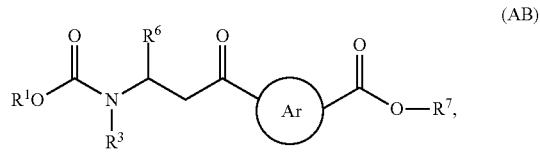

or as an enantiomeric mixture, or a composition comprised or consisting essentially of that intermediate or enantiomeric mixture;

(b) contacting the Formula AB tubuvaline intermediate or composition with a suitable reducing agent, in particular a chiral reducing agent, so as to form a tubuvaline compound of (R,R)-Formula 1a:

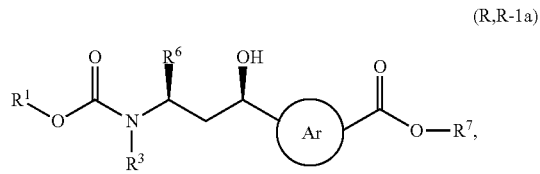

or a composition comprised or consisting essentially of that compound, optionally in salt form;

(c) contacting the (R,R)-Formula 1a tubuvaline compound or composition with a suitable hydrolysis agent so as to form a tubuvaline compound of (R,R)-Formula 2:

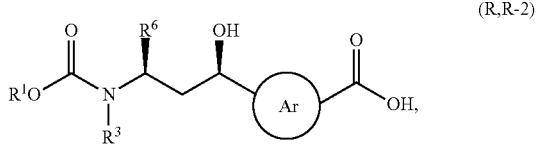
(R,R-2)

or a composition comprised or consisting essentially of that compound optionally in salt form; and (d) contacting the (R,R)-Formula 2 tubuvaline compound or composition, with a suitable acylating agent so as to form the (R,R)-Formula 2a tubuvaline composition or compound, optionally in salt form, wherein the variable groups of Formulae A, B, AB and (R,R)-Formula 1a and (R,R)-Formula 2 are as defined for (R,R)-Formula 2a.

7. The method of embodiment 6, wherein the method further comprises the step of separating from the tubuvaline composition the diastereomer of the Formula 1, 2 or 2a tubuvaline compound having inverted stereochemistry of the carbon atom to which $R^6$ is attached, so as to obtain:

a purified tubuvaline composition comprised or consisting essentially of the (R,R)-Formula 1a, (R,R)-Formula 2 or (R,R)-Formula 2a tubuvaline compound, optionally in salt form, and no more than about 10% w/w of the diastereomer having inverted $R^6$ stereochemistry relative to the (R,R)-Formula 1a, (R,R)-Formula 2 or (R,R)-Formula 2a tubuvaline compound, in particular, no more than about 5% w/w, more particularly, no more that about 1% w/w, or a purified tubuvaline composition in which the (R,R)-Formula 1a, (R,R)-Formula 2 or (R,R)-Formula 2a tubuvaline compound is in about 80% diastereomeric excess (d.e.) or greater, in particular, in about 90% d.e., about 95% d.e. or about 97% d.e relative to the diastereomer having inverted $R^6$ stereochemistry.

8. A method for preparing a tubuvaline compound of (R,R)-Formula 1b:

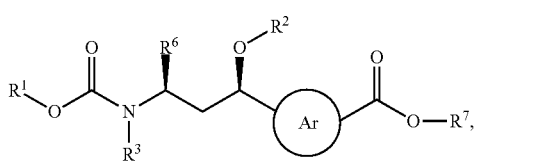
(R,R-1b)

or a composition comprised or consisting essentially of that compound, optionally in salt form, wherein: the circled Ar is a 1,3-phenylene or a 5- or 6-membered nitrogen-containing 1,3-heteroarylene, optionally substituted at the remaining positions; $R^1$ is phenyl, t-butyl, 9-fluorenyl or allyl, optionally substituted, or other moiety so that $R^1$—OC(=O)— is a suitable nitrogen protecting group;

$R^2$ is optionally substituted saturated $C_1$-$C_8$ alkyl, optionally substituted unsaturated $C_3$-$C_8$ alkyl, optionally substituted $C_2$-$C_8$ alkenyl or optionally substituted $C_2$-$C_8$ alkynyl, or $R^2$ is $R^{2A}$ wherein $R^{2A}$ is —$CH_2R^{2C}$, wherein $R^{2C}$ is optionally substituted saturated $C_1$-$C_8$ ether or optionally substituted unsaturated $C_2$-$C_8$ ether;

$R^3$ is optionally substituted saturated $C_1$-$C_8$ alkyl, optionally substituted unsaturated $C_3$-$C_8$ alkyl or optionally substituted $C_3$-$C_8$ heteroalkyl; $R^6$ is optionally substituted $C_1$-$C_8$ alkyl; and $R^7$ is optionally substituted saturated $C_1$-$C_{20}$ alkyl, optionally substituted unsaturated $C_1$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moeity so that $R^7$—O— provides for a suitable carboxylic acid protecting group, the method comprising the steps of:

(a) contacting a compound of Formula A:

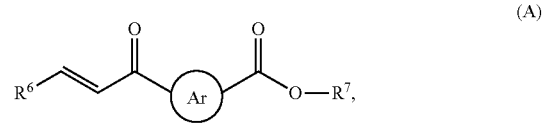
(A)

with a compound of Formula B:

$R^3NHC(O)OR^1$ (B), in a suitable polar, aprotic solvent in the presence of a suitable transition metal (II) or transition metal (III) catalyst, in particular, one comprised of a transition metal selected from the group consisting of Cu(II), Zn(II) and Yb(III), so as to form a tubuvaline intermediate of Formula AB:

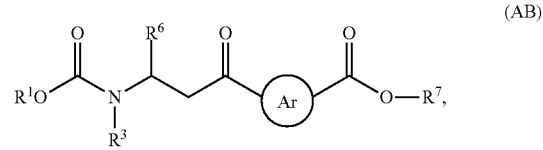
(AB)

or as an enantiomeric mixture, or a composition comprised or consisting essentially of that intermediate or enantiomeric mixture;

(b) contacting the Formula AB tubuvaline intermediate or composition, with a suitable reducing agent, in particular, a chiral reducing agent, so as to form a tubuvaline compound of (R,R)-Formula 1a:

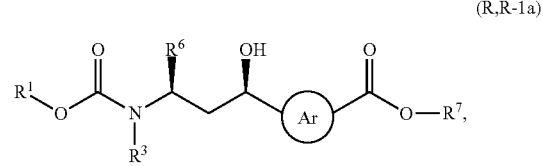
(R,R-1a)

or a composition comprised or consisting essentially of that compound, optionally in salt form; and contacting the (R,R)-Formula 1a tubuvaline compound or composition with a suitable alkylating agent so as to form the (R,R)-Formula 1b tubuvaline composition or compound, optionally in salt form, wherein the variable groups of Formulae A, B and AB and (R,R)-Formula 1a are as defined for (R,R)-Formula 1b.

9. The method of embodiment 8, wherein the method further comprises the step of separating from the tubuvaline composition the diastereomer of the (R,R)-Formula 1a or (R,R)-Formula 1b tubuvaline compound having inverted stereochemistry of the carbon atom to which $R^6$ is attached from the tubuvaline composition so as to obtain:

a purified tubuvaline composition comprised or consisting essentially of the (R,R)-Formula 1a or (R,R)-Formula 1b tubuvaline compound, optionally in salt form, and no more than about 10% w/w of the diastereomer having inverted $R^6$ stereochemistry relative to the (R,R)-Formula 1a or (R,R)-Formula 1b tubuvaline compound, in particular, no more than about 5% w/w, more particularly, no more that about 1% w/w, or a purified tubuvaline composition in which the (R,R)-Formula 1a or (R,R)-Formula 1b tubuvaline compound is in about 80% diastereomeric excess (d.e.) or greater, in particular in about 90% d.e., about 95% d.e. or about 97% d.e relative to the diastereomer having inverted $R^6$ stereochemistry.

10. A method for preparing a tubuvaline compound of (R,R)-Formula 2b:

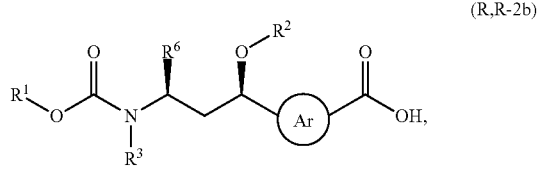

(R,R-2b)

or a composition comprised or consisting essentially of that compound, optionally in salt form, wherein: the circled Ar is a phenylene or a 5- or 6-membered nitrogen-containing heteroarylene, optionally substituted at the remaining positions; $R^1$ is phenyl, t-butyl, 9-fluorenyl or allyl, optionally substituted, or other moiety so that $R^1$—OC(=O)— is a suitable protecting group;

$R^2$ is optionally substituted saturated $C_1$-$C_8$ alkyl, optionally substituted unsaturated $C_3$-$C_6$ alkyl, optionally substituted $C_2$-$C_6$ alkenyl or optionally substituted alkynyl, or $R^2$ is $R^{2A}$ wherein $R^{2A}$ is —$CH_2R^{2C}$, wherein $R^{2C}$ is optionally substituted saturated $C_1$-$C_8$ ether, optionally substituted unsaturated $C_2$-$C_8$ ether; and $R^3$ is optionally substituted saturated $C_1$-$C_8$ alkyl, optionally substituted unsaturated $C_3$-$C_8$ alkyl or optionally substituted $C_3$-$C_8$ heteroalkyl; and $R^6$ is optionally substituted $C_1$-$C_8$ alkyl, the method comprising the steps of:

(a) contacting a compound of Formula A:

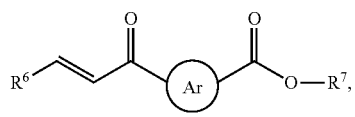

(A)

wherein $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$—$C_{20}$ heterocyclyl, or other moiety so that $R^7$—O— provides a suitable carboxylic acid protecting group, with a compound of Formula B: $R^3NHC(O)OR^1$ (B), in a suitable polar, aprotic solvent in the presence of a suitable transition metal (II) or transition metal (III) catalyst, in particular, one comprising a transition metal selected from the group consisting of Cu(II), Zn(II) and Yb(III), so as to form a tubuvaline intermediate, optionally in salt form, of Formula AB:

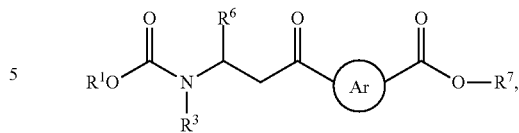

(AB)

or as an enantiomeric mixture, or a composition comprised or consisting essentially of that intermediate or enantiomeric mixture;

(b) contacting the Formula AB tubuvaline intermediate or composition with a suitable reducing agent, in particular, a chiral reducing agent, so as to form a tubuvaline compound of (R,R)-Formula 1a

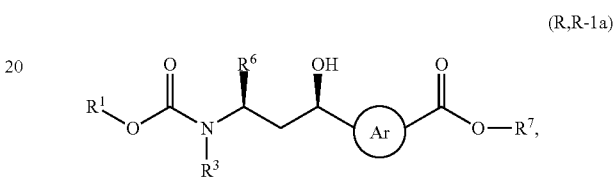

(R,R-1a)

or a composition comprised o consisting essentially of that compound, optionally in salt form;

(e) contacting the (R,R)-Formula 1a tubuvaline compound or composition with a suitable alkylating agent so as to form a tubuvaline compound, optionally in salt form, of (R,R)-Formula 1b:

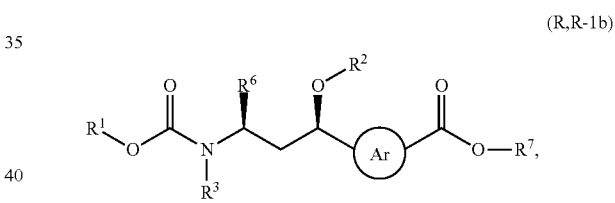

(R,R-1b)

wherein $R^2$ is a previously defined for (R,R)-Formula 2b, or a composition comprised or consisting essentially of that compound; and (f) contacting the (R,R)-Formula 1b tubuvaline compound or composition with a suitable hydrolysis agent so as to form the (R,R)-Formula 2b tubuvaline compound, optionally in salt form or composition, wherein the variable group(s) of Formulae A, B and AB and (R,R)-Formula 1a and (R,R)-Formula 1b are as defined for (R,R)-Formula 2b.

11. The method of embodiment 10, wherein the method further comprises the step of separating the tubuvaline composition the diastereomer of the (R,R)-Formula 1a, (R,R)-Formula 1b or (R,R)-Formula 2b tubuvaline compound having inverted stereochemistry of the carbon atom to which $R^6$ is attached from the tubuvaline composition so as to obtain:

a purified tubuvaline composition comprised or consisting essentially of the (R,R)-Formula 1a, (R,R)-Formula 1b or (R,R)-Formula 2b tubuvaline compound, optionally in salt form, and no more than about 10% w/w of the diastereomer having inverted $R^6$ stereochemistry relative to the (R,R)-Formula 1a or (R,R)-Formula 1b tubuvaline compound, in particular, no more than about 5% w/w, more particularly, no more that about 1% w/w, or a purified tubuvaline composition in which the (R,R)-Formula 1a, (R,R)-Formula 1b or (R,R)-Formula 2b tubuvaline compound is in about 80% diastereomeric excess (d.e.) or greater, in particular in about 90% d.e., about 95% d.e. or about 97% d.e relative to the diastereomer having inverted $R^6$ stereochemistry.

12. The method of embodiment 6 or 7 wherein the acylating agent has the structure of $R^{2B}C(O)Cl$ or $[R^{2B}C(O)]_2O$, wherein $R^{2B}$ is saturated $C_1$-$C_6$ alkyl, unsaturated $C_3$-$C_8$ alkyl, $C_2$-$C_8$ alkenyl or optionally substituted $C_2$-$C_4$ alkynyl.

13. The method of embodiment 12, wherein $R^{2B}$ is —$CH_3$, —$CH_2CH_3$, —$CH_2CH_2CH_3$, —$CH_2CH$=$CH_2$, —$CH_2CH(CH_3)_2$, —$CH_2C(CH_3)_3$, —$CH_2C(CH_3)$=$CH_2$, —$CH$=$CH_2$ or —$CHC$≡$CH$, in particular —$CH_3$.

14. The method of any one of embodiments 8 to 11, wherein the alkylating reagent is $R^{2A}X$ or $R^{2C}$—$CH_2X$, wherein $R^{2A}$ is $C_1$-$C_8$ alkyl, $R^{2C}$ is $C_1$-$C_8$ ether, and X is Br, I, -OTs, -OMs or other suitable leaving group.

15. The method of any one of the preceding embodiments, wherein the transition (II) metal catalyst is comprised of Cu(II).

16. The method of embodiment 15, wherein the transition (II) metal catalyst is comprised of $Cu(OTf)_2$, $Cu(SbF_6)_2$, or $CuCl_2$, in particular $Cu(OTf)_2$.

17. The method of any one of the preceding embodiments, wherein the suitable polar, aprotic solvent is acetonitrile, dichloromethane, THF, dioxane, or a mixture of two or three of these solvents, in particular, dichloromethane.

18. The method of any one of the preceding embodiments, wherein the chiral reducing agent comprises $BH_3$-DMS.

19. The method of embodiment 18, wherein the chiral reducing agent further comprises (S)-(–)-CBS.

20. The method of claim any one of the preceding embodiments, wherein the circled Ar is a 5-membered nitrogen-containing 1,3-heteroarylene, optionally substituted at the remaining positions.

21. The method of any one of embodiments 2 to 20, wherein the (R,R)-Formula 1a tubuvaline compound has the structure of:

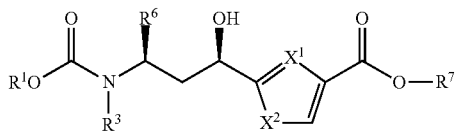

wherein: $X^1$ is =N—; and $X^2$ is S, O, or $N(R^{X2})$—, or $X^1$ is =$C(R^{X1})$—; and $X^2$ is $NR^{X2}$, wherein $R^{X1}$ and $R^{X2}$ are independently selected from the group consisting of —H, —$CH_3$ or —$CH_2CH_3$; and $R^1$ is phenyl, t-butyl, 9-fluorenyl or allyl, optionally substituted, or other moiety so that $R^1$—OC(=O)— is a suitable nitrogen protecting group; and $R^3$ is optionally substituted saturated $C_1$-$C_6$ alkyl, optionally substituted unsaturated $C_3$-$C_6$ alkyl or optionally substituted $C_3$-$C_6$ heteroalkyl; $R^6$ is $C_1$-$C_6$ alkyl; and $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl or optionally substituted $C_3$-$C_{20}$ hetero-cyclyl, or other moeity so that $R^7$—O— provides a suitable carboxylic acid protecting group.

22. The method of any one of embodiments 4 to 7, wherein the (R,R)-Formula 2 tubuvaline compound, optionally in salt form, has the structure of:

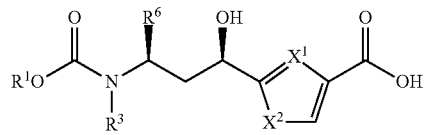

wherein: X is NH or O; and $X^1$ is =N—; and $X^2$ is S, O, or —$N(R^{X2})$—, or $X^1$ is =$C(R^{X1})$—; and $X^2$ is —$N(R^{X2})$—, wherein $R^{X1}$ and $R^{X2}$ are independently selected from the group consisting of —H, —$CH_3$ and —$CH_2CH_3$; and $R^1$ is phenyl, t-butyl, 9-fluorenyl or allyl, optionally substituted, or other moiety so that $R^1$—OC(=O)— is a suitable amino protecting group; $R^3$ is optionally substituted saturated $C_1$-$C_6$ alkyl, optionally substituted unsaturated $C_3$-$C_6$ alkyl or optionally substituted $C_3$-$C_6$ heteroalkyl; and $R^6$ is $C_1$-$C_6$ alkyl.

23. The method of embodiment 6 or 7 or the method of embodiment 10 or 11, wherein the (R,R)-Formula 2a or (R,R)-Formula 2b tubuvaline compound, optionally in salt form, has the structure of:

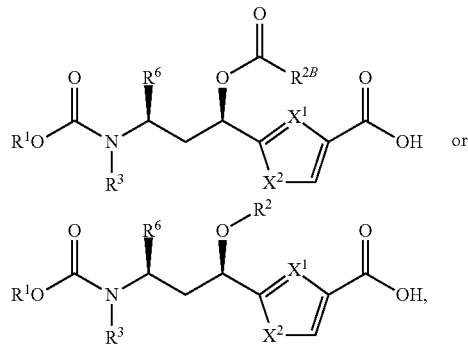

respectively, wherein: $R^1$ is optionally substituted phenyl, t-butyl, 9-fluorenyl or allyl, or other moeity so that $R^1$—OC(=O)— is a suitable nitrogen protecting group;

$R^2$ is optionally substituted saturated $C_1$-$C_8$ alkyl, optionally substituted unsaturated $C_3$-$C_6$ alkyl, optionally substituted $C_2$-$C_6$ alkenyl or optionally substituted alkynyl, or $R^2$ is $R^{2A}$ wherein $R^{2A}$ is —$CH_2R^{2C}$;

X is NH or O; and $X^1$ is =N—; and $X^2$ is S, O, or $NR^{X2}$, or $X^1$ is =$CR^{X1}$; and $X^2$ is $NR^{X2}$, wherein $R^{X1}$ and $R^{X2}$ are independently selected from the group consisting of —H, —$CH_3$ or —$CH_2CH_3$; $R^{2B}$ and $R^{2C}$ are as previously defined; and $R^3$ is optionally substituted saturated $C_1$-$C_6$ alkyl, optionally substituted unsaturated $C_3$-$C_6$ alkyl or optionally substituted $C_3$-$C_6$ heteroalkyl; and $R^6$ is $C_1$-$C_6$ alkyl.

24. The method of embodiment 21, 22 or 23, wherein $X^1$ is =N.

25. The method of claim any one of embodiments 21 to 24, wherein $X^2$ is S.

26. The method of any one of the preceding embodiments, wherein $R^3$ is optionally substituted $C_1$-$C_4$ alkyl.

27. The method of embodiment 26, wherein $R^3$ is methyl.

28. The method of any one of the preceding embodiments, wherein $R^6$ is $C_1$-$C_4$ alkyl.

29. The method of embodiment 28, wherein $R^6$ is isopropyl.

30. The method of any one of the preceding embodiments, wherein $R^1$ is t-butyl.

31. The method of embodiment 21, wherein the (R,R)-Formula 1a tubuvaline compound has the structure of:

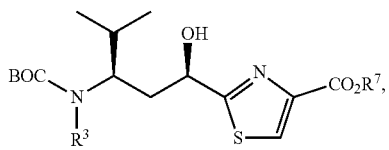

wherein $R^3$ is optionally substituted $C_1$-$C_4$ alkyl.

32. The method of embodiment 31, wherein the (R,R)-Formula 1a tubuvaline compound has the structure of:

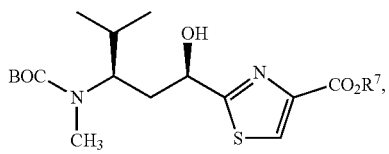

wherein $R^7$ is —$CH_3$ or —$CH_2CH_3$.

33. The method of embodiment 22 or 23, wherein the (R,R)-Formula 2, (R,R)-Formula 2a and (R,R)-Formula 2b tubuvaline compounds, each optionally in salt form, have the structures of:

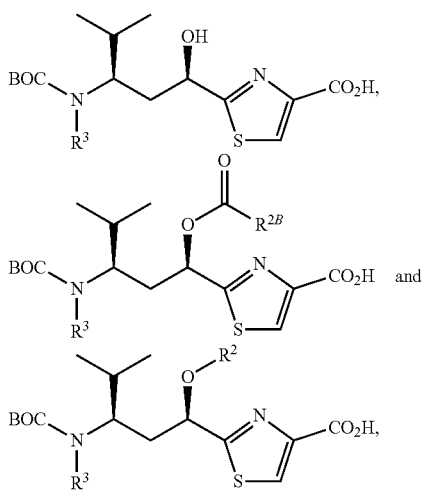

respectively, wherein $R^2$ is saturated $C_1$-$C_4$ alkyl, in particular, —$CH_3$, —$CH_2CH_3$, —$CH_2CH_2CH_3$, or $R^2$ is $R^{2A}$, wherein $R^{2A}$ is —$CH_2R^{2C}$, wherein $R^{2C}$ is $C_1$-$C_4$ ether, in particular $R^{2C}$ is —$OCH_3$ or —$OCH_2CH_3$;

$R^{2B}$ is saturated $C_1$-$C_4$ alkyl, unsaturated $C_3$-$C_6$ alkyl, or $C_2$-$C_6$ alkenyl, in particular —$CH_3$, —$CH_2CH_3$, —$CH(CH_3)_2$, —$CH_2CH(CH_3)_2$, —$CH_2C(CH_3)_3$, —$CH_2CH=CH_2$, —$CH_2C(CH_3)=CH_2$, —$CH=CH_2$, —$CH=CHCH_3$, or —$C(CH_3)=CH_2$; and $R^3$ is optionally substituted $C_1$-$C_4$ alkyl, in particular, —$CH_3$ or —$CH_2CH_2CH_3$.

34. A method for preparing a tubulysin intermediate of (R,R)-Formula Ti-1:

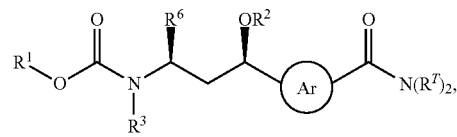

or a composition comprising or consisting essentially of the intermediate, optionally in salt form, wherein: the circled Ar is a 5- or 6-membered nitrogen-containing 1,3-heteroarylene, optionally substituted at the remaining positions;

$R^1$ is phenyl, t-butyl, 9-fluorenyl or allyl, optionally substituted, or other moeity so that $R^1$—OC(=O)— is a suitable nitrogen protecting group;

$R^2$ is —H or optionally substituted saturated $C_1$-$C_6$ alkyl, optionally substituted unsaturated $C_3$-$C_6$ alkyl, optionally substituted $C_2$-$C_6$ alkenyl or optionally substituted $C_2$-$C_6$ alkynyl, or $R^2$ is $R^{2A}$ wherein $R^{2A}$ is —$CH_2R^{2C}$, wherein $R^{2C}$ is optionally substituted saturated $C_1$-$C_6$ ether or optionally substituted unsaturated $C_2$-$C_6$ ether, or $R^{2A}$ is —C(=O)$R^{2B}$, wherein $R^{2B}$ is optionally substituted saturated $C_1$-$C_6$ alkyl, optionally substituted unsaturated $C_3$-$C_6$ alkyl, optionally substituted $C_2$-$C_6$ alkenyl or optionally substituted $C_2$-$C_6$ alkynyl;

$R^3$ is optionally substituted saturated $C_1$-$C_8$ alkyl, optionally substituted unsaturated $C_3$-$C_8$ alkyl, or optionally substituted $C_3$-$C_8$ heteroalkyl;

$R^6$ is optionally substituted $C_1$-$C_8$ alkyl; and one $R^T$ is hydrogen, optionally substituted saturated $C_1$-$C_8$ alkyl or optionally substituted unsaturated $C_3$-$C_8$ alkyl, and the other $R^T$ is optionally substituted $C_1$-$C_8$ alkyl, optionally substituted saturated $C_1$-$C_8$ alkyl, optionally substituted unsaturated $C_3$-$C_8$ alkyl, or optionally substituted $C_3$-$C_8$ heteroalkyl, the method comprising the steps of:

(a) contacting a tubuvaline compound, optionally in salt form, of (R,R)-Formula 2, (R,R)-Formula 2a or (R,R)-Formula 2b, wherein the (R,R)-Formula 2, (R,R)-Formula 2a and (R,R)-Formula 2b tubuvaline compounds have the structures of:

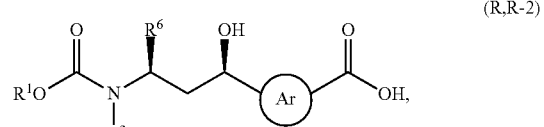

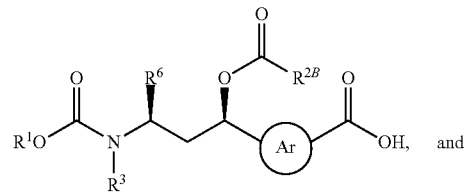

-continued

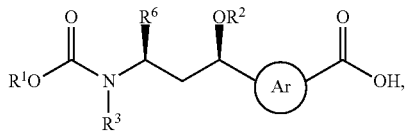
(R,R-2b)

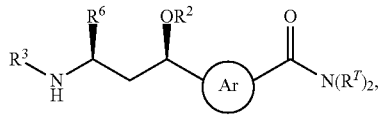
(R,R-Ti-2)

respectively, or a composition comprised or consisting of one of these tubuvaline compounds, wherein $R^1$ is phenyl, t-butyl, 9-fluorenyl or allyl, optionally substituted, or other moeity so that $R^1$—OC(=O)— is a suitable nitrogen protecting group, and $R^2$ is optionally substituted saturated $C_1$-$C_6$ alkyl, optionally substituted unsaturated $C_3$-$C_6$ alkyl, optionally substituted $C_2$-$C_6$ alkenyl or optionally substituted $C_2$-$C_6$alkynyl, or $R^2$ is $R^{2A}$ wherein $R^{2A}$ is —CH$_2$R$^{2C}$, wherein $R^{2C}$ is optionally substituted saturated $C_1$-$C_6$ ether or optionally substituted unsaturated $C_2$-$C_6$ ether and the remaining variable groups of (R,R)-Formula 2, (R,R)-Formula 2a and (R,R)-Formula 2b are as defined for (R,R)-Formula Ti, wherein the (R,R)-Formula 2, (R,R)-Formula 2a and (R,R)-Formula 2b tubuvaline compounds or compositions, are prepared according to the methods of embodiments 7, 9 and 11, respectively, with an amine compound of Formula C having the structure of HN(R$^T$)$_2$, optionally in salt form, wherein each R$^T$ is as defined for (R,R)-Formula Ti-1, in the presence of a first coupling agent and optionally in the presence of a first hindered base so as to form the (R,R)-Formula Ti-1 tubulysin intermediate, or a composition comprised of consisting essentially of that intermediate, optionally in salt form, wherein the (R,R)-Formula Ti-1 tubulysin intermediate has the structure of (R,R)-Formula 3, (R,R)-Formula 3a or (R,R)-Formula 3b:

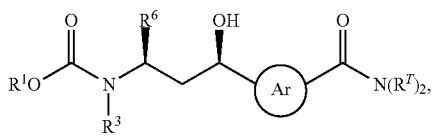
(R,R-3)

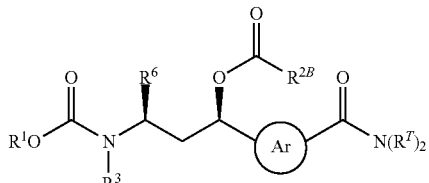
(R,R-3a)

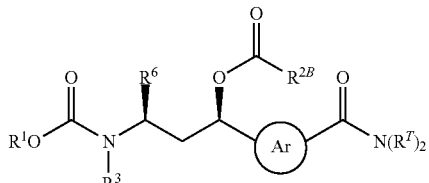
(R,R-3b)

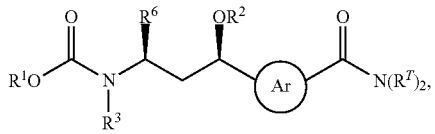

wherein $R^2$ retains its meaning from (R,R)-Formula 2b and the remaining variable groups of (R,R)-Formula 3, (R,R)-Formula 3a, and (R,R)-Formula 3b are as defined for Formula C and (R,R)-Formula Ti-1.

35. A method for preparing a tubulysin intermediate of (R,R)-Formula Ti-2:

or a composition comprised or consisting essentially of that intermediate, optionally in salt form, wherein: the circled Ar is a 5- or 6-membered nitrogen-containing 1,3-heteroarylene, optionally substituted at the remaining positions, wherein:

$R^2$ is —H or optionally substituted saturated $C_1$-$C_8$ alkyl, optionally substituted unsaturated $C_3$-$C_8$ alkyl, optionally substituted $C_2$-$C_8$ alkenyl or optionally substituted $C_2$-$C_8$alkynyl, or $R^2$ is $R^{2A}$, wherein $R^{2A}$ is —CH$_2$R$^{2C}$, wherein $R^{2C}$ is optionally substituted $C_1$-$C_8$ ether, optionally substituted $C_2$-$C_8$ alkenyl, or optionally substituted $C_2$-$C_8$ alkynyl, or $R^{2A}$ is —C(=O)R$^{2B}$, wherein $R^{2B}$ is optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$ alkynyl; and $R^3$ is optionally substituted saturated $C_1$-$C_8$ alkyl, optionally substituted unsaturated $C_3$-$C_8$ alkyl, or optionally substituted $C_3$-$C_8$ heteroalkyl;

$R^6$ is optionally substituted $C_1$-$C_8$ alkyl; and one R$^T$ is hydrogen, optionally substituted saturated $C_1$-$C_8$ alkyl or optionally substituted unsaturated $C_3$-$C_8$ alkyl, and the other R$^T$ is optionally substituted $C_1$-$C_8$ alkyl, optionally substituted saturated $C_1$-$C_8$ alkyl, optionally substituted unsaturated $C_3$-$C_8$ alkyl, or optionally substituted $C_3$-$C_8$ heteroalkyl, the method comprising the steps of:

(g) contacting a tubuvaline compound of (R,R)-Formula 2, (R,R)-Formula 2a or (R,R)-Formula 2b, wherein the (R,R)-Formula 2, (R,R)-Formula 2a and (R,R)-Formula 2b tubuvaline compounds have the structures of:

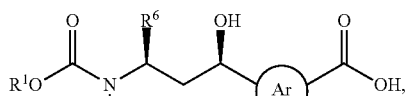
(R,R-2)

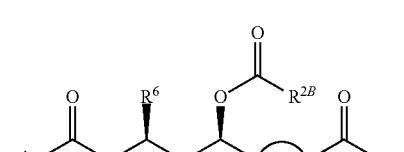
(R,R-2a)

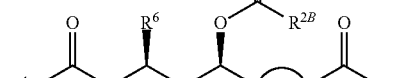
(R,R-2b)

respectively, or a composition comprised or consisting essentially of one of those compounds, optionally in salt form, or wherein $R^1$ is phenyl, t-butyl, 9-fluorenyl or allyl, optionally substituted, or other moeity so that $R^1$—OC(=O)— is a suitable nitrogen protecting groups; and $R^2$ is optionally substituted saturated $C_1$-$C_8$ alkyl, optionally substituted unsaturated $C_3$-$C_8$ alkyl, optionally substituted $C_2$-$C_8$ alkenyl or optionally substituted $C_2$-$C_8$ alkynyl, or $R^2$ is $R^{2A}$, wherein $R^{2A}$ is —$CH_2R^{2C}$, and the remaining variable groups are as defined for (R,R)-Formula Ti-2, wherein the (R,R)-Formula 2, (R,R)-Formula 2a and (R,R)-Formula 2b tubuvaline compounds, each optionally in salt form, or compositions are prepared according to the methods of embodiments 7, 9 and 11, respectively, with an amine of Formula C having the structure of $HN(R^T)_2$, optionally in salt form, wherein each $R^T$ is as defined for (R,R)-Formula Ti-2, in the presence of a first coupling agent and optionally in the presence of a first hindered base so as to form a (R,R)-Formula Ti-1 tubulysin intermediate having the structure of (R,R)-Formula 3, (R,R)-Formula 3a or (R,R)-Formula 3b:

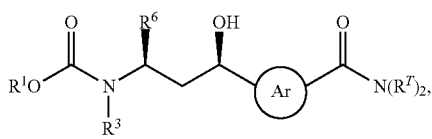
(R,R-3)

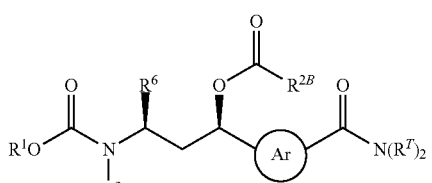
(R,R-3a)

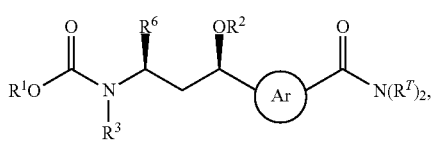
(R,R-3b)

or a composition comprised or consisting essentially of one of those tubulysin intermediates, optionally in salt form and/or as an activated ester thereof, wherein $R^1$ and $R^2$ are as defined for (R,R)-Formula 2b and the remaining variable groups are as defined for (R,R)-Formula Ti-2; and (h) contacting the (R,R)-Formula 3, (R,R)-Formula 3a, or (R,R)-Formula 3b tubulysin intermediate, optionally in salt form, or composition with a suitable first deprotecting agent so as to form the (R,R)-Formula Ti-2 tubulysin intermediate or composition, wherein the (R,R)-Formula Ti-2 tubulysin intermediate has the structure of (R,R)-Formula 4, (R,R)-Formula 4a or (R,R)-Formula 4b:

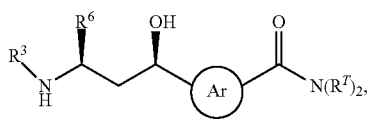
(R,R-4)

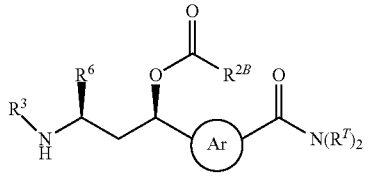
(R,R-4a)

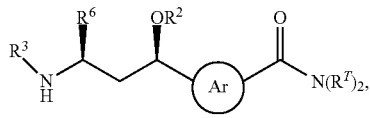
(R,R-4b)

respectively, wherein $R^2$ is as defined for (R,R)-Formula 2b and the remaining variable groups are as defined for (R,R)-Formula Ti-2.

36. A method for preparing a tubulysin intermediate or tubulysin compound having the structure of

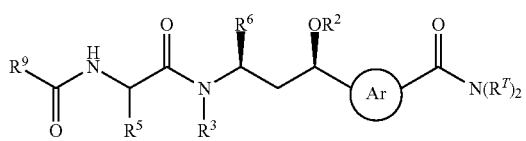

or a composition comprised of that tubulysin compound or intermediate, optionally in salt form, wherein: the circled Ar is a 5- or 6-membered nitrogen-containing 1,3-heteroarylene optionally substituted at the remaining positions;

$R^2$ is —H or optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$ alkynyl, or $R^2$ is $R^{2A}$, wherein $R^{2A}$ is —$CH_2R^{2C}$, wherein $R^{2C}$ is optionally substituted saturated $C_1$-$C_8$ ether or optionally substituted unsaturated $C_2$-$C_8$ ether, or $R^{2A}$ is —C(=O)$R^{2B}$, wherein $R^{2B}$ is optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$ alkynyl; and $R^3$ is optionally substituted saturated $C_1$-$C_8$ alkyl, optionally substituted saturated $C_3$-$C_8$ alkyl, or optionally substituted $C_3$-$C_8$ heteroalkyl; $R^5$ and $R^6$ are independently optionally substituted $C_1$-$C_8$ alkyl;

one $R^T$ is hydrogen, optionally substituted saturated $C_1$-$C_8$ alkyl or optionally substituted unsaturated $C_3$-$C_8$ alkyl, and the other $R^T$ is optionally substituted $C_1$-$C_8$ alkyl, optionally substituted saturated $C_1$-$C_8$ alkyl, optionally substituted unsaturated $C_3$-$C_8$ alkyl, or optionally substituted $C_3$-$C_8$ heteroalkyl; and $R^9$ is —$OR^{14}$, so that the tubulysin intermediate is (R,R)-Formula Ti-3, wherein $R^{14}$ independently of $R^1$ is optionally substituted phenyl, t-butyl, 9-fluorenyl, or allyl or other moiety so that $R^{14}$—OC(=O)— is independently a suitable nitrogen protecting group; and or $R^9$ has the structure of:

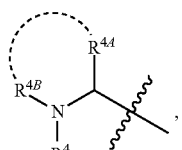

or a salt thereof, so that the tubulysin compound is (R,R)-Formula T, wherein $R^4$ is $C_1$-$C_4$ alkyl; $R^{4a}$ is hydrogen or optionally substituted $C_1$-$C_8$ alkyl; $R^{4B}$ is optionally substituted $C_1$-$C_8$ alkyl, or both together with the nitrogen atom to which they are attached, as indicated by the curved dashed line, define a optionally substituted 5-, 6-, 7-, or 8-membered nitrogen-containing heterocyclyl; and the wavy line indicates the site of covalent attachment to the remainder of the (R,R)-Formula T tubulysin compound, the method comprising the steps of:

(g) contacting a tubuvaline intermediate of (R,R)-Formula 2, (R,R)-Formula 2a or (R,R)-Formula 2b, or a composition comprised or consisting essentially of one of those intermediates, optionally in salt form, wherein the (R,R)-Formula 2, (R,R)-Formula 2a and (R,R)-Formula 2b tubuvaline compounds have the structures of:

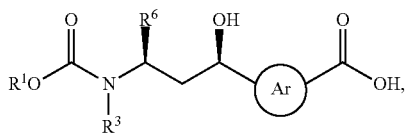
(R,R-2)

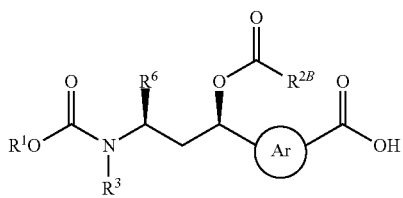
(R,R-2a)

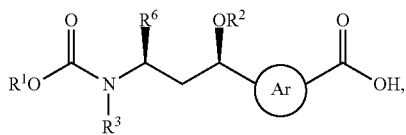
(R,R-2b)

wherein $R^2$ is optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$ alkynyl, or $R^2$ is $R^{2A}$, wherein $R^{2A}$ is —$CH_2R^{2C}$, wherein the remaining variable groups are as defined for (R,R)-Formula Ti-3, and wherein the (R,R)-Formula 2, (R,R)-Formula 2a or (R,R)-Formula 2b tubuvaline compound or composition is prepared according to embodiment 7, 9 or 11, respectively, with an amine of Formula C having the structure of $HN(R^T)_2$, optionally in salt form, wherein each $R^T$ is as defined for (R,R)-Formula Ti-3, in the presence of a first coupling agent and optionally in the presence of a first hindered base, so as to form a (R,R)-Formula Ti-1 tubulysin intermediate, optionally in salt form, or a composition comprised of that intermediate or salt, wherein the (R,R)-Formula Ti-1 tubulysin intermediate has the structure of (R,R)-Formula 3, (R,R)-Formula 3a or (R,R)-Formula 3b:

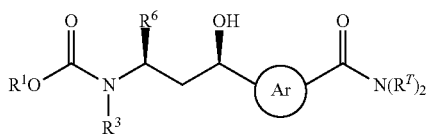
(R,R-3)

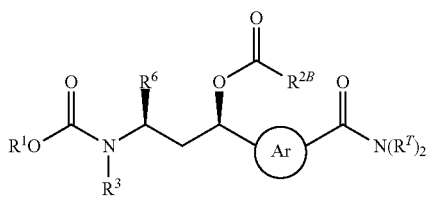
(R,R-3a)

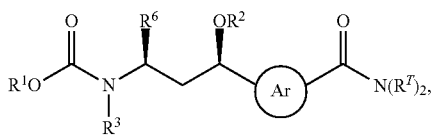
(R,R-3b)

wherein $R^1$ and $R^2$ are as defined for (R,R)-Formula 2, (R,R)-Formula 2a and (R,R)-Formula 2b, and the remaining variable groups are as defined for (R,R)-Formula Ti-3;

(h) contacting the (R,R)-Formula 3, (R,R)-Formula 3a, or (R,R)-Formula 3b tubulysin intermediate or composition thereof, with a suitable first deprotecting agent so as to form a (R,R)-Formula Ti-2 tubulysin intermediate, wherein the (R,R)-Formula Ti-2 tubulysin intermediate has the structure of (R,R)-Formula 4, (R,R)-Formula 4a or (R,R)-Formula 4b:

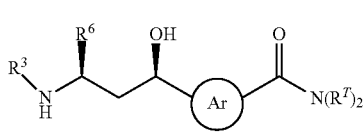
(R,R-4)

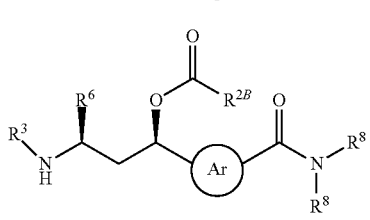
(R,R-4a)

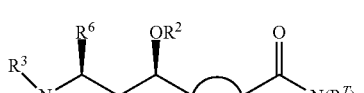
(R,R-4b)

wherein the variable groups retain their meanings from (R,R)-Formula 3, (R,R)-Formula 3a, or (R,R)-Formula 3b;

(i) contacting the (R,R)-Formula 4, (R,R)-Formula 4a or (R,R)-Formula 4b tubulysin intermediate, or composition thereof, with a protected amino acid of Formula D2, optionally in salt form, having the structure of:

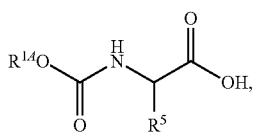
(D2)

or and activated ester thereof, wherein $R^{1A}$, independently of $R^1$, is optionally substituted phenyl, t-butyl, 9-fluorenyl, or allyl or other moiety so that $R^{1A}$—OC(=O)— is independently a suitable nitrogen protecting group and $R^5$ is as defined for (R,R)-Formula Ti-3, in the presence of a second coupling agent and optionally in the presence of a second hindered base, so as to form a (R,R)-Formula Ti-3 tubulysin intermediate, or composition thereof, comprised or consisting essentially of that intermediate, optionally in salt form, wherein the (R,R)-Formula Ti-3 tubulysin intermediate has the structure of (R,R)-Formula 5, (R,R)-Formula 5a or (R,R)-Formula 5b:

(R,R-5)
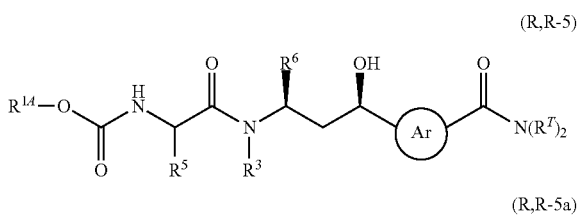

(R,R-5a)
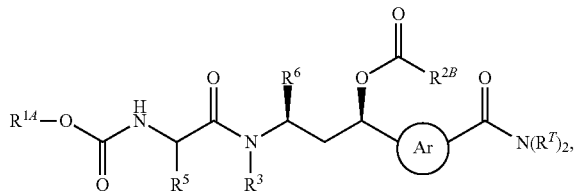

(R,R-5b)
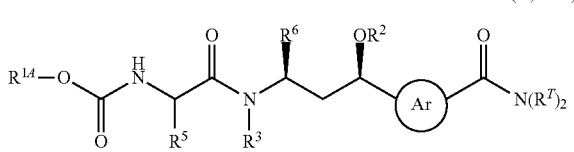

wherein the variable groups are as defined for D1 and remaining variable groups retain their meanings from (R,R)-Formula 4, (R,R)-Formula 4a or (R,R)-Formula 4b, or (i') contacting the (R,R)-Formula 4, (R,R)-Formula 4a or (R,R)-Formula 4b tubulysin intermediate or composition comprised or consisting essentially of one of these intermediates, optionally in salt form, with a dipeptide of Formula D1-D2, optionally in salt form, having the structure of:

(D1-D2)
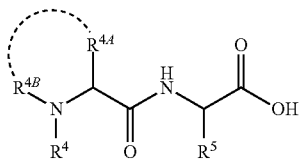

or an activated ester thereof, in the presence of a second coupling agent and optionally in the presence of a second hindered base, wherein $R^4$, $R^{4A}$, $R^{4B}$ and $R^5$ are as defined for (R,R)-Formula Ti-3 so as to form the (R,R)-Formula T tubulysin compound, or composition comprised or consisting essentially of that compound, optionally in salt form, wherein the (R,R)-Formula T tubulysin compound so prepared has the structure of (R,R)-Formula T1, (R,R)-Formula T1A or (R,R)-Formula T1B:

(R,R-T1)
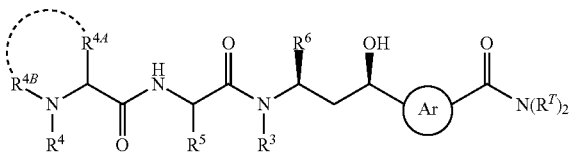

(R,R-T1A)
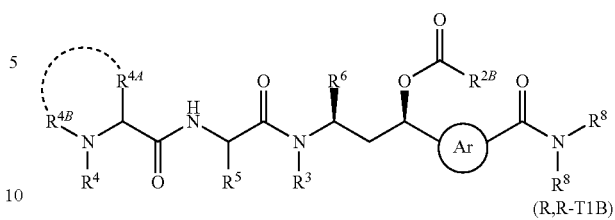

(R,R-T1B)
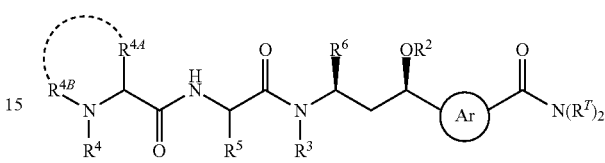

wherein $R^2$ is optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$ alkynyl, or $R^2$ is $R^{2A}$, wherein $R^{2A}$ is —$CH_2R^{2C}$, and remaining variable groups retain their meaning from dipeptide D1-D2 and (R,R)-Formula 4, (R,R)-Formula 4a or (R,R)-Formula 4b.

37. A method of preparing a tubulysin compound of (R,R)-Formula T (R,R-T)
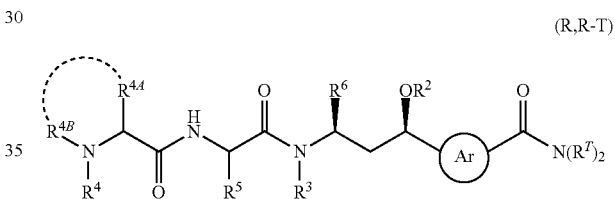

or a composition comprised or consisting essentially of that compound, optionally in salt form, wherein the circled Ar is a 5- or 6-membered nitrogen-containing 1,3-heteroarylene, optionally substituted at the remaining positions;

$R^2$ is —H or optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$alkynyl, or $R^2$ is $R^{2A}$, wherein $R^{2A}$ is —$CH_2R^{2C}$, wherein $R^{2C}$ is optionally substituted saturated $C_1$-$C_8$ ether or optionally substituted unsaturated $C_2$-$C_8$ ether, or $R^{2A}$ is —C(=O)$R^{2B}$, wherein $R^{2B}$ is optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$ alkynyl;

$R^3$ is optionally substituted saturated $C_1$-$C_8$ alkyl, optionally substituted unsaturated $C_3$-$C_8$ alkyl, or optionally substituted $C_3$-$C_8$ heteroalkyl; $R^4$ is $C_1$-$C_4$ alkyl; $R^{4a}$ is hydrogen or optionally substituted $C_1$-$C_8$ alkyl; $R^{4B}$ is optionally substituted $C_1$-$C_8$ alkyl, or both together with the nitrogen atom to which they are attached, as indicated by the curved dashed line, define a optionally substituted 5-, 6-, 7-, or 8-membered nitrogen-containing heterocyclyl; and $R^5$ and $R^6$ are independently optionally substituted $C_1$-$C_8$ alkyl;

one $R^T$ is hydrogen, optionally substituted saturated $C_1$-$C_8$ alkyl or optionally substituted unsaturated $C_3$-$C_8$ alkyl, and the other $R^T$ is optionally substituted $C_1$-$C_8$ alkyl, optionally substituted saturated $C_1$-$C_8$ alkyl, optionally substituted unsaturated $C_3$-$C_8$ alkyl, or optionally substituted $C_3$-$C_8$ heteroalkyl; the method comprising the steps of:

(i) contacting a tubulysin intermediate, wherein the compound has the structure of (R,R)-Formula Ti-3:

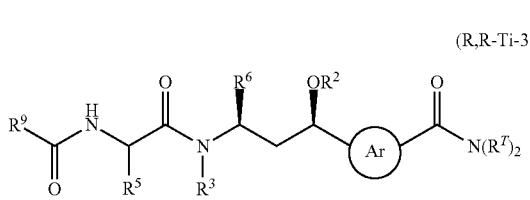
(R,R-Ti-3)

or a composition comprising or consisting essentially of that tubulysin intermediate, wherein $R^9$ is —$OR^{14}$, wherein $R^{14}$ is optionally substituted phenyl, t-butyl, 9-fluorenyl, or allyl or other moeity so that $R^{14}$—OC(=O)— is a suitable nitrogen protecting group, and the remaining variable groups are as defined for (R,R)-Formula T; and wherein the (R,R)-Formula Ti-3 tubulysin intermediate is prepared according to steps (g) and (h) of embodiment 36, with a second suitable deprotecting agent so as to provide a tubulysin intermediate of (R,R)-Formula Ti-4:

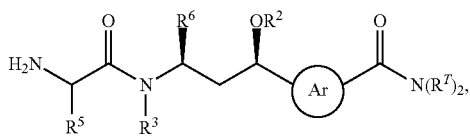
(R,R-Ti-4)

or a composition comprised or consisting essentially of that intermediate, optionally in salt form, wherein the variable groups retain their meanings from (R,R)-Formula Ti-3; and (i') contacting the (R,R)-Formula Ti-4 tubulysin intermediate, optionally in salt form, or composition with a dipeptide of Formula D1-D2, optionally in salt form, having the structure of:

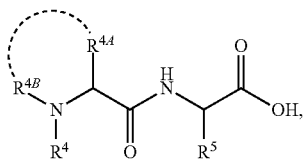
(D1-D2)

or an activated ester thereof, in the presence of a third coupling agent and optionally in the presence of a third hindered base so as to form the (R,R)-Formula T tubulysin compound or composition thereof having the structure of (R,R)-Formula T1, (R,R)-Formula T1A or (R,R)-Formula T1B:

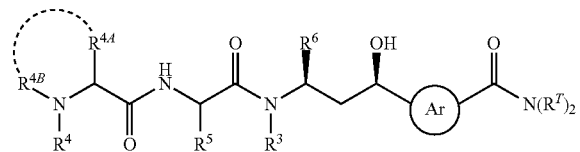
(R,R-T1)

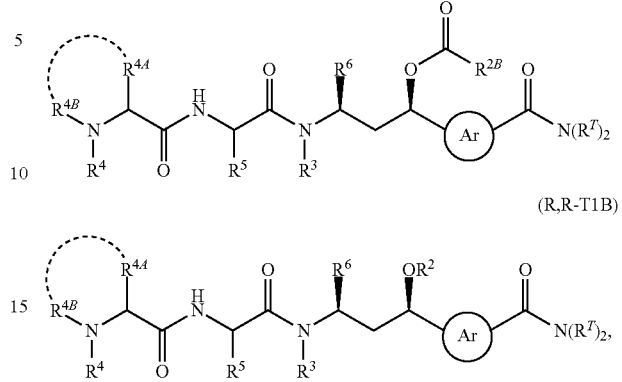
(R,R-T1A)

(R,R-T1B)

or composition comprised or consisting essentially of that compound, optionally in salt form, wherein $R^2$ is optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$ alkynyl, or $R^2$ is $R^{2A}$, wherein $R^{2A}$ is —$CH_2R^{2C}$, wherein $R^{2B}$ and $R^{2C}$ and the remaining variable groups are as defined for (R,R)-Formula T.

38. A method of preparing a tubulysin compound of (R,R)-Formula T1A:

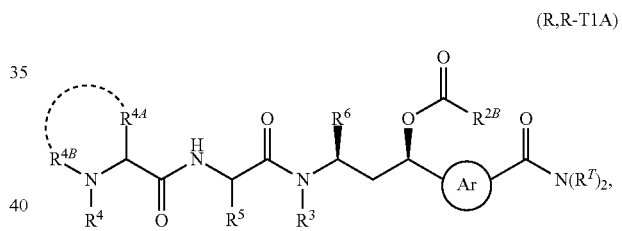
(R,R-T1A)

or a composition comprised or consisting essentially of that compound, optionally in salt form, wherein the circled Ar is a 5- or 6-membered nitrogen-containing 1,3-heteroarylene, optionally substituted at the remaining positions; $R^{2B}$ is optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$ alkynyl; $R^3$ is optionally substituted saturated $C_1$-$C_8$ alkyl, optionally substituted unsaturated $C_3$-$C_8$ alkyl, or optionally substituted $C_3$-$C_8$ heteroalkyl;

$R^4$ is $C_1$-$C_4$ alkyl; $R^{4a}$ is hydrogen or optionally substituted $C_1$-$C_8$ alkyl; $R^{4B}$ is optionally substituted $C_1$-$C_8$ alkyl, or both together with the nitrogen atom to which they are attached, as indicated by the curved dashed line, define a optionally substituted 5-, 6-, 7-, or 8-membered nitrogen-containing heterocyclyl; and $R^5$ and $R^6$ are independently optionally substituted $C_1$-$C_8$ alkyl;

one $R^T$ is hydrogen, optionally substituted saturated $C_1$-$C_8$ alkyl or optionally substituted unsaturated $C_3$-$C_8$ alkyl, and the other $R^T$ is optionally substituted $C_1$-$C_8$ alkyl, optionally substituted saturated $C_1$-$C_8$ alkyl, optionally substituted unsaturated $C_3$-$C_8$ alkyl, or optionally substituted $C_3$-$C_8$ heteroalkyl; the method comprising the steps of:

(i) contacting a tubulysin intermediate of (R,R)-Formula 5:

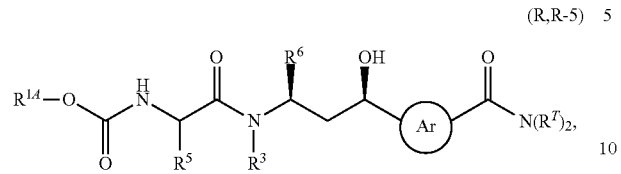
(R,R-5)

or a composition comprising or consisting essentially of that compound, wherein $R^{1A}$ is optionally substituted phenyl, t-butyl, 9-fluorenyl, or allyl or other moeity so that $R^{1A}$—OC(=O)— are independently suitable nitrogen protecting groups, and the remaining variable groups are as defined for (R,R)-Formula T1A, wherein the tubulysin intermediate is prepared according to steps (g)-(i) of embodiment 36, with a second suitable deprotecting agent so as to provide a tubulysin intermediate of (R,R)-Formula 6:

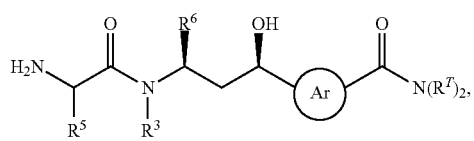
(R,R-6)

or a composition comprised or consisting essentially of that compound, optionally in salt form; and (i") contacting the (R,R)-Formula 6 tubulysin intermediate or composition with un-natural amino acid of Formula D1 having the structure of:

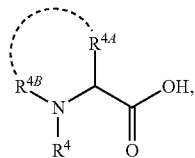
(D1)

optionally in salt form, or an activated ester thereof, optionally in the presence of a third hindered base, wherein the variable groups of D1 as defined for (R,R)-Formula T1A in the presence of a third coupling agent so as to provide the (R,R)-Formula T1A tubulysin composition or compound, optionally in salt form.

39. The method of any one of embodiments 34 to 38, wherein one $R^T$ of —N($R^T$)$_2$ is —H or $C_1$-$C_4$ alkyl and the other $R^T$ is optionally substituted ($C_6$-$C_{10}$ aryl)-$C_1$-$C_4$ alkyl- or optionally substituted ($C_5$-$C_{10}$ heteroaryl)-$C_1$-$C_4$ alkyl, or one $R^T$ is $C_1$-$C_4$ alkyl, and the other $R^T$ is an independently selected $C_1$-$C_4$ alkyl optionally substituted by —CO$_2$H or an ester thereof, and/or by an optionally substituted phenyl.

40. The method of any one of embodiments 34 to 38, wherein —N($R^T$)$_2$ is —NH($C_1$-$C_6$ alkyl), wherein the $C_1$-$C_6$ alkyl is a saturated $C_1$-$C_4$ alkyl or an unsaturated $C_3$-$C_6$ alkyl and is substituted by —CO$_2$H or an ester thereof, and/or by an optionally substituted phenyl, in particular —NH(CH$_3$), —NHCH$_2$CH$_2$Ph, and —NHCH$_2$—CO$_2$H, —NHCH$_2$CH$_2$CO$_2$H and —NHCH$_2$CH$_2$CH$_2$CO$_2$H.

41. The method of any one of embodiments 34 to 38, wherein —NH($R^T$)$_2$ has the structure of:

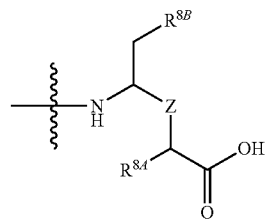

or a salt or $C_1$-$C_6$ ester thereof, wherein the wavy line indicates the site of covalent attachment to the remainder of the tubulysin intermediate or tubulysin compound; Z is optionally substituted $C_1$-$C_4$ alkylene, or optionally substituted $C_2$-$C_6$ alkenylene; $R^{8A}$ is optionally substituted $C_1$-$C_4$ alkyl; and $R^{SB}$ is optionally substituted phenyl, or optionally substituted 5- or 6-membered heteroaryl.

42. The method of embodiment 41, wherein —NH($R^T$)$_2$ has the structure of:

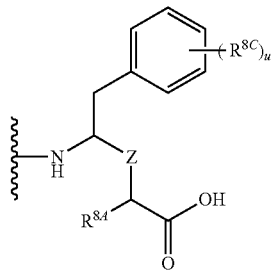

or a salt or $C_1$-$C_6$ ester thereof, wherein subscript u is 0, 1, 2 or 3, Z is $C_1$-$C_4$ alkylene or $C_2$-$C_6$ alkylene; $R^{8C}$ is absent when subscript u is 0 and 1, 2 or 3 independently selected $R^{8C}$ substituents are present when subscript u is 1, 2 or 3, respectively; and $R^{8A}$ is —H or $C_1$-$C_4$ alkyl; and each $R^{8C}$ when present is independently selected from the group consisting halogens, O-linked substituents and N-linked substituents, in particular from the group consisting of —OH and NH$_2$.

43. The method of embodiment 42, wherein —NH($R^T$)$_2$ has the structure of:

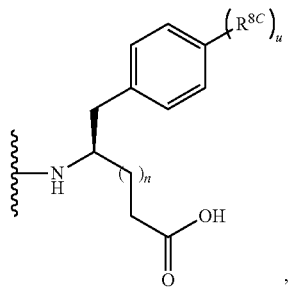

201

-continued

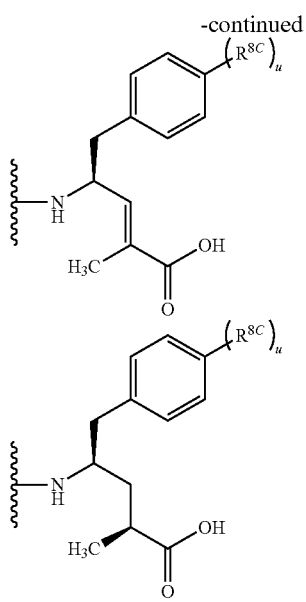

or a salt or $C_1$-$C_6$ ester thereof, in particular, methyl, ethyl or allyl ester, wherein subscript u is 0 or 1; subscript n is 0, 1 or 2; and $R^{8C}$, when present, is —OH or —$NH_2$.

44. The method of any one of embodiments 34 to 43, wherein the circled Ar is a 5-membered nitrogen-containing 1,3-heteroarylene optionally substituted at the remaining positions.

45. The method of embodiment 44, wherein the 5-membered nitrogen-containing 1,3-heteroarylene has the structure of:

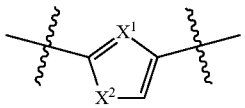

202 wherein: $X^1$ is =N—; and $X^2$ is S, O, or N($R^{X2}$)—, or $X^1$ is =C($R^{X1}$)—; and $X^2$ is $NR^{X2}$, wherein $R^{X1}$ and $R^{X2}$ are independently selected from the group consisting of —H, —$CH_3$ and —$CH_2CH_3$.

46. The method of embodiment 36, 37 or 38, wherein the tubulysin compound has the structure of:

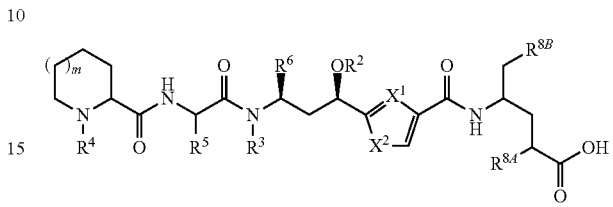

or a salt or $C_1$-$C_4$ ester thereof, wherein subscript m is 0 or 1; $R^2$ is —H or $R^2$ is $R^{2A}$, wherein $R^{2A}$ is optionally substituted $C_1$-$C_4$ alkyl, or $R^{2A}$—$CH_2R^{2C}$, wherein $R^{2C}$ is —$OCH_3$, —$OCH_2CH_3$ or optionally substituted $C_2$-$C_6$ alkenyl, or $R^{2A}$ is —C(O)$R^{2B}$, wherein $R^{2B}$ is optionally substituted saturated $C_1$-$C_4$ alkyl or optionally substituted unsaturated $C_3$-$C_6$ alkyl; and $X^1$ is =N—; and $X^2$ is S, O, or N($R^{X2}$)—, or $X^1$ is =C($R^{X1}$)—; and $X^2$ is $NR^{X2}$, wherein $R^{X1}$ and $R^{X2}$ are independently selected from the group consisting of —H, —$CH_3$ and —$CH_2CH_3$.

47. The method of embodiment 45 or 46, wherein $X^1$ is =N—.

48. The method of any one of embodiments 36 to 47, wherein $R^5$ is —CH($CH_3$)$CH_2CH_3$.

49. The method of embodiment 48, wherein the tubulysin compound has the structure of:

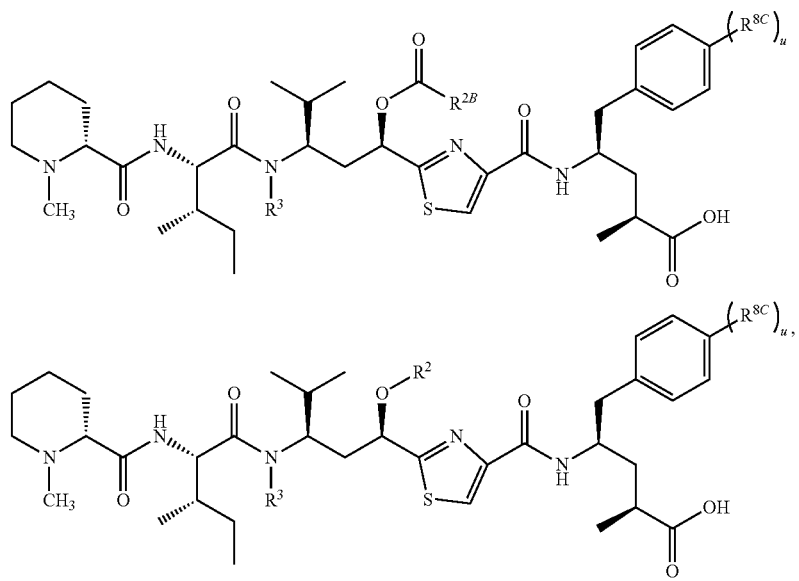

or a salt or $C_1$-$C_4$ ester thereof, in particular, methyl, ethyl or allyl, wherein subscript u is 0 or 1; $R^2$ is saturated $C_1$-$C_4$ alkyl, unsaturated $C_3$-$C_6$ alkyl or $C_2$-$C_6$ alkenyl, or $R^2$ is $R^{2A}$, wherein $R^{2A}$ is —$CH_2R^{2C}$, wherein $R^{2C}$ is saturated $C_1$-$C_6$ ether or unsaturated $C_2$-$C_6$ ether; $R^3$ is —$CH_3$, —$CH_2CH_3$, —$CH_2CH_2CH_3$ or —$C(R^{3A})(R^{3A})C(=O)$—$X^C$, wherein $X^C$ is —$OR^{3B}$ or —$N(R^{3C})(R^{3C})$, wherein each of $R^{3A}$, $R^{3B}$ and $R^{3c}$ are independently selected from the group consisting of —H and —$CH_3$; and $R^{8C}$ when present is —OH.

50. The method of embodiment 49, wherein $R^2$ is —$CH_3$, —$CH_2CH_3$, —$CH_2CH_2CH_3$, —$CH(CH_3)_2$, —$CH_2CH(CH_3)_2$, —$CH_2C(CH_3)_3$, —$CH=CH_2$, or —$C(CH_3)=CH_2$, or $R^{2A}$—$CH_2R^{2C}$, wherein $R^{2C}$ is —$OCH_3$ or —$OCH_2CH_3$; $R^{2B}$ is $CH_3$, —$CH_2CH_3$, —$CH(CH_3)_2$, —$CH_2CH(CH_3)_2$, —$CH_2C(CH_3)_3$, —$CH_2CH=CH_2$, —$CH_2C(CH_3)=CH_2$, —$CH=CH_2$, —$CH=CHCH_3$, or —$C(CH_3)=CH_2$; and $R^3$ is —$CH_3$ or —$CH_2CH_3$.

51. The method of any one of embodiments 1 to 50, wherein $R^6$ is —$CH(CH_3)_2$.

52. The method of embodiment 51, wherein the tubulysin compound has the structure of:

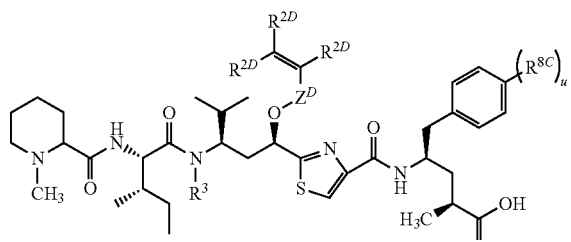

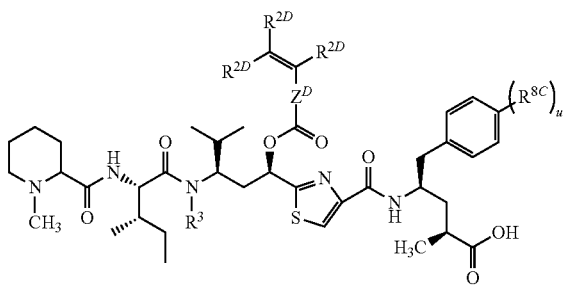

or a salt or $C_1$-$C_4$ ester thereof, in particular, methyl, ethyl or allyl ester, wherein subscript u is 0 or 1; $R^{8C}$ when present is —OH; $Z^D$ is absent or —$CH_2$—; each $R^{2D}$ is independently selected from the group consisting of —H and —$CH_3$; and $R^3$ is —$CH_3$, —$CH_2CH_3$ or —$CH_2CH_2CH_3$.

53. The method of embodiment 51, wherein the tubulysin compound has the structure of:

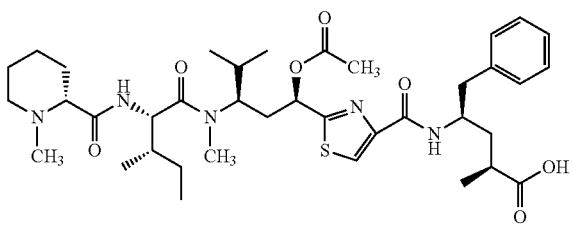

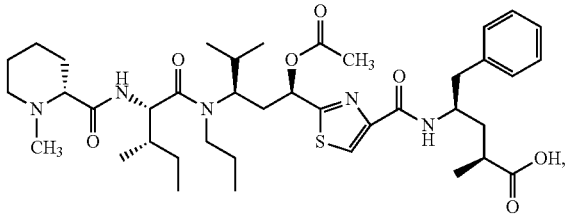

or a salt, or methyl, ethyl or allyl ester thereof.

54. The method of embodiment 51, wherein the tubulysin compound has the structure of:

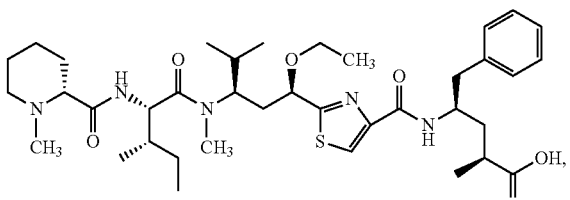

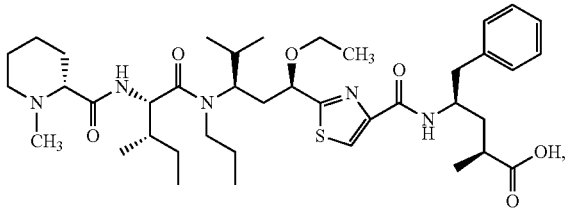

or a salt or methyl, ethyl or allyl ester thereof.

55. The method of any one of embodiments 34 to 54, wherein the transition (II) metal is Cu(II).

56. The method of embodiment 55, wherein the transition metal catalysis is comprised of $Cu(OTf)_2$, $Cu(SbF_6)_2$, or $CuCl_2$.

57. The method of any one of embodiments 34 to 56, wherein the suitable polar aprotic solvent is acetonitrile, dichloromethane, THF, dioxane, or a mixture of two or three of these solvents, in particular dichloromethane.

58. The method of any one of embodiments 34 to 57, wherein the chiral reducing agent comprises $BH_3$-DMS.

59. The method of embodiment 58, wherein the chiral reducing agent further comprises (S)-(−)-CBS.

60. The method of any one of embodiments 34 to 59, wherein $R^1$ and/or $R^{1A}$ is t-butyl and the first, second and/or third deprotecting agent is comprised of HCl or TFA.

61. The method of embodiment 60, wherein $R^1$ and $R^{1A}$ is t-butyl and the first, second and third deprotecting agent is TFA/$CH_2Cl_2$.

62. The method of any one of embodiments 34 to 61, wherein the first, second and third coupling agents are independently selected from the group consisting of N-(β-Dimethylaminopropyl)-N'-ethylcarbodiimide hydrochloride (EDC. HCl), 2-ethoxy-1-ethoxycarbonyl-1,2-dihydroquinoline (EEDQ), (1-Cyano-2-ethoxy-2-oxoethylidenaminooxy) dimethylamino-morpholino-carbenium hexafluorophosphate (COMU), N-(β-Dimethylaminopropyl)-N'-ethylcarbodiimide hydrochloride/N-Hydroxysuccinimide, O-(7-Azabenzotriazol-1-yl)-N,N,N',N'-tetramethyluronium hexafluorophosphate (HATU), Diphenyl phosphoryl azide (DPPA), Chloro-N,N,N',N'-bis(tetramethylene)formamidinium tetrafluoroborate, Fluoro-N,N,N',N'-bis(tetramethylene)formamidinium hexafluorophosphate, N,N'-Dicyclohexylcarbodiimide, N-(β-Dimethylaminopropyl)-N'-ethylcarbodiimide hydrochloride, 1,1'-Carbonyldiimidazole, 2-Chloro-1,3-dimethylimidazolidinium tetrafluoroborate, (Benzotriazol-1-yloxy)tripyrrolidinophosphonium hexafluorophosphate, O-(7-Azabenzotriazol-1-yl)-N,N,N',N'-tetramethyluronium hexafluorophosphate, 2-Chloro-1-methylpyridinium iodide, and Propylphosphonic anhydride.

63. The method of any one of embodiments 34 to 61, wherein the first, second and third coupling agents are independently selected from the group consisting of HATU and COMU.

64. A composition comprising or consisting essentially of tubuvaline compounds having the structures of:

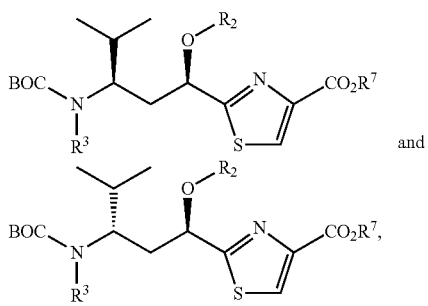

and each optionally in salt form, and tubuvaline impurities having the structures of:

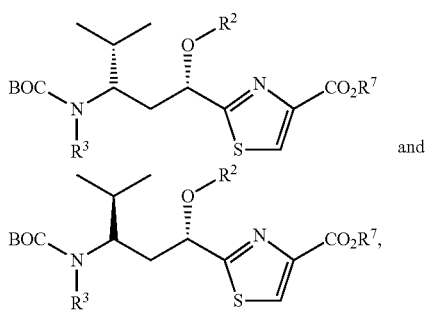

each optionally in salt form and having identical variable groups wherein $R^2$ is selected from the group consisting of —H optionally substituted saturated $C_1$-$C_4$ alkyl and $R^{2A}$, wherein $R^{2A}$ is —C(=O)$R^{2B}$, wherein $R^{2B}$ is optionally substituted saturated $C_1$-$C_4$ alkyl, in particular $R^2$ is —H or —C(=O)CH$_3$; $R^3$ in is selected from the group consisting of —CH$_3$, —CH$_2$CH$_3$ and —CH$_2$CH$_2$CH$_3$, in particular —CH$_3$; $R^7$ is $C_1$-$C_4$ saturated alkyl, in particular —CH$_2$CH$_3$; and wherein the composition has no more than an combined amount of about 5% w/w to about 10% w/w of the tubuvaline impurities relative to the combined amount of the tubuvaline compounds.

65. The composition of embodiment 64, wherein the composition has no more than an amount of about 1 w/w % to about 3% w/w, in particular no more than about 1.5% of the tubuvaline impurities relative to the combined amount of the tubuvaline compounds.

66. A composition comprising or consisting essentially of a tubuvaline compound having the structures of:

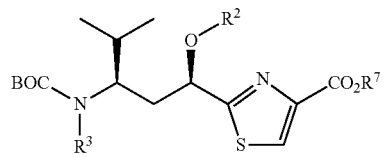

optionally in salt form, and
a tubuvaline impurity having the structures of:

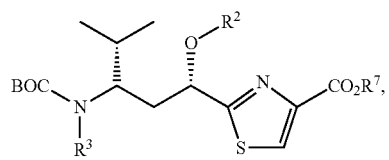

optionally in salt form, wherein $R^2$ in the tubuvaline compound and tubuvaline impurity is —H or —C(=O)$R^{2B}$, wherein $R^{2B}$ is optionally substituted saturated $C_1$-$C_4$ alkyl, in particular $R^2$ is —H or —C(=O)CH$_3$; $R^3$ in each of the tubuvaline compounds and tubulysin impurities is-CH$_3$, —CH$_2$CH$_3$ or —CH$_2$CH$_2$CH$_3$, in particular —CH$_3$; $R^7$ is $C_1$-$C_4$ saturated alkyl, in particular —CH$_2$CH$_3$; and wherein the composition has no more than amount of about 3% w/w to about 5% w/w of the tubuvaline impurity relative to the amount of the tubuvaline compound.

67. The composition of embodiment 66, wherein the composition has no more than an amount of about 1 w/w % to about 3% w/w, in particular nor more than about 1.5% of the tubuvaline impurity relative to the tubuvaline compound.

68. The composition of embodiment 66 or 67, wherein the composition has 0.5% w/w or less or is essentially free of other tubuvaline impurities having the structures of:

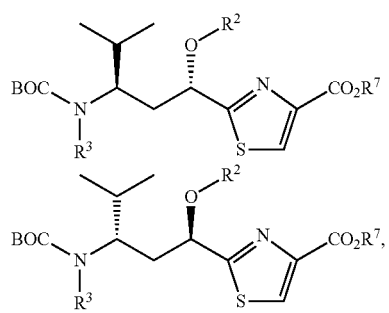

and optionally in salt forms, wherein $R^2$, $R^3$ and $R^7$ are identical to the tubulysin impurities of embodiment 68.

69. The composition of any one of embodiment 64 to 68, wherein $R^2$ is —H; $R^3$ is —CH$_3$; and $R^7$ is —CH$_2$CH$_3$.

70. A Drug Linker composition comprised or consisting essentially of a Drug Linker compound in suitable salt form and having a quaternized tubulysin Drug Unit (D$^+$) prepared from quaternization of a tubuvaline composition of any one of embodiments 64 to 69.

71. The Drug Linker composition of embodiment 70 wherein the composition is comprised or consists essentially of a Drug Linker compound having the structure of:

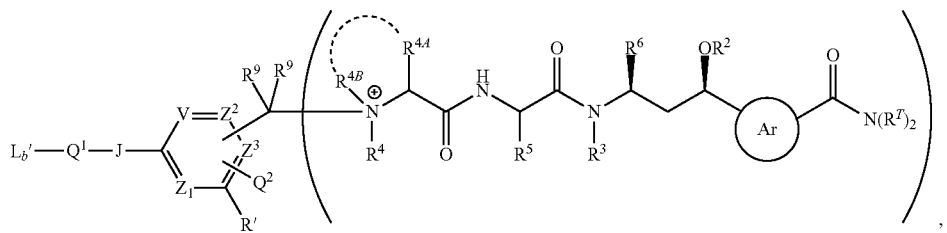

in suitable salt form, and a Drug Linker impurity having the structure of:

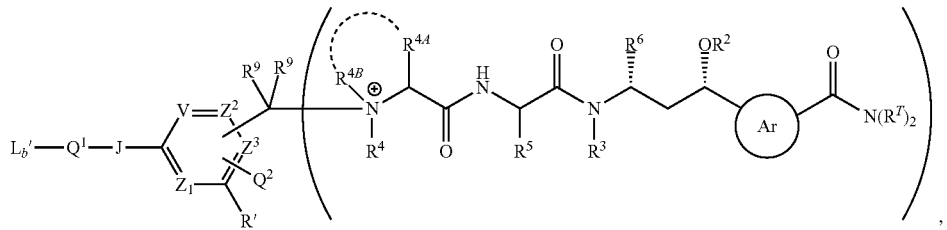

also in salt form, wherein the Drug Linker impurity is no more than 10% w/w of the composition relative to the Drug Linker compound and whose variable group identities are the same as the Drug Linker compound, and the quaternized moiety in parenthesis is $D^+$, wherein the circled Ar is a 5-membered nitrogen-containing 1,3-heteroarylene, optionally substituted at the remaining positions, the curved dashed line indicates optional cyclization; $R^2$ is —H or optionally substituted saturated $C_1$-$C_8$ alkyl, or $R^2$ is $R^{2A}$, wherein $R^{2A}$ is —$CH_2R^{2C}$, wherein $R^{2C}$ is optionally substituted $C_1$-$C_8$ ether, optionally substituted $C_2$-$C_8$ alkenyl, or optionally substituted $C_2$-$C_8$ alkynyl, or $R^{2A}$ is —C(=O)$R^{2B}$, wherein $R^{2B}$ is optionally substituted saturated $C_1$-$C_8$ alkyl, optionally substituted unsaturated $C_3$-$C_8$ alkyl, optionally substituted $C_2$-$C_8$ alkenyl, or optionally substituted $C_2$-$C_8$ alkynyl;

$R^3$ is optionally substituted saturated $C_1$-$C_8$ alkyl, optionally substituted unsaturated $C_3$-$C_8$ alkyl, or optionally substituted $C_3$-$C_8$ heteroalkyl; $R^4$ is $C_1$-$C_4$ alkyl; $R^{4A}$ is hydrogen or optionally substituted $C_1$-$C_8$ alkyl; and $R^{4B}$ is optionally substituted $C_1$-$C_8$ alkyl, in absence of cyclization, or $R^{4A}$ and $R^{4B}$ together with the nitrogen atom to which both are attached, when cyclization is present, define a optionally substituted 5-, 6-, 7-, or 8-membered nitrogen-containing heterocyclyl; and $R^5$ and $R^6$ are independently optionally substituted $C_1$-$C_8$ alkyl; one $R^T$ is hydrogen, optionally substituted saturated $C_1$-$C_8$ alkyl or optionally substituted unsaturated $C_3$-$C_8$ alkyl, and the other $R^T$ is optionally substituted $C_1$-$C_8$ alkyl, optionally substituted saturated $C_1$-$C_8$ alkyl, optionally substituted unsaturated $C_3$-$C_8$ alkyl, or optionally substituted $C_3$-$C_8$ heteroalkyl;

$L_b'$ is a ligand covalent binding precursor; $Q^1$ is $A_a$-$W_w$, wherein A is an optional Stretcher Unit so that subscript a is 0 when A is absent or 1 when A is present and is a single unit or has two, three or four subunits; $Q^2$ is $W'_{w'}$-$E'$-, wherein $Q^2$, when present, is bonded to V, $Z^1$, $Z^2$ or $Z^3$; subscript w is 0 or 1 so that W is absent or present, respectively, and subscript w' is 0 or 1 so that W'-E' is absent or present, respectively, and wherein w+w' is 1 so that one and only one of W, W' is present, wherein:

when subscript w is 1 so that W is present, then W is a Peptide Cleavable Unit that is capable of selective cleavage by an intracellular or regulatory protease in comparison to serum proteases, or W is a non-enzymatically cleavable moiety that is more susceptible to cleavage by glutathione through disulfide exchange under hypoxic conditions, or is more reactive to hydrolysis under lower pH conditions present in lysosomes in comparison to physiological pH of serum; and when subscript w' is 1 so that W' is present, then J replaces J' and W' comprises a Glucuronide Cleavable Unit having the formula of:

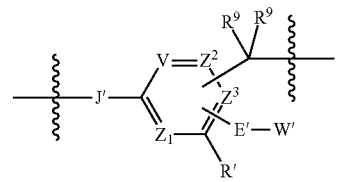

wherein W'-E' provides a glycosidic bond cleavable by a glycosidase located intracellularly, wherein W' is a carbohydrate moiety; J or E' and J' independently are —O—, —S— or —N($R^{33}$)—, wherein $R^{33}$ is hydrogen or optionally substituted $C_1$-$C_8$ alkyl; V, $Z^1$, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, an electron donating group, -$Q^2$, or —C($R^9$)($R^9$)—$D^+$, wherein at least one of V, $Z^1$, $Z^2$ and $Z^3$ is =C($R^{24}$)— when w is 1, and at least two of V, $Z^1$, $Z^2$ and $Z^3$ are =C($R^{24}$)— when w' is 1, provided that when w is 1, $Q^2$ is absent and one and only one $R^{24}$ is —C($R^9$)($R^9$)-$D^+$ so that —C($R^9$)($R^9$)-$D^+$ is bonded to one of V, $Z^1$, $Z^2$, $Z^3$ when that variable group is =C($R^{24}$)— and the $Q^1$-J- and —C($R^8$)($R^9$)-$D^+$ substituents are ortho or para to each other, and provided that when w' is 1, one any only one $R^{24}$ is —C($R^8$)($R^9$)-$D^+$ so that —C($R^8$)($R^9$)-$D^+$ is bonded to one of V, $Z^1$, $Z^2$, $Z^3$ when that variable group is =C(R$^{24}$)— and one and only one other R$^{24}$ is Q$^2$ so that Q$^2$ is bonded to another one of V, Z$^1$, Z$^2$, Z$^3$ when that variable group is =C(R$^{24}$)—, and the Q$^2$ and —C(R$^8$)(R$^9$)-D$^+$ substituents are ortho or para to each other; each R$^9$ is independently hydrogen, C$_1$-C$_8$ alkyl, C$_2$-C$_8$ alkenyl, C$_2$-C$_8$ alkynyl, C$_6$-C$_{24}$ aryl or C$_5$-C$_{24}$ heteroaryl, optionally substituted, or both R$^9$ together with the carbon atom to which both are attached define an optionally substituted C$_3$-C$_8$ carbocyclo or an optionally substituted, saturated or partially unsaturated C$_5$-C$_8$ heterocyclo; R' is hydrogen or is halogen, —NO$_2$, —CN or other electron withdrawing group when subscript w' is 1, or is hydrogen or an electron donating group, when subscript w is 1; and wherein said protease cleavage, disulfide exchange, acid hydrolysis or glycosidase cleavage results in release of D$^+$ as a tubulysin compound from the Drug Linker compound.

72. The Drug Linker composition of embodiment 71, wherein the Drug Linker compound has the structure of:

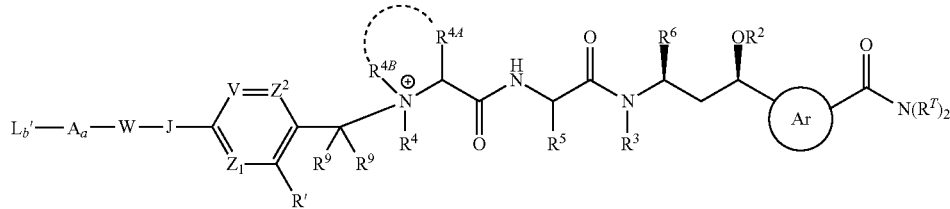

in suitable salt form, and the Drug Linker impurity has the structure of:

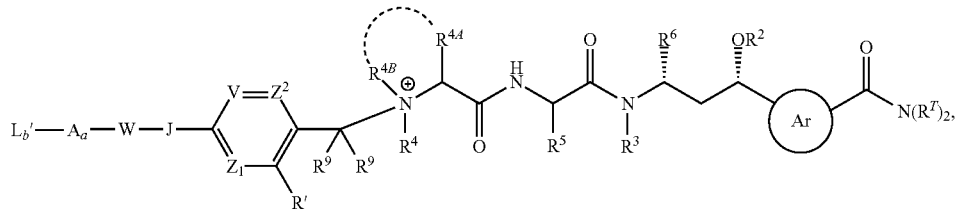

also in salt form, wherein subscript a is 0 or 1, indicating the absence or presence of A, respectively.

73. The Drug Linker composition of embodiment 71, wherein the Drug Linker compound has the structure of:

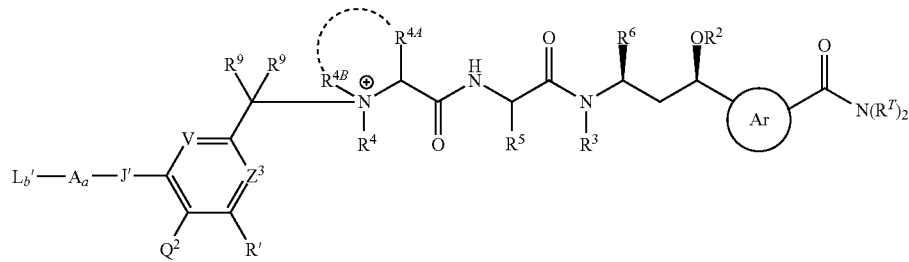

in suitable salt form, and the Drug Linker impurity has the structure of:

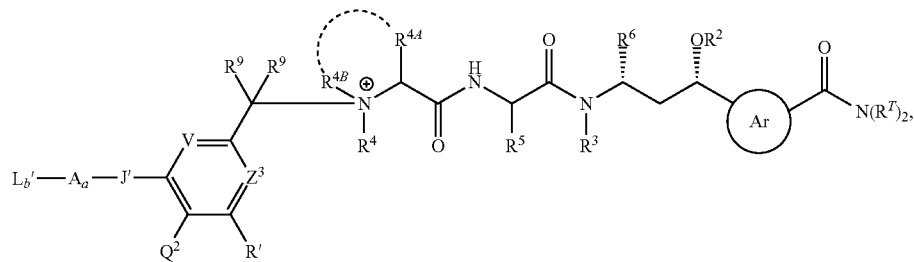

also in salt form, wherein subscript a is 0 or 1, indicating the absence or presence of A, respectively; and $Q^2$ is $W'_{w'}$-E'-, wherein subscript w' is 1.

74. The Drug Linker composition of embodiment 71, wherein the Drug Linker compound has the structure of:

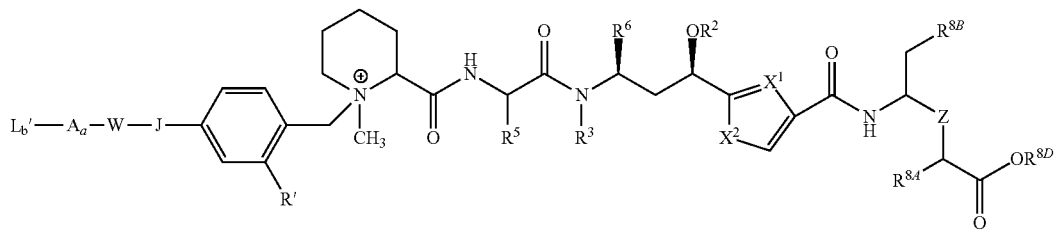

in suitable salt form, and the Drug linker impurity has the structure of:

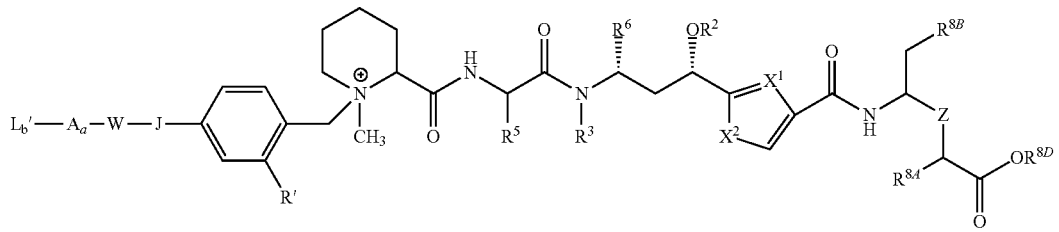

also in salt form, wherein R' is an electron donating group; J is —NH—; W is comprised of a dipeptide residue, whose C-terminus is attached to J as an amide bond, wherein the amide bond is capable of cleavage by a regulatory protease to initiate release of $D^+$ as a tubulysin compound; $X^1$ is =N—; and $X^2$ is S, O, or $N(R^{X2})$—, or $X^1$ is =C($R^{X1}$)—; and $X^2$ is $NR^{X2}$, wherein $R^{X1}$ and $R^{X2}$ are independently selected from the group consisting of —H, —$CH_3$ and —$CH_2CH_3$; and Z is optionally substituted $C_1$-$C_4$ alkylene or optionally substituted $C_2$-$C_6$ alkenylene; $R^{8A}$ is optionally substituted $C_1$-$C_4$ alkyl; $R^{8B}$ is optionally substituted phenyl, or optionally substituted 5- or 6-membered heteroaryl; and $R^{8D}$ is —H or provides for a suitable ester functional group, in particular, $R^{8D}$ is —H, —$CH_3$, —$CH_2CH_3$ or —$CH_2$—CH=$CH_2$.

75. The Drug Linker composition of embodiment 71, wherein the Drug Linker compound has the structure of:

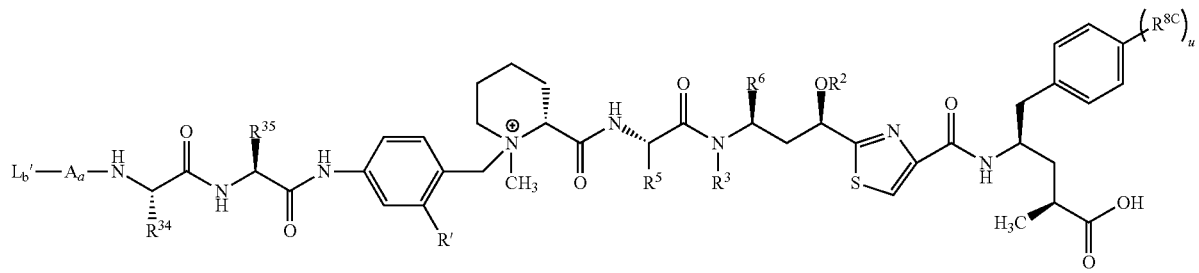

in suitable salt form, and the Drug linker impurity has the structure of:

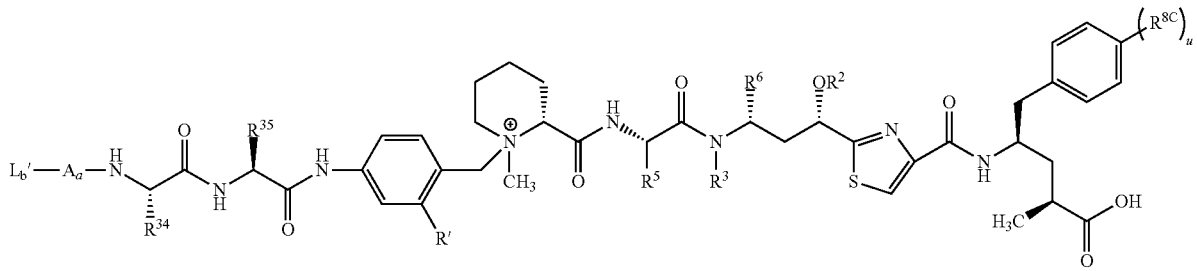

also in salt form, wherein: R' is —H or an electron donating group; $R^{34}$ is isopropyl; $R^{35}$ is —CH$_3$, isopropyl, —CH$_2$CH$_2$CH$_2$NH(C=O)NH$_2$ or —CH$_2$CH$_2$CO$_2$H; $R^{8C}$ is —OH or is absent; $R^2$ is saturated C$_1$-C$_6$ alkyl, unsaturated C$_3$-C$_6$ alkyl, or $R^2$ is $R^{2A}$, wherein $R^{2A}$ is —OCH$_2$R$^{2C}$, wherein $R^{2C}$ is saturated C$_1$-C$_6$ ether or unsaturated C$_2$-C$_6$ alkyl, or $R^{2A}$ is —C(=O)R$^{2B}$, wherein $R^{2B}$ is saturated C$_1$-C$_6$ alkyl, unsaturated C$_3$-C$_6$ alkyl or optionally substituted C$_2$-C$_6$ alkenyl; and subscript u is 0 or 1.

76. The Drug Linker composition of embodiment 75, wherein the Drug Linker compound has the structure of:

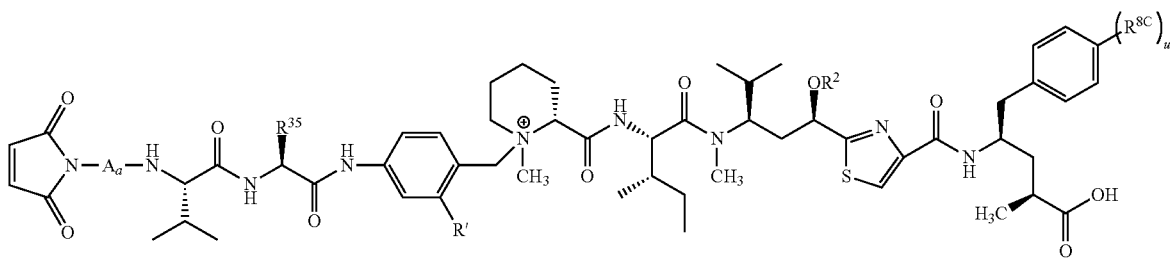

in suitable salt form, and the Drug linker impurity has the structure of:

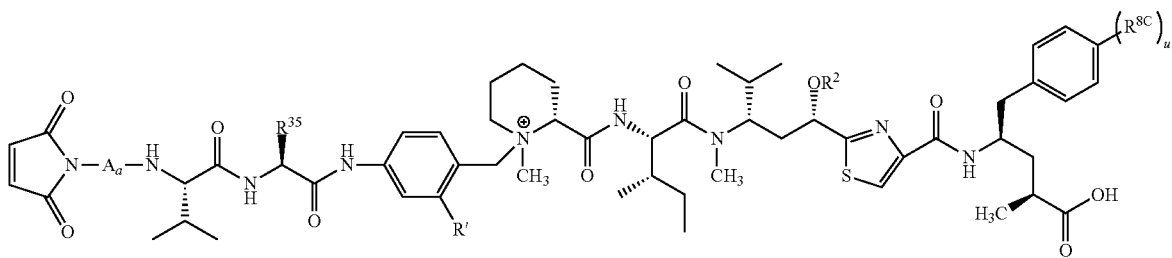

also in salt form, wherein: R' is —H or an electron donating group; $R^{35}$ is —CH$_3$, isopropyl, —CH$_2$CH$_2$CH$_2$NH(C=O)NH$_2$ or —CH$_2$CH$_2$CO$_2$H; $R^{8C}$ is —OH or is absent; $R^2$ is saturated C$_1$-C$_6$ alkyl or unsaturated C$_3$-C$_6$ alkyl, or $R^2$ is $R^2$, wherein $R^2$ is —CH$_2$R$^{2C}$, wherein $R^{2C}$ is saturated C$_3$-C$_6$ ether, or $R^{2A}$ is —C(=O)R$^{2B}$, wherein $R^{2B}$ is saturated C$_3$-C$_6$ alkyl or unsaturated C$_3$-C$_6$ alkyl; and subscript u is 0 or 1.

77. The Drug Linker composition of embodiment 76, wherein the Drug Linker compound has the structure of:

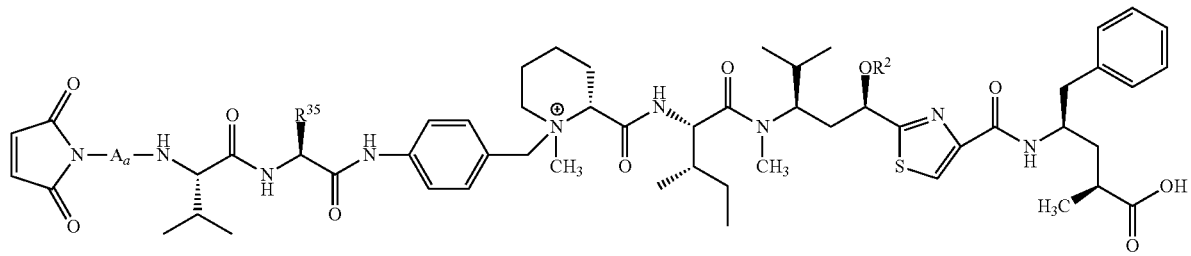

in suitable salt form, and the Drug linker impurity has the structure of:

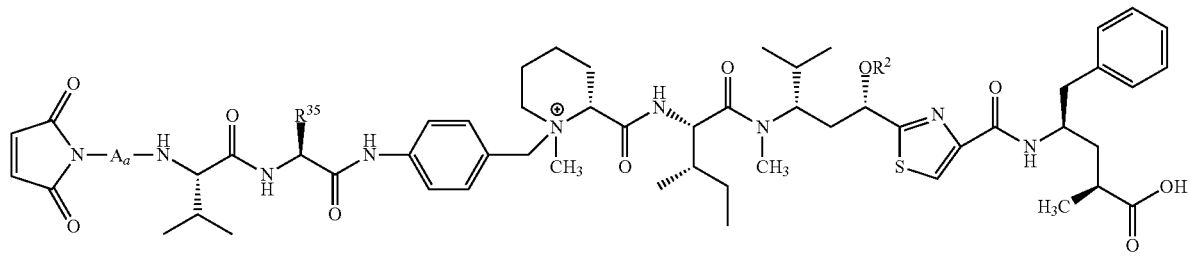

also in salt form, wherein: $R^{35}$ is —CH$_3$, isopropyl, —CH$_2$CH$_2$CH$_2$—NH(C=O)NH$_2$ or —CH$_2$CH$_2$CO$_2$H; and $R^2$ is saturated C$_1$-C$_6$ alkyl or unsaturated C$_3$-C$_6$ alkyl, or $R^2$ is $R^{2A}$ wherein $R^2$ is —C(=O)R$^{2B}$, wherein R$^{2B}$ is saturated C$_1$-C$_6$ alkyl or unsaturated C$_3$-C$_6$ alkyl, in particular, $R^2$ is —CH$_3$ or CH$_2$CH$_3$ or —C(=O)CH$_3$.

78. The Drug Linker composition of embodiment 77, wherein the Drug Linker compound has the structure of:

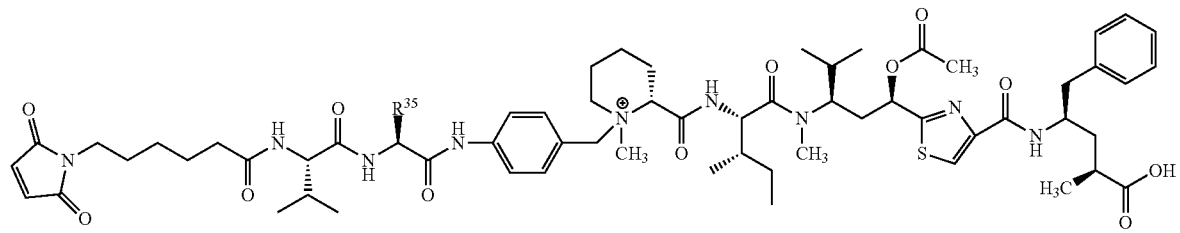

in suitable salt form, and the Drug linker impurity has the structure of:

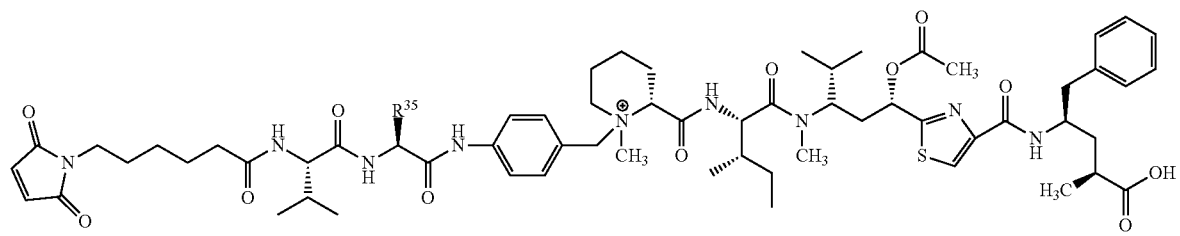

also in salt form, wherein $R^{35}$ is —CH$_3$ or —CH$_2$CH$_2$CH$_2$NH(C=O)NH.

79. The Drug Linker composition of embodiment 71, wherein the Drug Linker compound has the structure of:

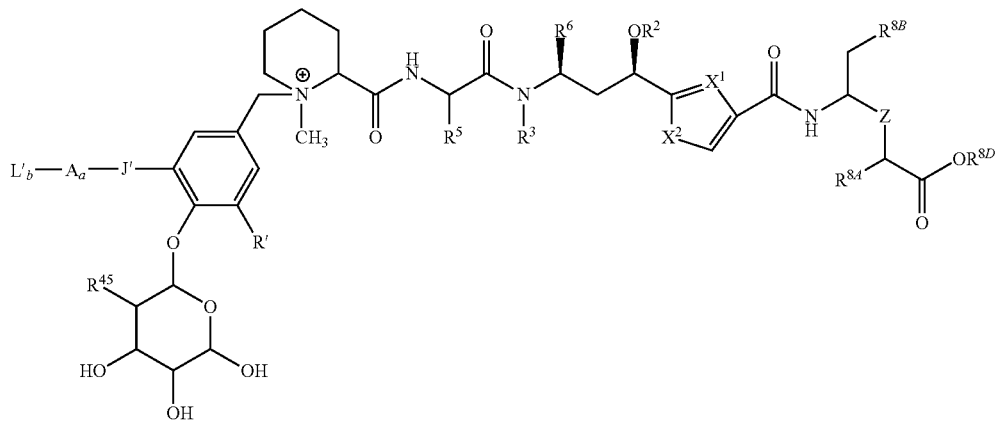

in suitable salt form, and the Drug linker impurity has the structure of:

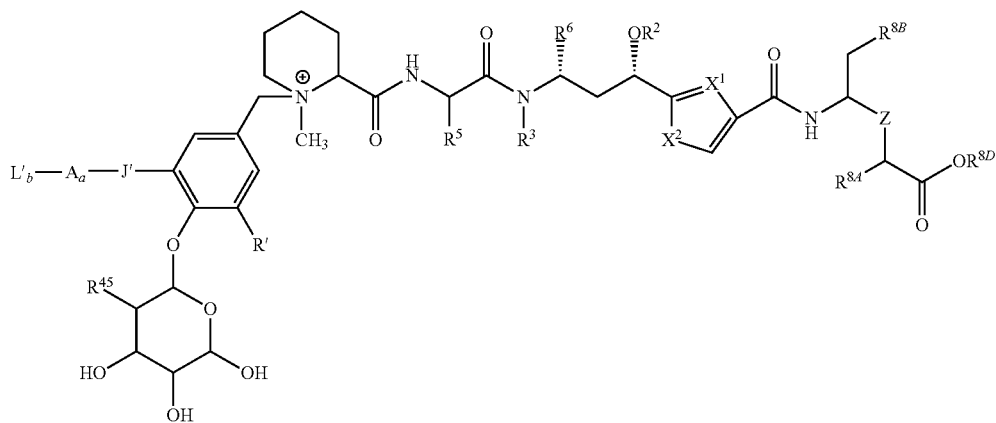

also in salt form, wherein R' is an electron withdrawing group; J is —NH—; $X^1$ is =N—; and $X^2$ is S, O, or $N(R^{X2})$—, or $X^1$ is =C($R^{X1}$)—; and $X^2$ is $NR^{X2}$, wherein $R^{X1}$ and $R^{X2}$ are independently selected from the group consisting of —H, —CH$_3$ and —CH$_2$CH$_3$; and Z is optionally substituted $C_1$-$C_4$ alkylene or optionally substituted $C_2$-$C_6$ alkenylene; $R^{8A}$ is optionally substituted $C_1$-$C_4$ alkyl; $R^{8B}$ is optionally substituted phenyl, or optionally substituted 5- or 6-membered heteroaryl; $R^{8D}$ is —H or provides for a suitable ester functional group, in particular, $R^{8D}$ is —H, —CH$_3$, —CH$_2$CH$_3$ or —CH$_2$—CH=CH$_2$; and $R^{45}$ is —OH or —C(=O)O$R^{45A}$, wherein $R^{45A}$ provides for a suitable ester functional group, in particular, $R^{45A}$ is —CH$_3$, —CH$_2$CH$_3$ or —CH$_2$—CH=CH$_2$.

80. The Drug Linker composition of embodiment 79, wherein the Drug Linker compound has the structure of:

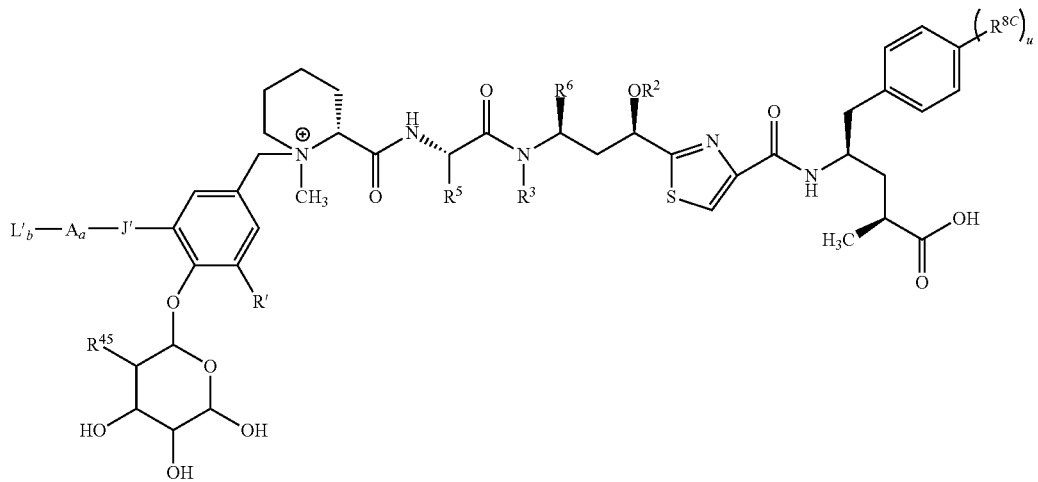

in suitable salt form, and the Drug linker impurity has the structure of:

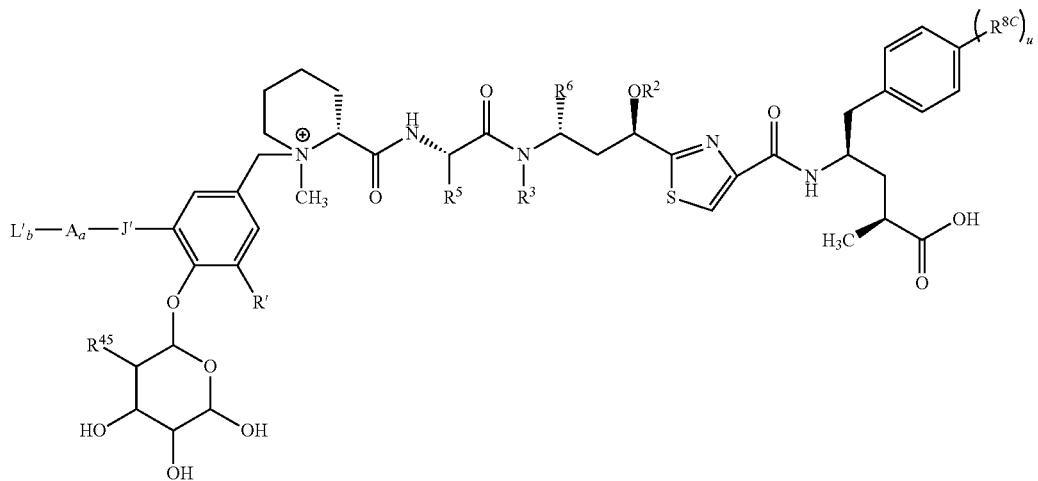

also in salt form, wherein R' is —H, halogen, —CN or —NO₂; $R^{8C}$ is —OH or is absent; $R^2$ is saturated $C_1$-$C_6$ alkyl, unsaturated $C_3$-$C_6$ alkyl, or R2 is R2A, wherein $R^{2A}$ is —OCH₂$R^{2C}$, wherein $R^{2C}$ is $C_1$-$C_6$ ether or substituted $C_2$-$C_6$ alkenyl, or $R^{2A}$ is —C(=O)$R^{2B}$, wherein $R^{2B}$ is saturated $C_1$-$C_6$ alkyl, unsaturated $C_3$-$C_6$ alkyl or optionally substituted $C_2$-$C_6$ alkenyl; and subscript u is 0 or 1; and A is a natural or unnatural amino acid residue or other amine-containing acid so that the A-J bond is stable under physiological conditions or is resistant to protease cleavage; and $L_b'$ is comprised of a maleimide ($M^1$) moeity.

81. The Drug Linker composition of embodiment 80, wherein the Drug Linker compound has the structure of:
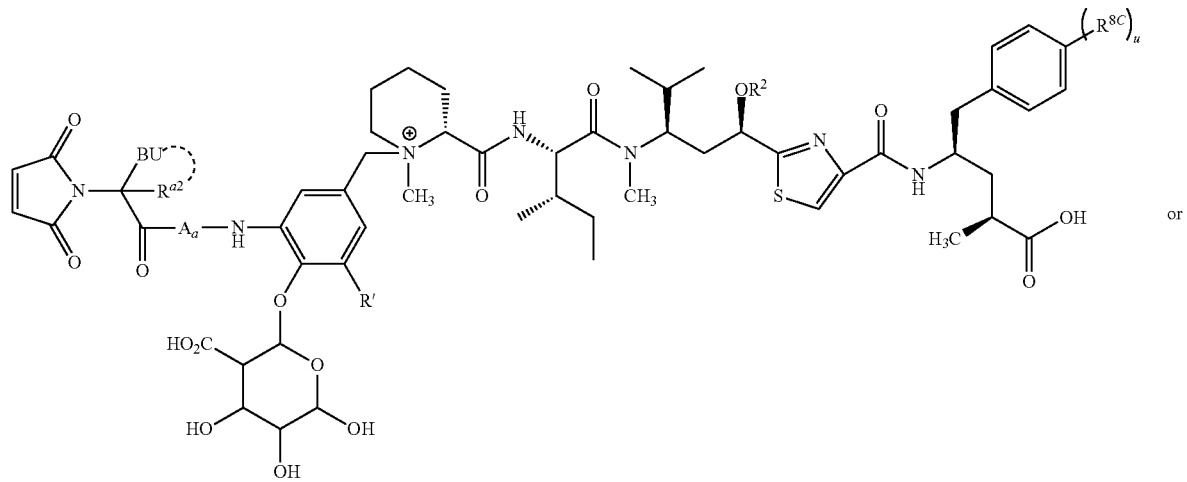
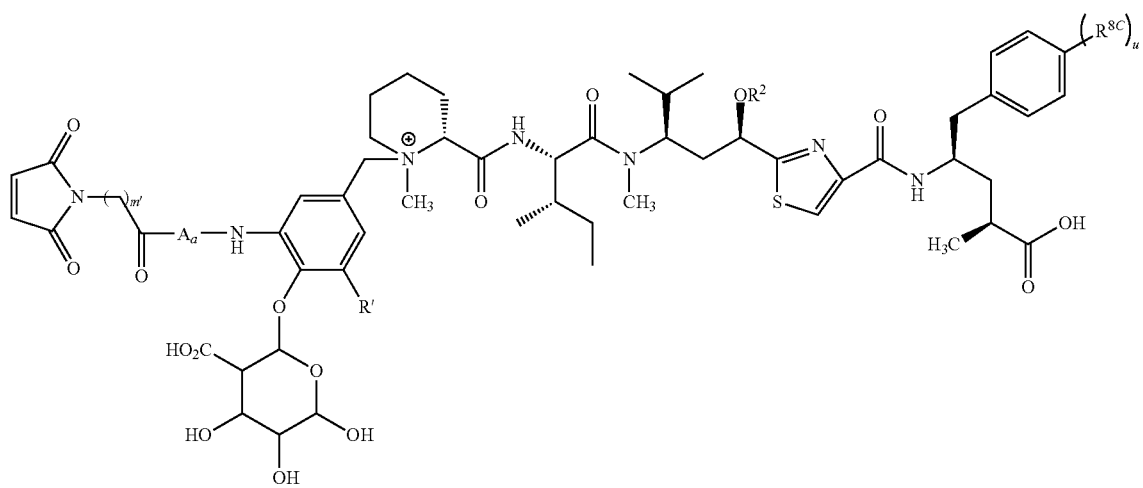
in suitable salt form, and the Drug linker impurity has the structure of:
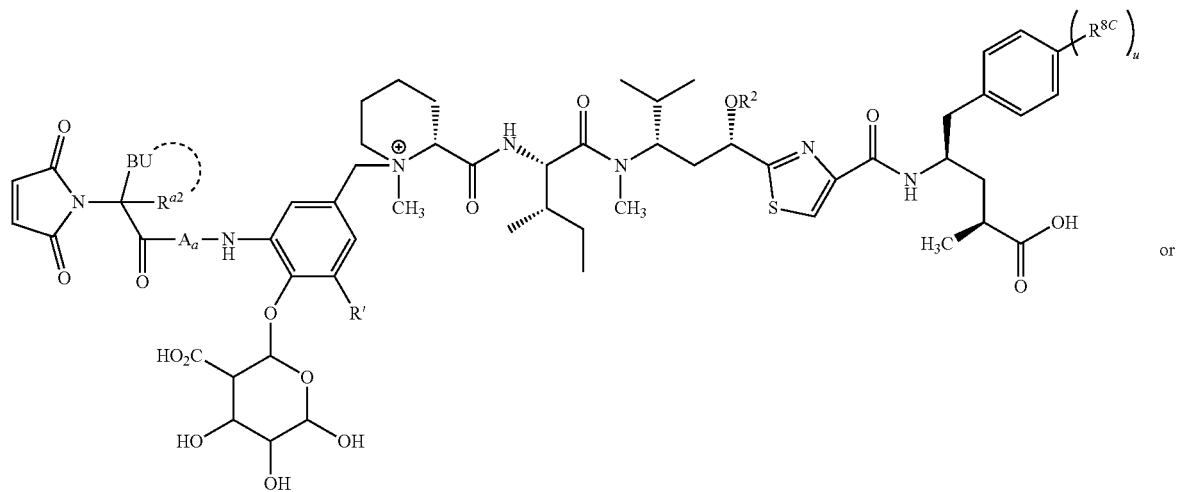 or -continued

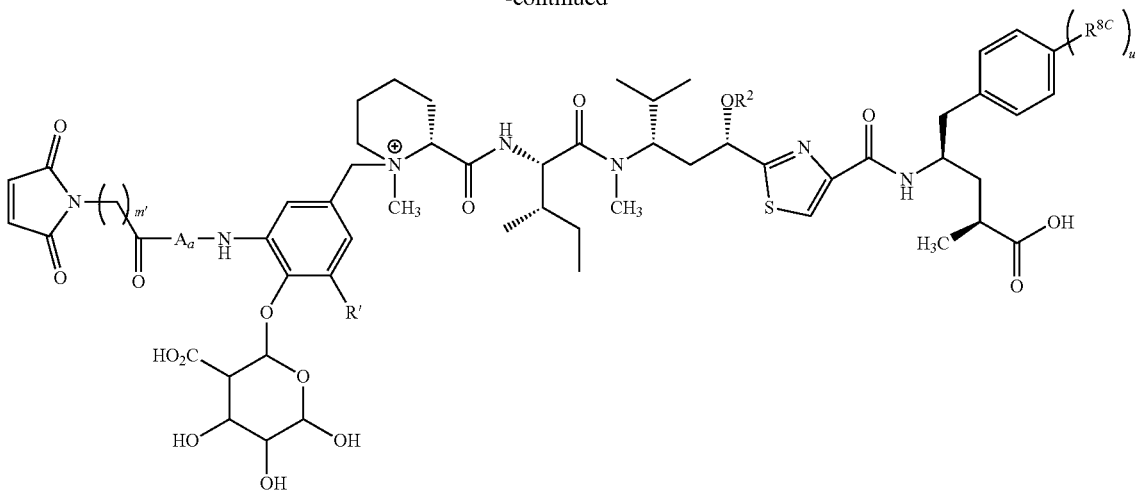

also in salt form, wherein subscript a is 1; subscript m' ranges from 1 to 5; and BU is a Basic Unit, the basic nitrogen atom of which is optionally protonated or protected with a suitable nitrogen protecting group; $R^2$—H or $C_1$-$C_6$ alkyl; and the curved dashed line indicates optional cyclization between BU and $R^{a2}$, provided cyclization is absent when BU is an acyclic Basic Unit, wherein the acyclic Basic Unit has the formula of —$[C(R^{a1})(R^{a1})]$—$[C(R^{a1})(R^{a1})]_{0-3}$—$N(R^{a3})(R^{a3})$, wherein each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or $R^{a3}$ together with the nitrogen atom to which both are attached define an optionally substituted $C_3$-$C_6$ heterocyclyl in which the basic nitrogen is a skeletal atom; and provided cyclization is present when BU is a cyclic basic Unit for which $R^{a2}$ is $C_1$-$C_6$ alkyl cyclized to BU so that BU and $R^2$ together with the carbon atom to which both are attached define an optionally substituted 4-, 5- or 6-membered ring system.

82. The Drug Linker composition of embodiment 81, wherein the Drug Linker compound has the structure of:

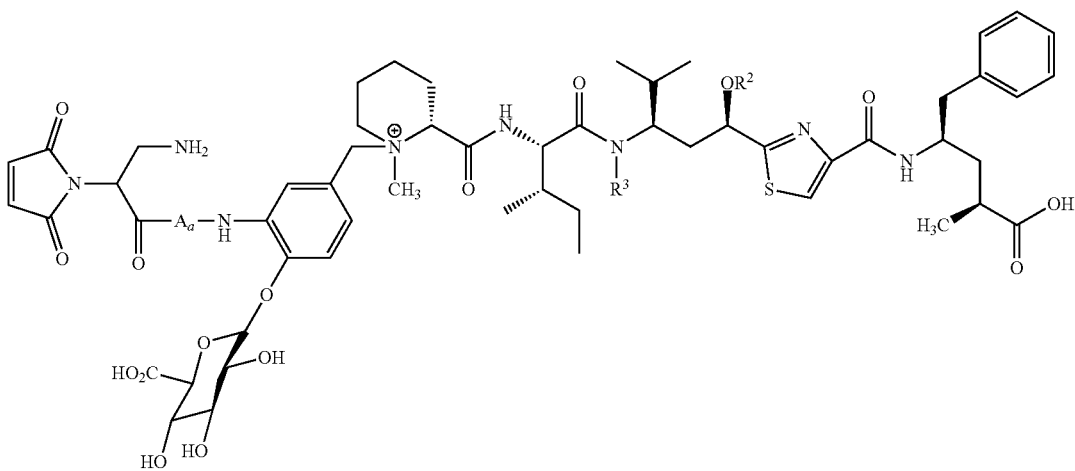

in suitable salt form, and the Drug linker impurity has the structure of:
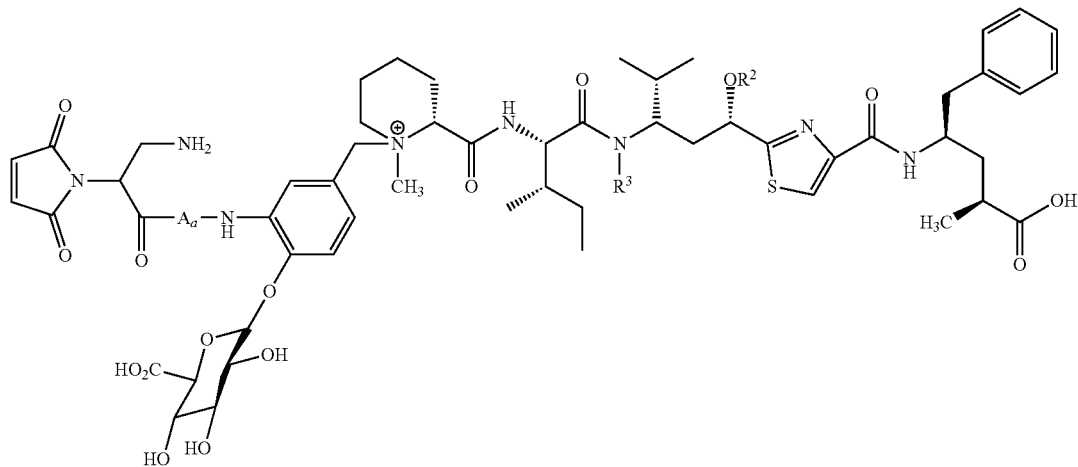
also in salt form, or wherein the Drug Linker compound has the structure of:
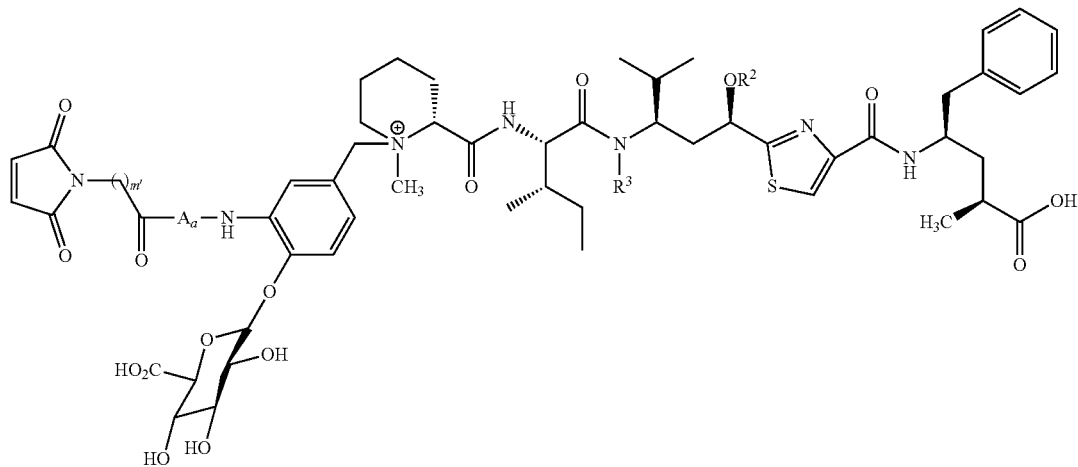
in suitable salt form, and the Drug linker impurity has the structure of:
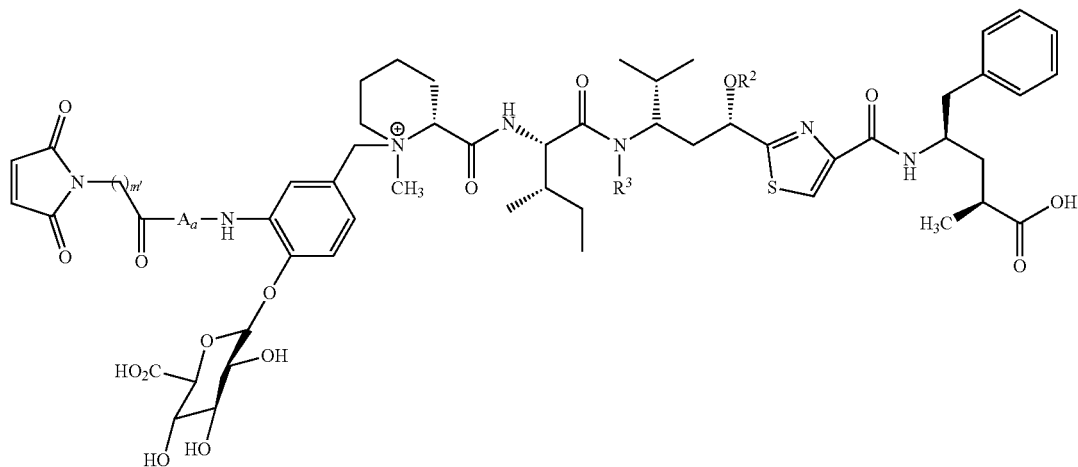

also in salt form, wherein subscript a is 1 so that A is present, preferably as an α-amino acid or β-amino acid residue; subscript m' ranges from 1 to 5; $R^2$ is saturated $C_1$-$C_6$ alkyl, or $R^2$ is $R^{2A}$, wherein $R^{2A}$ is —C(=O)$R^{2B}$, wherein $R^{2B}$ is saturated $C_1$-$C_6$ alkyl or unsaturated $C_3$-$C_6$ alkyl, in particular, $R^2$ is —CH$_3$, —CH$_2$CH$_3$ or —C(=O)CH$_3$; and $R^3$ is —CH$_3$ or —CH$_2$CH$_2$CH$_3$.

83. The Drug Linker composition of embodiment 82, wherein the Drug Linker compound has the structure of:

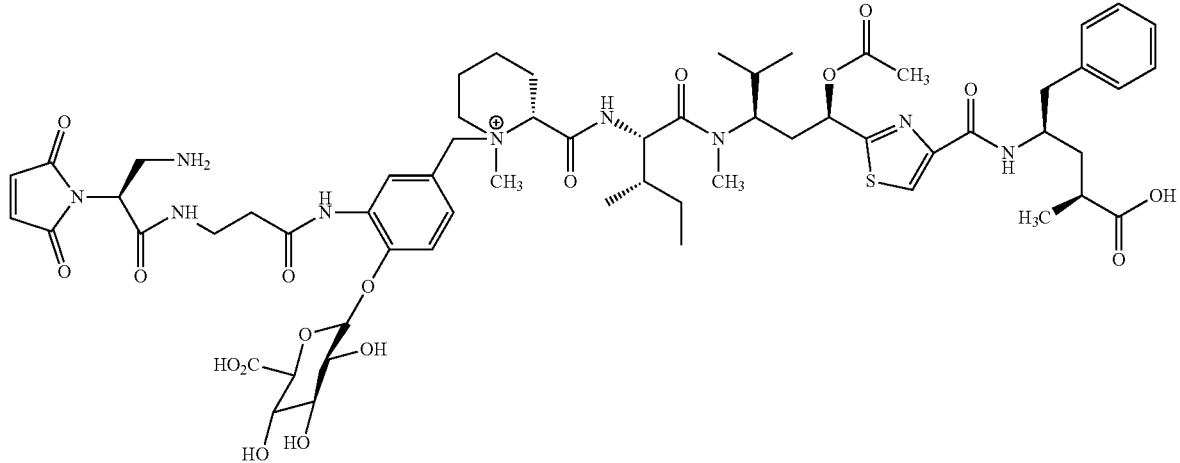

in suitable salt form, and the Drug linker impurity has the structure of:

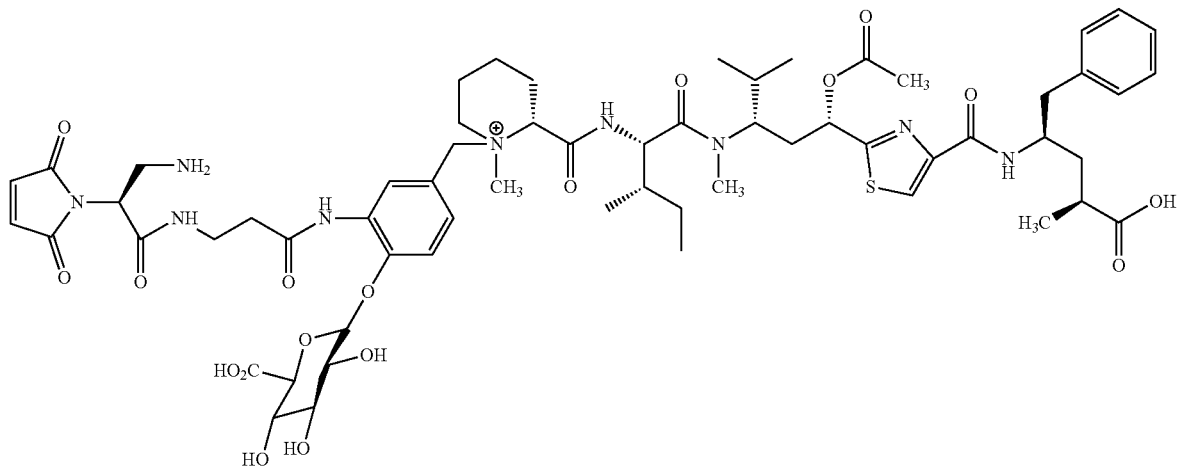

84. The Drug Linker composition of embodiment 81, wherein the Drug Linker compound has the structure of:

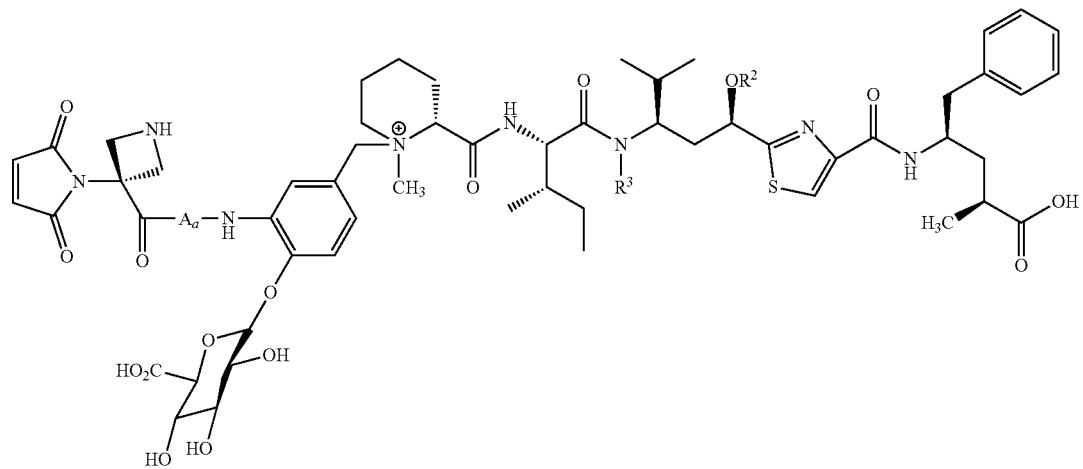

in suitable salt form, and the Drug linker impurity has the structure of:

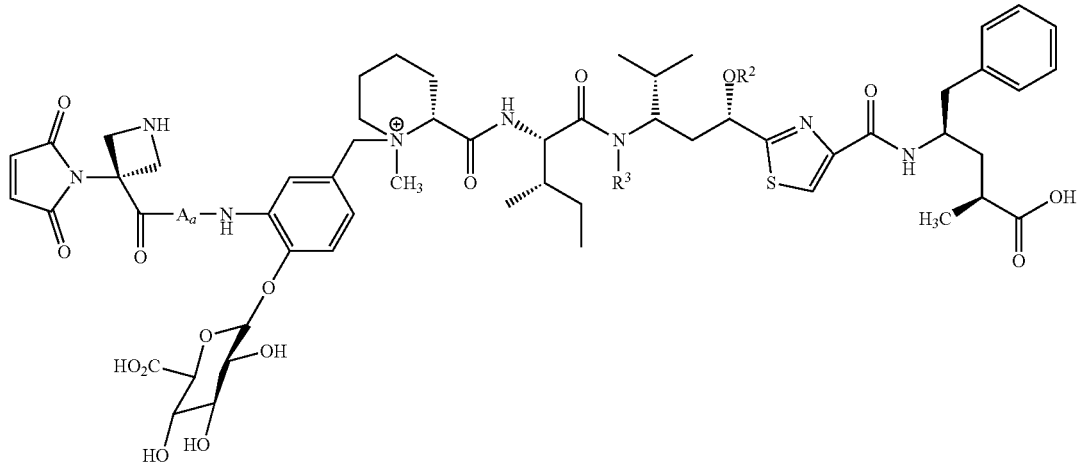

also in salt form, wherein subscript a is 1; $R^2$ is saturated $C_1$-$C_6$ alkyl, or $R^2$ is $R^{2A}$, wherein $R^{2A}$ is —C(=O)$R^{2B}$, wherein $R^{2B}$ is saturated $C_1$-$C_6$ alkyl or unsaturated $C_3$-$C_6$ alkyl, in particular, $R^2$ is —CH$_3$, CH$_2$CH$_3$ or —C(=O)CH$_3$; and $R^3$ is —CH$_3$ or —CH$_2$CH$_2$CH$_3$.

85. The Drug Linker composition of embodiment 84, wherein the Drug Linker compound has the structure of:

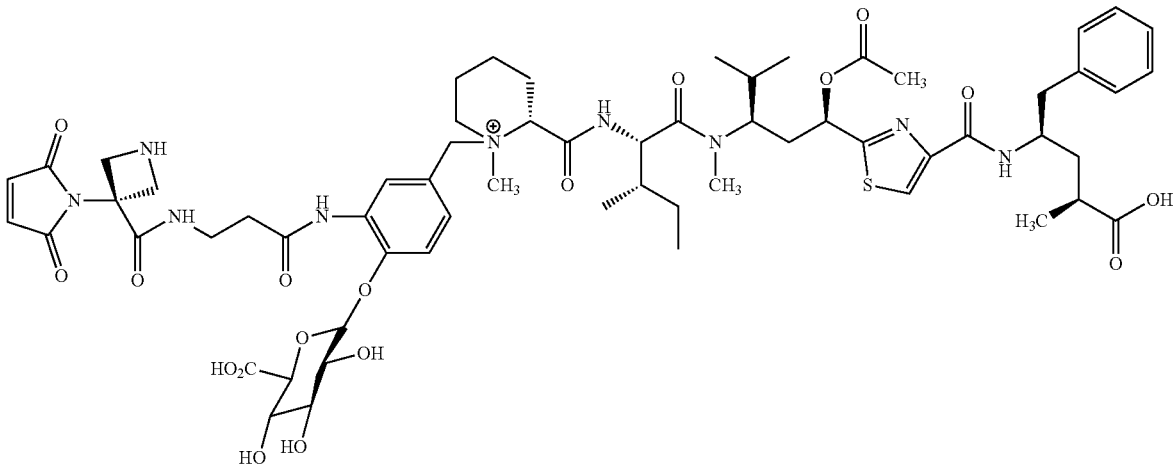

in suitable salt form, and the Drug linker impurity has the structure of:

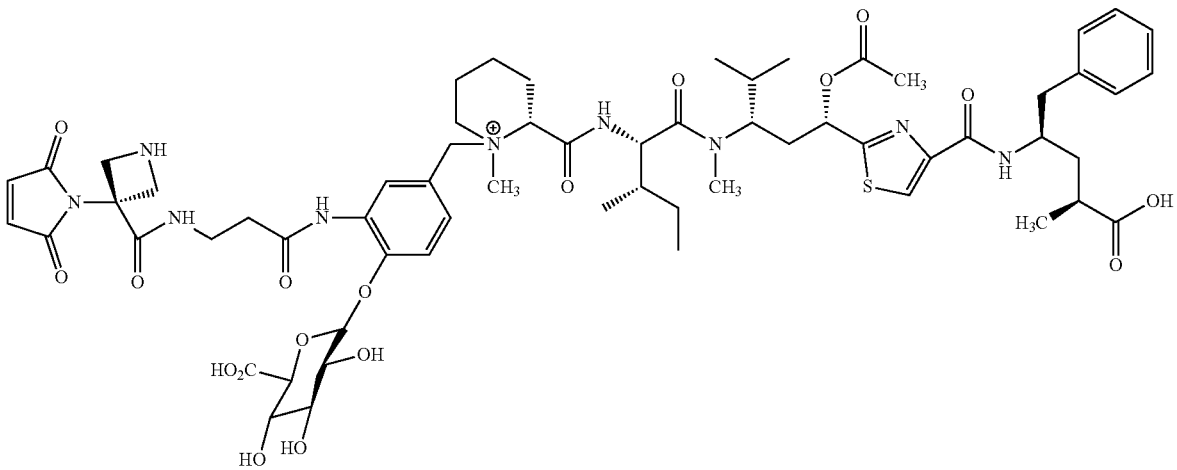

also in salt form.

86. A Ligand Drug Conjugate composition of formula: L-($L_b$-$L_O$-$D^+$)$_p$, or a salt thereof, in particular a pharmaceutically acceptable salt, wherein L is a Ligand Unit from a targeting agent, in particular an antibody Ligand Unit so as to define a Antibody Drug Conjugate; $L_b$ is a covalent bind moiety; $L_O$ is a secondary linker that is present; and subscript p is a number ranging from 1 to 20, 1 to 16 or 1 to 8, wherein the Ligand Drug Conjugate composition is prepared by contacting the targeting moiety with a Drug Linker composition of any one of embodiments 70 to 85 in a suitable aqueous-based solvent at a pH of about 7.0 to about 7.5 wherein said contacting condenses a reactive functional group of the targeting moeity and the reactive functional group of $L_b$' of the Drug Linker compound of the Drug Linker composition to form a covalent bond between L and $L_b$ by converting $L_b$' to $L_b$ and the targeting moeity to the Ligand Unit.

87. A compound having the structure of:

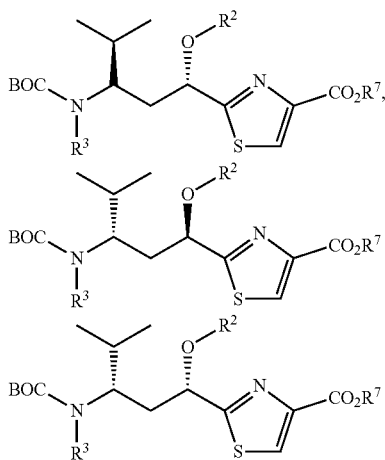

wherein $R^2$ is —H, $C_1$-$C_4$ alkyl or $R^{2A}$, wherein $R^{2A}$ is —C(=O)$R^{2B}$, wherein $R^{2B}$ is optionally substituted saturated $C_1$-$C_4$ alkyl or optionally substituted $C_3$-$C_6$ unsaturated alkyl, in particular $R^2$ is —H, —C(=O)$CH_3$, —$OCH_3$ or —$OCH_2CH_3$; $R^3$ is-$CH_3$, —$CH_2CH_3$ or —$CH_2CH_2CH_3$, in particular —$CH_3$; and $R^7$ is —H or $C_1$-$C_4$ saturated alkyl, in particular —H or —$CH_2CH_3$.

88. The compound of embodiment 87 wherein $R^2$ is —H or —$CH_2CH_3$; $R_3$ is —$CH_3$, —$CH_2CH_3$ or —$CH_2CH_2CH_3$; and $R^7$ is —H, —$CH_3$ or —$CH_2CH_3$.

89. The compound of embodiment 87, wherein $R^2$ is —H or —C(=O)$R^{2B}$, $R^3$ is —$CH_3$, —$CH_2CH_3$ or —$CH_2CH_2CH_3$ and $R^7$ is —H.

90. The compound of embodiment 88, wherein $R^2$ is —$CH_2CH_3$, $R^3$ is —$CH_3$, or —$CH_2CH_2CH_3$ and $R^7$ is —H or —$CH_2CH_3$.

91. The compound of embodiment 89, wherein $R^2$ is —H, $R^3$ is —$CH_3$, or —$CH_2CH_2CH_3$ and $R^7$ is —H.

92. The compound of embodiment 87, wherein the compound has the structure of:

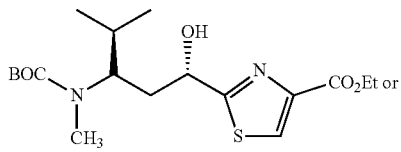

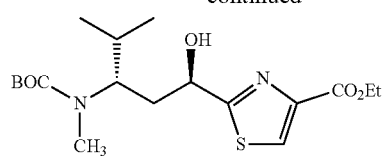

93. The compound of embodiment 87, optionally in salt form, wherein the compound has the structure of:

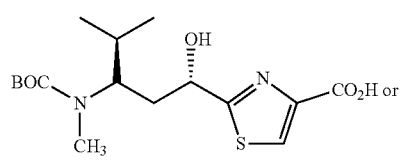

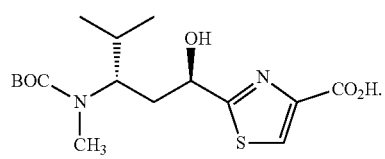

94. The compound of embodiment 87, optionally in salt form, wherein the compound has the structure of:

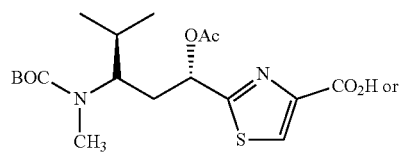

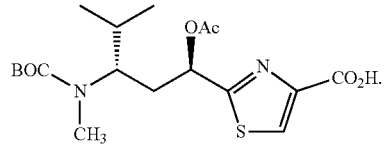

95. The compound of embodiment 87, wherein the compound has the structure of:

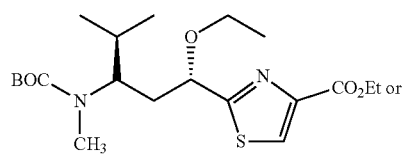

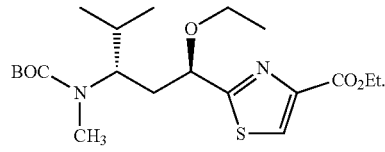

96. The compound of embodiment 87, wherein the compound has the structure of:

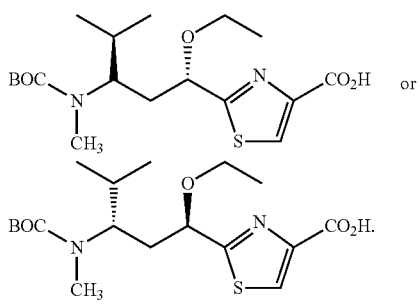

or

1A. A compound having the structure of:

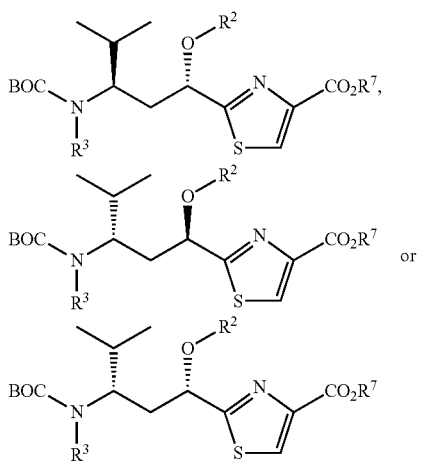

or optionally in salt form, wherein R² is selected from the group consisting of —H, C₁-C₄ alkyl and R²ᴬ, wherein R²ᴬ is —C(=O)R²ᴮ, wherein R²ᴮ is optionally substituted saturated C₁-C₄ alkyl or optionally substituted C₃-C₆ unsaturated alkyl; R³ is-CH₃, —CH₂CH₃ or —CH₂CH₂CH₃; and R⁷ is —H or C₁-C₄ saturated alkyl.

2A. The compound of embodiment 1A, wherein R² is —H, —CH₂CH₃ or —C(=O)R²ᴮ; R₃ is —CH₃—CH₂CH₃ or —CH₂CH₂CH₃; and R⁷ is —H, —CH₃ or —CH₂CH₃.

3A. The compound of embodiment 1A, wherein R² is —C(=O)R²ᴮ, R³ is —CH₃, or —CH₂CH₂CH₃ and R⁷ is —H or —CH₂CH₃.

4A. The compound of embodiment 1A, wherein R² is —CH₂CH₃, R³ is —CH₃, or —CH₂CH₂CH₃ and R⁷ is H or —CH₂CH₃.

5A. The compound of embodiment 1A, wherein R² is —H, R³ is —CH₃, or —CH₂CH₂CH₃ and R⁷ is —H.

6A. The compound of embodiment 1A, wherein the compound has the structure of:

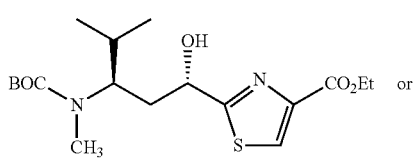

or

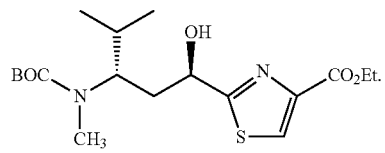

7A. The compound of embodiment 1A, optionally in salt form, wherein the compound has the structure of:

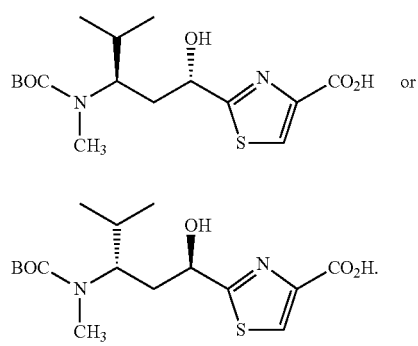

or

8A. The compound of embodiment 1A, optionally in salt form, wherein the compound has the structure of:

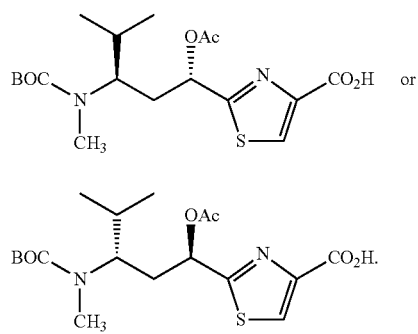

9A. The compound of embodiment 1A, wherein the compound has the structure of:

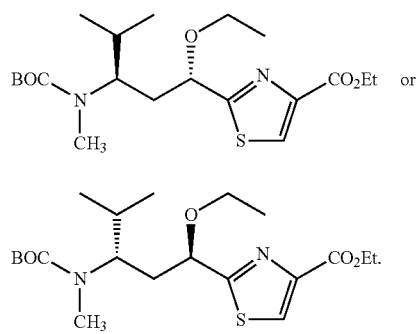

or

10A. The compound of embodiment 1A, wherein the compound has the structure of:

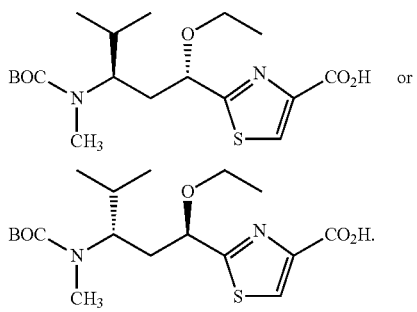

11A. The compound of embodiment 1A, wherein the compound has the structure of:

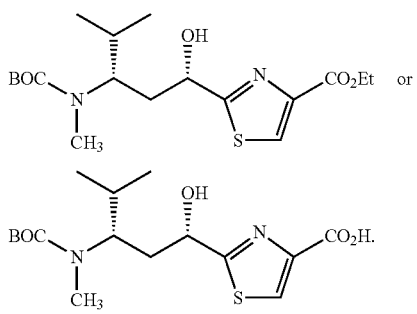

12A. The compound of embodiment 1A, wherein the compound has the structure of:

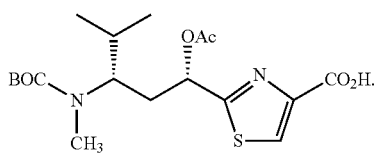

13A. The compound of embodiment 1A, wherein the compound has the structure of:

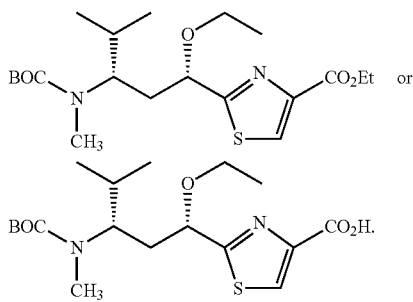

14A. A composition comprised of a tubuvaline compound of (R,R)-Formula 1a, optionally in salt form, having the structure of:

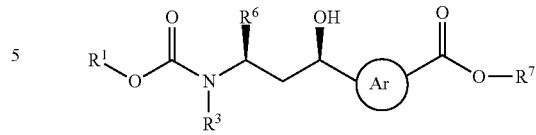
(R,R-1a)

and one or more optical isomers thereof as optical impurities, wherein the (R,R)-Formula 1a tubuvaline compound, or salt thereof, is the predominate optical isomer, and wherein its corresponding enantiomer, (S,S)-Formula 1a, optionally in salt form, is the major optical impurity, which has the structure of:

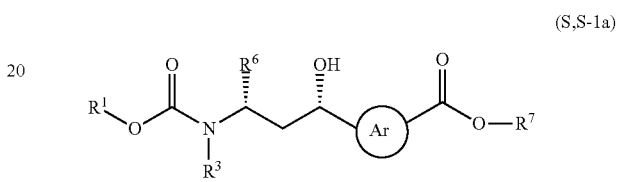
(S,S-1a)

wherein: the circled Ar is a 1,3-phenylene or a 5- or 6-membered nitrogen-containing 1,3-heteroarylene, optionally substituted at the remaining positions; $R^1$ is phenyl, t-butyl, 9-fluorenyl or allyl, optionally substituted, or other moeity so that $R^1$—OC(=O)— is a suitable nitrogen protecting group;

$R^3$ is optionally substituted saturated $C_1$-$C_8$ alkyl, optionally substituted unsaturated $C_3$-$C_8$ alkyl or optionally substituted $C_3$-$C_8$ heteroalkyl; $R^6$ is optionally substituted $C_1$-$C_8$ alkyl; and $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moeity so that $R^7$—O— provides for a suitable carboxylic acid protecting group, in particular, (R,R)-Formula 1a has the structure of:

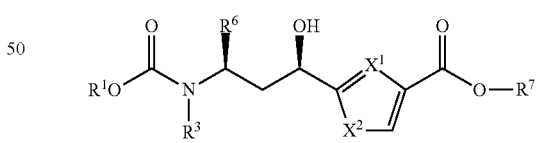

and (S,S)-Formula 1a has the structure of:

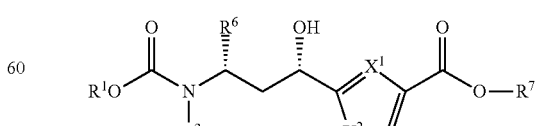

wherein: $X^1$ is =N—; and $X^2$ is S, O, or N($R^{X2}$)—, or $X^1$ is =C($R^{X1}$)—; and $X^2$ is N$R^{X2}$, $R^{X1}$ and $R^{X2}$ are independently selected from the group consisting of —H, —$CH_3$ or —CH₂CH₃; and wherein the remaining variable group are as previously defined, more particularly, (R,R)-Formula 1a has the structure of:

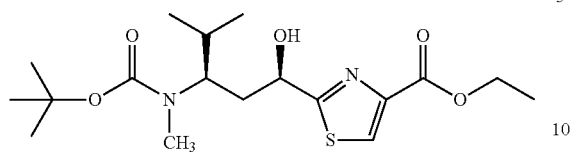

and (S,S)-Formula 1a has the structure of:

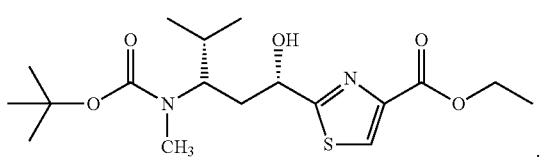

15A. The composition of embodiment 14A, wherein the tubuvaline composition is comprised of the (R,R)-Formula 1a tubuvaline compound, or salt thereof, as the predominate optical isomer and has no more than about 5% w/w of the diastereomeric tubuvaline compound, (R,S)-Formula 1a, relative to the total amount of optical isomers present in the composition, in particular, no more than about 1.5% w/w, more particularly, no more that about 1.0% w/w, or is essentially free of the diastereomer, as determined by chiral HPLC, wherein the diastereomeric tubuvaline compound, optionally in salt form, has the structure of:

(R,S-1a)

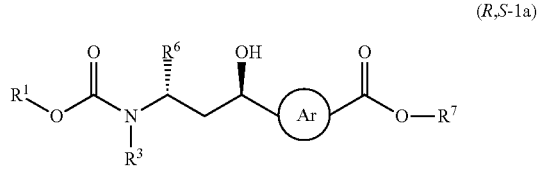

in particular (R,S)-Formula 1a has the structure of:

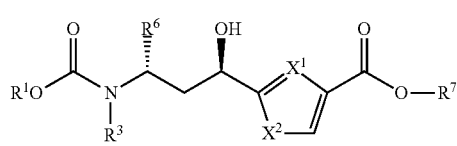

wherein the variable groups remain as previously defined for (R,R)-Formula 1a and (S,S)-Formula 1a, more particularly, (R,S)-Formula 1a has the structure of:

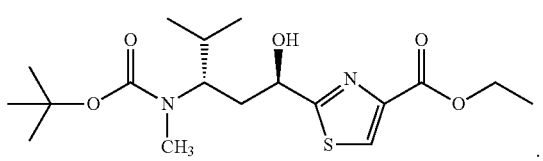

16A. The composition of embodiment 15A, wherein the composition is essentially free of the diastereomer (R,S)-Formula 1a, and is essentially free of its corresponding enantiomer, (S,R)-Formula 1a, as determined by chiral HPLC, which has the structure of:

(S,R-1a)

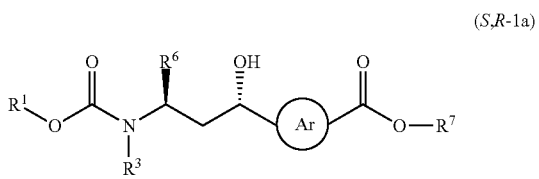

in particular, (S,R)-Formula 1a has the structure of:

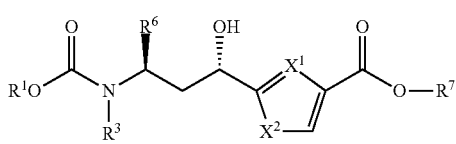

wherein the variable groups remain as previously defined for (R,R)-Formula 1a, (S,S)-Formula 1a and (R,S)-Formula 1a, more particularly, (S,R)-Formula 1a has the structure of:

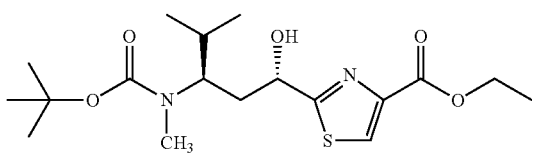

17A. The embodiment of embodiment 14A, 15A or 16A, wherein the composition contains no more that about 3% w/w, in particular no more than about 2% w/w or no more than about 1.5% w/w of the optical impurity of (S,S)-Formula 1a, as determined by chiral HPLC, relative to the total amount of optical isomers present in the composition.

18A. A composition comprised of a tubuvaline compound of (R,R)-Formula 2, optionally in salt form, having the structure of:

(R,R-2)

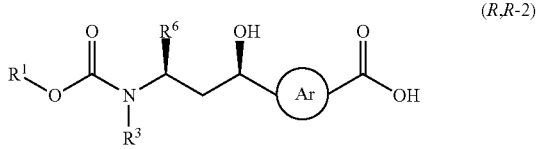

and one or more optical isomers thereof as optical impurities, wherein the (R,R)-Formula 2 tubuvaline compound, or salt thereof, is the predominate optical isomer, and wherein its corresponding enantiomer, (S,S)-Formula 2, optionally in salt form, is the major optical impurity, which has the structure of:

(S,S-2)

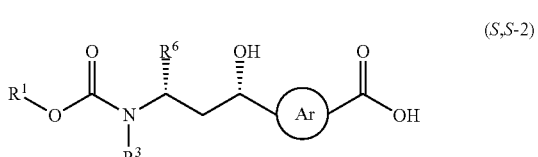

wherein:

the circled Ar is a 1,3-phenylene or a 5- or 6-membered nitrogen-containing 1,3-heteroarylene, optionally substituted at the remaining positions; $R^1$ is phenyl, t-butyl, 9-fluorenyl or allyl, optionally substituted, or other moeity so that $R^1$—OC(=O)— is a suitable nitrogen protecting group; $R^3$ is optionally substituted saturated $C_1$-$C_8$ alkyl, optionally substituted unsaturated $C_3$-$C_8$ alkyl or optionally substituted $C_3$-$C_8$ heteroalkyl; $R^6$ is optionally substituted $C_1$-$C_8$ alkyl; and $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moeity so that $R^7$—O— provides for a suitable carboxylic acid protecting group, in particular, wherein (R,R)-Formula 2 has the structure of

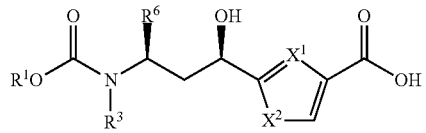

or a salt thereof, and (S,S)-Formula 2 has the structure of:

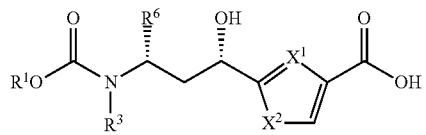

or a salt thereof, wherein: $X^1$ is =N—; and $X^2$ is S, O, or N($R^{X2}$)—, or $X^1$ is =C($R^{X1}$)—; and $X^2$ is N$R^{X2}$, wherein $R^{X1}$ and $R^{X2}$ are independently selected from the group consisting of —H, —$CH_3$ or —$CH_2CH_3$; and the remaining variable groups are as previously defined, more particularly, (R,R)-Formula 2 has the structure of:

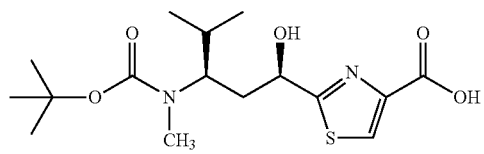 [SMILES: CC(C)[C@@H](C[C@@H](O)c1nc(C(=O)O)cs1)N(C)C(=O)OC(C)(C)C]

or a salt thereof, and (S,S)-Formula 2, optionally in salt form, has the structure of:

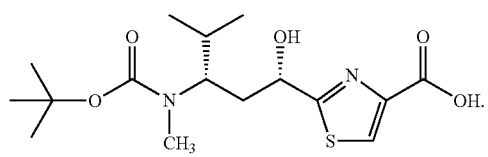 [SMILES: CC(C)[C@H](C[C@H](O)c1nc(C(=O)O)cs1)N(C)C(=O)OC(C)(C)C]

19A. The composition of embodiment 18A, wherein the tubuvaline composition is comprised of the (R,R)-Formula 2 tubuvaline compound, or salt thereof, as the predominate optical isomer and has no more than about 5% w/w of the diastereomeric tubuvaline compound, (R,S)-Formula 2, relative to the total amount of optical isomers present in the composition, in particular, no more than about 1.5% w/w, more particularly, no more that about 1.0% w/w, or is essentially free of the diastereomer, as determined by chiral HPLC, wherein the diastereomeric tubuvaline compound, optionally in salt form, has the structure of (R,S)-Formula 2:

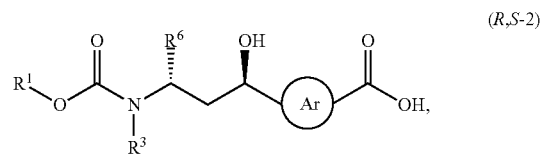

wherein the variable groups remain as previously defined, in particular, wherein (R,S)-Formula 2 has the structure of:

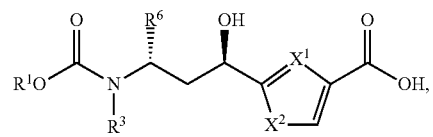

or a salt thereof, wherein: $X^1$ is =N—; and $X^2$ is S, O, or N($R^{X2}$)—, or $X^1$ is =C($R^{X1}$)—; and $X^2$ is N$R^{X2}$, $R^{X1}$ and $R^{X2}$ are independently selected from the group consisting of —H, —$CH_3$ or —$CH_2CH_3$; and wherein the remaining variable groups are as previously defined, more particularly, wherein (R,S)-Formula 2, optionally in salt form, has the structure of:

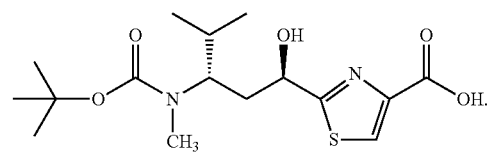

20A. The composition of embodiment 19A, wherein the composition is essentially free of the diastereomer, (R,S)-Formula 2, or salt thereof, and is essentially free, as determined by chiral HPLC, of its corresponding enantiomer, (S,R)-Formula 2, which has the structure of:

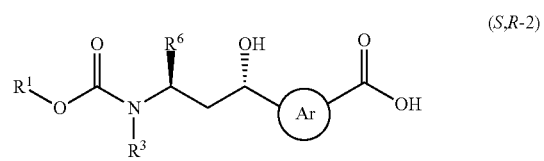

or salt thereof, in particular, wherein (S,R)-Formula 2 has the structure of:

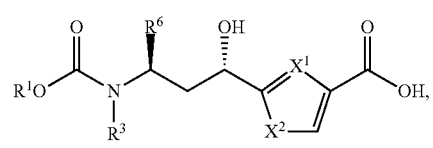

or salt thereof, wherein the variable groups are as previously defined for (R,R)-Formula 1a, (R,S)-Formula 1a and (S,S)-Formula 1a, more particularly, wherein (S,R)-Formula 2, optionally in salt form, has the structure of:

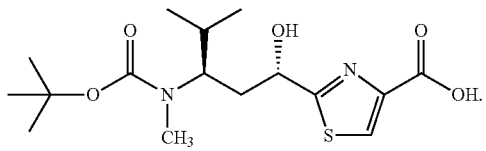 [SMILES: CC(C)[C@@H](C[C@H](O)c1nc(C(=O)O)cs1)N(C)C(=O)OC(C)(C)C]

21A. The composition of embodiment 18A, 19A or 20A, wherein the composition contains no more that about 3% w/w, in particular no more than about 2% w/w or no more than about 1.5% w/w of the optical impurity of (S,S)-Formula 2, as determined by chiral HPLC, relative to the total amount of optical isomers present in the composition.

22A. A composition comprised of a tubuvaline compound of (R,R)-Formula 2a, optionally in salt form, having the structure of:

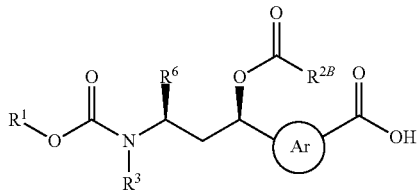

(R,R-2a)

and one or more optical isomers thereof as optical impurities, wherein the (R,R)-Formula 2a tubuvaline compound, or salt thereof, is the predominate optical isomer, and wherein its corresponding enantiomer, (S,S)-Formula 2a, optionally in salt form, is the major optical impurity, which has the structure of:

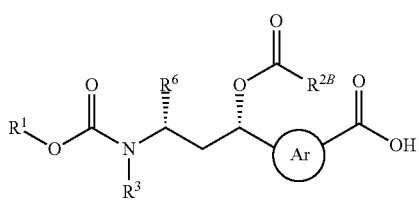

(S,S-2a)

wherein: the circled Ar is a 1,3-phenylene or a 5- or 6-membered nitrogen-containing 1,3-heteroarylene, optionally substituted at the remaining positions; $R^1$ is phenyl, t-butyl, 9-fluorenyl or allyl, optionally substituted, or other moiety so that $R^1$—OC(=O)— is a suitable nitrogen protecting group; $R^3$ is optionally substituted saturated $C_1$-$C_8$ alkyl, optionally substituted unsaturated $C_3$-$C_8$ alkyl or optionally substituted $C_3$-$C_8$ heteroalkyl; $R^6$ is optionally substituted $C_1$-$C_8$ alkyl; and $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moiety so that $R^7$—O— provides for a suitable carboxylic acid protecting group, in particular, wherein (R,R)-Formula 2a has the structure of:

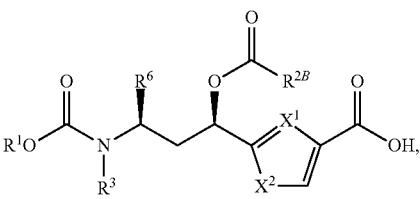

or salt thereof, and (S,S)-Formula 2a has the structure of:

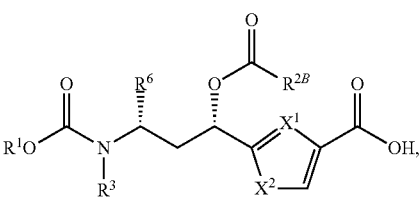

or salt thereof, wherein: $X^1$ is =N—; and $X^2$ is S, O, or N($R^{X2}$)—, or $X^1$ is =C($R^{X1}$)—; and $X^2$ is N$R^{X2}$, wherein $R^{X1}$ and $R^{X2}$ are independently selected from the group consisting of —H, —$CH_3$ or —$CH_2CH_3$; and wherein the remaining variable groups are as previously defined, more particularly, wherein (R,R)-Formula 2a has the structure of:

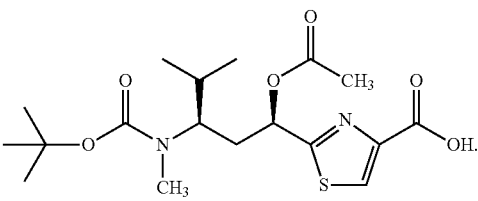 [SMILES: CC(=O)O[C@H](C[C@H](C(C)C)N(C)C(=O)OC(C)(C)C)c1nc(C(=O)O)cs1]

or salt thereof, and (S,S)-Formula 2a, optionally in salt form, has the structure of:

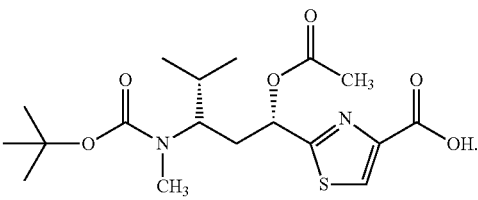

23A. The composition of embodiment 22A, wherein the tubuvaline composition is comprised of the (R,R)-Formula 2a tubuvaline compound, or salt thereof, as the predominate optical isomer and has no more than about 5% w/w of the diastereomeric tubuvaline compound, (R,S)-Formula 2a, relative to the total amount of optical isomers present in the composition, in particular, no more than about 1.5% w/w, more particularly, no more that about 1.0% w/w, or is essentially free of the diastereomer, as determined by chiral HPLC, wherein the diastereomeric tubuvaline compound, optionally in salt form, has the structure of (R,S)-Formula 2a:

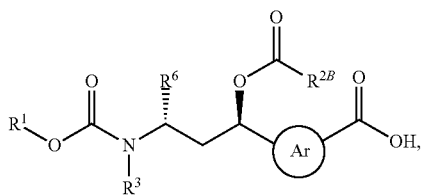

(R,S-2a)

in particular, wherein (R,S)-Formula 2a has the structure of:

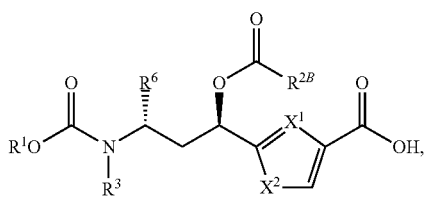

or salt thereof, wherein the variable groups remain as previously defined for (R,R)-Formula 2a and (S,S)-Formula 2a, more particularly, (R,S)-Formula 2a, optionally in salt form, has the structure of:

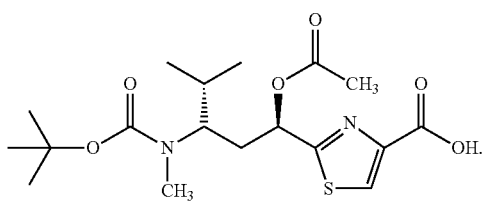

24A. The composition of embodiment 23A, wherein the composition is essentially free of the diastereomer, (R,S)-Formula 2a, and is essentially free, as determined by chiral HPLC, of its corresponding enantiomer, (S,R)-Formula 2a, which has the structure of:

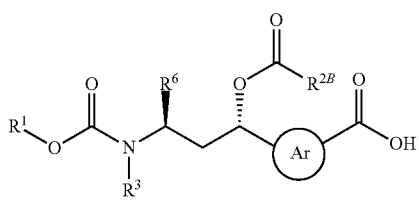

(S,R-2a)

in particular, wherein (S,R)-Formula 2a has the structure of

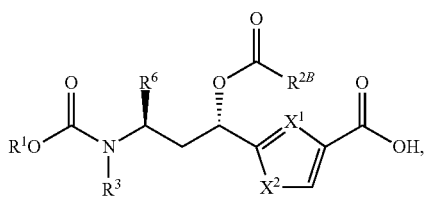

or salt thereof, wherein the variable groups remain as previously defined for (R,R)-Formula 2a, (S,S)-Formula 2a and (R,S)-Formula 2a, more particularly, (S,R)-Formula 2a, optionally in salt form, has the structure of:

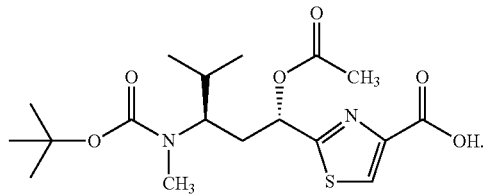 [SMILES: CC(=O)O[C@@H](C[C@H](C(C)C)N(C)C(=O)OC(C)(C)C)c1nc(C(=O)O)cs1]

25A. The composition of embodiment 22A, 23A or 24A, wherein the composition contains no more that about 3% w/w, in particular no more than about 2% w/w or no more than about 1.5% w/w of the optical impurity of (S,S)-Formula 2a, as determined by chiral HPLC, relative to the total amount of optical isomers present in the composition.

26A. A method for preparing a composition of any one of embodiments 14A-17A, the method comprising the steps of:

(a) contacting a compound of Formula A:

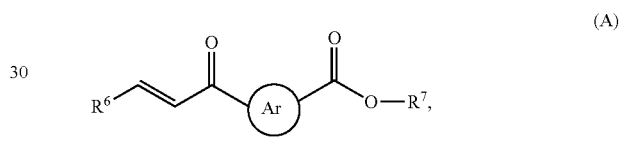

(A)

wherein $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl, optionally substituted $C_3$-$C_{20}$ heterocyclyl, or other moiety so that $R^7$—O— provides for a suitable carboxylic acid protecting group, with a compound of Formula B:

$R^3NHC(O)OR^1$ (B), in a suitable polar, aprotic solvent in the presence of a suitable transition metal (II) or transition metal (III) catalyst, in particular, one comprising a transition metal selected from the group consisting of Cu(II), Zn(II) and Yb(III), so as to form a composition comprised of an enantiomeric mixture of tubuvaline intermediates represented by Formula AB:

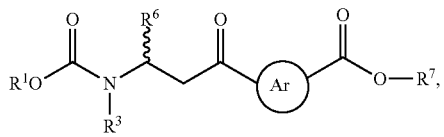

(AB)

(b) contacting the enantiomeric mixture with a suitable chiral reducing agent so as to form a composition comprised of essentially an equimolar mixture of diastereomers, wherein the diastereomeric mixture is represented by Formula R-1a,

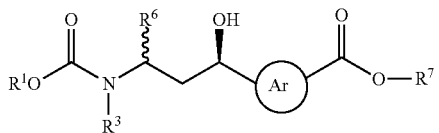

(R-1a)

wherein the composition is further comprised of essentially an equimolar mixture of optical impurities that are enantiomers of the diastereomers.

(b') separating the diastereomers from the composition of the Formula R-1a diastereomeric mixture so that the composition, which is comprised of (R,R)-Formula 1a as the predominate optical isomer and having (S,S)-Formula 1a as the major optical impurity, is obtained, wherein the predominate optical isomer and the predominate optical impurity, each optionally in salt form, have the structures of:

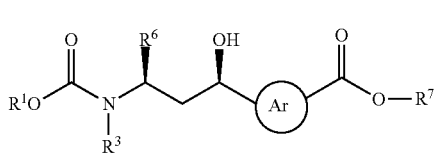

(R,R-1a)

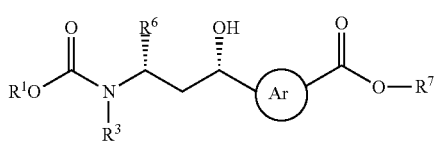

(S,S-1a)

respectively, wherein the variable groups of AB, Formula R-1a, R,R-Formula 1a and (S,S)-Formula 1a retain the previous meanings from the Formula A and Formula B compounds.

27A. The method of embodiment 26A, wherein the transition (II) metal catalyst is comprised of Cu(II), in particular Cu(OTf)$_2$, Cu(SbF$_6$)$_2$, or CuCl$_2$, more particularly Cu(OTf)$_2$.

28A. The method of embodiment 26A or 27A, wherein the suitable polar, aprotic solvent is acetonitrile, dichloromethane, THF, dioxane, or a mixture of two or three of these solvents, in particular, dichloromethane.

29A. The method of embodiment 26A, 27A or 28A, wherein the chiral reducing agent is a chiral oxazaborolidine prepared from contacting BH$_3$-DMS in THF with a suitable chiral ligand, in particular (S)-(–)-CBS.

30A. A method for preparing a composition of any one of embodiments 18A-21A, the method comprising the steps of:

(c) contacting the composition obtained from steps (a), (b) and step (b') of any one of embodiments 26A-29A with an suitable hydrolysis agent, wherein the predominate optical isomer of the composition so obtained is (R,R)-Formula 2, optionally in salt form, having the structure of:

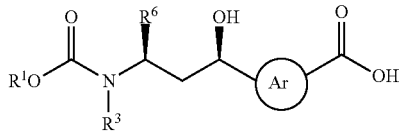

(R,R-2)

and the major optical impurity is (S,S)-Formula 2, optionally in salt form, having the structure of:

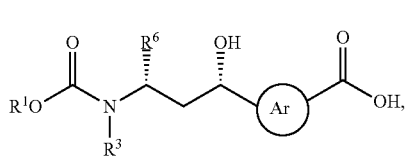

(S,S-2)

wherein the variable groups of R,R-Formula 2 and S,S-Formula 2 retain the previous meanings from the Formula A and Formula B compounds.

31. A method for preparing a composition of any one of embodiments 22A-25A, the method comprising the steps of:

(c) contacting the composition obtained from steps (a), (b) and step (b') of embodiment 26A-29A with an suitable hydrolysis agent to obtain a composition comprised of (R,R)-Formula 2 as the predominate optical isomer, optionally in salt form, which has the structure of:

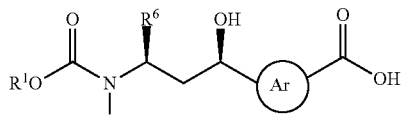

and further comprised of its enantiomer, optionally in salt form, as the major optical impurity, which has the structure of:

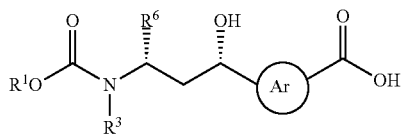

step (d) contacting the composition so obtained with a suitable acylating agent to obtain a composition comprised (R,R)-Formula 2a as the predominate optical isomer and (S,S)-Formula 2a as the major optical impurity, wherein the predominate optical isomer and the predominate optical isomer, each optionally in salt form, have the structures of:

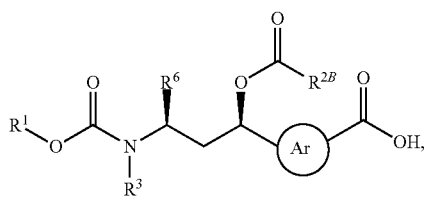

(R,R-2a)

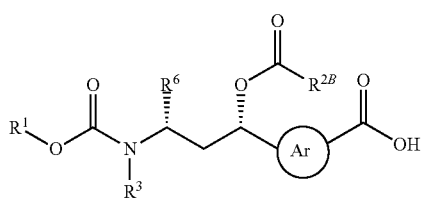

(S,S-2a)

wherein R$^{2B}$ is saturated C$_1$-C$_6$ alkyl, unsaturated C$_3$—C alkyl, C$_2$-C$_8$ alkenyl or C$_2$-C$_4$ alkynyl, optionally substituted, in particular —CH$_3$, —CH$_2$CH$_3$, —CH$_2$CH$_2$CH$_3$, —CH$_2$CH=CH$_2$, —CH$_2$CH(CH$_3$)$_2$, —CH$_2$C(CH$_3$)$_3$, —CH$_2$C(CH$_3$)=CH$_2$, —CH=CH$_2$ or —CHC≡CH, more particularly, —CH₃, and the remaining variable groups retain the previous meanings of the Formula A and Formula B compounds.

32A. The method of any one of embodiments 26A-31A, wherein the optical purity of the composition from step (b') is substantially or essentially retained by the composition obtained from step (c) and/or step (d).

33A. The method of any one of embodiments 26A-32A, wherein said step (b') separation is by silica gel flash chromatography.

34A. The method of claim any one embodiments 26A-33A, wherein the circled Ar is a 5-membered nitrogen-containing 1,3-heteroarylene, optionally substituted at the remaining positions.

35A. The method of claim any one embodiments 26A-34A, wherein compound A and compound B of step (a) have the structures of:

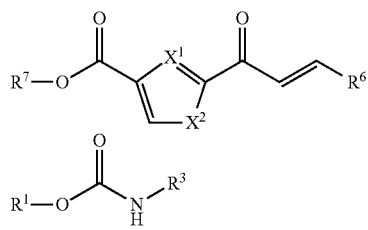

wherein, $X^1$ is =N—; and $X^2$ is S, O, or N($R^{X2}$)—, or $X^1$ is =C($R^{X1}$)—; and $X^2$ is N$R^{X2}$, wherein $R^{X1}$ and $R^{X2}$ are independently selected from the group consisting of —H, —CH₃ or —CH₂CH₃; $R^1$ is phenyl, t-butyl, 9-fluorenyl or allyl, optionally substituted, or other moeity so that $R^1$—OC(=O)— is a suitable nitrogen protecting group, in particular t-butyl; and $R^3$ is optionally substituted saturated $C_1$-$C_6$ alkyl, optionally substituted unsaturated $C_3$-$C_6$ alkyl or optionally substituted $C_3$-$C_6$ heteroalkyl, in particular —CH₃ or —CH₂CH₂CH₃; $R^6$ is $C_1$-$C_6$ alkyl, in particular —CH(CH₃)₂; and $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl or optionally substituted $C_3$-$C_{20}$ heterocyclyl, or other moeity so that $R^7$—O— provides a suitable carboxylic acid protecting group, in particular R7 is —CH₃ or —CH₂CH₃, in particular, compound A and compound B have the structures of:

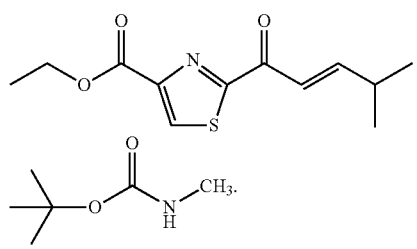

36A. A composition comprised of a compound, optionally in salt form, having the structure of:

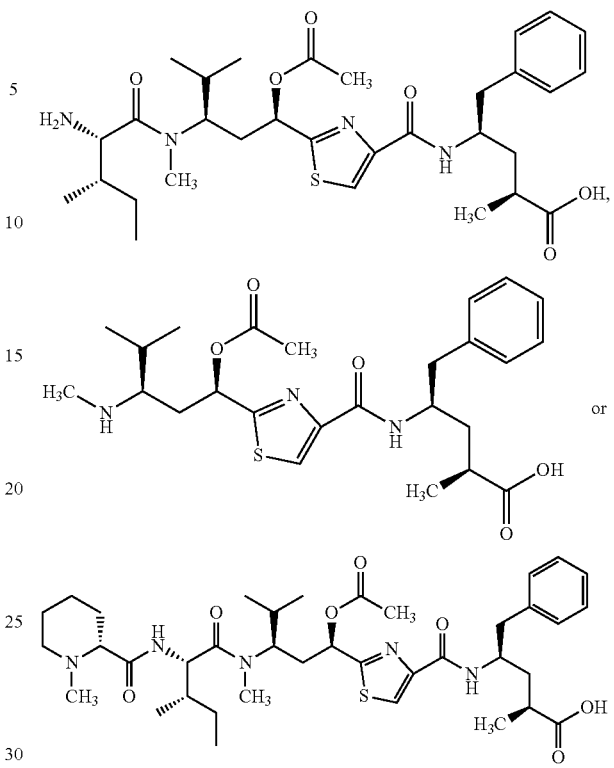

as the predominate optical isomer, and a corresponding optical impurity, optionally in salt form, having the structure of:

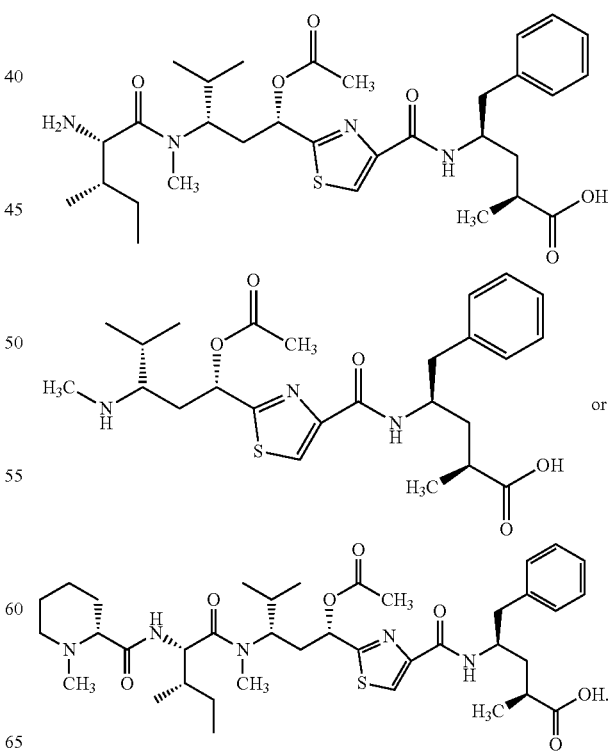

37A. The composition of embodiment 36A, wherein the composition is essentially free of the corresponding optical impurity of:

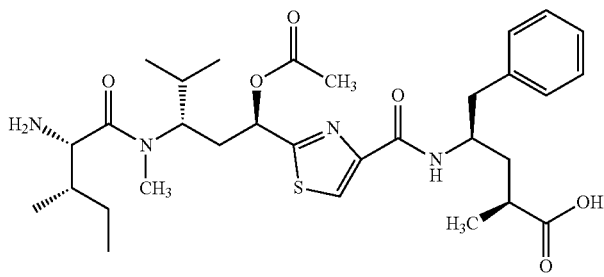

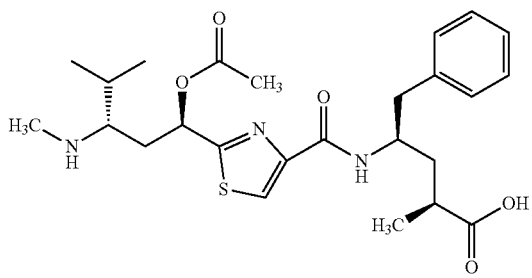

or

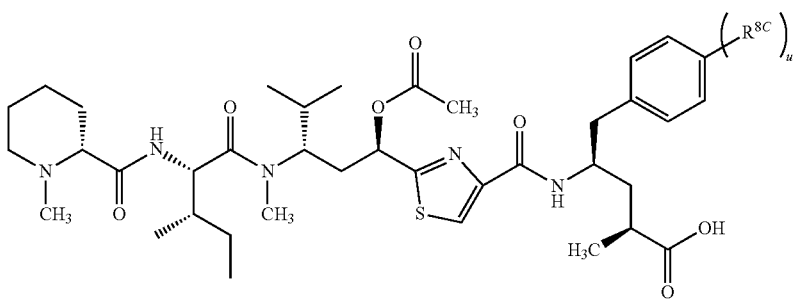

and is essentially free of the corresponding optical impurity having the structure of:

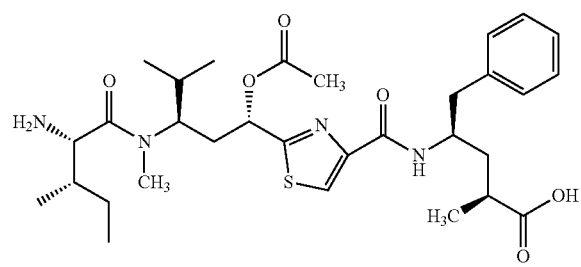

or

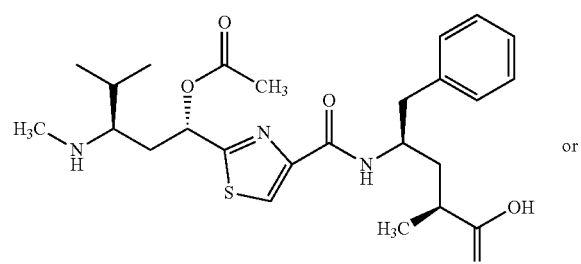

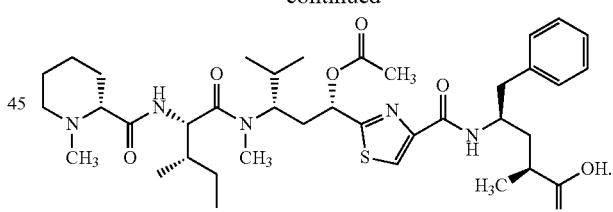

38A. The composition of embodiment 37A, wherein the composition is prepared from a composition of claim 24A, wherein the composition of embodiment 24A contains no more that about 3% w/w, in particular no more than about 2% w/w or no more than about 1.5% w/w of the optical impurity of (S,S)-Formula 2a, as determined by chiral HPLC, relative to the total amount of optical isomers present in the composition.

39A. A Drug Linker composition, wherein the composition is comprised of a Drug Linker compound having the structure of:

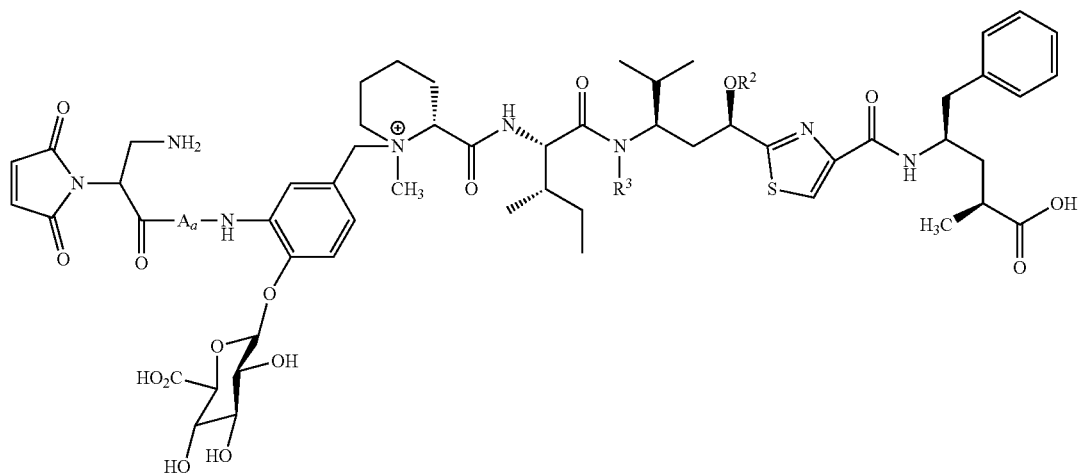
in suitable salt form, and a Drug linker impurity having the structure of:
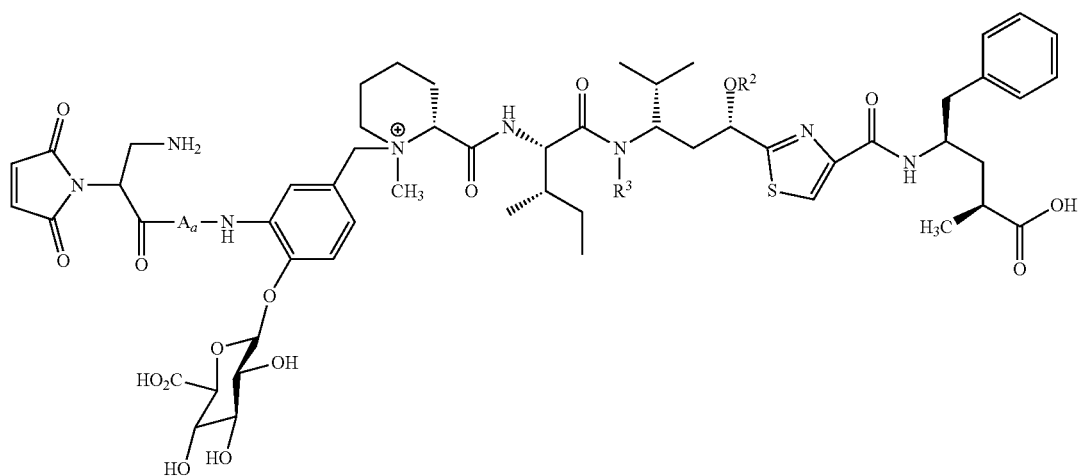
also in salt form, or wherein the Drug Linker compound has the structure of:
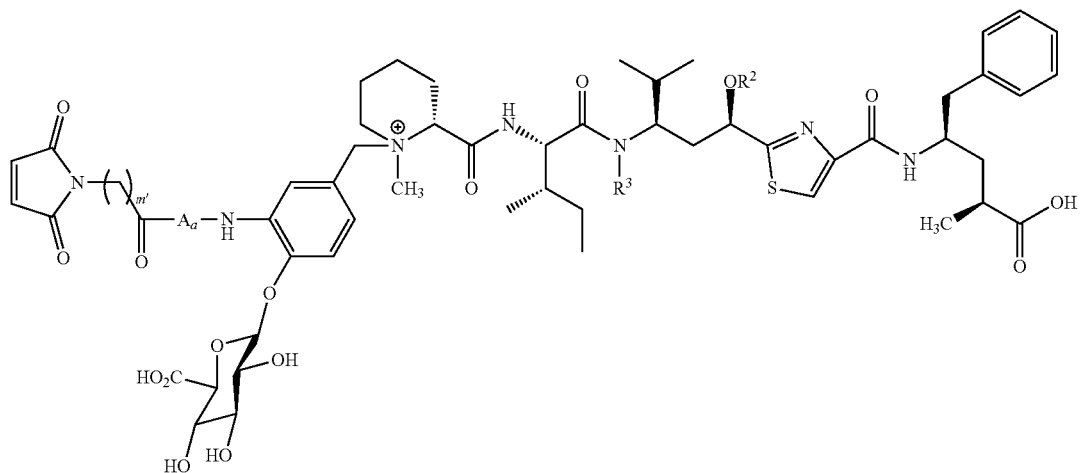

in suitable salt form, and the Drug linker impurity has the structure of:

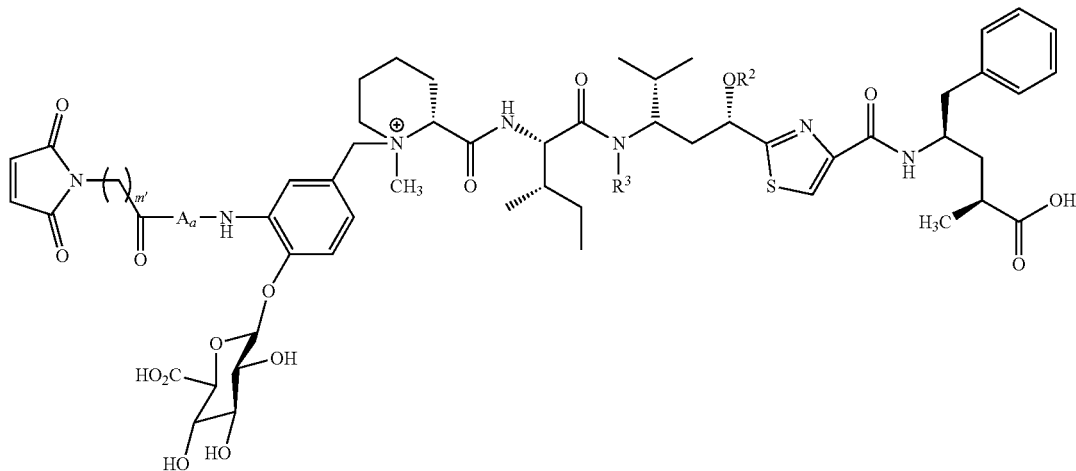

also in salt form, wherein subscript a is 1 so that A is present, preferably as an α-amino acid or β-amino acid residue; subscript m' ranges from 1 to 5; $R^2$ is saturated $C_1$-$C_6$ alkyl, or $R^2$ is $R^{2A}$, wherein $R^{2A}$ is —C(=O)$R^{2B}$, wherein $R^{2B}$ is saturated $C_1$-$C_6$ alkyl or unsaturated $C_3$-$C_6$ alkyl, in particular, $R^2$ is —$CH_3$, —$CH_2CH_3$ or —C(=O)$CH_3$; and $R^3$ is —$CH_3$ or —$CH_2CH_2CH_3$.

40A. The Drug Linker composition of embodiment 39A, wherein $R^2$ is $R^{2A}$, wherein $R^{2A}$ is —C(=O)$CH_3$ and $R^3$ is —$CH_3$, and wherein the composition is prepared from a composition of embodiment 36A, 37A or 38A.

41A. A Ligand Drug Conjugate composition having the structure of Formula 1:

wherein L is a Ligand Unit, LU is a Linker Unit and $D^+$ is a quaternized tubulysin Drug Unit; and subscript p ranges from 2 to 12, wherein a plurality of Ligand Drug Conjugate compounds of the composition have identical quaternized tubulysin Drug Units having the structure of (R,R)-Formula $D^+$:

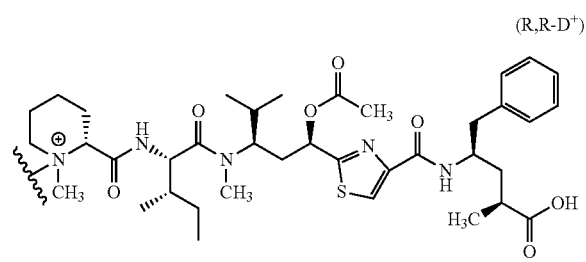

in pharmaceutically acceptable salt form, wherein the wavy line indicate the site of covalent attachment to LU, and wherein at least one compound of the composition has at least one quaternized tubulysin Drug Unit having the structure of (S,S)-Formula $D^+$:

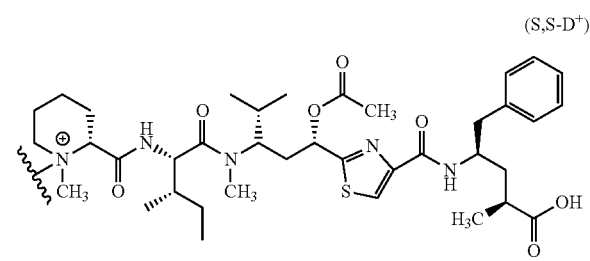

with the remainder having identical (R,R)-Formula $D^+$ structures.

42A. The Ligand Drug Conjugate composition of embodiment 41A, wherein the Ligand Drug Conjugate composition is prepared from a Drug Linker composition of embodiment 39A or 40A.

43A. The Ligand Drug Conjugate composition of claim 41A or 42A, wherein the Ligand Unit is an antibody Ligand Unit directed to a cancer cell antigen, in particular CD30, CD33 or CD70.

EXAMPLES

General Reaction Schemes.

Beginning from commercially available materials, preparation of BOC-protected tubuvaline by the literature route described by and the present route involving a transition (II) metal catalyzed aza-Michael reaction are shown in Schemes 1 and 2, respectively.

Scheme 1. Preparation of BOC-protected tubuvaline based upon literature precedent

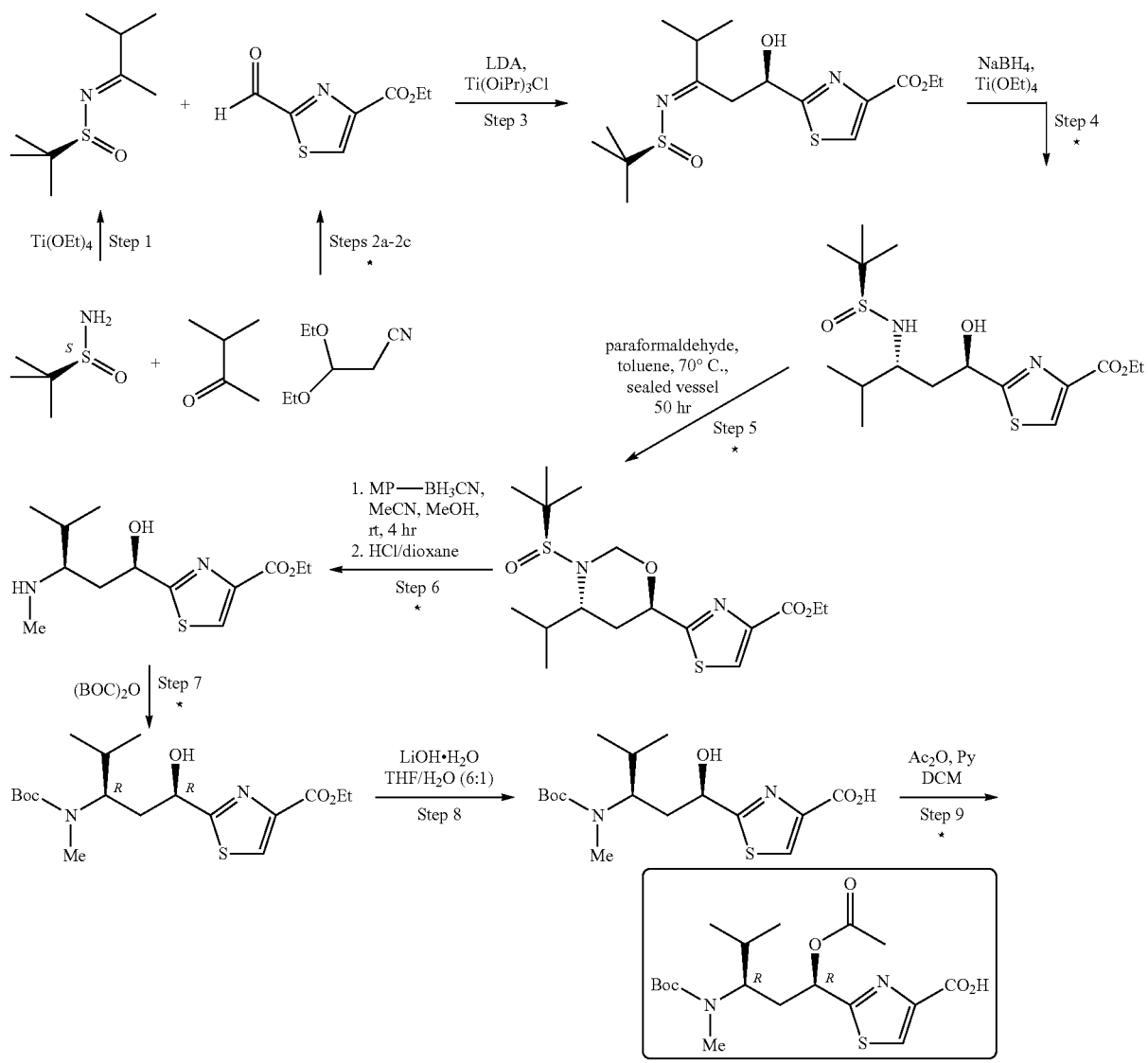

* Flash chromatography

The reaction sequence of Scheme 1 through step 6 to prepare desacetyl-tubuvaline ethyl ester is described by Ellman et al. *J. Org. Chem.* (2008) 73: 4326-4396 for which the starting material ethyl 2-formylthiazole-4-carboxylate for step 3 is prepared in 3 steps (steps 2a-2c) from commercially available diethoxyacetonitrile and 3-bromopyruvate (78% overall yield), as reported by Ellman et al. *J. Amer. Chem. Soc.* (2006) 128; 16018-16019 using the method of Inami, K. and Shiba, T. *Bull. Chem. Soc. (Jpn)* (1985) 58: 352-360. Preparation of that thiazole intermediated required flash chromatography for purification of the intermediate ethyl 2-(diethoxymethyl)-4-thiazolecarboxylate. Preparation of ethyl 2-((1R,3R)-3-((tert-butoxycarbonyl)(methyl)-amino)-1-hydroxy-4-methylpentyl)thiazole-4-carboxylate (BOC-protected tubuvaline) then requires BOC protection of the secondary amine of desacetyl-tubuvaline ethyl ester provided by step 6 followed by hydrolysis of the ethyl ester and acylation of the hydroxyl group (steps 7-9). Thus, Scheme 1 requires 10 steps from commercially available material to provide BOC-protected tubuvaline.

Scheme 2. Preparation of BOC-protected tubuvaline by transition (II) metal catalysis of an aza-Michael conjugate addition reaction.

Cys+ pyruvaldehyde → step 1a → step 1b

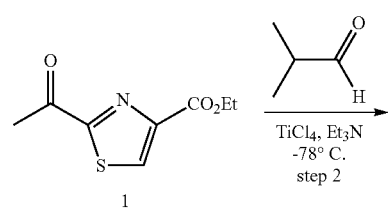

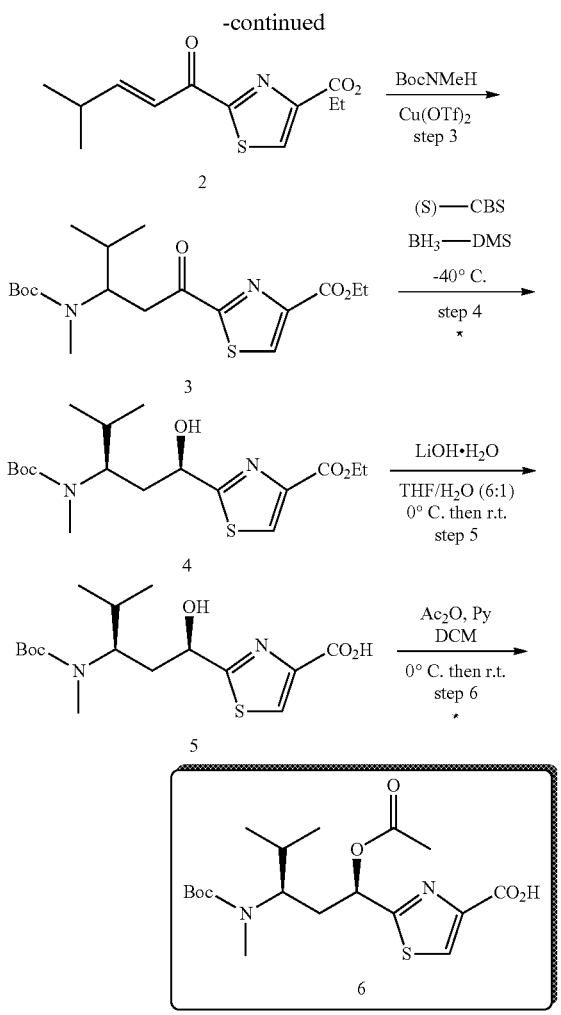

The intermediate ethyl (E)-2-(4-methylpent-2-enoyl)thiazole-4-carboxylate (2) was prepared by condensation of isobutyradehyde with ethyl 2-acetylthiazole-4-carboxylate (1) in step 2 of Scheme 2 according to the method of Zanda et al. *Angew. Chem. Int'l. Ed.* (2007) 46: 3526-3529. The thiazole starting material was obtained in 2 steps (steps 1a and 1b) starting from cysteine and pyruvaldehyde (52% overall yield) as reported by Zanda et al. Thus, Scheme 2 involved 7 steps from commercially available material, which is in contrast to the 10 steps required by Scheme 1.

Transition-metal catalyzed aza-Michael conjugate addition of BOC-NHMe to compound 2 in step 3 of Scheme 2 provides racemic ethyl 2-(3-((tert-butoxycarbonyl)-(methyl)amino)$_4$-methylpentanoyl)thiazole-4-carboxylate (3). Chiral ketone reduction of step 4 of Scheme 2 of compound 3, provides the diastereomeric alcohol ethyl 2-((1R,3R)-3-((tert-butoxycarbonyl)(methyl)-amino)-1-hydroxy-4-methylpentyl)thiazole-4-carboxylate (4) after subsequent removal of the undesired diastereomer by flash chromatography. In contrast, the desired (R,R)-diastereomer from step 6 of Scheme 1 was obtained using the (S)-sulfoxide of step 1 as a chiral auxiliary agent, which must be used in stoichiometric amount.

Preparation of the chiral ligand (S)-CBS, which is (S)-(−)-2-(diphenylhydroxy methyl)pyrrolidine, and its use in conjunction with BH$_3$-Me$_2$S for stereoselective reduction of ketones is described by Corey et al. *J. Amer. Chem. Soc.* (1987), 109: 5551-5553. That and other chiral ligands suitable for stereoselective reduction in Scheme 2 for preparation of tubuvaline analogs are further described by Corey et al. *Angew. Chem, Int'l. Ed.* (1998) 37: 1986-2012.

The overall yield of desacetyl-tubuvaline ethyl ester from step 6 of Scheme 1 was reported to be 40%; however, the reaction scale was such that only about 150 mg was obtained. Scale-up to gram scale proved more troublesome with the sealed tube reaction requiring 12 days at 85° C. (77% yield). Attempts to hasten the reaction time so as to be more consistent with manufacturing requirements by increasing the temperature (125° C., 60 hr) proved futile due to significantly reduced yield (41%). Furthermore, attempts to protect the secondary amine to permit acetylation so as to provide BOC-protected tubuvaline resulted in a disappointing 55% yield.

Aside from the troublesome sealed tube reaction, the greatest loss of material in Scheme 1 occurs, as previously mentioned, during BOC protection of intermediate ethyl 2-((1R,3R)-1-hydroxy-4-methyl-3-(methylamino)pentyl)thiazole-4-carboxylate (desacetyl-tubuvaline ethyl ester) of step 7. Without being bound by theory, it is believe that such an extensive loss late in the reaction sequence in introducing a BOC protecting group, which should be a straightforward protection step, is due to a retro aza-Michael reaction. That aza-Michael reaction in the forward direction, as shown in step 2 of Scheme 2, allowed for direct introduction of the BOC-protected methylamino moiety early in the reaction sequence. Although there was incomplete conversion of (E)-2-(4-methylpent-2-enoyl)thiazole-4-carboxylate to rac-ethyl 2-(3-((tert-butoxycarbonyl)(methyl)amino)$_4$-methylpentanoyl)thiazole-4-carboxylate in step 3, loss of material occurred earlier in a shorter reaction sequence so that the overall yield of ethyl 2-((1R,3R)-3-((tert-butoxycarbonyl)(methyl)amino)-1-hydroxy-4-methylpentyl)thiazole-4-carboxylate (BOC-protected tubuvaline) prepared according to Scheme 2 was 15.9% compared to 5.3% from Scheme 2 when conducted on multigram scale. Furthermore, in addition to the inability to scale up the sealed tube reaction of Scheme 1 and the loss of material during BOC-protection, Scheme 2 is also impractical from a manufacturing perspective since a total of 7 chromatographic purifications is required.

General Information.

All commercially available anhydrous solvents were used without further purification. Silica gel chromatography was performed on a CombiFlash Rf+ system. All commercially available anhydrous solvents were used without further purification. Silica gel chromatography was performed on a CombiFlash Rf+ system. Analytical HPLC was performed with an Agilent 1200 HPLC using a Phenomenex Kinetex XB—C18 RP column (150×4.5 mm, 2.6 m), PN:00F-4496-E0, at ambient temperature with detection at 240 nm, eluting (1.0 mL/min) with a linear gradient of 5% to 95% acetonitrile/water (0.1% formic acid) over 35 min (Method A) or eluting with a linear gradient of 25% to 90% acetonitrile/water (0.1% formic acid) over 15 min (Method B). Chiral analytical chromatography was performed on an Agilent 1260 HPLC using a Chiral pak IB-3 (4.6×150 mm, 3 μm) column at ambient temperature, with detection at 220 nm, eluting (flow rate=1.0 mL/min) with an isocratic gradient of 60:40 water:acetonitrile (0.1% formic acid) over 30 min (Method C).

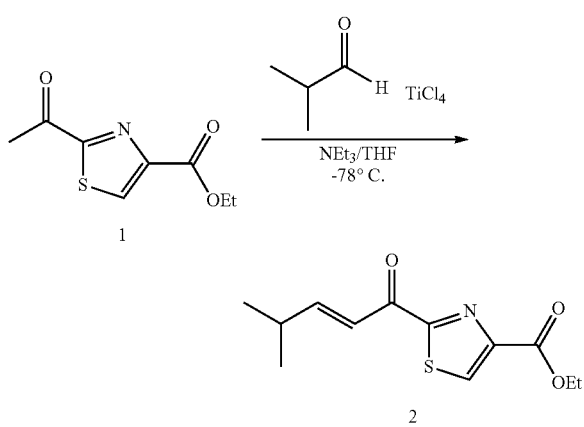

Example 1: Ethyl (E)-2-(4-methylpent-2-enoyl)thiazole-4-carboxylate

To a solution of ethyl 2-acetylthiazole-4-carboxylate (1, 11.6 g, 58.2 mmol) in dry THF (200 mL) was added 1 N solution of TiCl$_4$ in toluene (128 mL, 128 mmol) slowly at 0° C. The mixture was stirred for 30 min at 0° C. The solution was cooled to -78° C. Neat Et$_3$N (18 mL, 535 mmol) was added dropwise at −78° C. The stirring was continued for 10 min at −78° C. Isobutyradehyde (6.5 mL, 2.3 mmol) was added dropwise. The reaction mixture was stirred for 1 h at −78° C., whereupon the solution was allowed to warm to room temperature. The reaction was quenched with 50% sat. NH$_4$Cl aqueous solution followed by EtOAc. The aqueous phase was extracted with EtOAc five times. The collected organic phases were dried over anhydrous Na$_2$SO$_4$, filtered, and concentrated. The residue was purified by flash column purification, affording 9.2 g of the title compound (2, 63% isolated yield) as a yellow oil. $^1$H NMR is consistent with the literature (*J. Org. Chem.* 2016, 81, 10302-10320), MS [M+H] m/z=254.0598 (found).

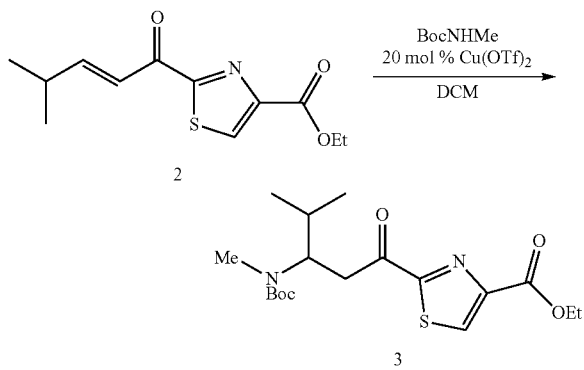

Example 2: Ethyl 2-(3-((tert-butoxycarbonyl)(methyl)amino)$_4$-methylpentanoyl)thiazole-4-carboxylate To a solution of ethyl (E)-2-(4-methylpent-2-enoyl)thiazole-4-carboxylate (2, 9.2 g, 36.36 mmol) in DCM (150 mL) was added BOC-NHMe (9.85 g, 75.09 mmol) in one portion at room temperature followed by Cu(OTf)$_2$ (2.72 g, 7.51 mmol) added in one portion at room temperature. The resulting reaction mixture was stirred for 15 h and then concentrated in vacuo to provide a residue that was purified by flash column affording 5.2 g of the title compound (3, 38% isolated yield). $^1$H NMR was consistent with its structure. MS [M+Na] m/z=407.1250 (found). HPLC (Method B): t$_R$=11.7 min.

Example 3: Variation in Transition Metal Catalyst and Solvent for the Aza-Michael Conjugate Addition Reaction Conversions of (E)-2-(4-methylpent-2-enoyl)thiazole-4-carboxylate (2) and BOC-NHMe to ethyl 2-(3-((tert-butoxycarbonyl)(methyl)amino)$_4$-methylpentanoyl)-thiazole-4-carboxylate (3) in the presence of 10 mole % of various transition (II) or transition (III) metal catalyst were determined, along with variations in solvent, by analyzing the reaction mixtures by RP-HPLC with monitoring at 220 nm. The conversions from those variations are presented in Table 1.

TABLE 1

Effect of transition metal catalyst and solvent on an aza-Michael conjugate addition reaction.

| Catalyst | Solvent | Conversion ( %) (220 nm) |
|---|---|---|
| Sn(OTf)$_2$* | ACN | 0 |
| Bi(NO$_3$)$_4$ | ACN | 0 |
| InCl$_3$/TMSCl | ACN | 0 |
| Cu(OTf)$_2$ | ACN | 0 |
| Cu(OTf)$_2$ | DCM | 39 |
| Yb(OTf)$_3$ | DCM | 39 |
| Zn(OTf)$_2$ | DCM | 39 |
| Pd(ACN)$_2$Cl$_2$ | DCM | 0 |
| Pd(PPh$_3$)$_2$Cl$_2$ | DCM | 0 |
| PtCl$_4$ | DCM | 0 |

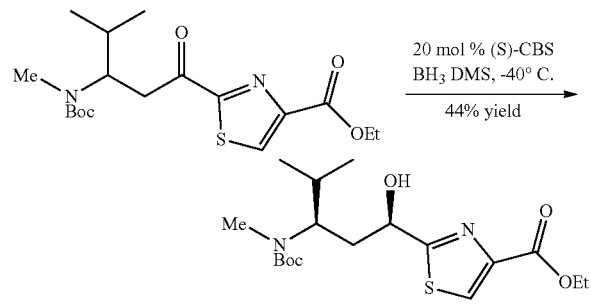

*Literature report for synthesis of ethyl 2-(3-((tert-butoxycarbonyl)amino) 4-methylpentanoyl)thiazole-4-carboxylate (desmethyl version of compound 3) by aza-Michael conjugate addition using Sn(OTf)$_2$ and BOC—NH$_2$ proceeded in 60% yield (Sani, M. et al. Angew. Chem. Int'l. Ed. (2007) 46: 3526-3529),whereas the same aza-Michael conjugate addition using BOC—NHMe resulted in no observable conversion to compound 3.

Example 4: Ethyl 2-((1R,3R)-3-((tert-butoxycarbonyl)(methyl)amino)-1-hydroxy-4-methylpentyl)thiazole-4-carboxylate To a solution of (S)-CBS catalyst (1.0 M in THF, 3.74 mL, 3.74 mmol) in THF (130 mL) was added BH$_3$.SMe$_2$ (2.0 M in THF, 9.85 mL, 19.68 mmol) at 0° C. After stirring for 10 min. the resulting reaction mixture was cooled to −40° C. whereupon a solution of ethyl 2-(3-((tert-butoxycarbonyl)(methyl)amino)-4-methylpentanoyl)thiazole-4-carboxylate (7.2 g, 18.75 mmol) in THF (65 mL) was added followed by stirring for 18 h while the temperature was allowed to gradually increase to room temperature. The reaction was then quenched with MeOH (130 mL) and solvent was removed under reduced pressure. The residue was purified by flash column purification, affording 3.27 g (44% isolated yield, 97.3% e.e.) of the title (1R,3R)-diastereomer of (R,R)-Formula 1a as an oil. MS [M+Na] m/z=409.1461 (found), which also provided the (1R,3S)-diastereomer of (R,S)-Formula 1a in purified form. Optical characterizations of those two diastereomers by chiral chromatography and optical rotation are as follows.

HPLC (Method C): $t_R$ (1R,3R)=17.2 min, $[\alpha]^{21.6}_D$ (c=10, MeCN) −7.7 deg.; $t_R$ (1R,3S)=7.7 min (Method C), $[\alpha]^{21.6}_D$ (c=10, MeCN)+37.3 deg.

The percent amounts of the title compound, (1R,3R)-BOC-desacetyl-Tuv-OEt, and optical isomers thereof prior and subsequent to flash chromatography are shown in Table 2 below.

Example 5: 2-((1R,3R)-3-((tert-Butoxycarbonyl)(methyl)amino)-1-hydroxy-4-methylpentyl)thiazole-4-carboxylic acid To a solution of ethyl 2-((1R,3R)-3-((tert-butoxycarbonyl)(methyl)amino)-1-hydroxy-4-methylpentyl)thiazole-4-carboxylate (1.4 g, 3.7 mmol) in THF (26 mL) was added a solution of LiOH monohydrate (0.19 g, 4.4 mmol) in water (5 mL) at 0° C. The resulting reaction solution was gradually warmed to room temperature for 16h followed by quenching with saturated KHSO$_4$ and dilution with EtOAc. The organic phase was collected and the remaining aqueous phase was extracted with EtOAc for two times. The combined organic extracts were washed with brine then dried over anhydrous Na$_2$SO$_4$, filtered, and concentrated to give the crude title compound (1.3 g, 96% isolated yield).

TABLE 2

Relative (%) amounts of optical isomers of BOC-desacetyl-Tuv-OEt

|  | (1R, 3R) | (1S, 3S) | (1S, 3R) | (1R, 3S) |
|---|---|---|---|---|
| Crude | 49.35 | 0.675 | 0.675 | 49.35 |
| Isolated | 98.65 | 1.35 | 0 | 0 |

(1R,3R)-BOC-desacetyl-Tuv-OEt prepared by extension of a previously reported stereoselective route (*J. Org. Chem.* 2008, 73: 4362-4369) is identical by analytical chiral chromatography to the major isolated optical isomer having (R,R)-Formula 1a is shown in Table 2 as are the $^1$H-NMR spectra.

For optical characterization of the two minor optical impurities of Table 2 of (S,R)-Formula 1a and (S,S)-Formula 1a found in the crude product, ethyl 2-(3-((tert-butoxycarbonyl)(methyl)amino)-4-methylpentanoyl)-thiazole-4-carboxylate was reduced with (R)-CBS catalyst to obtain those compounds as the major optical products. Optical characterizations of those two separated diastereomers are as follows:

HPLC (Method C): $t_R$ (1S,3R)=7.7 min., $[\alpha]^{22.0}_D$ (c=10, MeCN) −39.1 deg.; $t_R$ (1S,3S)=12.1 min, $[\alpha]^{21.9}_D$ (c=10, MeCN)+7.6 deg.

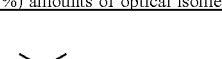

Other optical isomers of the (R,R)-Formula 2 title compound were similarly prepared by hydrolysis of each of the corresponding optical isomers described by Example 4. Optical rotations for each of the optical isomers are as follows. (R,R)-Formula 2: $[\alpha]^{22.0}_D$ (c=10, MeCN) −1.00 deg.; (R,S)-Formula 2: $[\alpha]^{22.0}_D$ (c=10, MeCN)+0.52 deg.; (S,S)-Formula 2: $[\alpha]^{22.0}_D$ (c=10, MeCN)+1.28 deg.; (S,R)-Formula 2: $[\alpha]^{22.0}_D$ (c=10, MeCN) −0.42 deg.

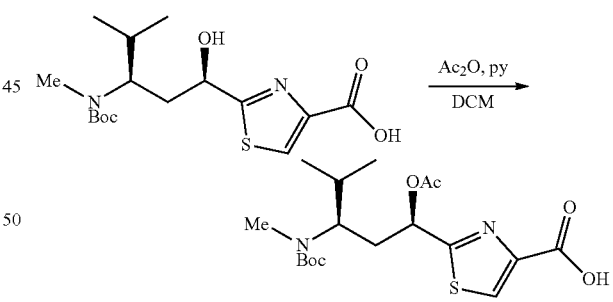

Example 6: 2-((1R,3R)-1-Acetoxy-3-((tert-butoxycarbonyl)(methyl)amino)-4-methylpentyl)thiazole-4-carboxylic acid To a solution of 2-((1R,3R)-3-((tert-butoxycarbonyl)(methyl)amino)-1-hydroxy-4-methylpentyl)thiazole-4-carboxylic acid (3.51 mmol) in DCM (25 mL) was added pyridine (1.5 mL, 18.42 mmol) at 0° C. over 5 minutes. To the solution was added Ac$_2$O (1.5 mL, 16.84 mmol) over 10 minutes. The ice bath was removed, and the reaction solution was allowed to warm up to room temperature for 16h. Water (10 mL) was added dropwise to the reaction mixture at 0° C. The ice bath was then removed, and the reaction mixture was stirred vigorously at RT for 1 hour. The solution was diluted with DCM (10 mL). The organic layer was collected. The aqueous phase was extracted with DCM for three times. The organic phase was extracted with 10% citric acid solution followed by water. The organic layer was dried over anhydrous Na$_2$SO$_4$, filtered, and concentrated to give crude material. The crude material was purified by flash chromatography, affording 1.215 g of the title compound (BOC-Tuv-OH) as a white foam (86% yield). $^1$H NMR (400 MHz, CDCl$_3$) is consistent with that reported for BOC-Tuv-OH (Columbo, R. et al. *J. Org. Chem.* (2016) 81: 10302-10320); [M+H] m/z=400.9301 (found), HPLC (Method A): t$_R$=19.24 min.

What is claimed is:

1. A method for preparing a composition comprising a tubuvaline compound of (R,R)-Formula 1a, or a salt thereof, having the structure of:

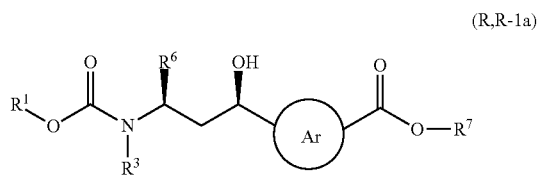

(R,R-1a)

and one or more optical isomers thereof as optical impurities, wherein the (R,R)-Formula 1a tubuvaline compound, or salt thereof, is the predominate optical isomer, and wherein its corresponding enantiomer, (S,S)-Formula 1a, or a salt thereof, is the major optical impurity and has the structure of:

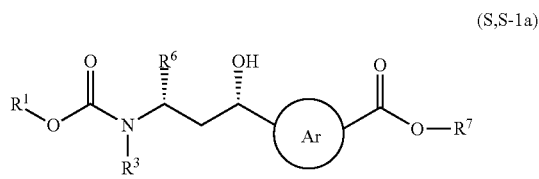

(S,S-1a)

wherein:
the circled Ar is a 1,3-phenylene or a 5- or 6-membered nitrogen-containing 1,3-heteroarylene, optionally substituted at the remaining positions;
R$^1$ is phenyl, t-butyl, 9-fluorenyl or allyl, optionally substituted, or other moeity so that R$^1$—OC(=O)— is a suitable nitrogen protecting group;
R$^3$ is optionally substituted saturated C$_1$-C$_8$ alkyl, optionally substituted unsaturated C$_3$-C$_8$ alkyl or optionally substituted C$_3$-C$_8$ heteroalkyl;
R$^6$ is optionally substituted C$_1$-C$_8$ alkyl; and
R$^7$ is optionally substituted saturated C$_1$-C$_{20}$ alkyl, optionally substituted unsaturated C$_3$-C$_{20}$ alkyl, optionally substituted C$_3$-C$_{20}$ heteroalkyl, optionally substituted C$_2$-C$_{20}$ alkenyl, optionally substituted C$_3$-C$_{20}$ heteroalkenyl, optionally substituted C$_2$-C$_{20}$ alkynyl, optionally substituted C$_3$-C$_{20}$ heteroalkynyl, optionally substituted C$_6$-C$_{24}$ aryl, optionally substituted C$_5$-C$_{24}$ heteroaryl, optionally substituted C$_3$-C$_{20}$ heterocyclyl, or other moeity so that R$^7$—O— provides for a suitable carboxylic acid protecting group, the method comprising the steps of:

(a) contacting a compound of Formula A:

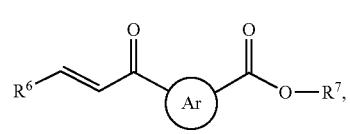

(A)

with a compound of Formula B:

 R$^3$NHC(O)OR$^1$  (B), in a suitable polar, aprotic solvent in the presence of a suitable transition metal (II) or transition metal (III) catalyst, so as to form a composition comprising an enantiomeric mixture of tubuvaline intermediates represented by Formula AB:

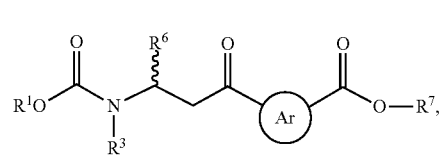

(AB)

(b) contacting the enantiomeric mixture with a suitable chiral reducing agent so as to form a composition comprising an equimolar mixture of diastereomers, wherein the diastereomeric mixture is represented by Formula R-1a,

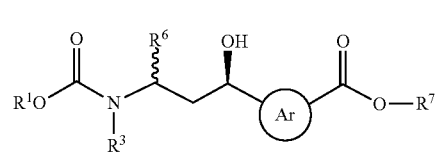

(R-1a)

or salts thereof, wherein the composition further comprises an equimolar mixture of optical impurities that are enantiomers of the diastereomers, and (b') separating the diastereomers from the composition of the Formula R-1a diastereomeric mixture so that the composition comprising (R,R)-Formula 1a as the predominate optical isomer and comprising (S,S)-Formula 1a as the major optical impurity is obtained, wherein the predominate optical isomer and the major optical impurities have the structures of:

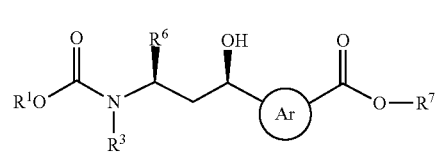

(R,R-1a)

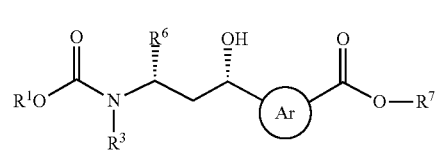

(S,S-1a)

or salts thereof, respectively.

2. The method of claim 1, wherein the suitable polar, aprotic solvent is acetonitrile, dichloromethane, THF, dioxane, or a mixture of two or three of these solvents.

3. The method of claim 2, wherein the chiral reducing agent is a chiral oxazaborolidine prepared from contacting BH$_3$-DMS in THF with a suitable chiral ligand.

4. A method for preparing a composition comprising a tubuvaline compound of (R,R)-Formula 2, or a salt thereof, having the structure of:

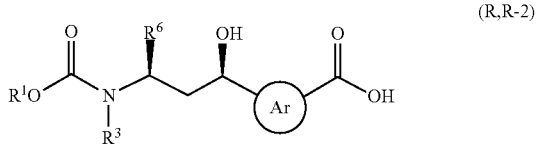
(R,R-2)

and one or more optical isomers thereof as optical impurities, wherein the (R,R)-Formula 2 tubuvaline compound, or salt thereof, is the predominate optical isomer, and wherein its corresponding enantiomer, (S,S)-Formula 2, or salt thereof, is the major optical impurity and has the structure of:

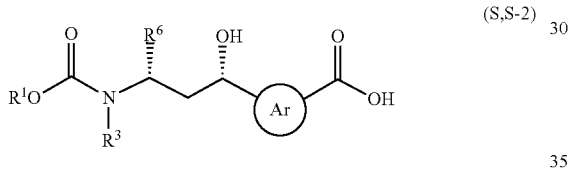
(S,S-2)

wherein:
the circled Ar is a 1,3-phenylene or a 5- or 6-membered nitrogen-containing 1,3-heteroarylene, optionally substituted at the remaining positions;
$R^1$ is phenyl, t-butyl, 9-fluorenyl or allyl, optionally substituted, or other moiety so that $R^1$—OC(=O)— is a suitable nitrogen protecting group;
$R^3$ is optionally substituted saturated $C_1$-$C_8$ alkyl, optionally substituted unsaturated $C_3$-$C_8$ alkyl or optionally substituted $C_3$-$C_8$ heteroalkyl; and
$R^6$ is optionally substituted $C_1$-$C_8$ alkyl, the method comprising the steps of:
(c) contacting the composition obtained from steps (a), (b) and step (b') of claim 1 with a suitable hydrolysis agent, wherein the predominate optical isomer of the composition so obtained is (R,R)-Formula 2, having the structure of:

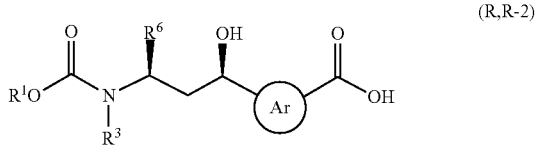
(R,R-2)

or a salt thereof, and the major optical impurity is (S,S)-Formula 2 having the structure of:

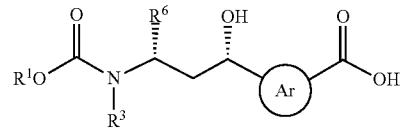
(S,S-2)

or a salt thereof.

5. A method for preparing a composition, comprising a tubuvaline compound of (R,R)-Formula 2a, or salt thereof, having the structure of:

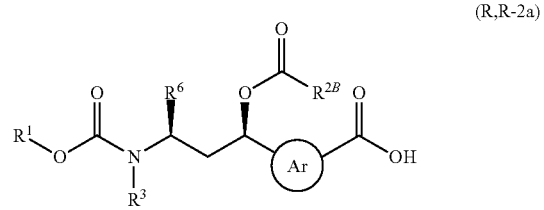
(R,R-2a)

and one or more optical isomers thereof as optical impurities, wherein the (R,R)-Formula 2a tubuvaline compound, or salt thereof, is the predominate optical isomer, and wherein its corresponding enantiomer, (S,S)-Formula 2a, or salt thereof, is the major optical impurity and has the structure of:

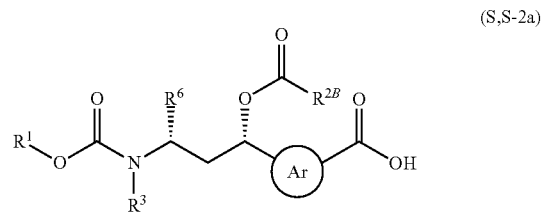
(S,S-2a)

wherein:
the circled Ar is a 1,3-phenylene or a 5- or 6-membered nitrogen-containing 1,3-heteroarylene, optionally substituted at the remaining positions;
$R^1$ is phenyl, t-butyl, 9-fluorenyl or allyl, optionally substituted, or other moiety so that $R^1$—OC(=O)— is a suitable nitrogen protecting group;
$R^3$ is optionally substituted saturated $C_1$-$C_8$ alkyl, optionally substituted unsaturated $C_3$-$C_8$ alkyl or optionally substituted $C_3$-$C_8$ heteroalkyl;
$R^6$ is optionally substituted $C_1$-$C_8$ alkyl; and
$R^{2B}$ is saturated $C_1$-$C_6$ alkyl, unsaturated $C_3$-$C_8$ alkyl, $C_2$-$C_8$ alkenyl or $C_2$-$C_4$ alkynyl, optionally substituted or $R^{2B}$ is —CH$_3$, —CH$_2$CH$_3$, —CH$_2$CH$_2$CH$_3$— CH$_2$CH=CH$_2$, —CH$_2$CH(CH$_3$)$_2$, —CH$_2$C(CH$_3$)$_3$, —CH$_2$C(CH$_3$)=CH$_2$, —CH=CH$_2$ or —CHCCH, the method comprising the steps of:
(c) contacting the composition obtained from steps (a), (b) and step (b') of claim 1 with a suitable hydrolysis agent to obtain a composition comprising (R,R)-Formula 2 having the structure of:

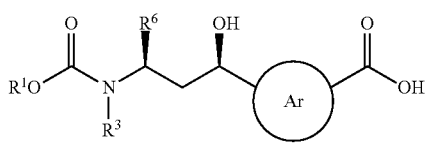

or salt thereof, as the predominate optical isomer and further comprising its enantiomer, having the structure of:

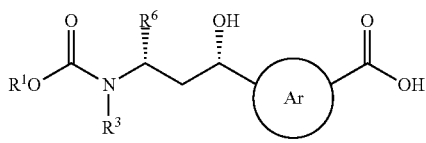

or a salt thereof, as the major optical impurity, and step (d): contacting the composition so obtained with a suitable acylating agent to obtain a composition comprising (R,R)-Formula 2a, or a salt thereof, as the predominate optical isomer and (S,S)-Formula 2a, or a salt thereof, as the major optical impurity, wherein the predominate optical isomer and the major optical impurity, have the structures of:

(R,R-2a)

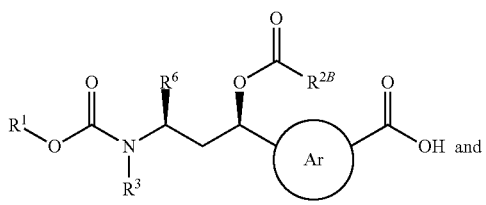

(S,S-2a)

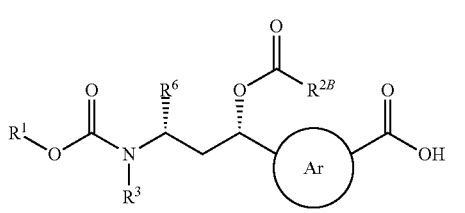

respectively.

6. The method of claim 4, wherein the optical purity of the composition from step (b') is substantially or essentially retained by the composition obtained from step (c).

7. The method of claim 1, wherein said step (b') separation is by silica gel flash chromatography.

8. The method of claim 1, wherein the circled Ar is a 5-membered nitrogen-containing 1,3-heteroarylene, optionally substituted at the remaining positions.

9. The method of claim 8, wherein compound A and compound B of step (a) have the structures of:

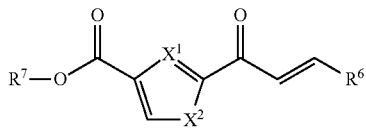

-continued

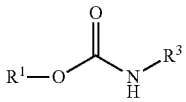

respectively, wherein, $X^1$ is =N—; and $X^2$ is S, O, or $N(R^{X2})$—, or $X^1$ is =$C(R^{X1})$—; and $X^2$ is $NR^{X2}$, wherein $R^{X1}$ and $R^{X2}$ are independently selected from the group consisting of —H, —$CH_3$ or —$CH_2CH_3$;

$R^1$ is phenyl, t-butyl, 9-fluorenyl or allyl, optionally substituted, or other moeity moiety so that $R^1$—OC(=O)— is a suitable nitrogen protecting group;

$R^3$ is optionally substituted saturated $C_1$-$C_6$ alkyl, optionally substituted unsaturated $C_3$-$C_6$ alkyl or optionally substituted $C_3$-$C_6$ heteroalkyl;

$R^6$ is $C_1$-$C_6$ alkyl; and $R^7$ is optionally substituted saturated $C_1$-$C_{20}$ alkyl, optionally substituted unsaturated $C_3$-$C_{20}$ alkyl, optionally substituted $C_3$-$C_{20}$ heteroalkyl, optionally substituted $C_2$-$C_{20}$ alkenyl, optionally substituted $C_3$-$C_{20}$ heteroalkenyl, optionally substituted $C_2$-$C_{20}$ alkynyl, optionally substituted $C_3$-$C_{20}$ heteroalkynyl, optionally substituted $C_6$-$C_{24}$ aryl, optionally substituted $C_5$-$C_{24}$ heteroaryl or optionally substituted $C_3$-$C_{20}$ heterocyclyl, or other moeity moiety so that $R^7$—O— provides a suitable carboxylic acid protecting group.

10. The method of claim 1, wherein the compound of (R,R)-Formula 1a, or a salt thereof, has the structure of:

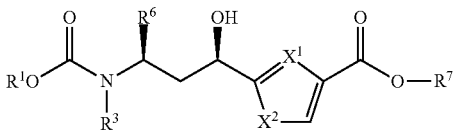

and its corresponding enantiomer of (S,S)-Formula 1a, or salt thereof, has the structure of:

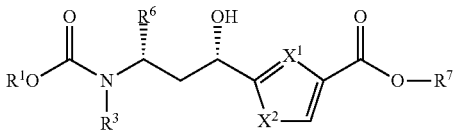

wherein $X^1$ is =N—; and $X^2$ is S, O, or $N(R^{X2})$—, or $X^1$ is =$C(R^{X1})$—; and $X^2$ is $NR^{X2}$, wherein $R^{X1}$ and $R^{X2}$ are independently selected from the group consisting of —H, —$CH_3$ or —$CH_2CH_3$.

11. The method of claim 1, wherein the compound of (R,R)-Formula 1a, or a salt thereof, has the structure of:

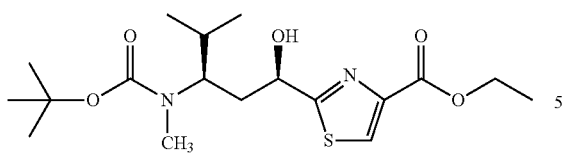

and its corresponding enantiomer of (S,S)-Formula 1a, or salt thereof, has the structure of:

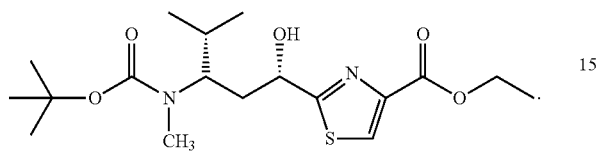

12. The method of claim 1, wherein the suitable transition metal (II) or transition metal (III) catalyst comprises a transition metal selected from the group consisting of Cu(II), Zn(II) and Yb(III).

13. The method of claim 1, wherein the transition (II) metal catalyst comprises Cu(II).

14. The method of claim 1, wherein the transition (II) metal catalyst is $Cu(OTf)_2$, $Cu(SbF_6)_2$, or $CuCl_2$.

15. The method of claim 1, wherein the suitable polar, aprotic solvent is dichloromethane.

16. The method of claim 1, wherein the chiral reducing agent is (S)-(−)-CBS.

17. The method of claim 4, wherein the compound of (R,R)-Formula 2, or a salt thereof, has the structure of:

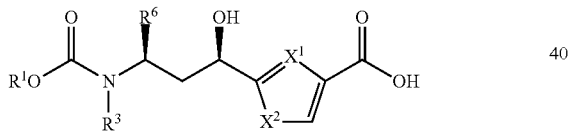

and its corresponding enantiomer of (S,S)-Formula 2, or salt thereof, has the structure of:

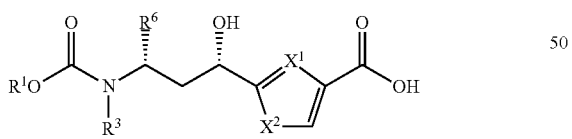

wherein
$X^1$ is =N—; and
$X^2$ is S, O, or $N(R^{X2})$—,
or
$X^1$ is =$C(R^{X1})$—; and
$X^2$ is $NR^{X2}$, wherein
$R^{X1}$ and $R^{X2}$ are independently selected from the group consisting of —H, —$CH_3$ or —$CH_2CH_3$.

18. The method of claim 4, wherein the compound of (R,R)-Formula 2, or a salt thereof, has the structure of:

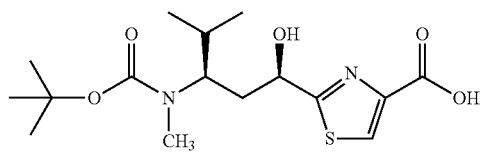 [SMILES: CC(C)[C@@H](C[C@@H](O)c1nc(C(=O)O)cs1)N(C)C(=O)OC(C)(C)C]

and its corresponding enantiomer of (S,S)-Formula 2, or salt thereof, has the structure of:

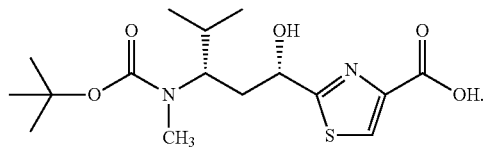 [SMILES: CC(C)[C@H](C[C@H](O)c1nc(C(=O)O)cs1)N(C)C(=O)OC(C)(C)C]

19. The method of claim 5, wherein the compound of (R,R)-Formula 2a, or a salt thereof, has the structure of:

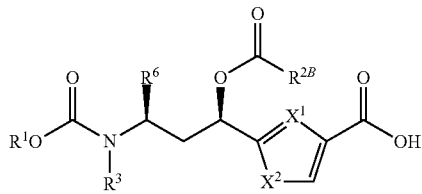

and its corresponding enantiomer of (S,S)-Formula 2a, or salt thereof, has the structure of:

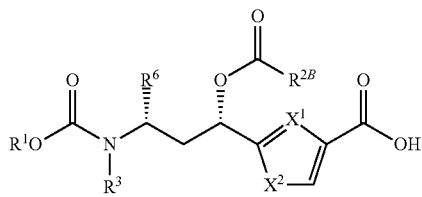

wherein
$X^1$ is =N—; and
$X^2$ is S, O, or $N(R^{X2})$—,
or
$X^1$ is =$C(R^{X1})$—; and
$X^2$ is $NR^{X2}$, wherein
$R^{X1}$ and $R^{X2}$ are independently selected from the group consisting of —H, —$CH_3$ or —$CH_2CH_3$.

20. The method of claim 5, wherein the compound of (R,R)-Formula 2a, or a salt thereof, has the structure of:

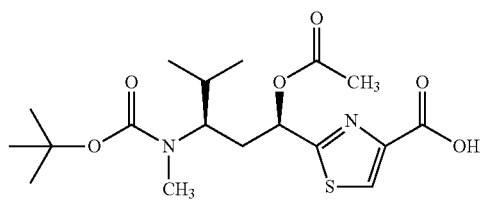 [SMILES: CC(=O)O[C@H](C[C@H](C(C)C)N(C)C(=O)OC(C)(C)C)c1nc(C(=O)O)cs1]

and its corresponding enantiomer of (S,S)-Formula 2a, or salt thereof, has the structure of:

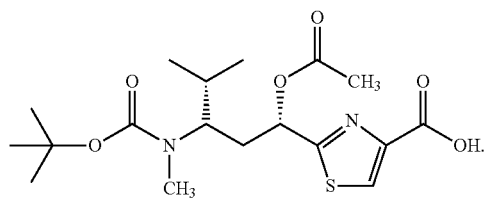
21. The method of claim 9, wherein
$R^1$ is t-butyl;
$R^3$ is —$CH_3$ or —$CH_2CH_2CH_3$;
$R^6$ is —$CH(CH_3)_2$; and
$R^7$ is —$CH_3$ or —$CH_2CH_3$.
22. The method of claim 9, wherein compound A and compound B have the structures of:
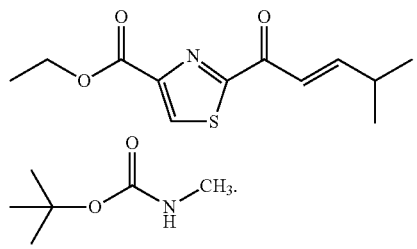
* * * * *